(12) United States Patent  (10) Patent No.: US 9,136,481 B2
Kang et al.  (45) Date of Patent: Sep. 15, 2015

(54) COMPOUND FOR AN ORGANIC PHOTOELECTRIC DEVICE, ORGANIC PHOTOELECTRIC DEVICE INCLUDING THE SAME, AND DISPLAY DEVICE INCLUDING THE ORGANIC PHOTOELECTRIC DEVICE

(75) Inventors: Dong-Min Kang, Uiwang-si (KR);
Mi-Young Chae, Uiwang-si (KR);
Myeong-Soon Kang, Uiwang-si (KR);
Sung-Hyun Jung, Uiwang-si (KR);
Ho-Kuk Jung, Uiwang-si (KR);
Nam-Heon Lee, Uiwang-si (KR);
Nam-Soo Kim, Uiwang-si (KR)

(73) Assignee: CHEIL INDUSTRIES, INC., Gum-si, Kyeongsangbuk-do (KR)

( * ) Notice: Subject to any disclaimer, the term of this patent is extended or adjusted under 35 U.S.C. 154(b) by 243 days.

(21) Appl. No.: 13/591,263

(22) Filed: Aug. 22, 2012

(65) Prior Publication Data
US 2012/0313091 A1 Dec. 13, 2012

Related U.S. Application Data

(63) Continuation of application No. PCT/KR2010/007058, filed on Oct. 14, 2010.

(30) Foreign Application Priority Data

Feb. 22, 2010 (KR) .................. 10-2010-0015901

(51) Int. Cl.
*C07D 413/14* (2006.01)
*H01L 51/46* (2006.01)
(Continued)

(52) U.S. Cl.
CPC .......... *H01L 51/0067* (2013.01); *C07D 401/14* (2013.01); *C07D 403/14* (2013.01);
(Continued)

(58) Field of Classification Search
None
See application file for complete search history.

(56) References Cited

U.S. PATENT DOCUMENTS 7,349,204 B2 3/2008 Tanaka et al.
7,803,468 B2 9/2010 Nariyuki et al.
(Continued)

FOREIGN PATENT DOCUMENTS

EP   1 718 121 A1  11/2006
JP   2006-128636 A  5/2006
(Continued)

OTHER PUBLICATIONS

Adachi, C., et al., "Electroluminescence in Organic Films with Three-Layer Structure," *Japanese Journal of Applied Physics*, vol. 27, No. 2, Feb. 1988, pp. L269-L271.
(Continued)

*Primary Examiner* — J. L. Yang
(74) *Attorney, Agent, or Firm* — Lee & Morse, P.C.

(57) ABSTRACT

A compound for an organic photoelectric device, an organic photoelectric device including the same, and a display device including the organic photoelectric device, the compound being represented by the following Chemical Formula 1:

[Chemical Formula 1]

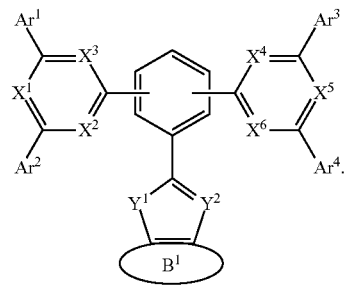

17 Claims, 7 Drawing Sheets

(51) Int. Cl.
*H01L 51/54* (2006.01)
*H01L 51/00* (2006.01)
*C07D 401/14* (2006.01)
*C07D 403/14* (2006.01)
*C07D 471/14* (2006.01)
*C07D 498/04* (2006.01)
*C07D 498/14* (2006.01)
*H01L 51/50* (2006.01)
*H01L 51/42* (2006.01)

(52) U.S. Cl.
CPC ............ *C07D413/14* (2013.01); *C07D 471/14* (2013.01); *C07D 498/04* (2013.01); *C07D 498/14* (2013.01); *H01L 51/0071* (2013.01); *H01L 51/0072* (2013.01); *H01L 51/42* (2013.01); *H01L 51/5012* (2013.01); *Y02E 10/549* (2013.01)

(56) References Cited

U.S. PATENT DOCUMENTS

| | | | |
|---|---|---|---|
| 2004/0124766 A1* | 7/2004 | Nakagawa et al. | ........... 313/504 |
| 2004/0251467 A1 | 12/2004 | Nakamura | |
| 2006/0057427 A1 | 3/2006 | Tsukahara et al. | |
| 2007/0257600 A1 | 11/2007 | Matsuura et al. | |

FOREIGN PATENT DOCUMENTS

| | | |
|---|---|---|
| JP | 2006-135184 A | 5/2006 |
| JP | 2006-235696 A | 9/2006 |
| JP | 2006-279014 A | 10/2006 |
| JP | 2007-015993 A | 1/2007 |
| KR | 10-2006-0114001 A | 11/2006 |
| KR | 10-0857655 B1 | 9/2008 |
| KR | 10-2009-0039598 A | 4/2009 |
| WO | WO 2009/051454 A2 * 4/2009 ............. C09K 11/06 |

OTHER PUBLICATIONS

Baldo, M. A., et al., "Very high-efficiency green organic light-emitting devices based on electrophosphorescence," *Applied Physics Letters*, vol. 75, No. 1, Jul. 5, 1999, pp. 4-6.

O'Brien, D. F., et al., "Improved energy transfer in electrophosphorescent devices," *Applied Physics Letters*, vol. 74, No. 3, Jan. 18, 1999, pp. 442-444.

Scholz, S., et al., "Photochemical reactions in organic semiconductor thin films," *Organic Electronics*, vol. 8, 2007, pp. 709-717.

Tang, C. W., et al., "Organic electroluminescent diodes," *Applied Physics Letters*, vol. 51, No. 12, Sep. 21, 1987, pp. 913-915.

International Search Report issued in PCT/KR2010/007058 having a mailing date of Jul. 8, 2011.

* cited by examiner

COMPOUND FOR AN ORGANIC PHOTOELECTRIC DEVICE, ORGANIC PHOTOELECTRIC DEVICE INCLUDING THE SAME, AND DISPLAY DEVICE INCLUDING THE ORGANIC PHOTOELECTRIC DEVICE

CROSS-REFERENCE TO RELATED APPLICATIONS

This application is a continuation of pending International Application No. PCT/KR2010/007058, entitled "Compound for Organic Photoelectric Device and Organic Photoelectric Device Including the Same," which was filed on Oct. 14, 2010, the entire contents of which are hereby incorporated by reference.

This application claims priority under 35 U.S.C. §119 to and the benefit of Korean Patent Application No. 10-2010-0015901 filed in the Korean Intellectual Property Office on Feb. 22, 2010, the entire contents of which are incorporated herein by reference.

BACKGROUND

1. Field

Embodiments relate to a compound for an organic photoelectric device, an organic photoelectric device including the same, and a display device including the organic photoelectric device.

2. Description of the Related Art

An organic photoelectric device is, in a broad sense, a device for transforming photo-energy to electrical energy, or conversely, a device for transforming electrical energy to photo-energy.

An organic photoelectric device may be classified as follows in accordance with its driving principles. One type of organic photoelectric device is an electronic device driven as follows: excitons are generated in an organic material layer by photons from an external light source; the excitons are separated into electrons and holes; and the electrons and holes are transferred to different electrodes as a current source (voltage source).

Another type of organic photoelectric device is an electronic device driven as follows: a voltage or a current is applied to at least two electrodes to inject holes and/or electrons into an organic material semiconductor positioned at an interface of the electrodes, and the device is driven by the injected electrons and holes.

Examples of an organic photoelectric device may include an organic light emitting diode, an organic solar cell, an organic photo conductor drum, and an organic transistor. The organic photoelectric device may include a hole injecting or transport material, an electron injecting or transport material, or a light emitting material.

For example, an organic light emitting diode (OLED) has recently drawn attention due to an increase in demand for flat panel displays. In general, organic light emission may refer to transformation of electrical energy to photo-energy.

SUMMARY

Embodiments are directed to a compound for an organic photoelectric device, an organic photoelectric device including the same, and a display device including the organic photoelectric device.

The embodiments may be realized by providing a compound for an organic photoelectric device, the compound being represented by the following Chemical Formula 1:

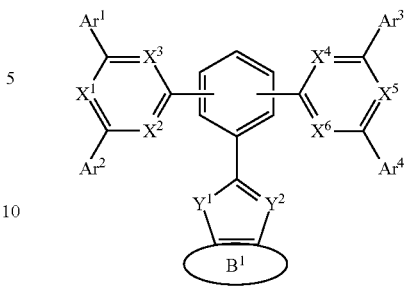

[Chemical Formula 1]

wherein, in Chemical Formula 1 $Ar^1$ to $Ar^4$ are each independently a substituted or unsubstituted C6 to C30 aryl group or a substituted or unsubstituted C3 to C30 heteroaryl group, $X^1$ to $X^6$ are each independently —N— or —CH—, provided that at least one of $X^1$ to $X^3$ is —N— and at least one of $X^4$ to $X^6$ is —N—, $Y^1$ is selected from the group of —O—, —S—, —NH— and —NR—, wherein R is selected from the group of a substituted or unsubstituted C6 to C30 aryl group, a substituted or unsubstituted C3 to C30 heteroaryl group, a substituted or unsubstituted C1 to C6 alkyl group, a substituted or unsubstituted C3 to C30 cycloalkyl group, a substituted or unsubstituted cyano group, a substituted or unsubstituted nitro group, a substituted or unsubstituted carbonyl group, and a substituted or unsubstituted amide group, $Y^2$ is —CH— or —N—, and $B^1$ is a substituted or unsubstituted C6 to C30 aryl group or substituted or unsubstituted C3 to C30 heteroaryl group and forms a fused ring with the moiety including $Y^1$ and $Y^2$.

The compound for an organic photoelectric device represented by Chemical Formula 1 may be represented by the following Chemical Formula 2:

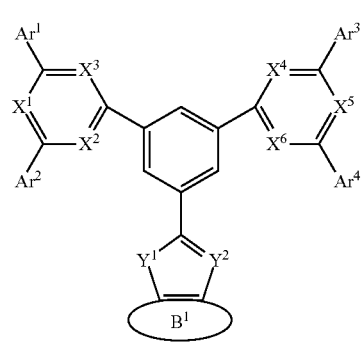

[Chemical Formula 2]

wherein, in Chemical Formula 2, $Ar^1$ to $Ar^4$ are each independently a substituted or unsubstituted C6 to C30 aryl group or a substituted or unsubstituted C3 to C30 heteroaryl group, $X^1$ to $X^6$ are each independently —N— or —CH—, provided that at least one of $X^1$ to $X^3$ is —N— and at least one of $X^4$ to $X^6$ is —N—, $Y^1$ is selected from the group of —O—, —S—, —NH—, and —NR—, wherein R is selected from the group of a substituted or unsubstituted C6 to C30 aryl group, a substituted or unsubstituted C3 to C30 heteroaryl group, a substituted or unsubstituted C1 to C6 alkyl group, a substituted or unsubstituted C3 to C30 cycloalkyl group, a substituted or unsubstituted cyano group, a substituted or unsubstituted nitro group, a substituted or unsubstituted carbonyl group, and a substituted or unsubstituted amide group, $Y^2$ is —CH— or —N—, and $B^1$ is a substituted or unsubstituted C6 to C30 aryl group or a substituted or unsubstituted C3 to C30 heteroaryl group and forms a fused ring with the moiety including $Y^1$ and $Y^2$.

$Ar^1$ to $Ar^4$ may each independently be a substituted or unsubstituted phenyl group, a substituted or unsubstituted naphthyl group, a substituted or unsubstituted anthracenyl group, a substituted or unsubstituted phenanthrenyl group, a substituted or unsubstituted perylenyl group, a substituted or unsubstituted chrysenyl group, a substituted or unsubstituted pyridinyl group, a substituted or unsubstituted pyridazinyl group, a substituted or unsubstituted quinolinyl group, or a substituted or unsubstituted isoquinolinyl group.

$B^1$ may be selected from the group of a substituted or unsubstituted phenyl group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted perylenyl group, a substituted or unsubstituted chrysenyl group, a substituted or unsubstituted pyridinyl group, a substituted or unsubstituted quinolinyl group, a substituted or unsubstituted benzoquinolinyl group, and a substituted or unsubstituted phenanthrolinyl group.

The embodiments may also be realized by providing a compound for an organic photoelectric device, the compound being represented by one of the following Chemical Formulae 3 to 186:

[Chemical Formula 3]

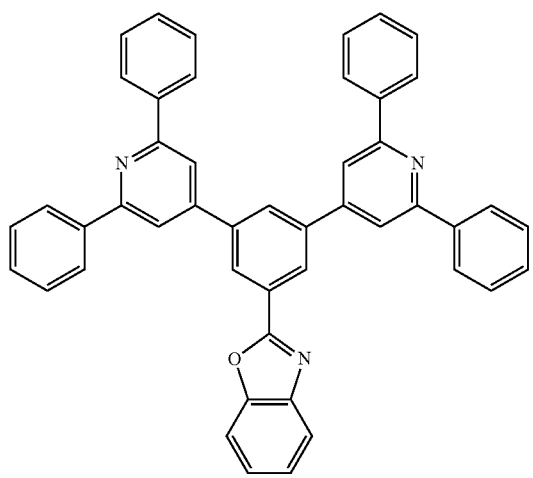

[Chemcial Formula 4]

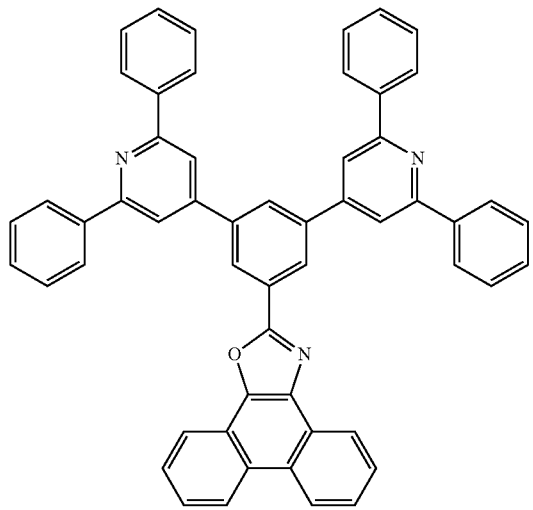

[Chemical Formula 5]

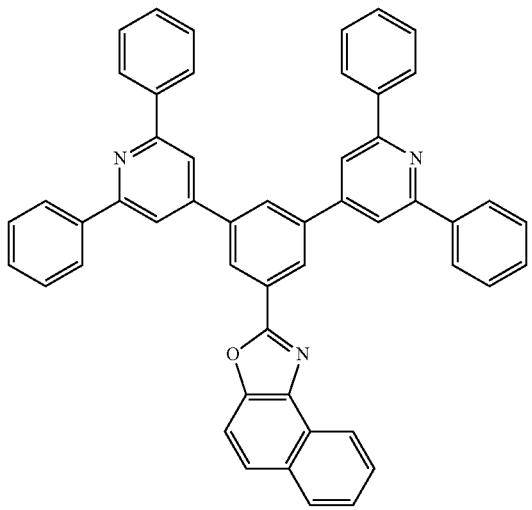

[Chemical Formula 6]

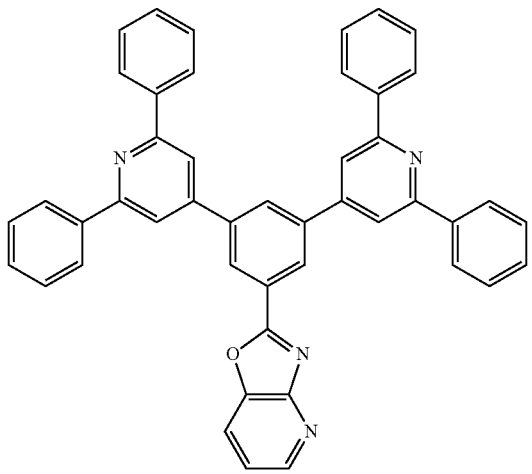

[Chemical Formula 7]

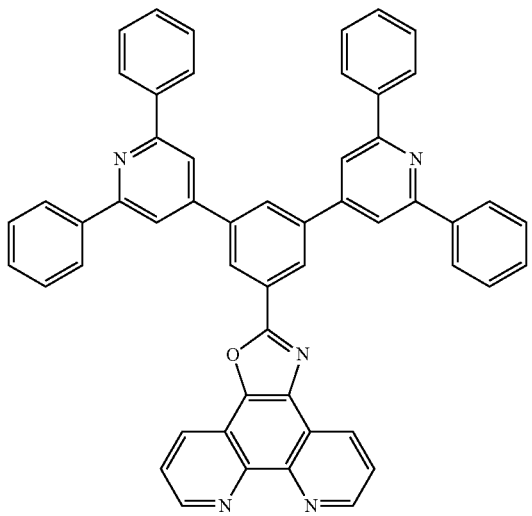

[Chemical Formula 8]
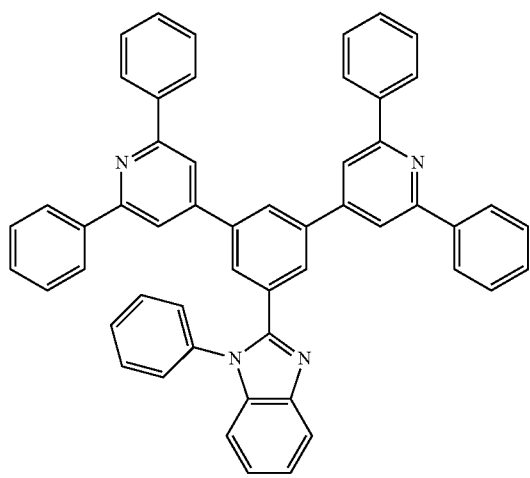
[Chemical Formula 9]
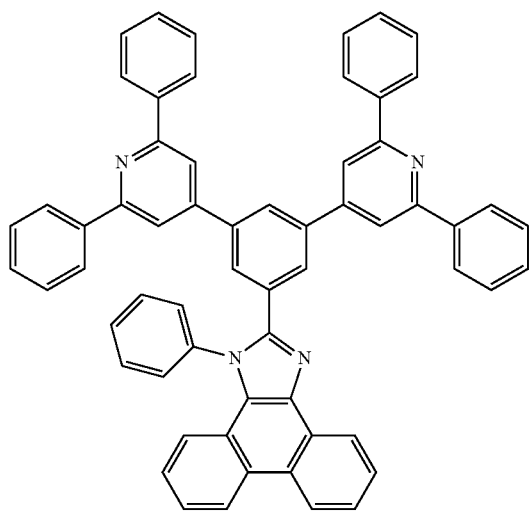
[Chemical Formula 10]
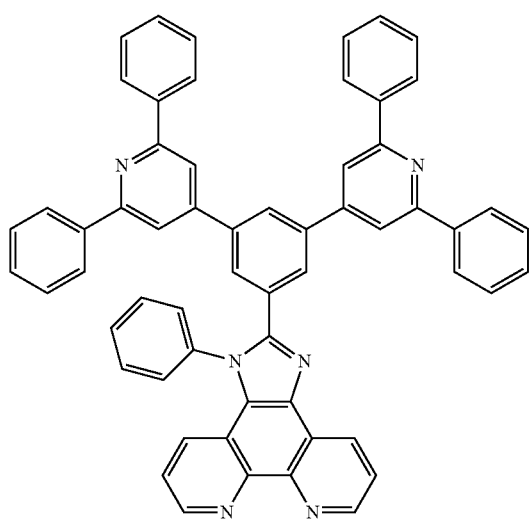
[Chemical Formula 11]
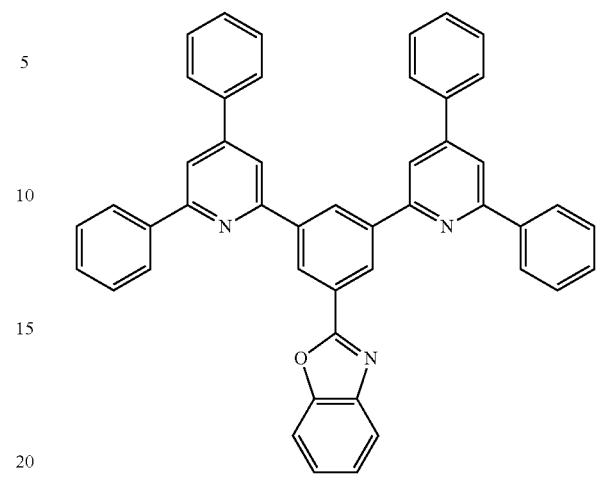
[Chemical Formula 12]
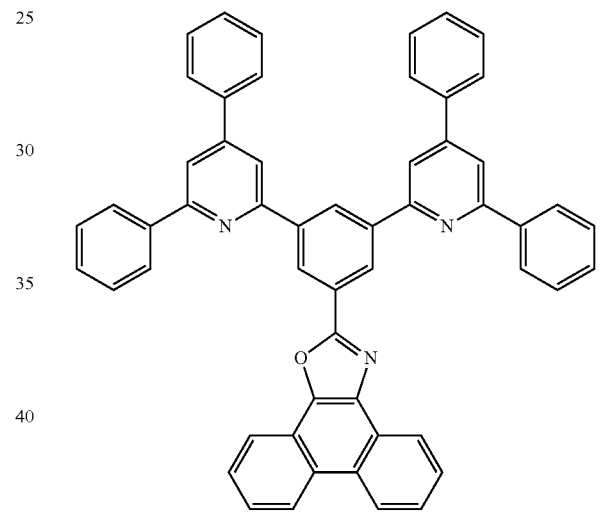
[Chemical Formula 13]
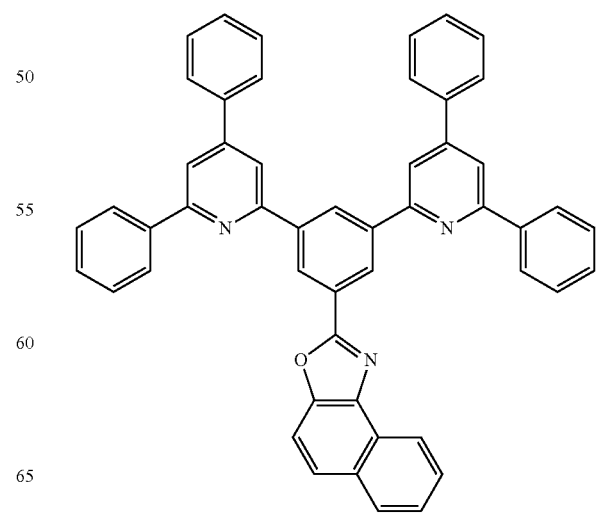

[Chemical Formula 14]
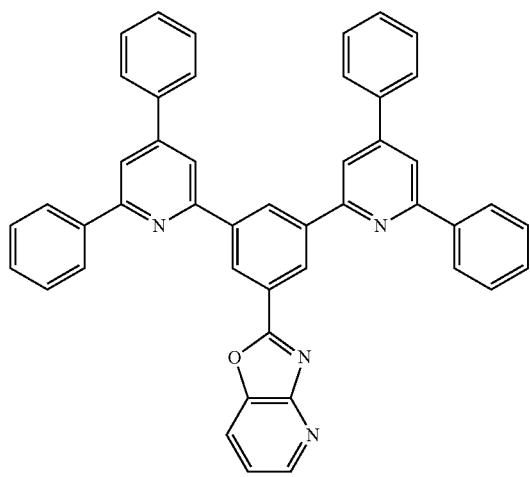
[Chemical Formula 15]
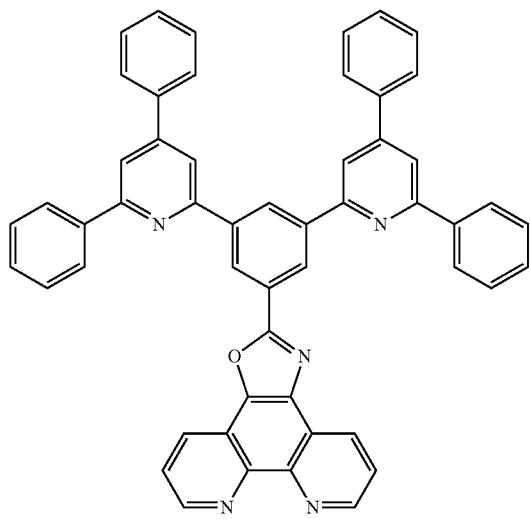
[Chemical Formula 16]
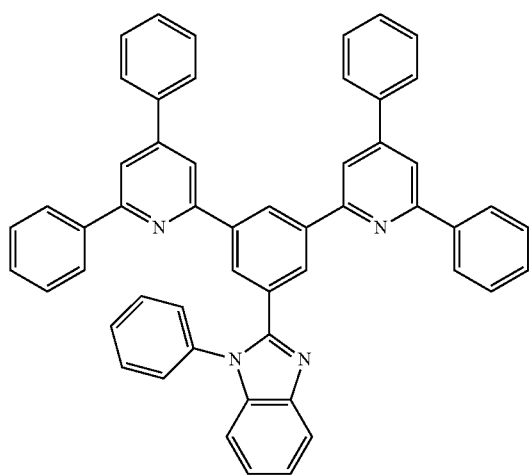
[Chemical Formula 17]
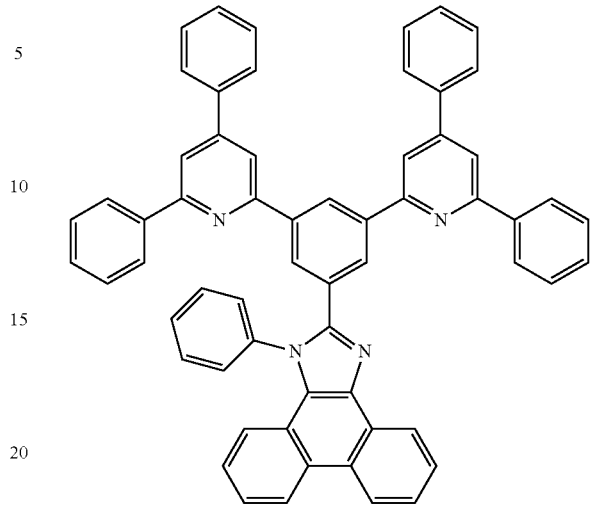
[Chemical Formula 18]
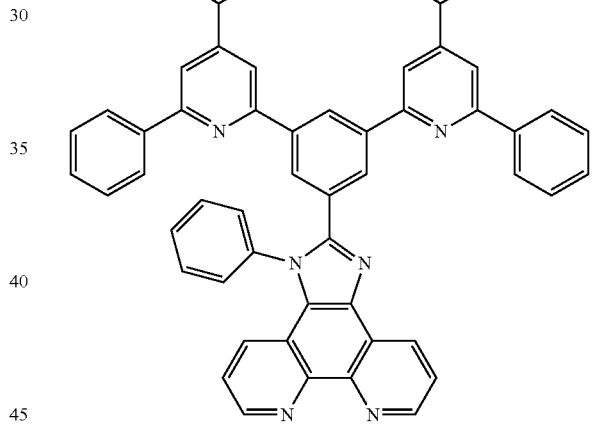
[Chemical Formula 19]
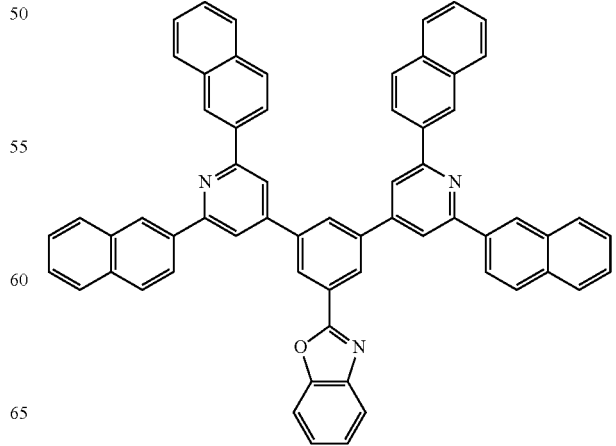

[Chemical Formula 20]
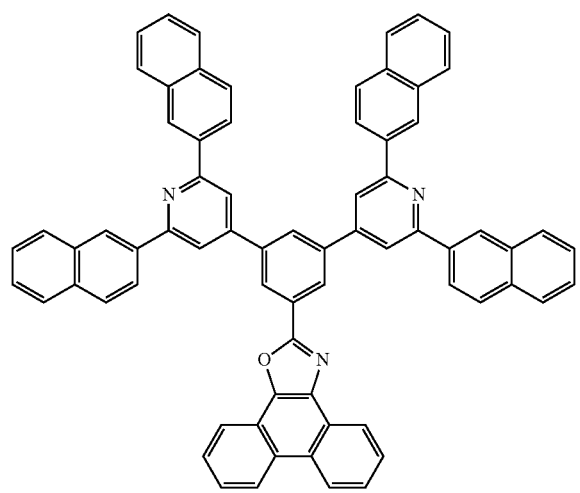
[Chemical Formula 23]
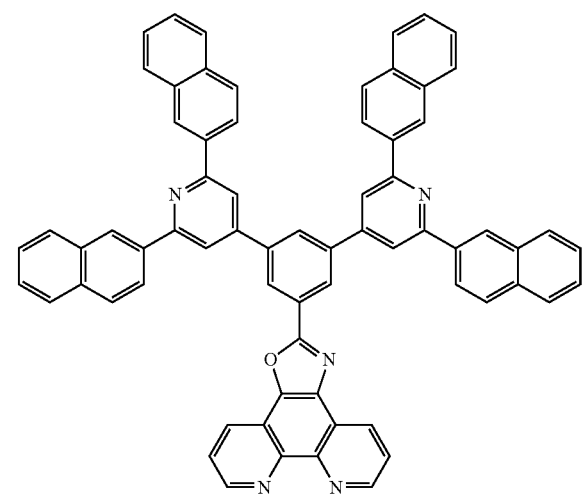
[Chemical Formula 21]
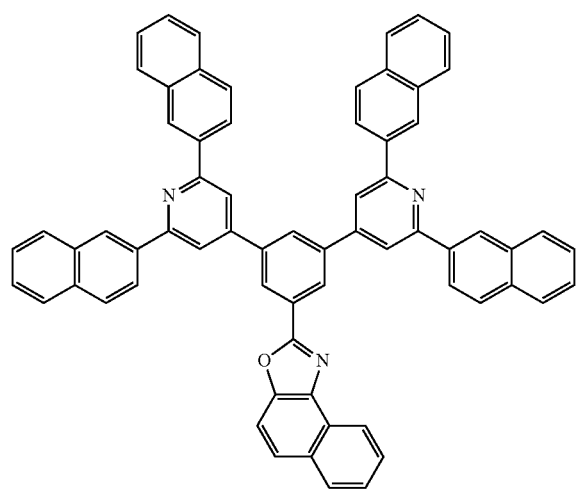
[Chemical Formula 24]
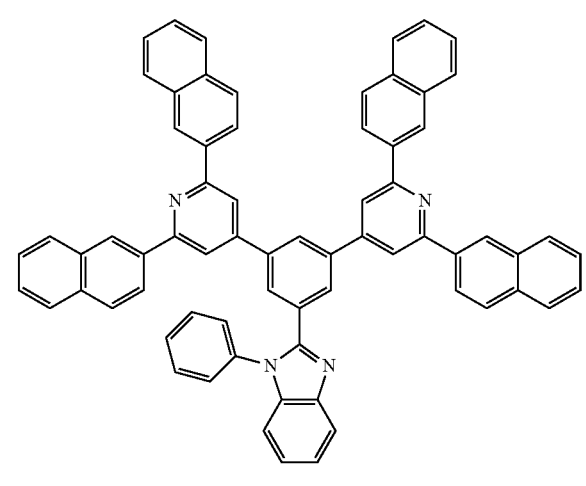
[Chemical Formula 22]
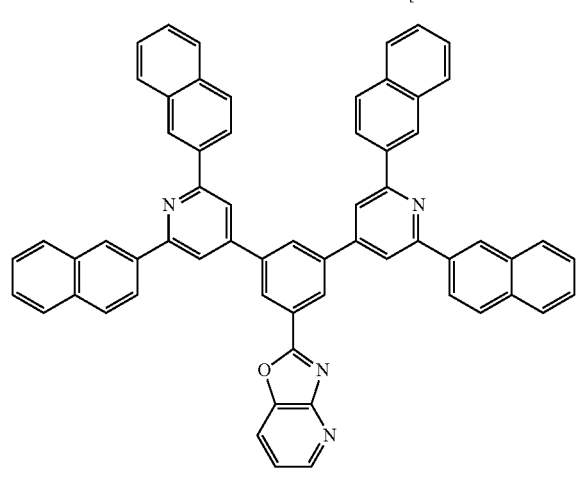
[Chemical Formula 25]
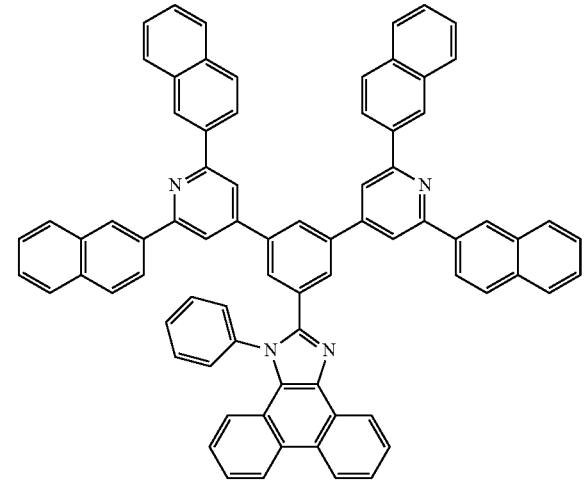

[Chemical Formula 26]
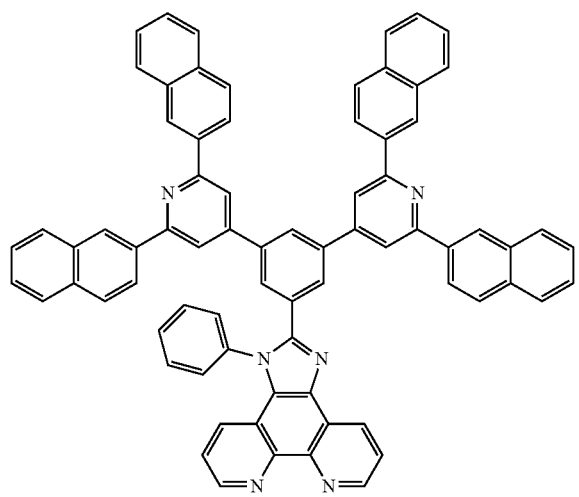
[Chemical Formula 29]
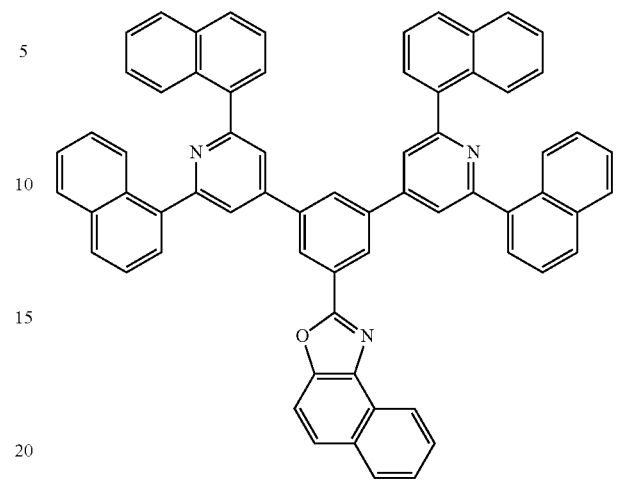
[Chemical Formula 27]
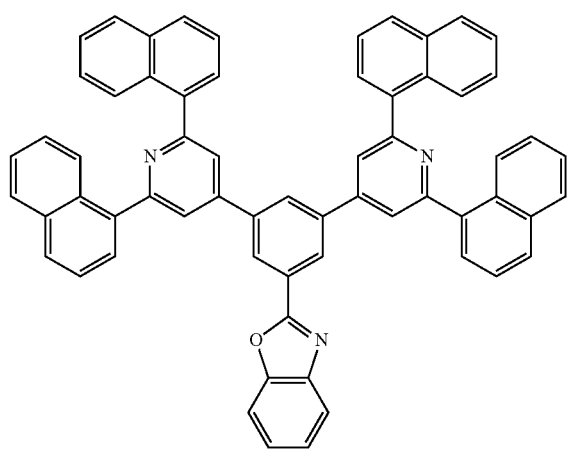
[Chemical Formula 30]
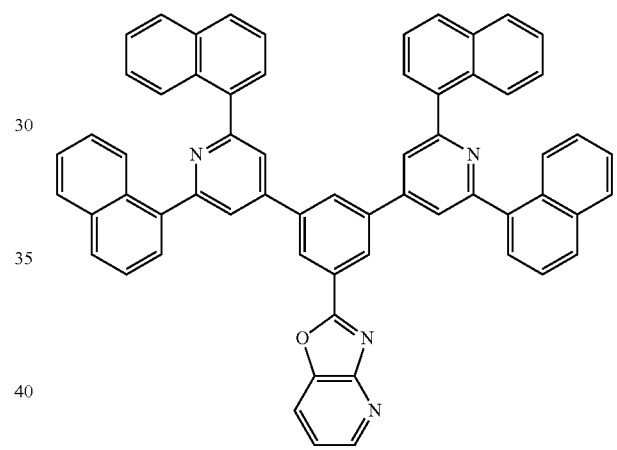
[Chemical Formula 28]
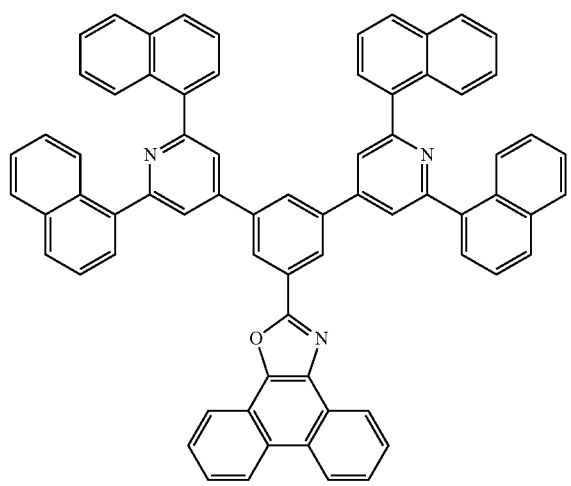
[Chemical Formula 31]
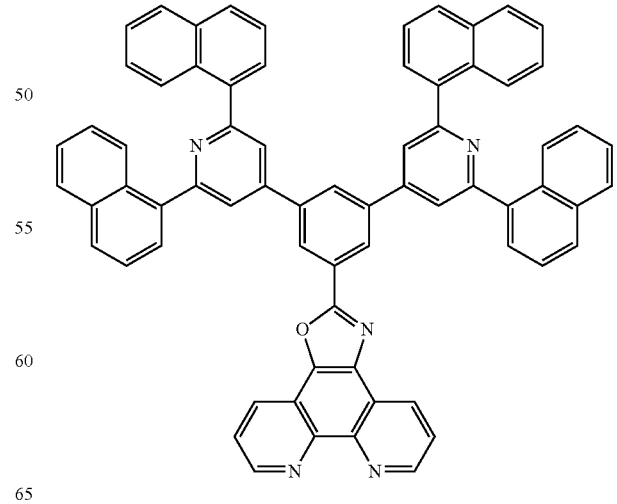

[Chemical Formula 32]
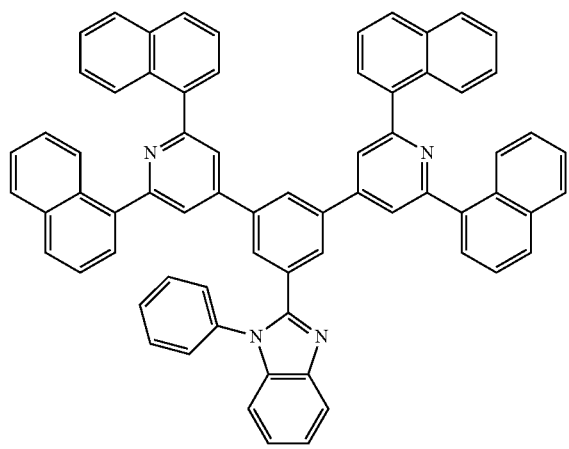
[Chemical Formula 33]
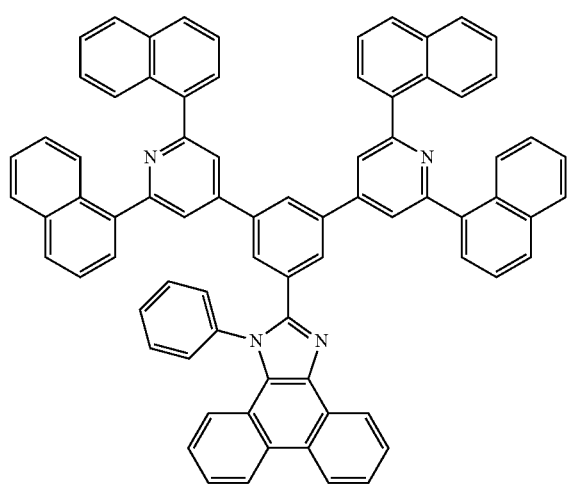
[Chemical Formula 34]
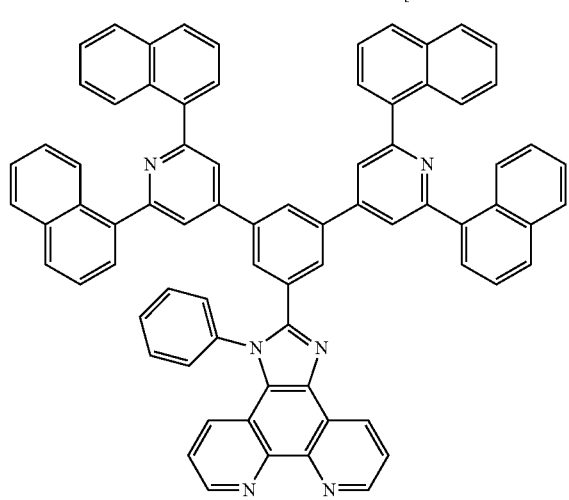
[Chemical Formula 35]
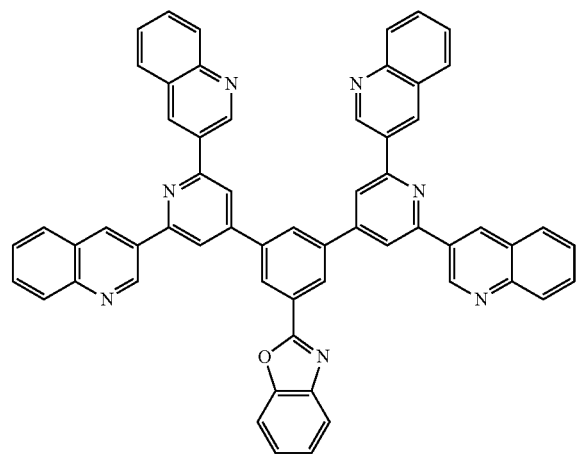
[Chemical Formula 36]
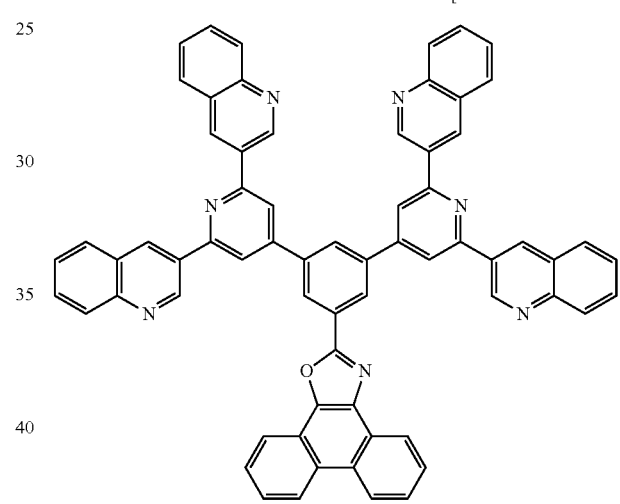
[Chemical Formula 37]
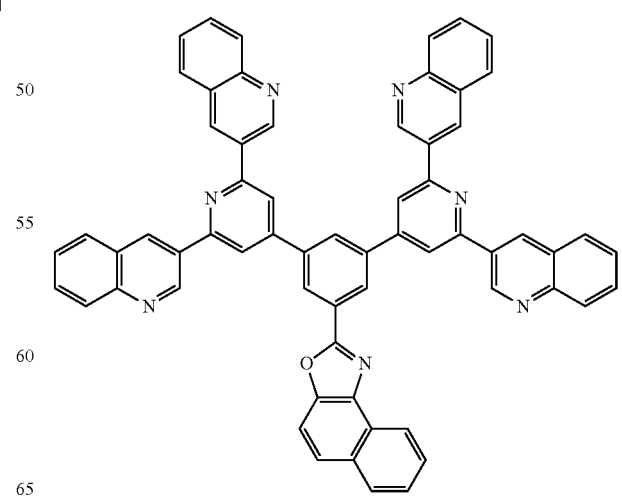

[Chemical Formula 38]
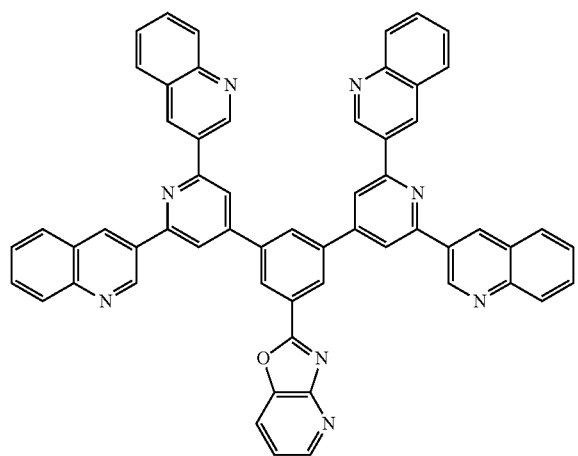
[Chemical Formula 39]
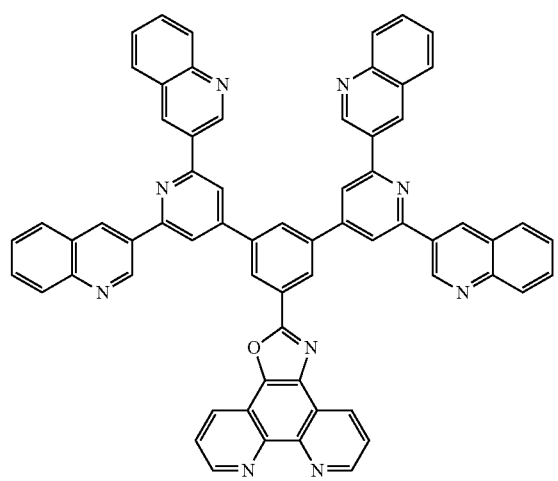
[Chemical Formula 40]
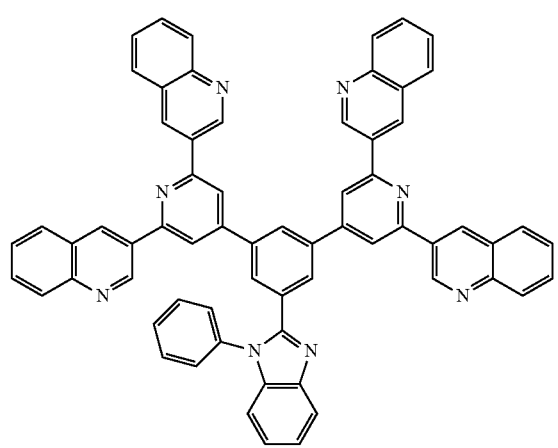
[Chemical Formula 41]
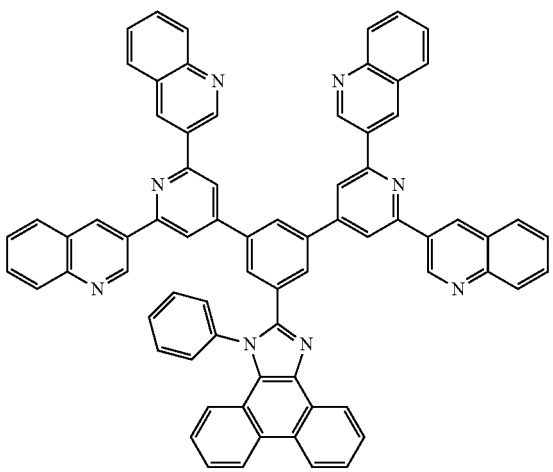
[Chemical Formula 42]
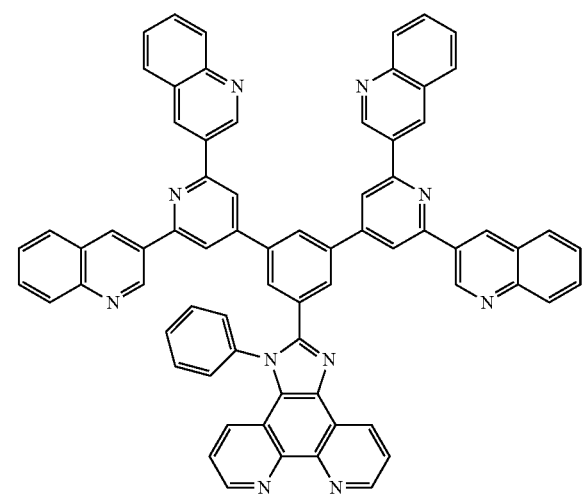
[Chemical Formula 43]
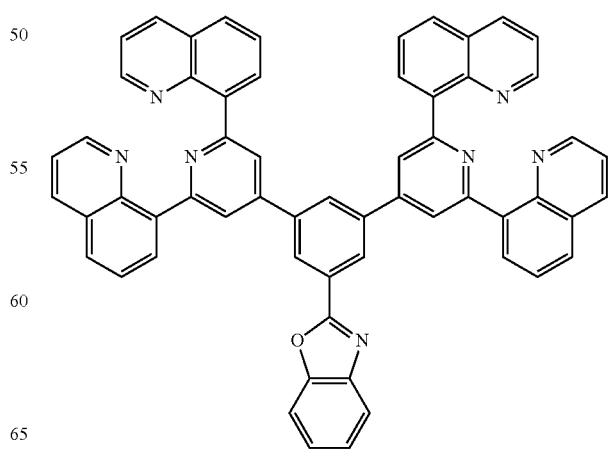

-continued
[Chemical Formula 44]
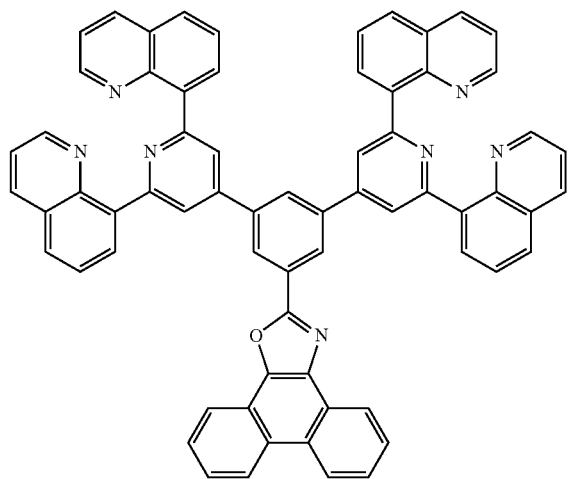
[Chemical Formula 45]
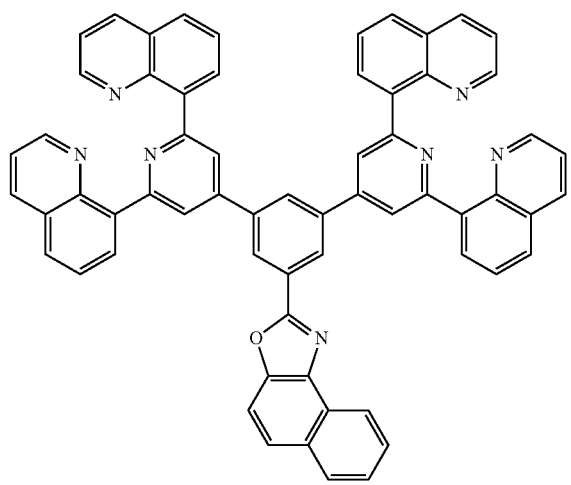
[Chemical Formula 46]
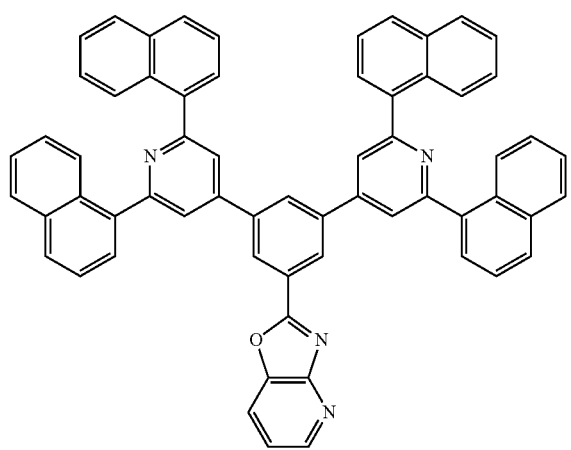
-continued
[Chemical Formula 47]
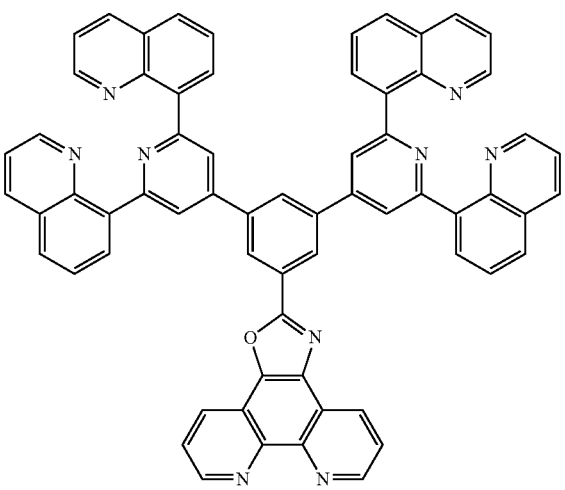
[Chemical Formula 48]
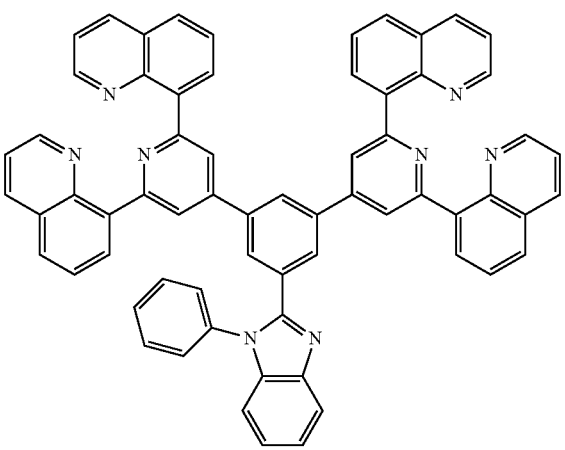
[Chemical Formula 49]
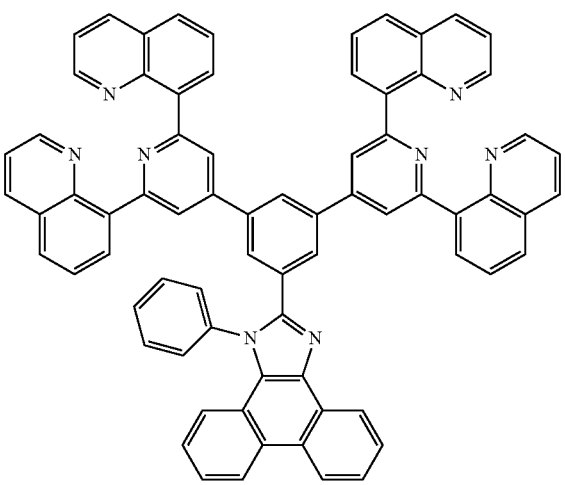

[Chemical Formula 50]
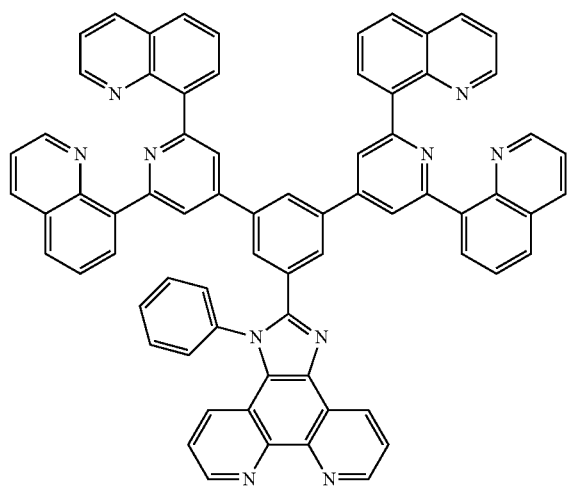
[Chemical Formula 53]
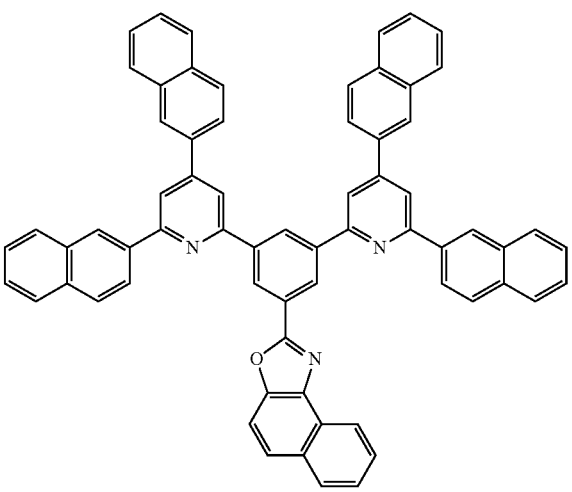
[Chemical Formula 51]
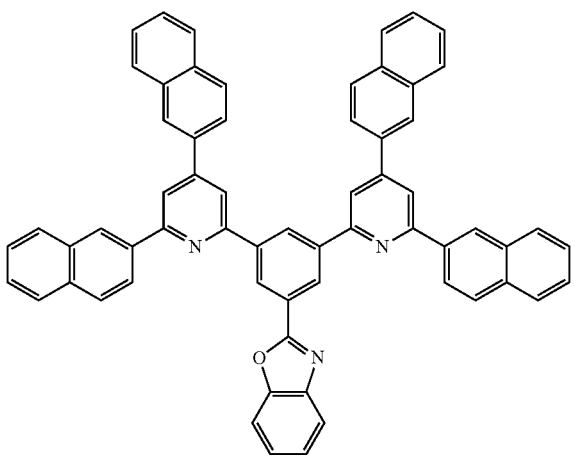
[Chemical Formula 54]
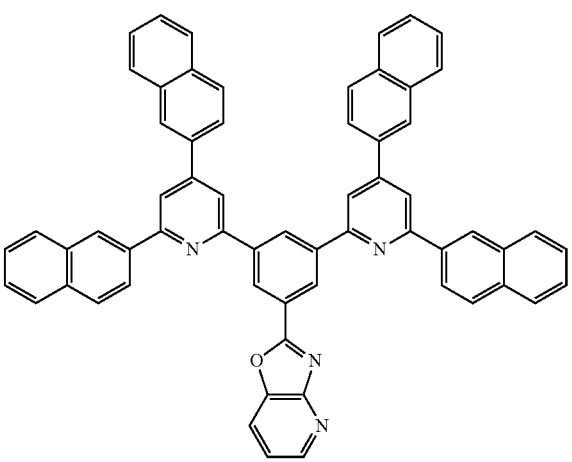
[Chemical Formula 52]
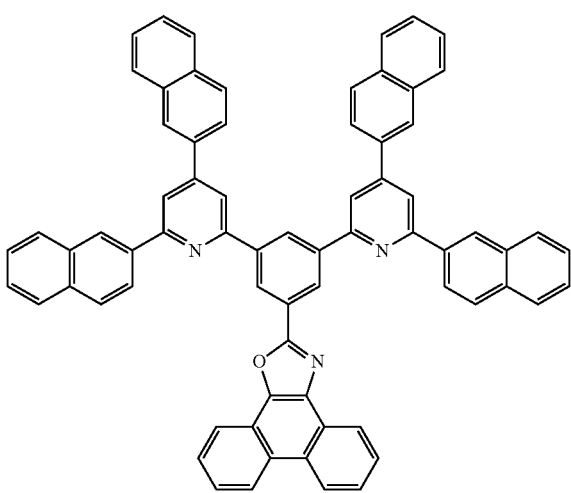
[Chemical Formula 55]
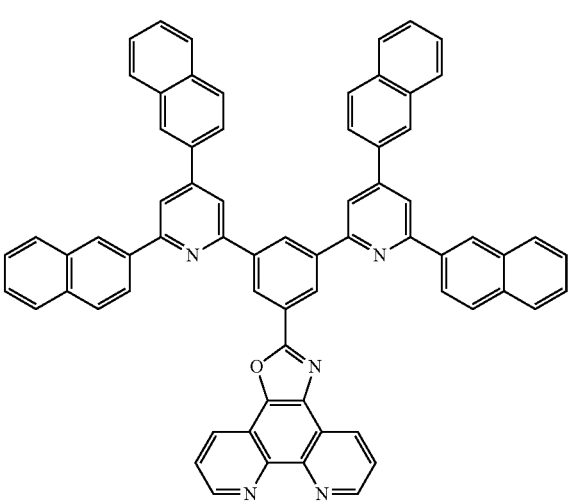

[Chemical Formula 56]
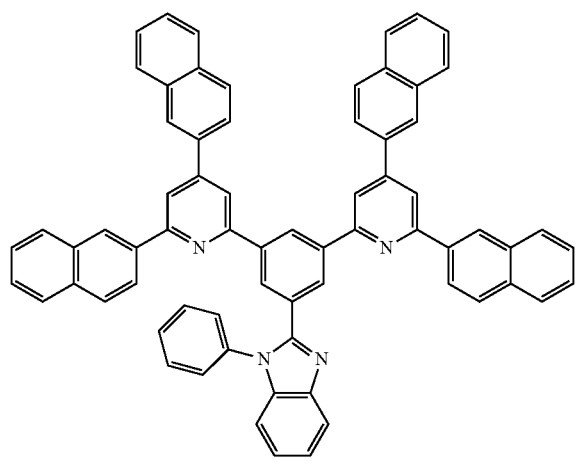
[Chemical Formula 57]
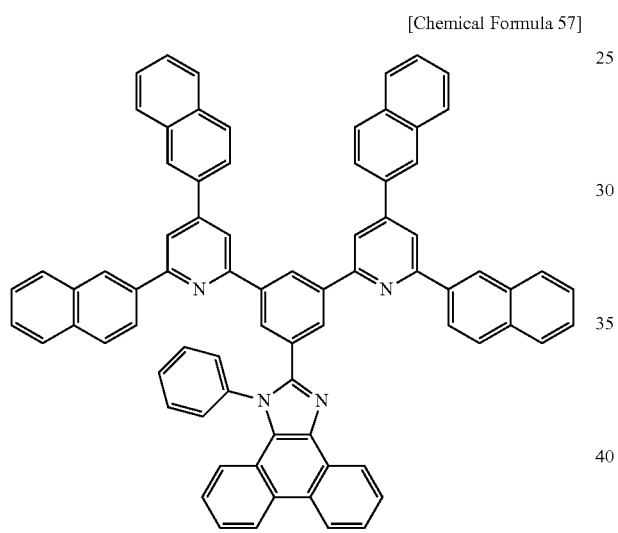
[Chemical Formula 58]
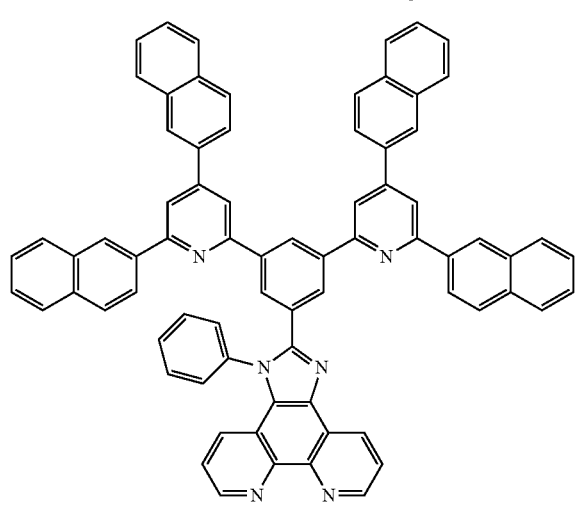
[Chemical Formula 59]
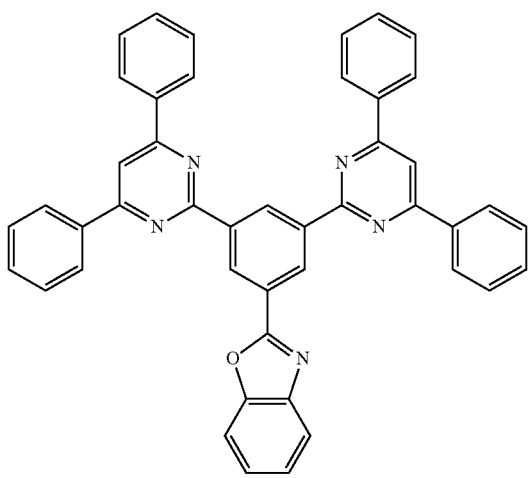
[Chemical Formula 60]
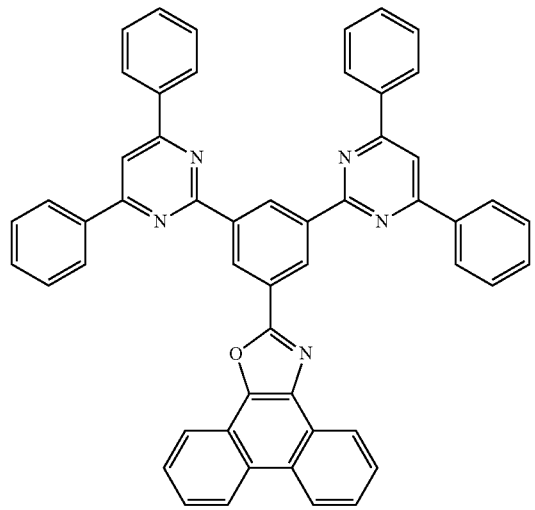
[Chemical Formula 61]
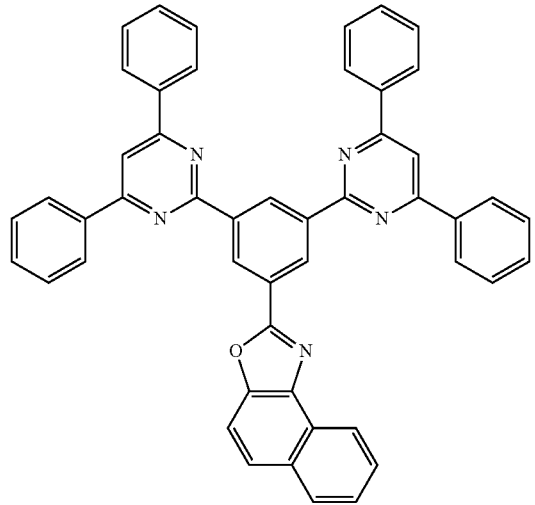

[Chemical Formula 62]
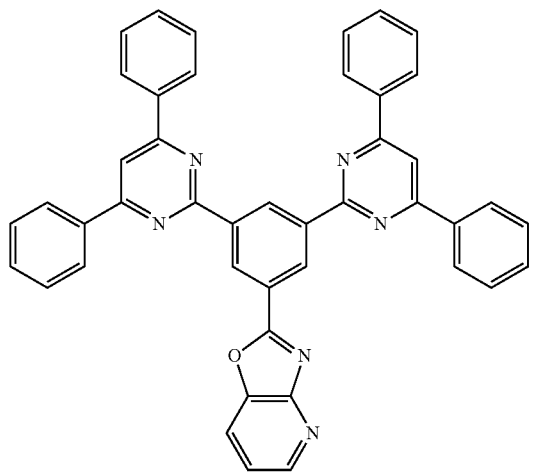
[Chemical Formula 63]
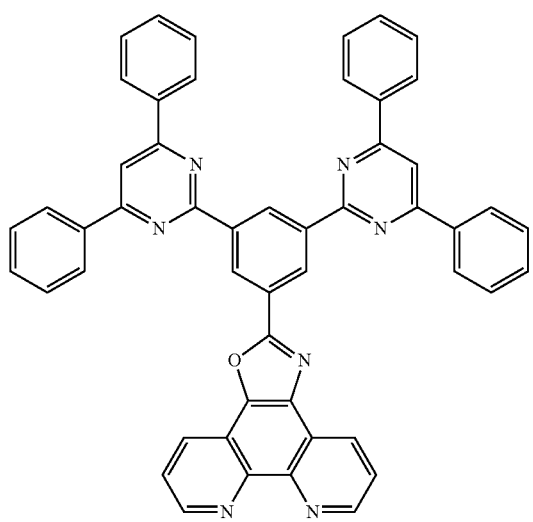
[Chemical Formula 64]
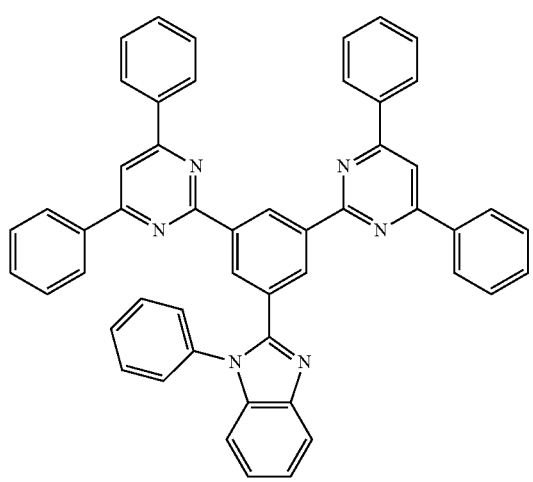
[Chemical Formula 65]
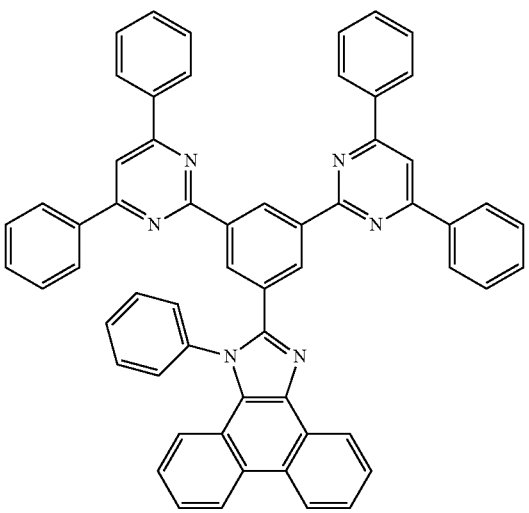
[Chemical Formula 66]
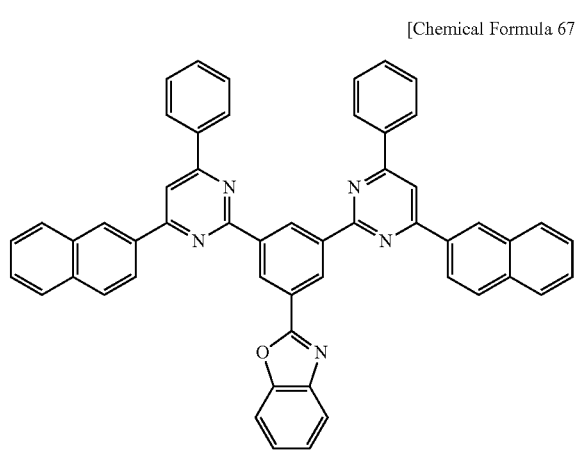
[Chemical Formula 67]

[Chemical Formula 68]
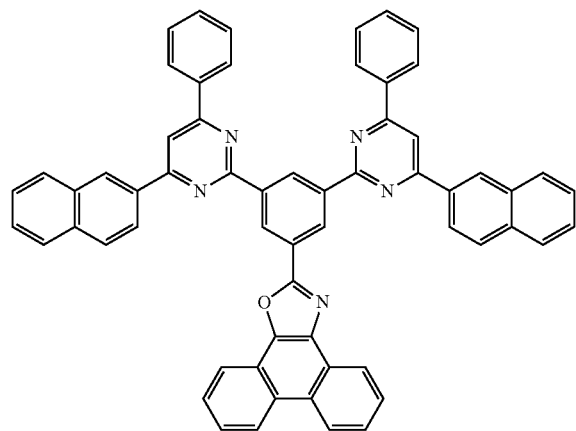
[Chemical Formula 69]
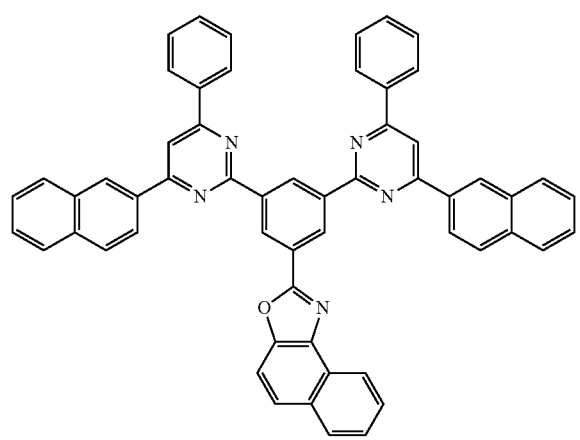
[Chemical Formula 70]
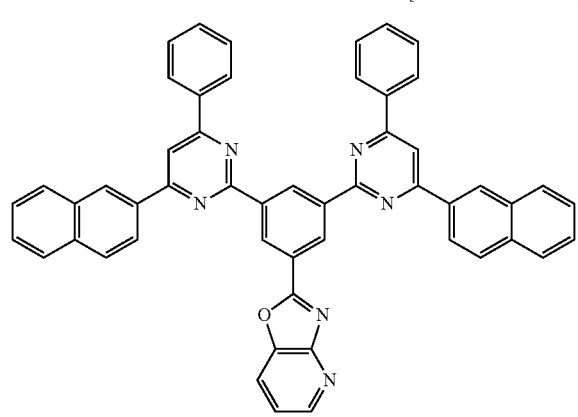
[Chemical Formula 71]
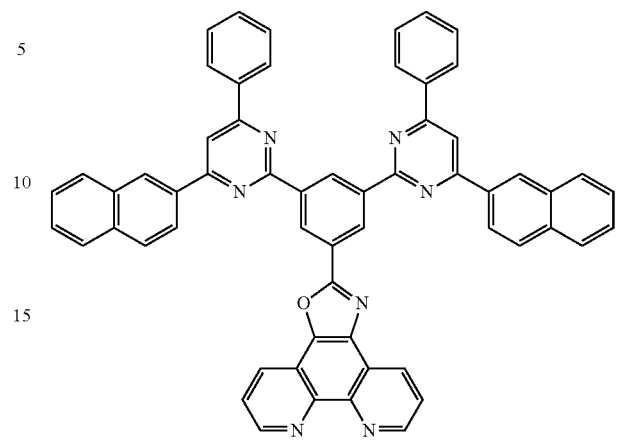
[Chemical Formula 72]
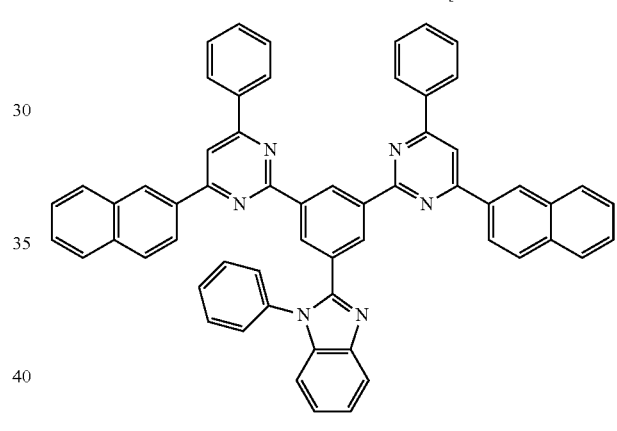
[Chemical Formula 73]
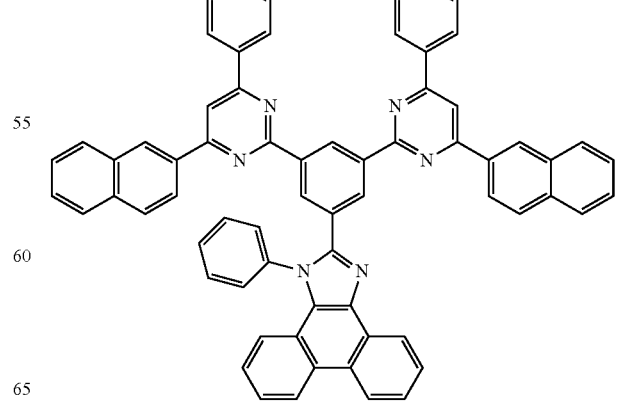

[Chemical Formula 74]
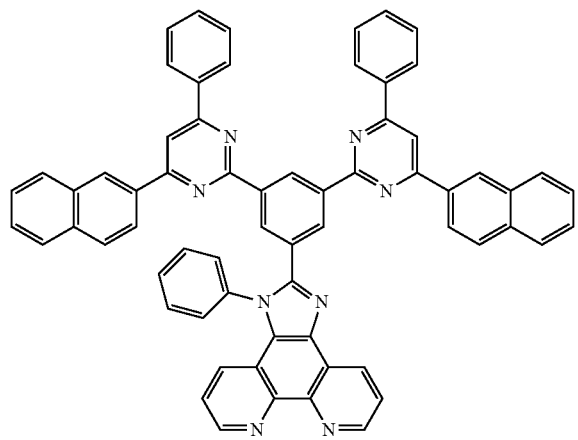
[Chemical Formula 75]
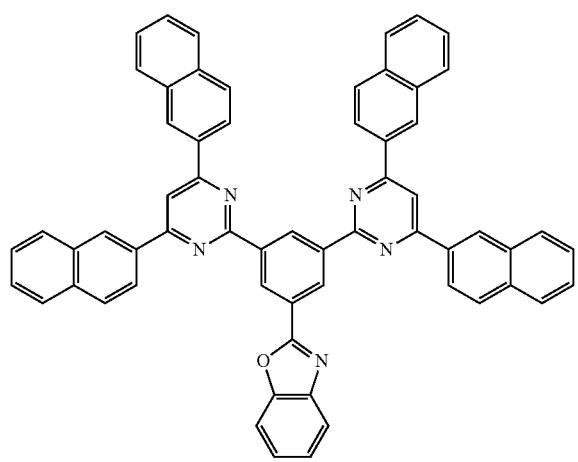
[Chemical Formula 76]
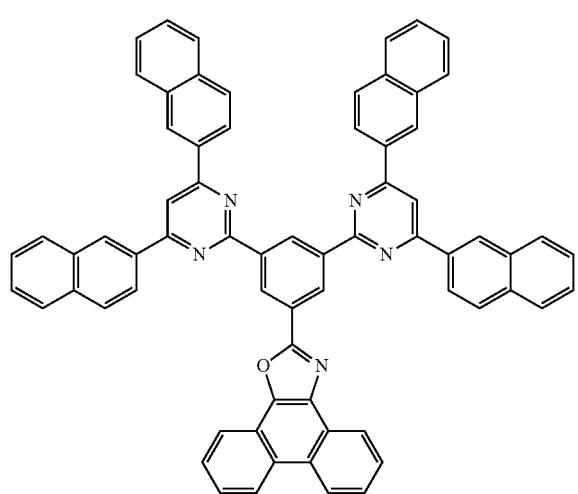
[Chemical Formula 77]
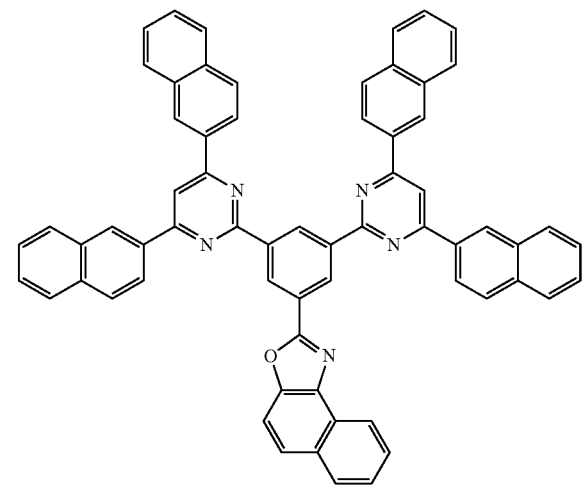
[Chemical Formula 78]
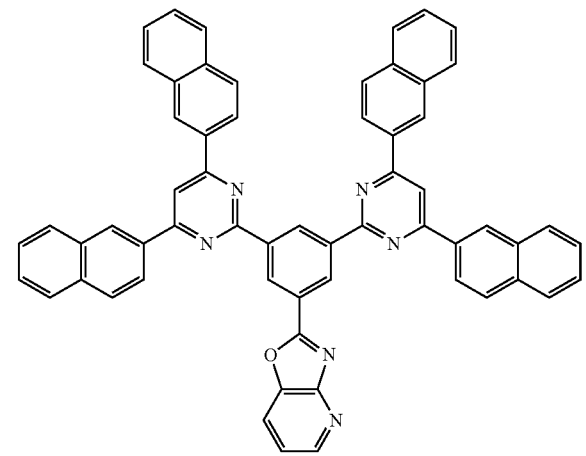
[Chemical Formula 79]
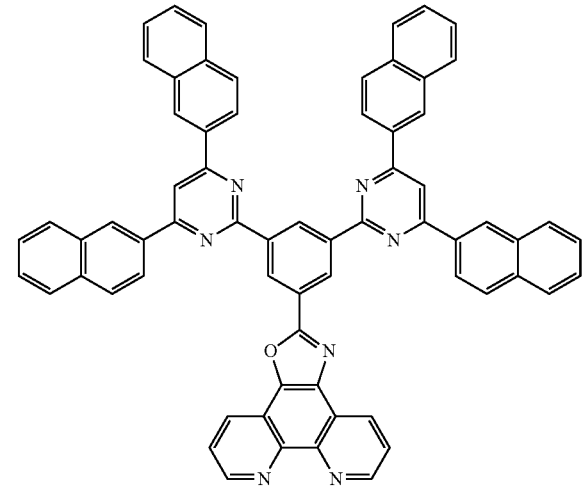

[Chemical Formula 80]
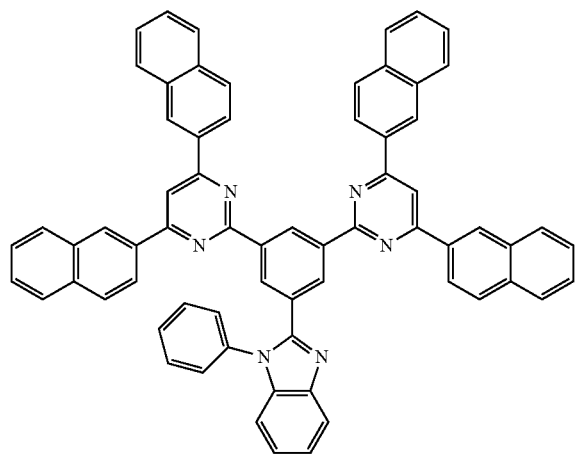
[Chemical Formula 83]
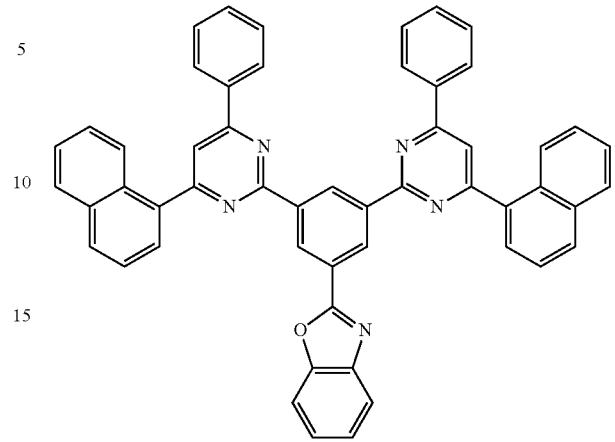
[Chemical Formula 81]
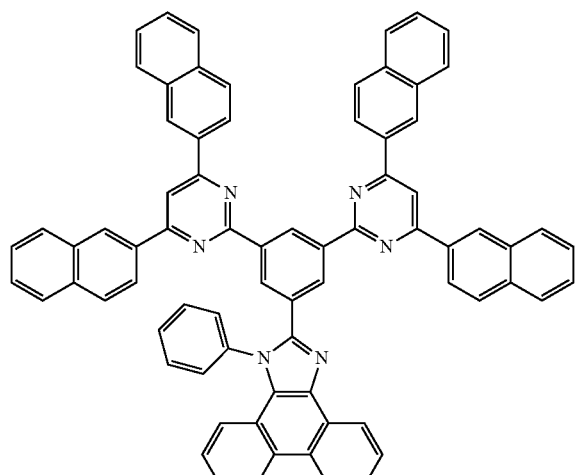
[Chemical Formula 84]
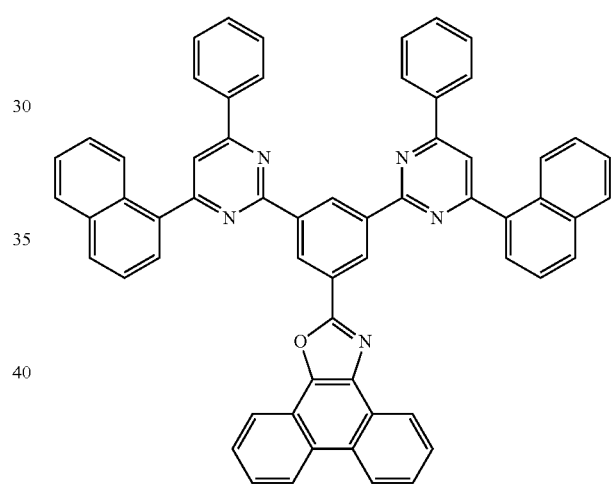
[Chemical Formula 82]
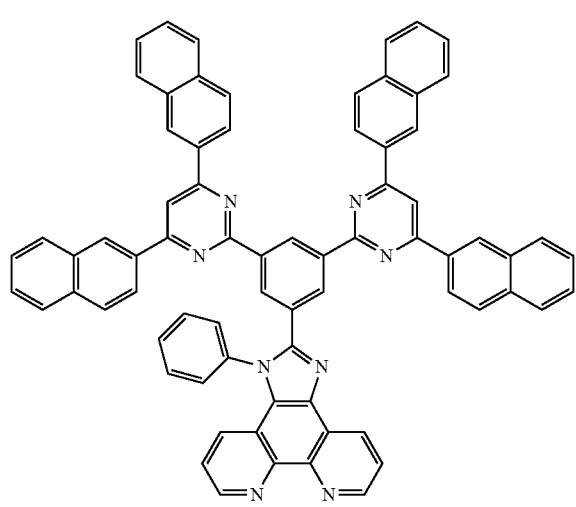
[Chemical Formula 85]
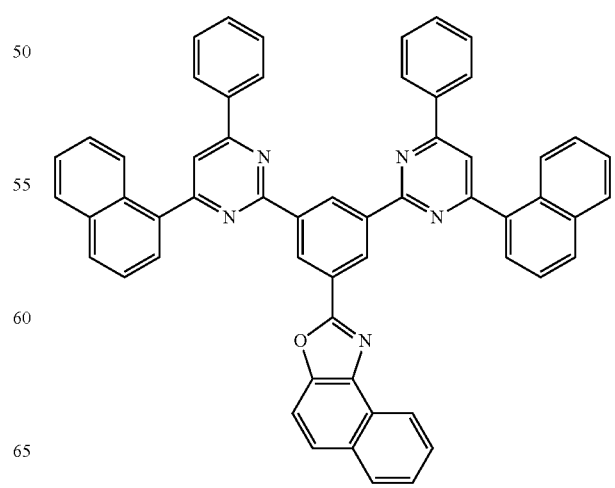

-continued
[Chemical Formula 86]
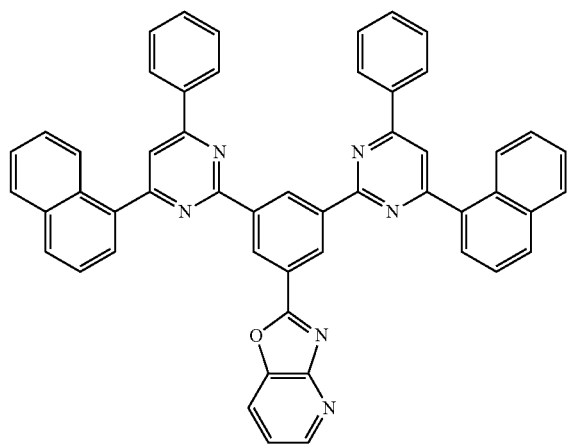
[Chemical Formula 87]
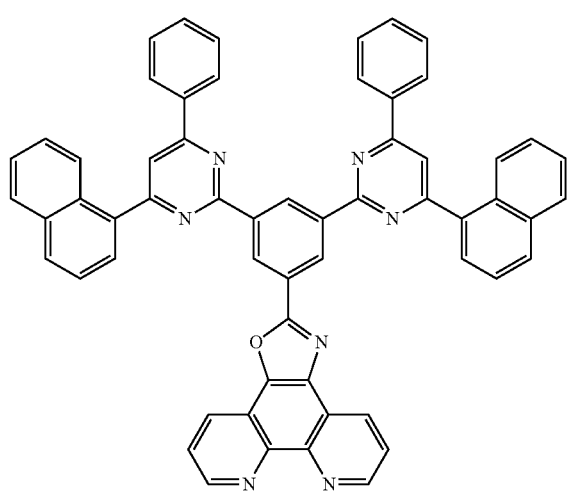
[Chemical Formula 88]
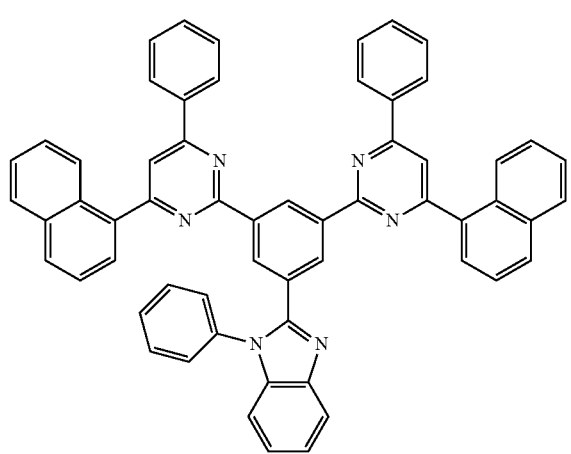
-continued
[Chemical Formula 89]
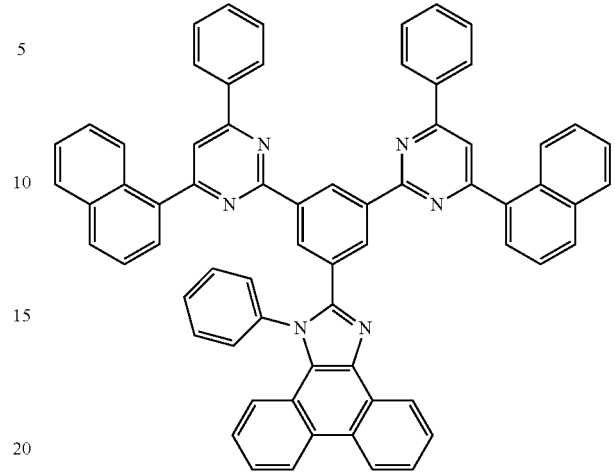
[Chemical Formula 90]
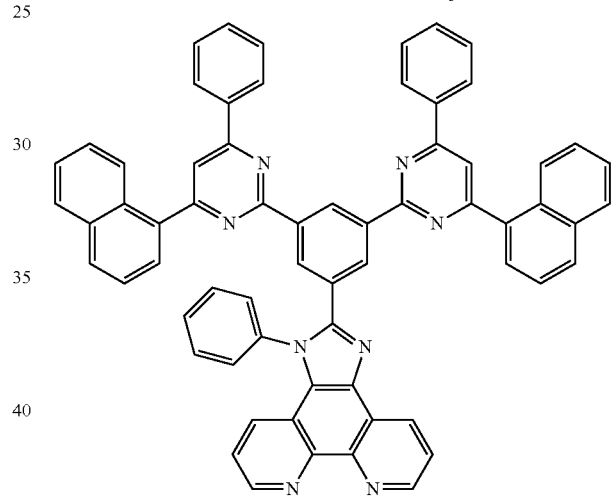
[Chemical Formula 91]
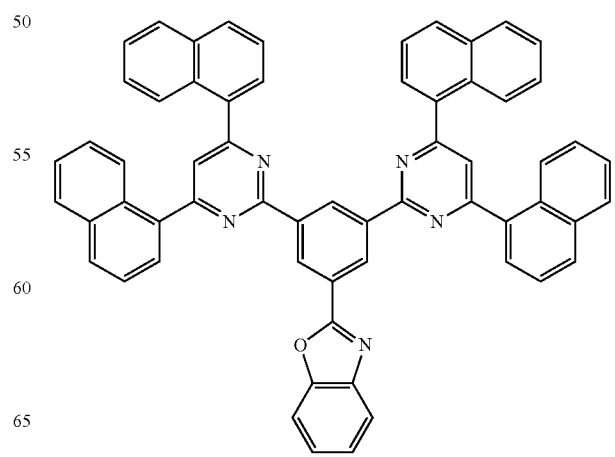

[Chemical Formula 92]
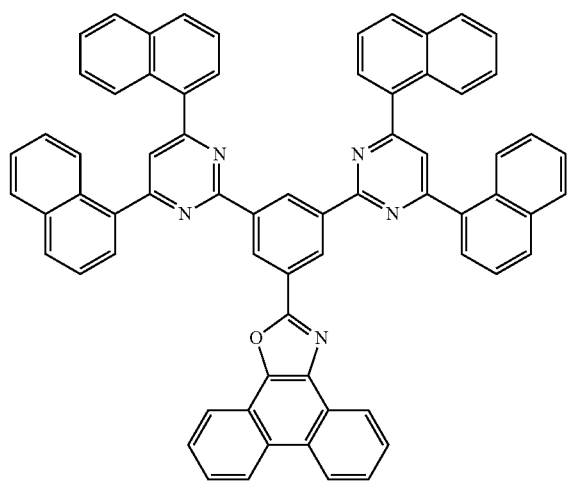
[Chemical Formula 93]
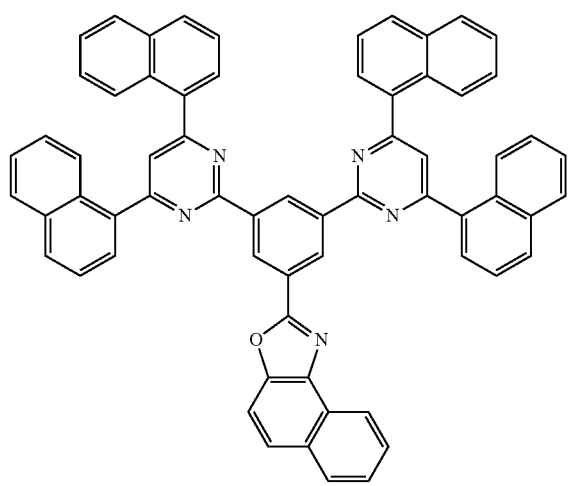
[Chemical Formula 94]
[Chemical Formula 95]
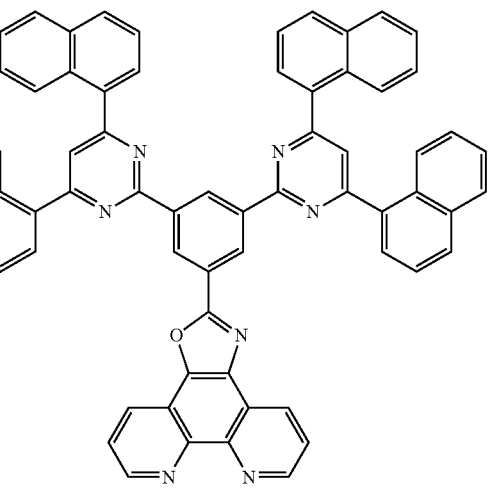
[Chemical Formula 96]
[Chemical Formula 97]
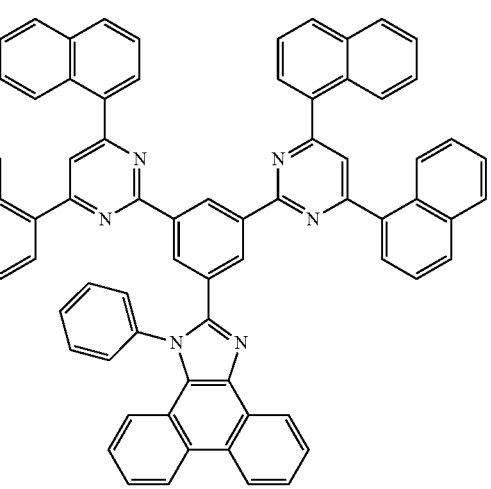

[Chemical Formula 98]
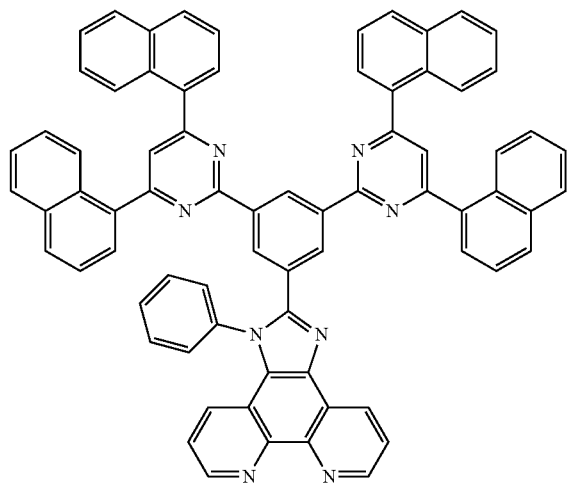
[Chemical Formula 99]
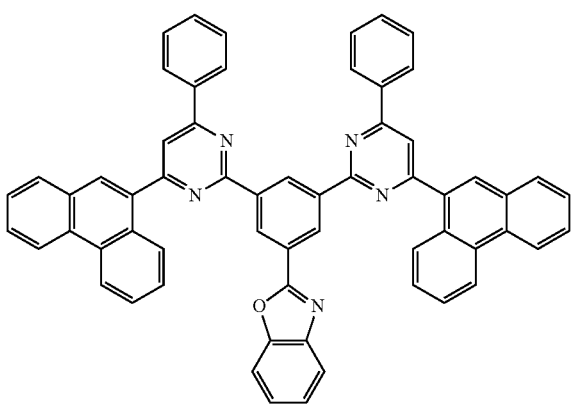
[Chemical Formula 100]
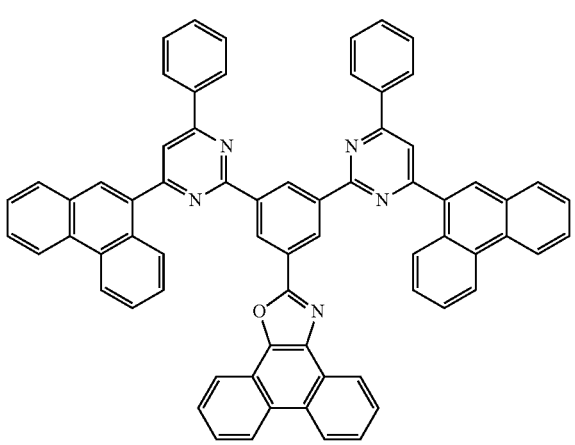
[Chemical Formula 101]
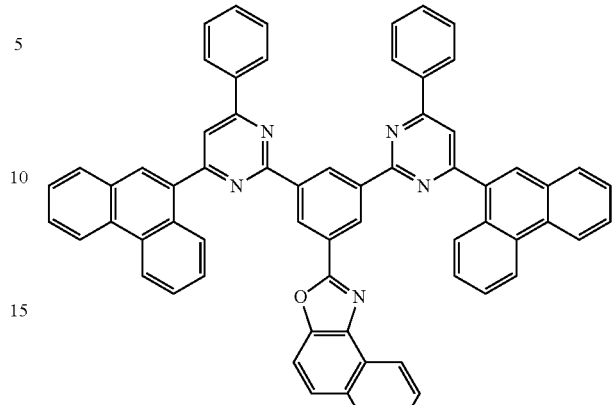
[Chemical Formula 102]
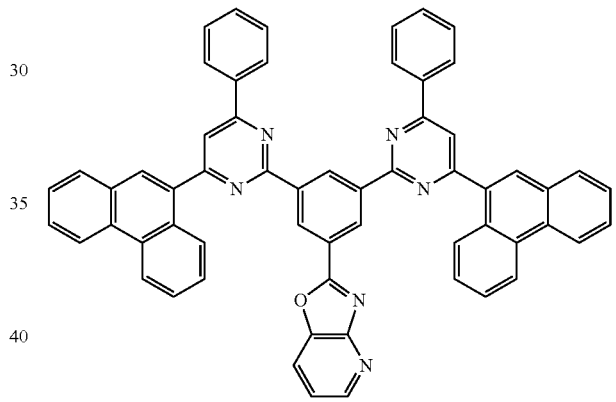
[Chemical Formula 103]
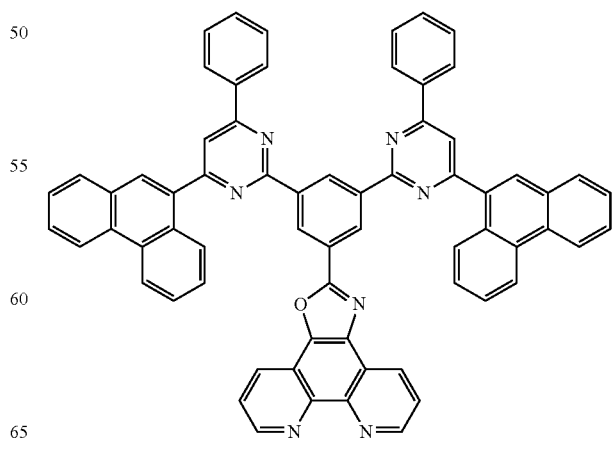

[Chemical Formula 104]
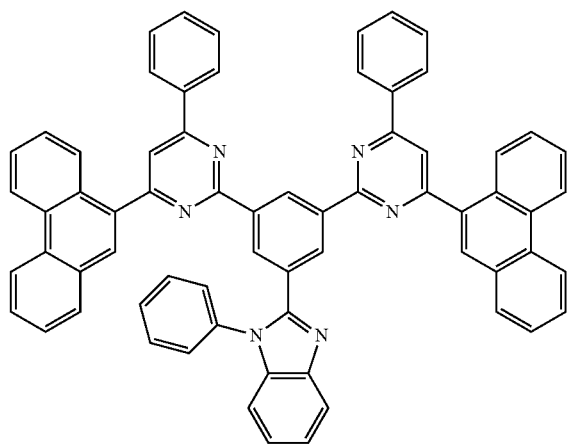
[Chemical Formula 105]
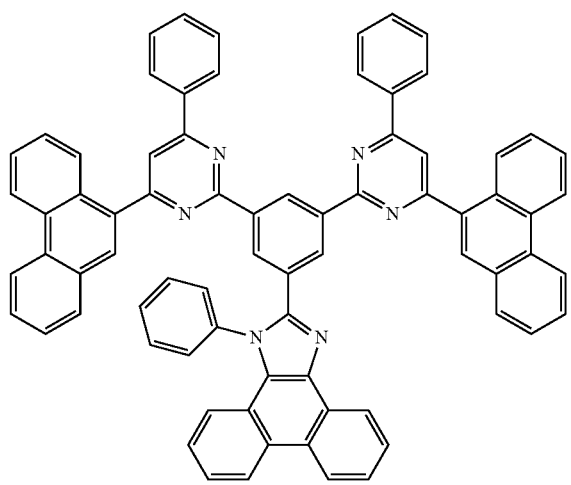
[Chemical Formula 106]
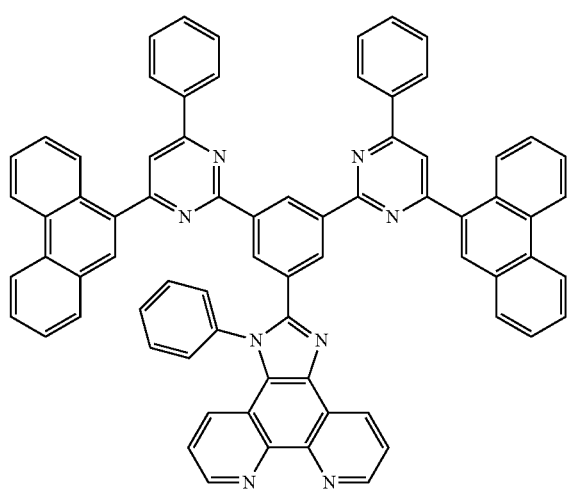
[Chemical Formula 107]
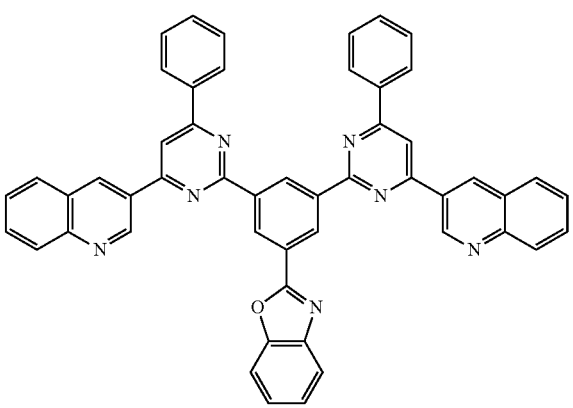
[Chemical Formula 108]
[Chemical Formula 109]
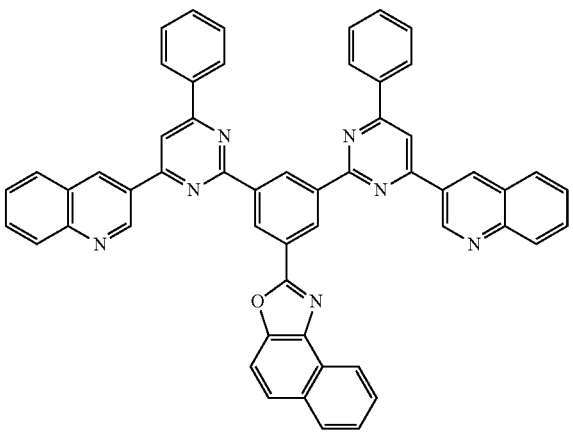

[Chemical Formula 110]
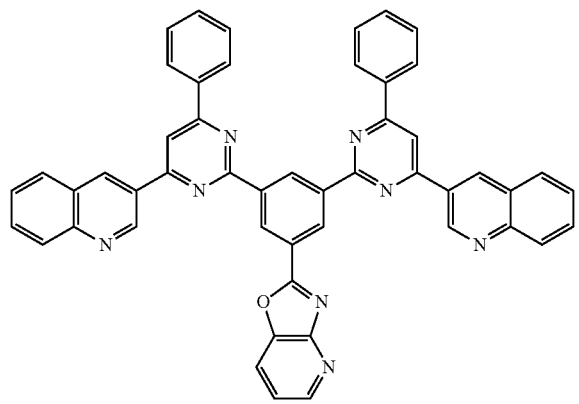
[Chemical Formula 113]
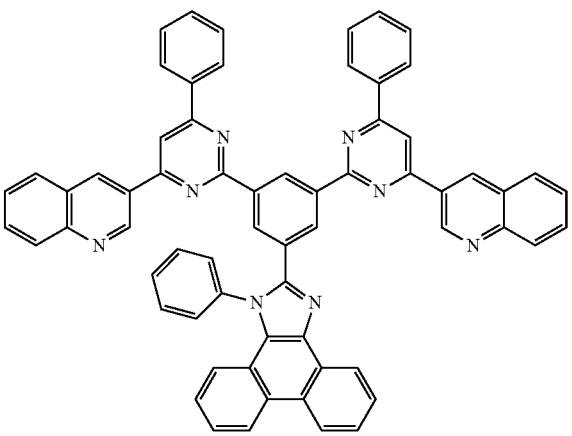
[Chemical Formula 111]
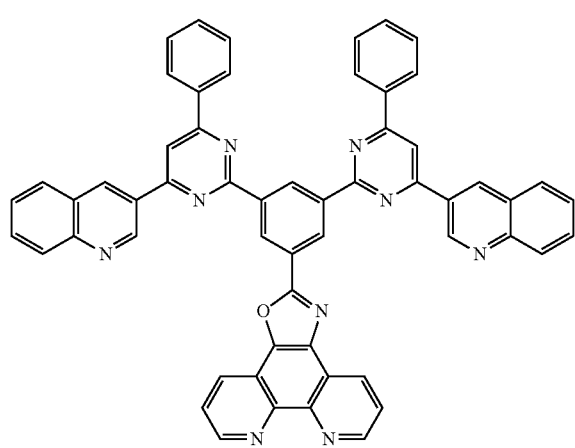
[Chemical Formula 114]
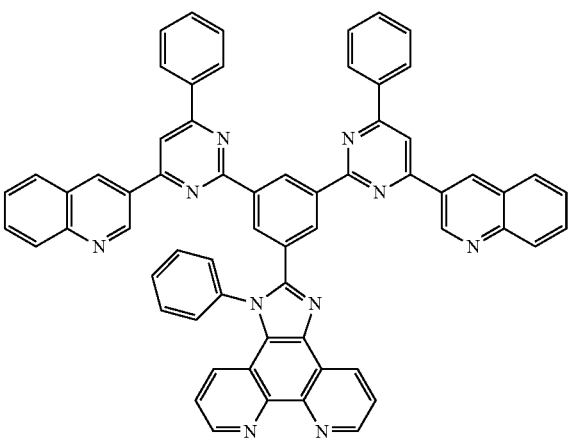
[Chemical Formula 112]
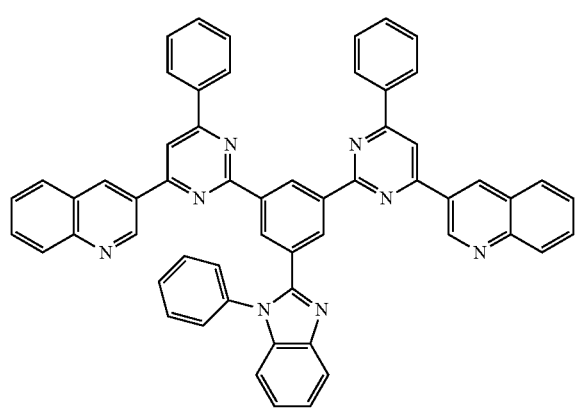
[Chemical Formula 115]
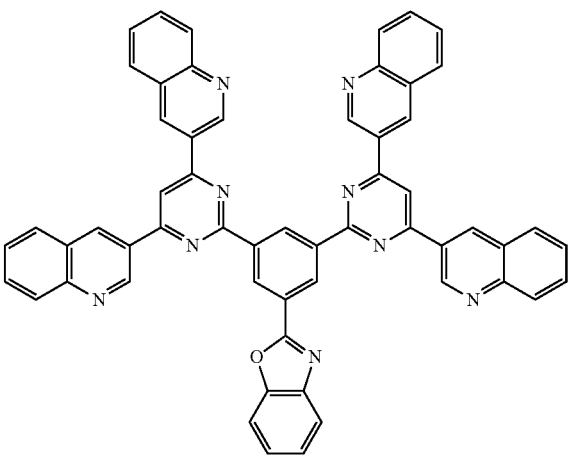

[Chemical Formula 116]
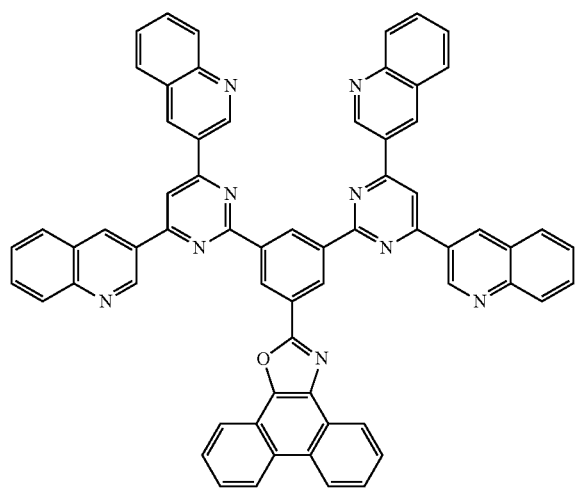
[Chemical Formula 117]
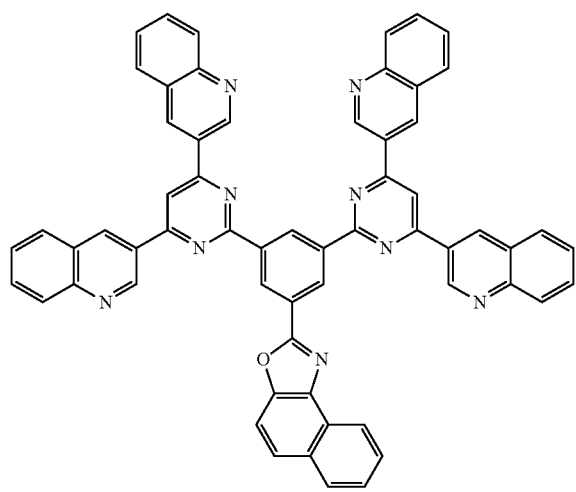
[Chemical Formula 118]
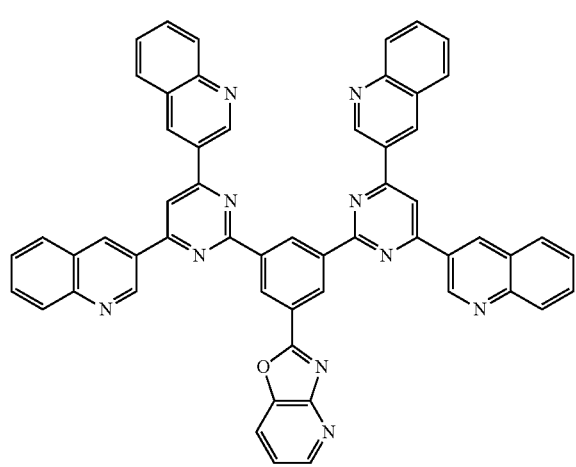
[Chemical Formula 119]
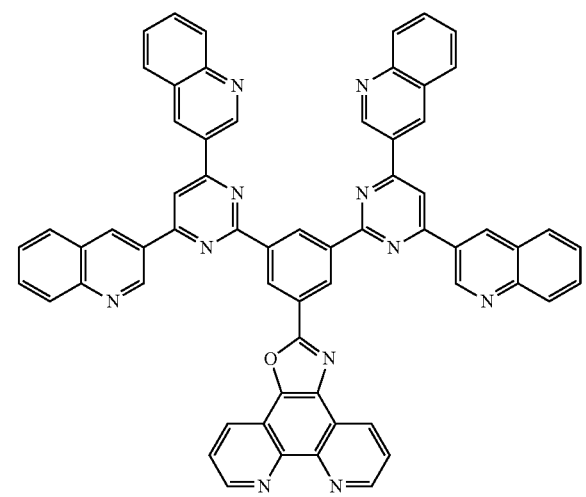
[Chemical Formula 120]
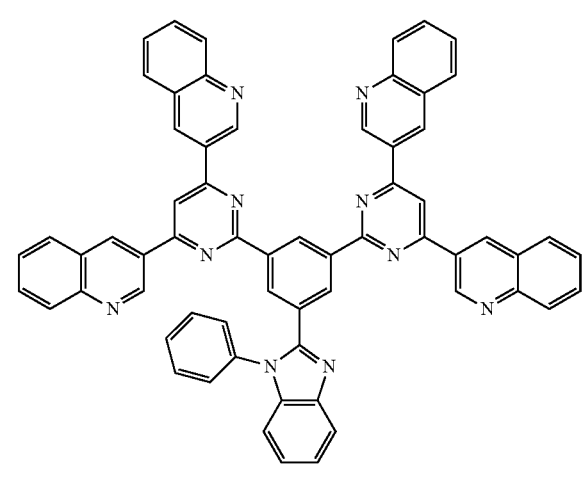
[Chemical Formula 121]
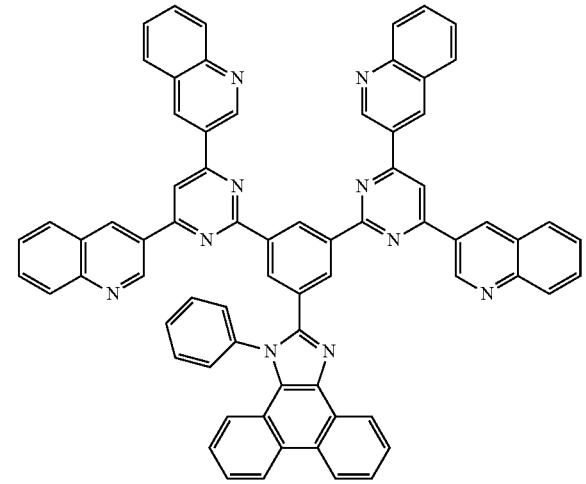

[Chemical Formula 122]
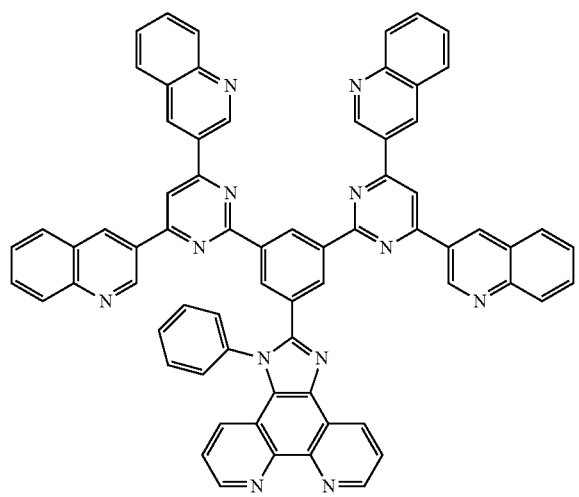
[Chemical Formula 123]
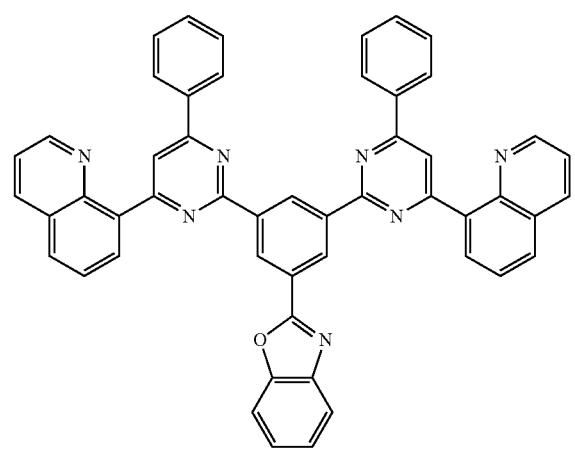
[Chemical Formula 124]
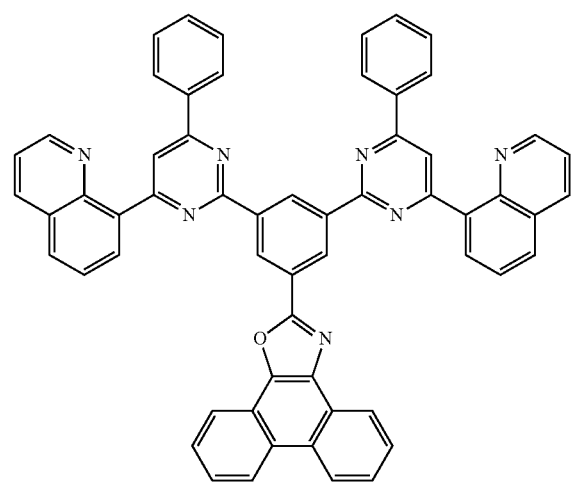
[Chemical Formula 125]
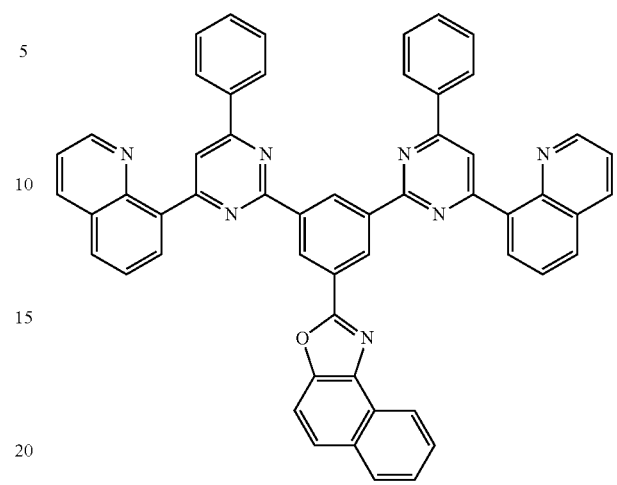
[Chemical Formula 126]
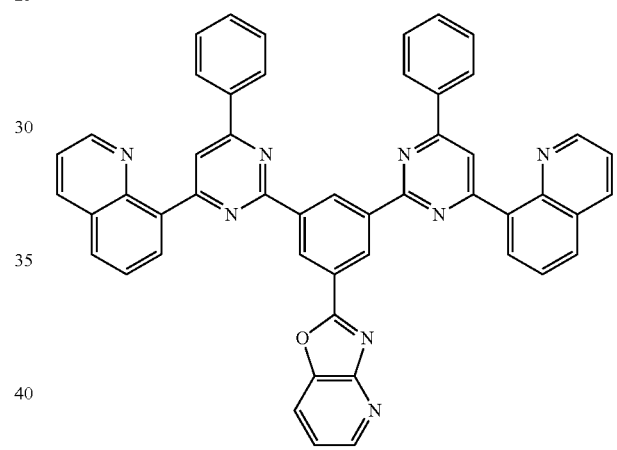
[Chemcial Formula 127]
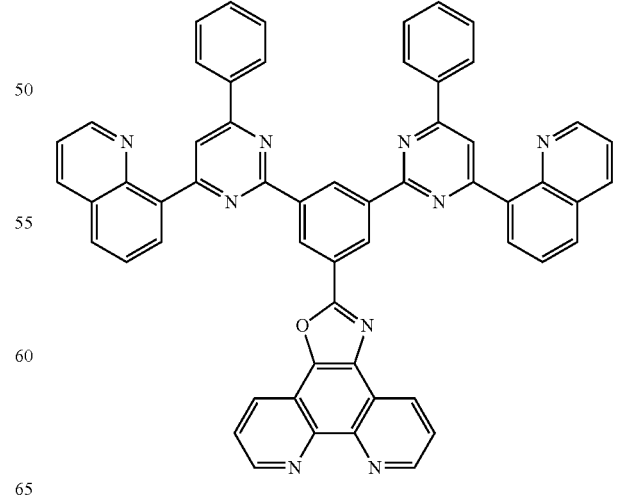

[Chemical Formula 128]
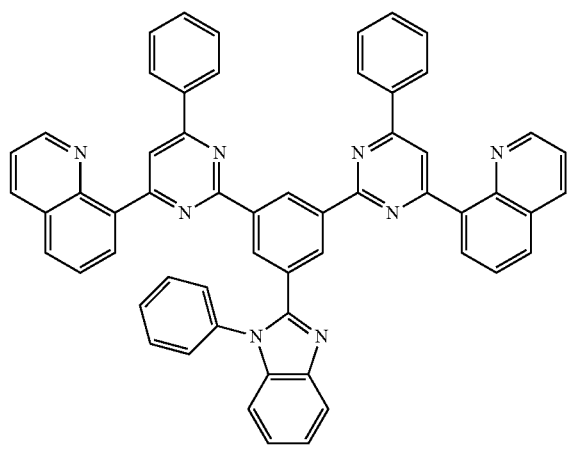
[Chemical Formula 129]
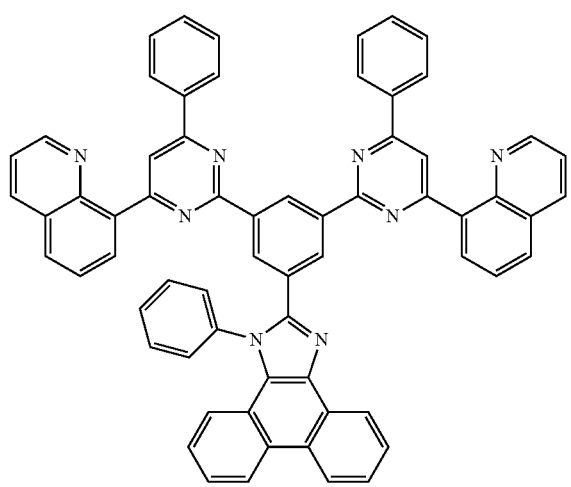
[Chemical Formula 130]
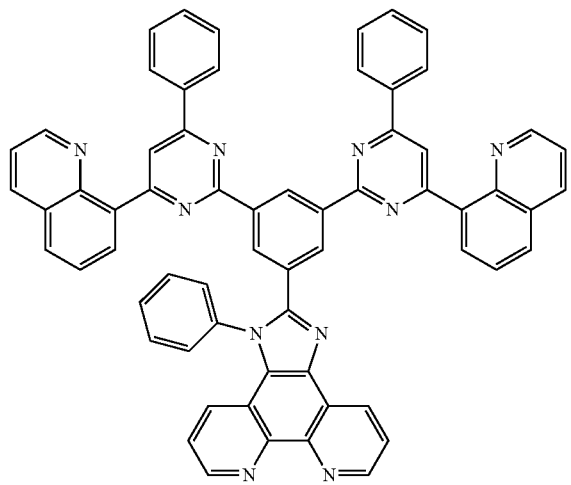
[Chemical Formula 131]
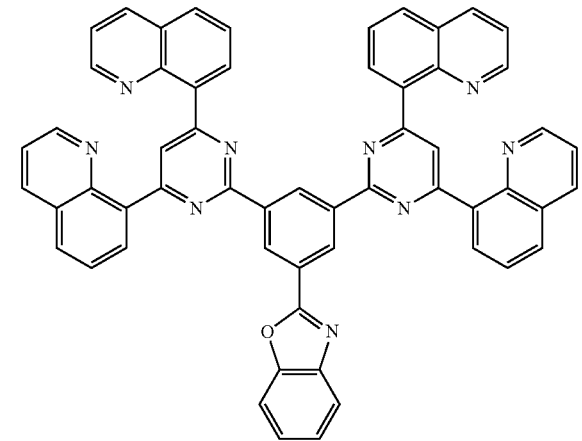
[Chemical Formula 132]
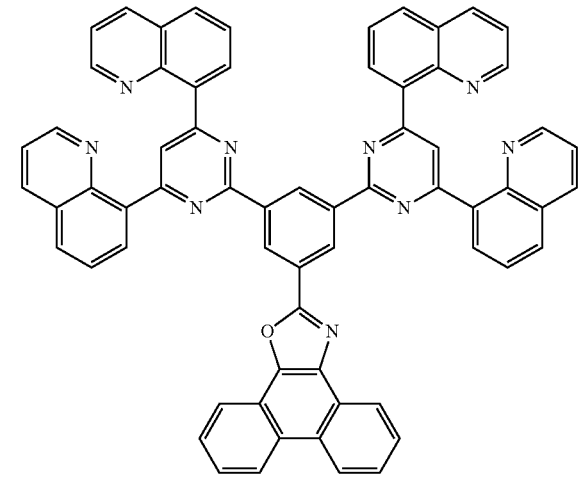
[Chemical Formula 133]
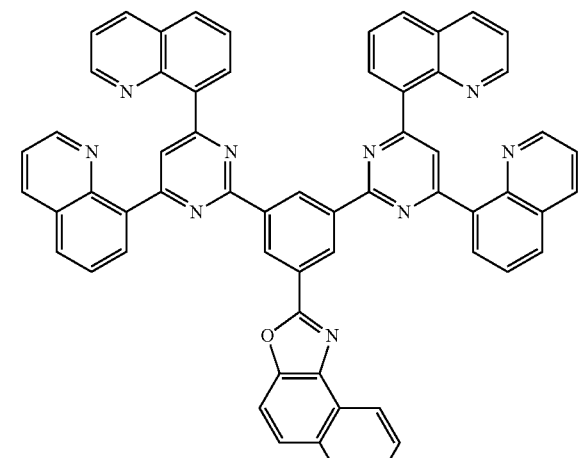

[Chemical Formula 134]
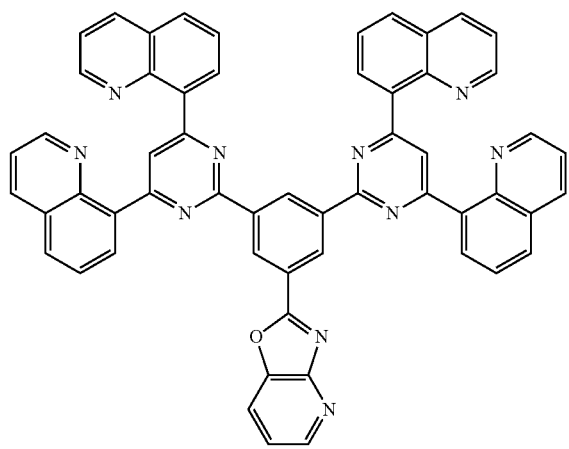
[Chemical Formula 135]
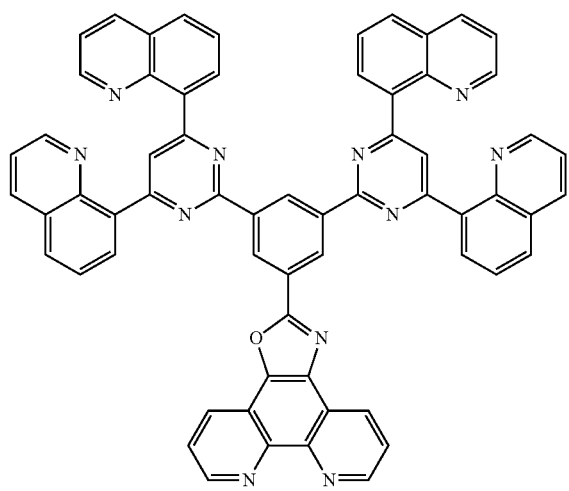
[Chemical Formula 136]
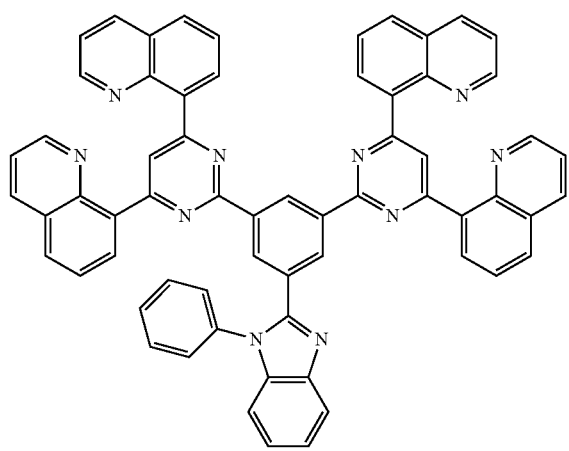
[Chemical Formula 137]
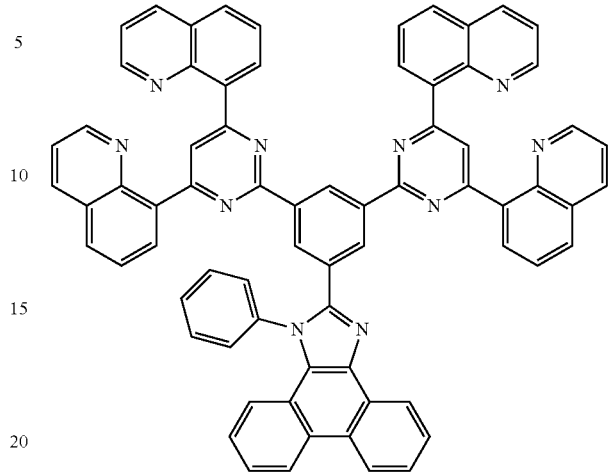
[Chemical Formula 138]
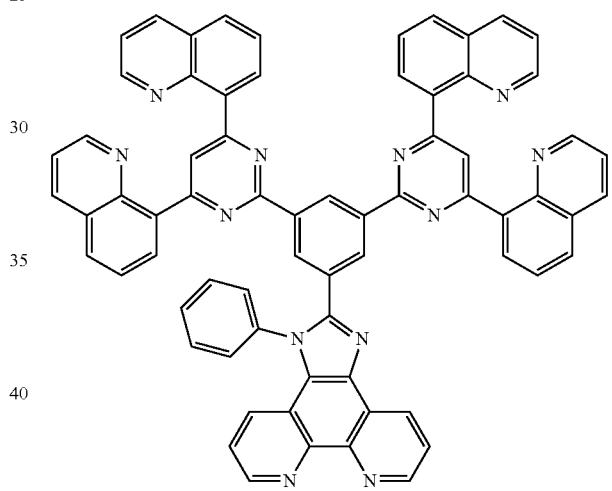
[Chemical Formula 139]
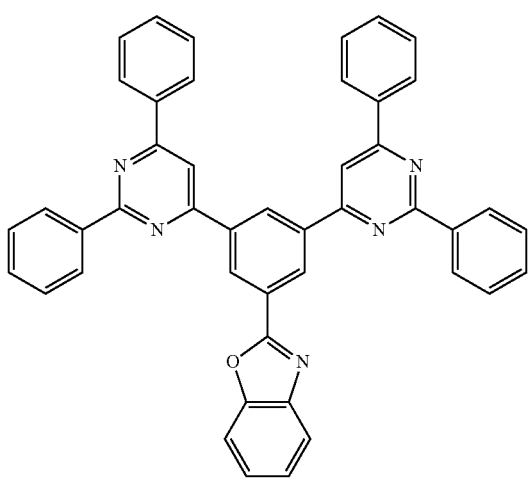

[Chemical Formula 140]
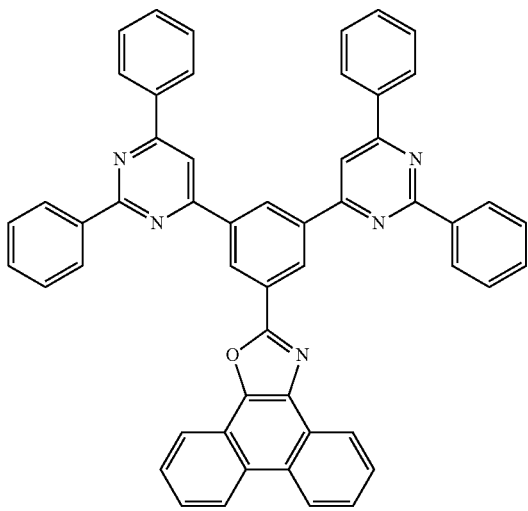
[Chemical Formula 141]
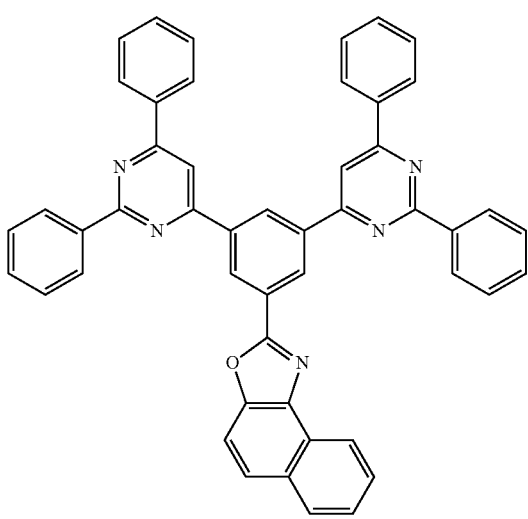
[Chemical Formula 142]
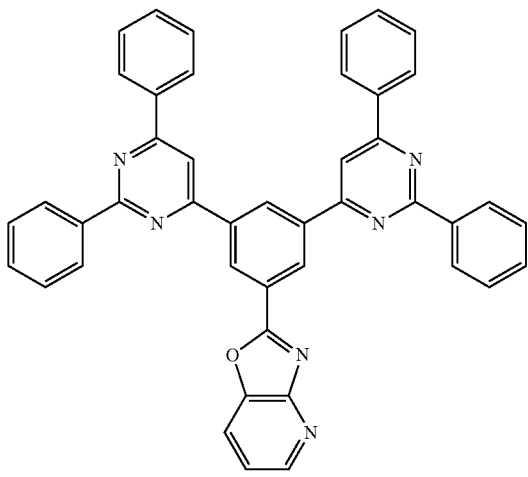
[Chemical Formula 143]
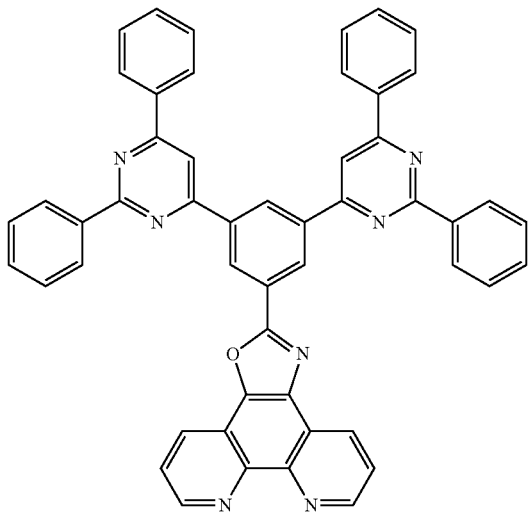
[Chemical Formula 144]
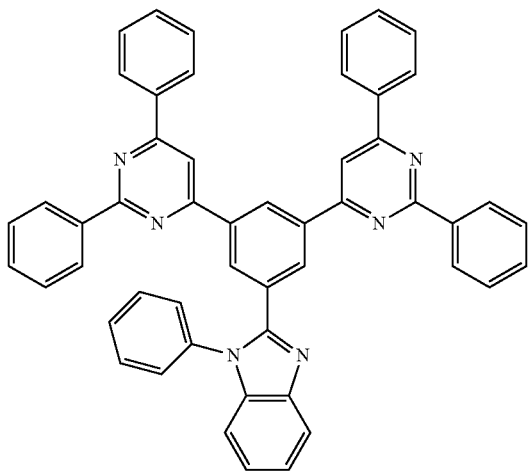
[Chemical Formula 145]
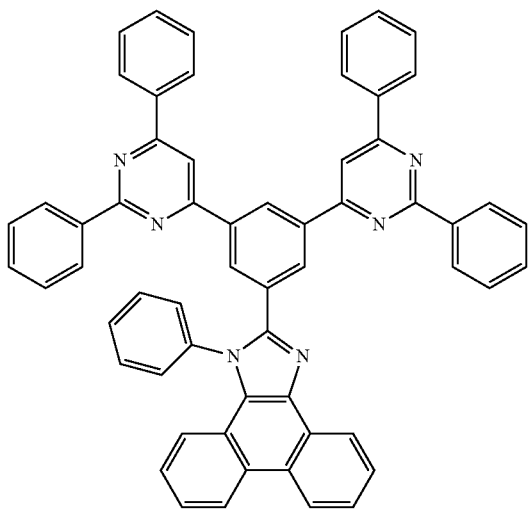

[Chemical Formula 146]
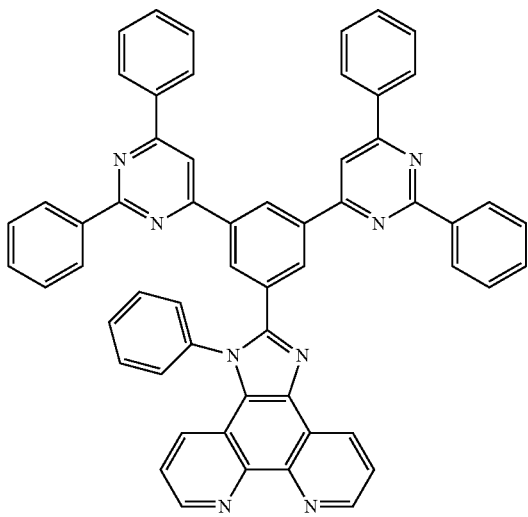
[Chemical Formula 147]
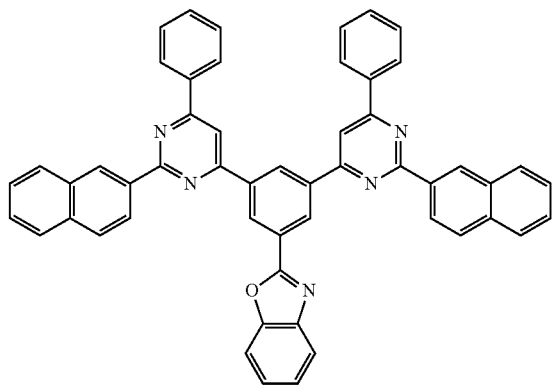
[Chemical Formula 148]
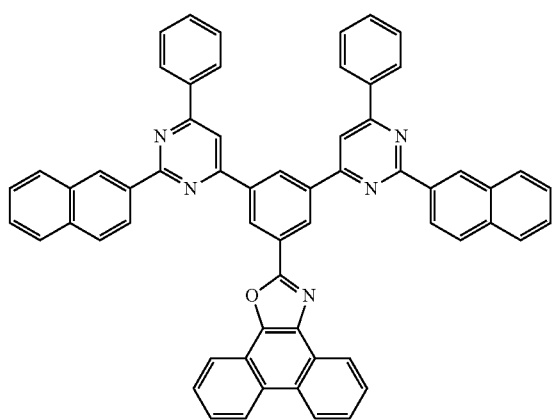
[Chemical Formula 149]
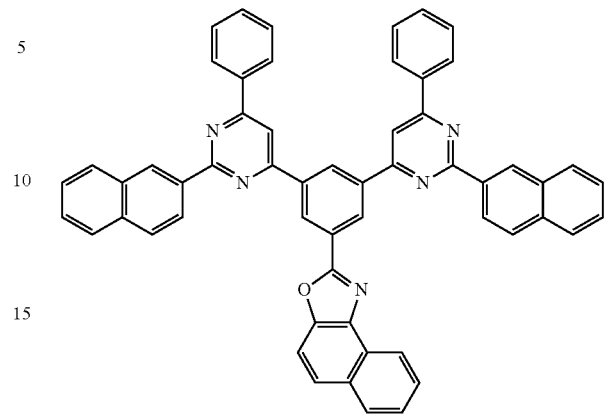
[Chemical Formula 150]
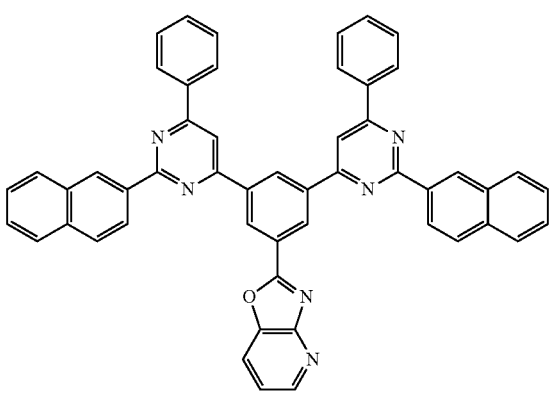
[Chemical Formula 151]
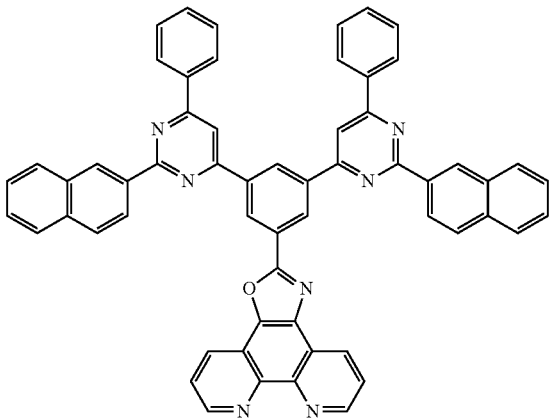

[Chemical Formula 152]
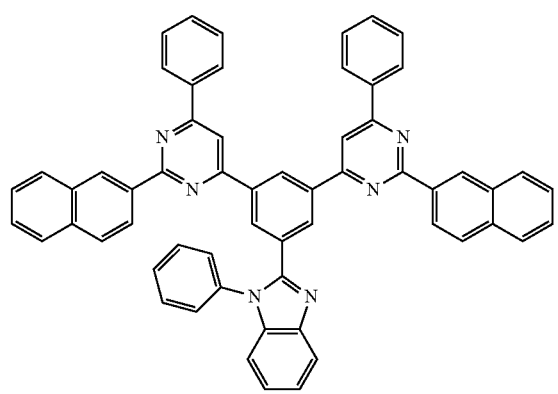
[Chemical Formula 153]
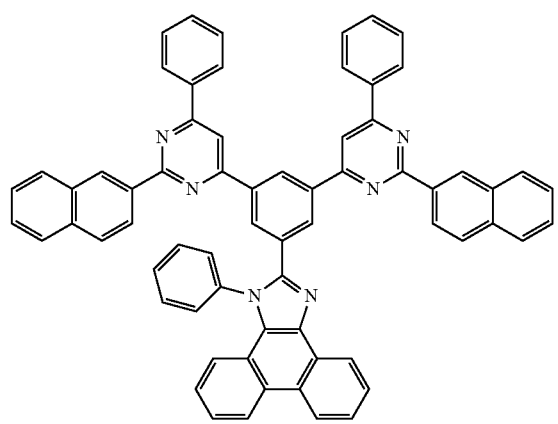
[Chemical Formula 154]
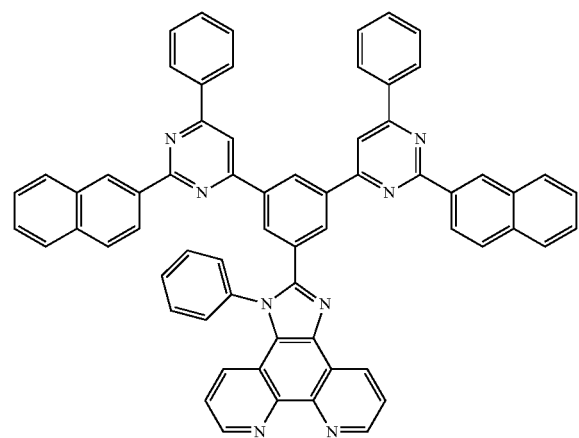
[Chemical Formula 155]
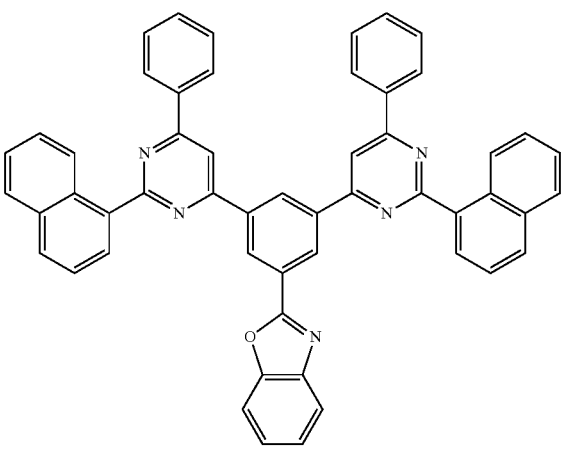
[Chemical Formula 156]
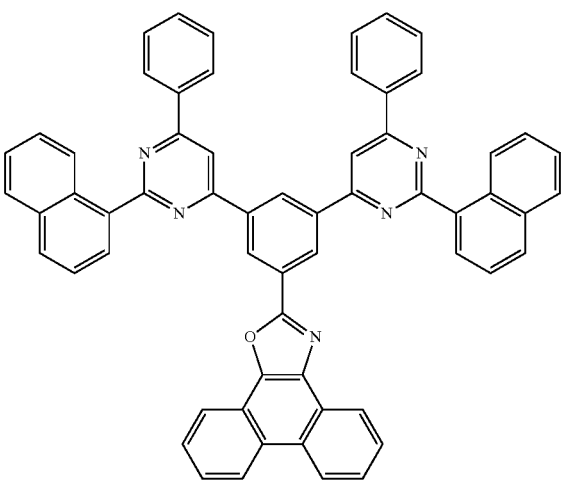
[Chemical Formula 157]
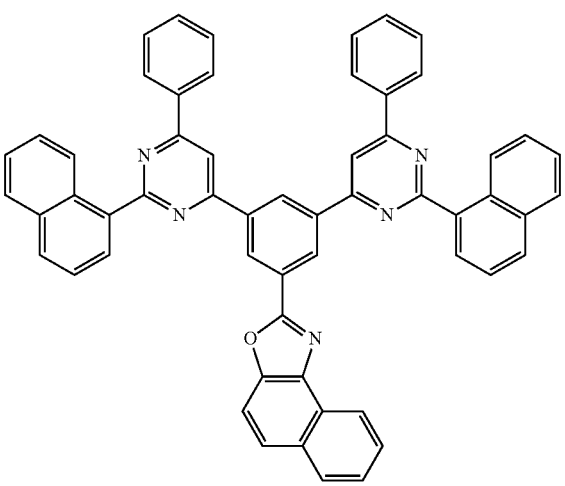

[Chemical Formula 158]
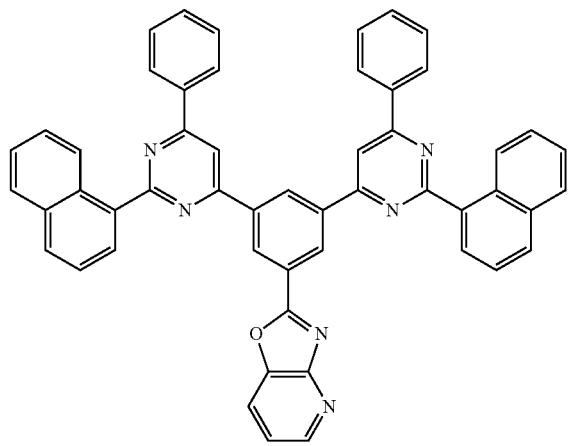
[Chemical Formula 161]
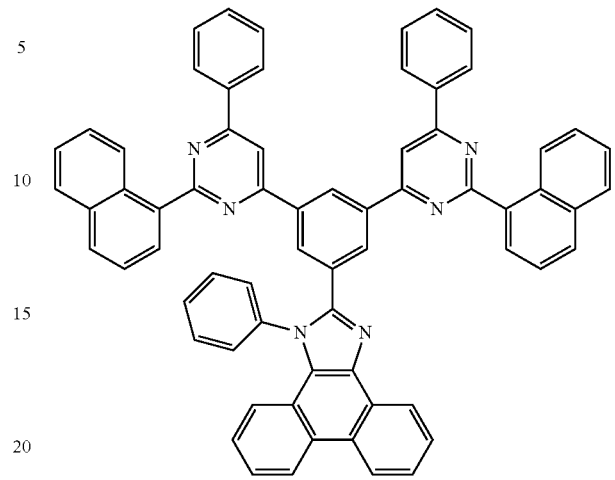
[Chemical Formula 159]
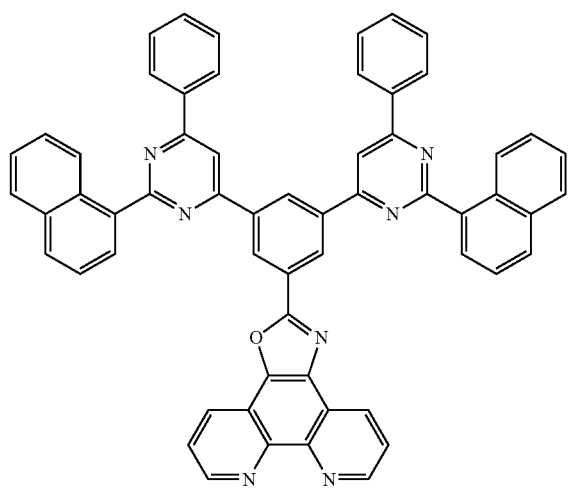
[Chemical Formula 162]
[Chemical Formula 160]
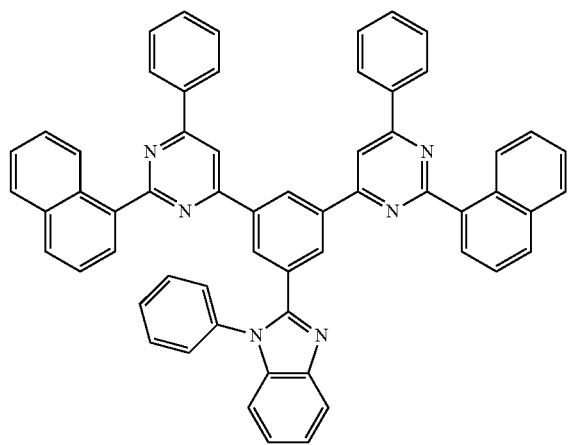
[Chemical Formula 163]
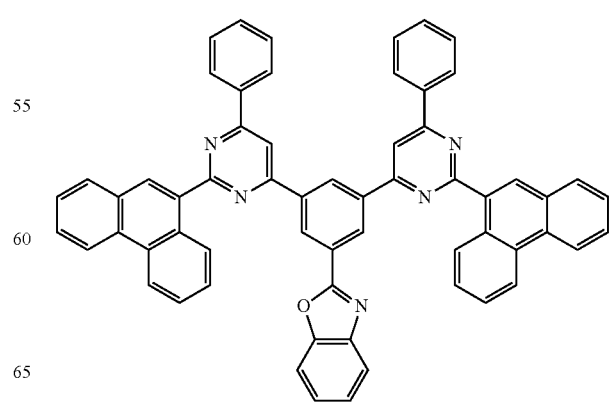

[Chemical Formula 164]
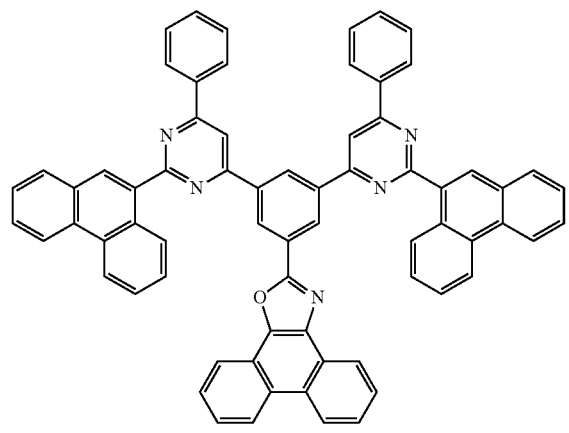
[Chemical Formula 167]
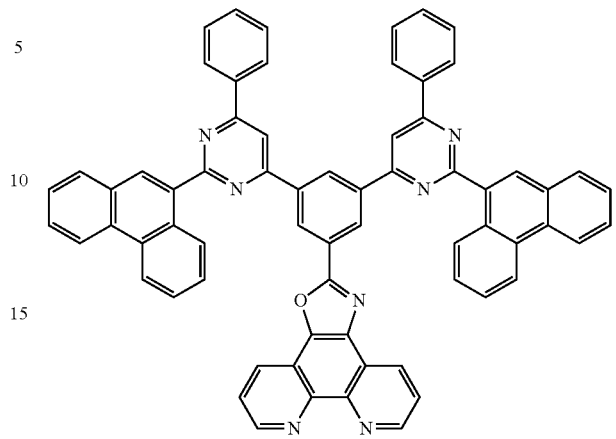
[Chemical Formula 165]
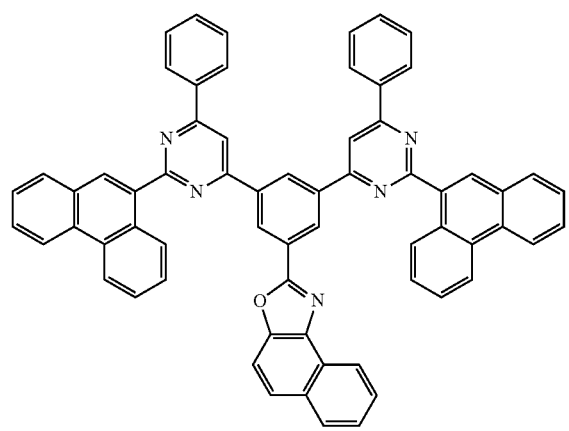
[Chemical Formula 168]
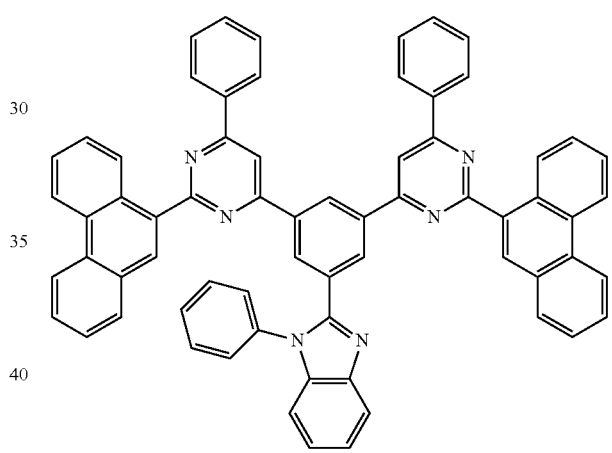
[Chemical Formula 166]
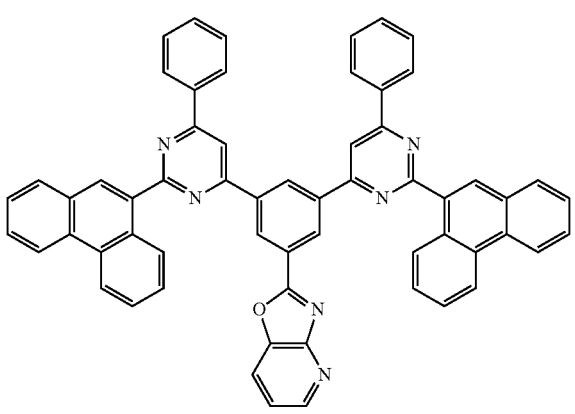
[Chemical Formula 169]
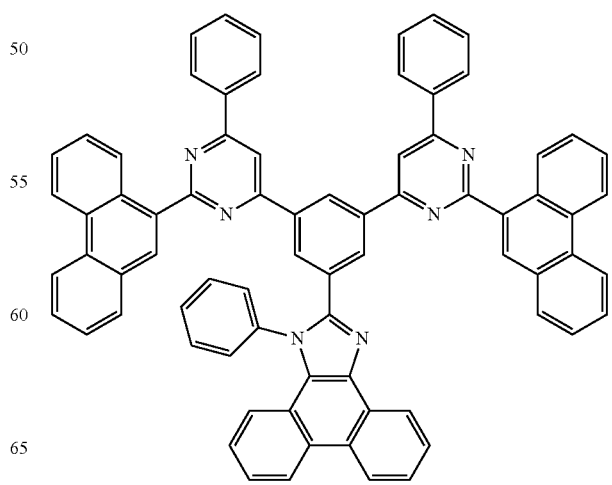

[Chemical Formula 170]
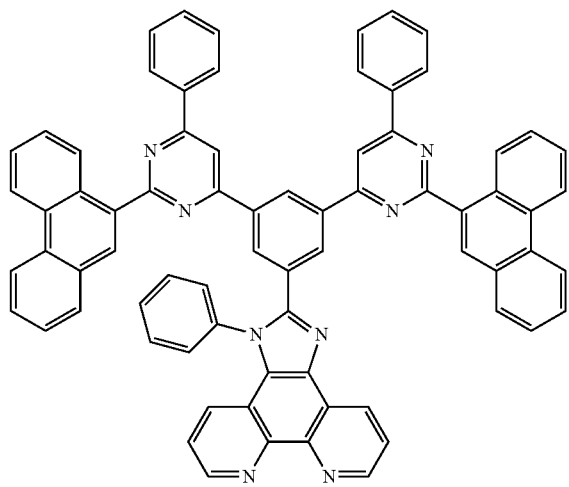
[Chemical Formula 171]
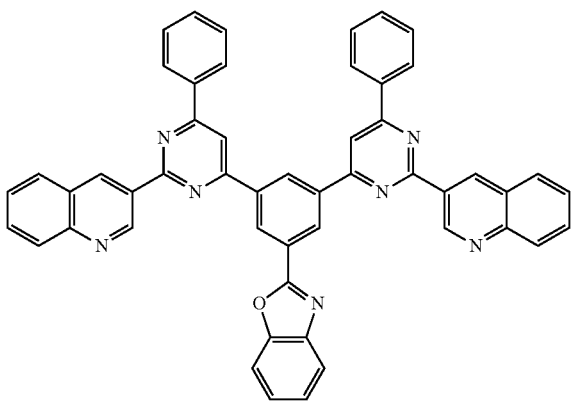
[Chemical Formula 172]
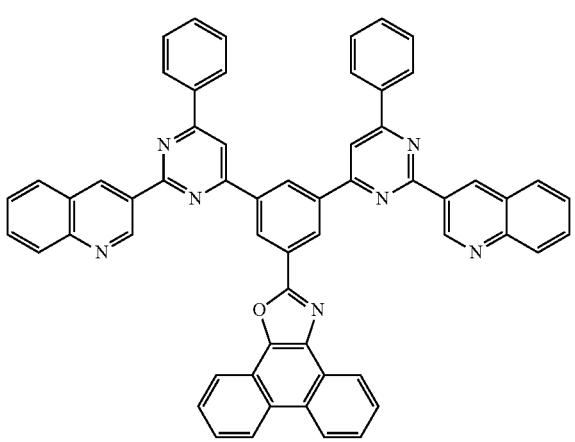
[Chemical Formula 173]
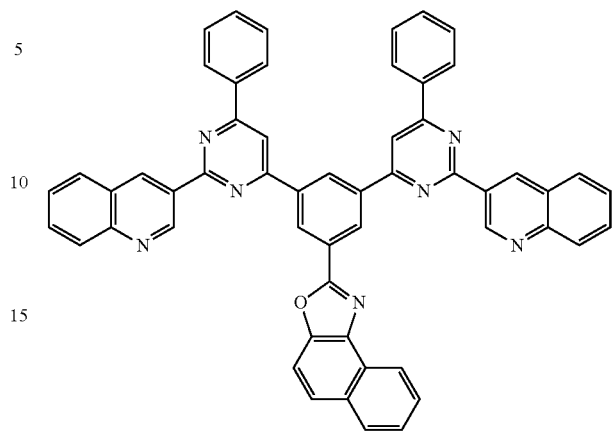
[Chemical Formula 174]
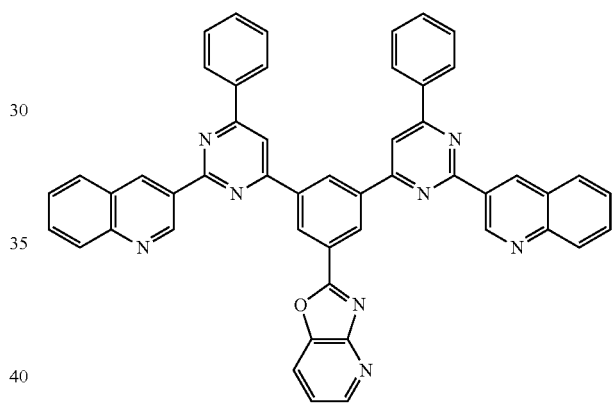
[Chemical Formula 175]
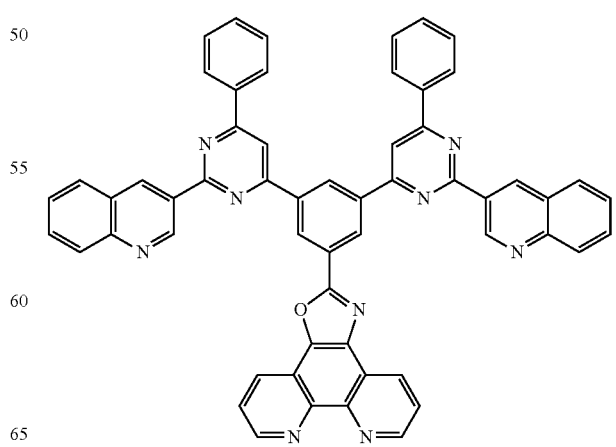

[Chemical Formula 176]
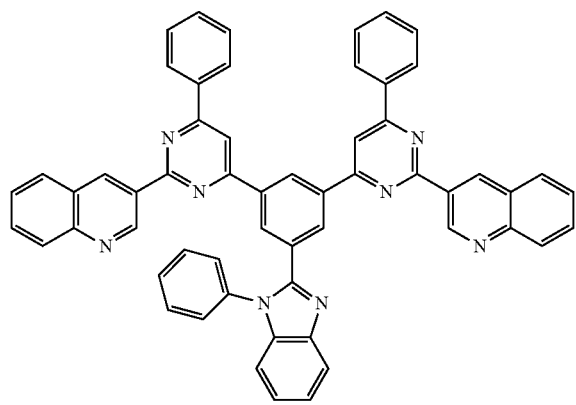
[Chemical Formula 177]
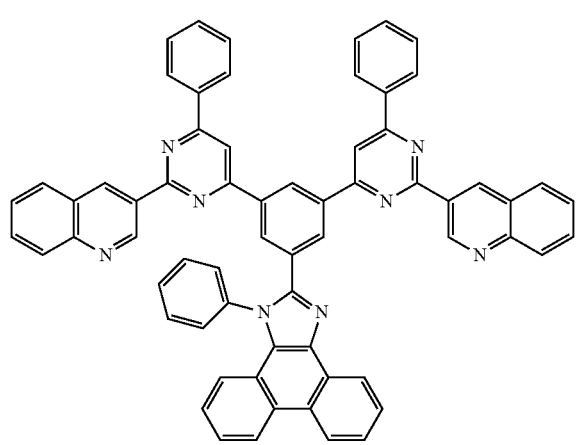
[Chemical Formula 178]
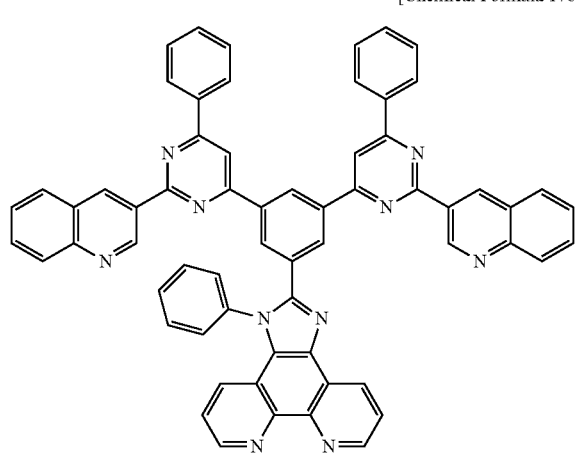
[Chemical Formula 179]
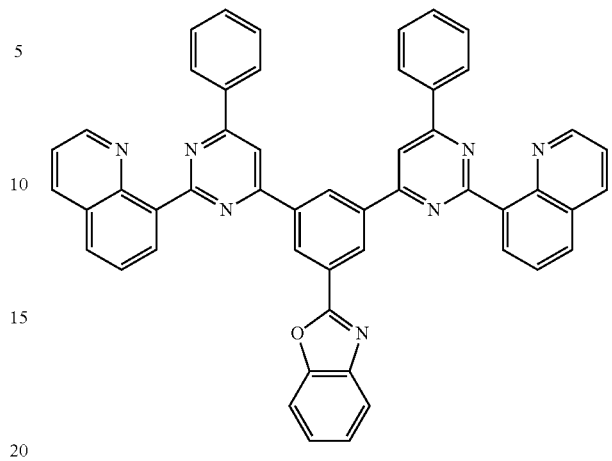
[Chemical Formula 180]
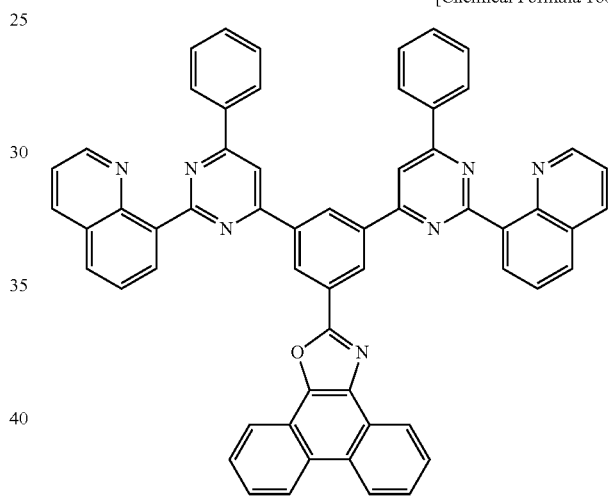
[Chemical Formula 181]
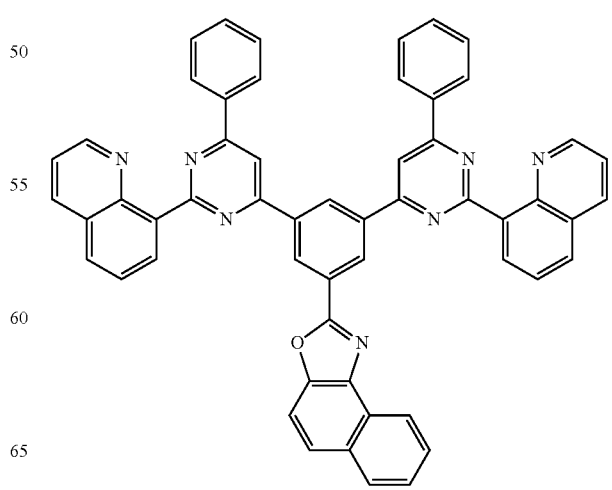

[Chemical Formula 182]

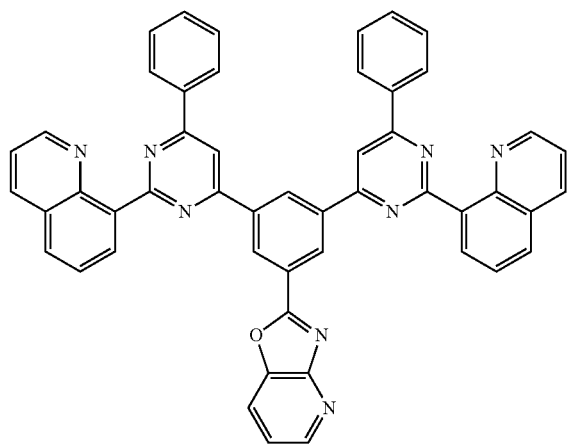

[Chemical Formula 185]

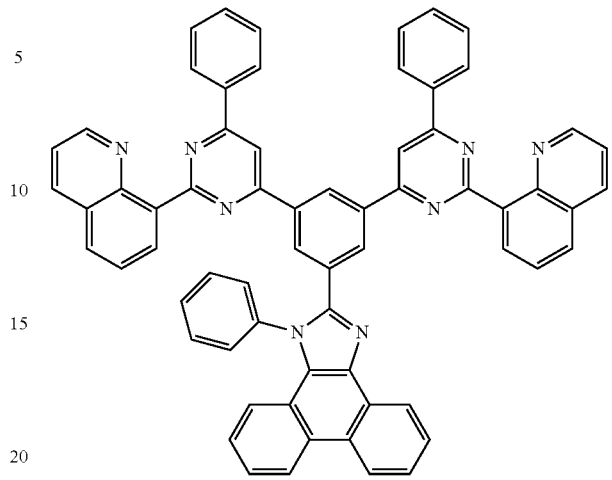

[Chemical Formula 183]

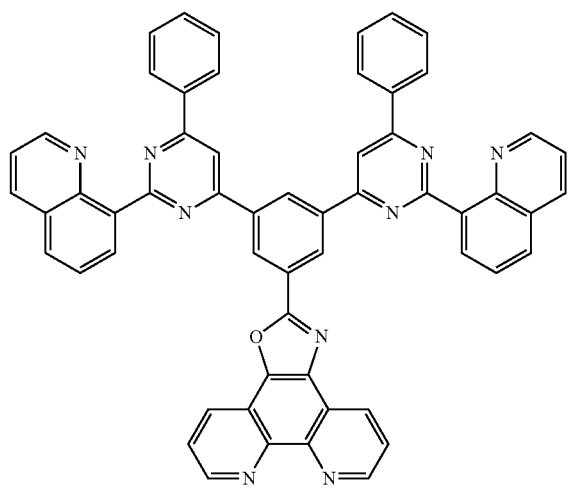

[Chemical Formula 186]

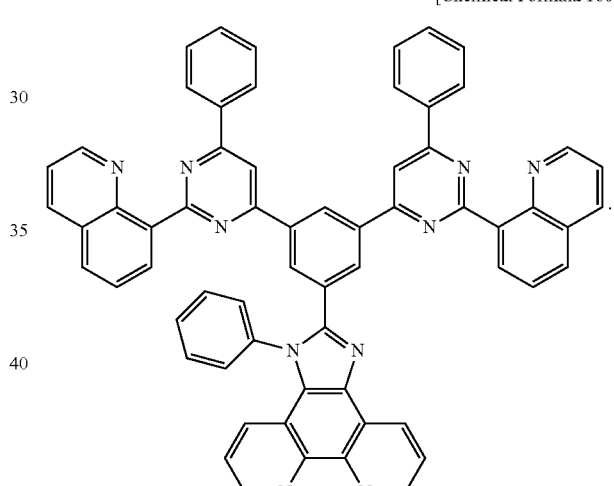

[Chemical Formula 184]

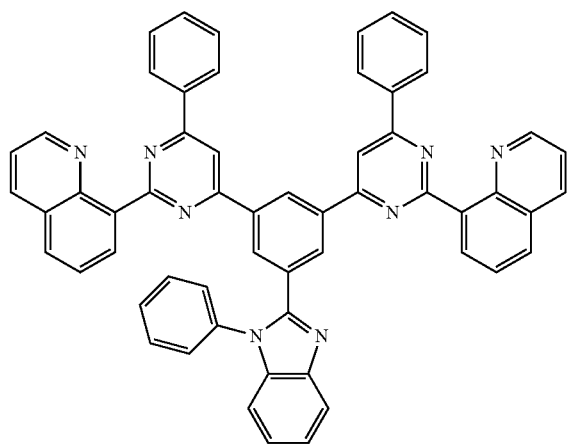

The embodiments may also be realized by providing an organic photoelectric device including an anode, a cathode, and at least one organic thin layer between the anode and the cathode, the at least one organic thin layer including the compound for an organic photoelectric device according to an embodiment.

The at least one organic thin layer may be selected from the group of an emission layer, a hole transport layer (HTL), a hole injection layer (HIL), an electron transport layer (ETL), an electron injection layer (EIL), a hole blocking layer, and a combination thereof.

The at least one organic thin layer may include one of an electron transport layer (ETL) and an electron injection layer (EIL), and the compound for an organic photoelectric device may be included in the electron transport layer (ETL) or the electron injection layer (EIL).

The at least one organic thin layer may include an emission layer, and the compound for an organic photoelectric device may be included in the emission layer.

The at least one organic thin layer may include an emission layer, and the compound for an organic photoelectric device may be a phosphorescent or fluorescent host material in the emission layer.

The at least one organic thin layer may include an emission layer, and the compound for an organic photoelectric device may be a fluorescent blue dopant material in the emission layer.

The organic photoelectric device may be selected from the group of an organic light emitting diode, an organic solar cell, an organic transistor, an organic photo-conductor drum, and an organic memory device.

The embodiments may also be realized by providing a display device including the organic photoelectric device according to an embodiment.

BRIEF DESCRIPTION OF THE DRAWINGS

Features will become apparent to those of ordinary skill in the art by describing in detail exemplary embodiments with reference to the attached drawings in which.

DETAILED DESCRIPTION

Figure 1:
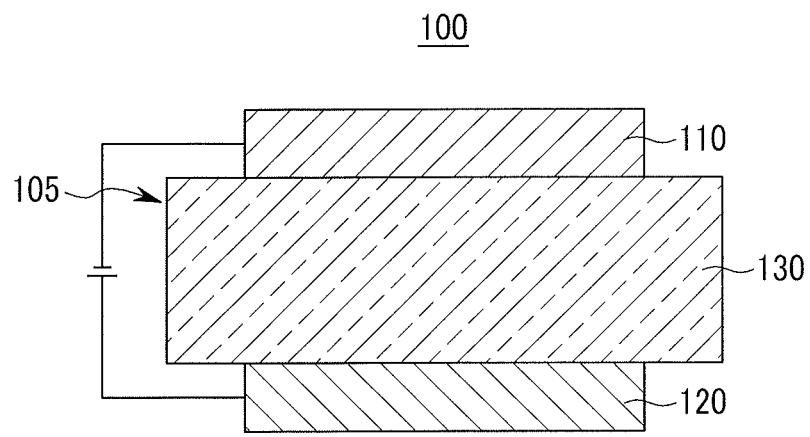
FIGS. 1 to 5 illustrate cross-sectional views of organic photoelectric devices according to various embodiments.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. In addition, it will also be understood that when a layer is referred to as being "between" two layers, it can be the only layer between the two layers, or one or more intervening layers may also be present. Like reference numerals refer to like elements throughout.

As used herein, when specific definition is not otherwise provided, the term "substituted" may refer to one substituted with a C1 to C30 alkyl group, a C1 to C10 alkylsilyl group, a C3 to C30 cycloalkyl group, a C6 to C30 aryl group, a C1 to C10 alkoxy group, a fluoro group, a C1 to C10 trifluoro alkyl group such as trifluoromethyl group, or a cyano group.

As used herein, when specific definition is not otherwise provided, the term "hetero" may refer to one including 1 to 3 hetero atoms selected from the group of N, O, S, and P, and remaining carbons in one functional group.

As used herein, when a definition is not otherwise provided, the term "combination thereof" may refer to at least two substituents bound to each other by a linker, or at least two substituents condensed to each other.

As used herein, when a definition is not otherwise provided, the term "alkyl" may refer to an aliphatic hydrocarbon group. The alkyl group may be a "saturated alkyl group" that does not include an alkene or alkyne moitey. An alkyl moiety may be an "unsaturated alkyl" moiety including at least one alkene or alkyne moiety. An "alkene" moiety may refer to a group including at least one carbon-carbon double bond, and "alkyne" moiety may refer to a group including at least one carbon-carbon triple bond. Regardless of being saturated or unsaturated, the alkyl may be branched, linear, or cyclic.

The alkyl group may be a C1 to C20 alkyl group. The alkyl group may be a C1 to C10 medium-sized alkyl group. The alkyl group may be a C1 to C6 lower alkyl group.

For example, a C1 to C4 alkyl group may have 1 to 4 carbon atoms and may be selected from the group of methyl, ethyl, propyl, iso-propyl, n-butyl, iso-butyl, sec-butyl, and t-butyl.

Examples of an alkyl group may include methyl, ethyl, propyl, isopropyl, butyl, isobutyl, t-butyl, pentyl, hexyl, ethenyl, propenyl, butenyl, cyclopropyl, cyclobutyl, cyclopentyl, cyclohexyl, and the like, which may be individually and independently substituted.

The term "aryl" may refer to an aryl group including a carbocyclic aryl (e.g., phenyl) having at least one ring having a covalent pi electron system. The term may also refer to monocyclic or fused ring polycyclic (i.e., rings sharing adjacent pairs of carbon atoms) groups. In addition, this term may also refer to a Spiro compound having a contact point of one carbon.

The term "heteroaryl" may refer to an aryl group including a heterocyclic aryl (e.g., pyridine) having at least one ring having a covalent pi electron system. The term may also refer to monocyclic or fused ring polycyclic (i.e., groups sharing adjacent pairs of carbon atoms) groups. In addition, the term may also refer to a spiro compound having a contact point of one carbon.

An embodiment provides a compound for an organic photoelectric device. The compound may have a structure in which three aryl groups and/or heteroaryl groups are bonded with a benzene core. In an implementation, the three substituents may be bonded in the 1, 3, and 5 positions of the benzene core.

The compound for an organic photoelectric device may be synthesized to have various energy band gaps by introducing various substituents into the core part and the substituents and accordingly, applied to satisfy various conditions required of an emission layer as well as an electron injection layer (EIL) and a transport layer.

The compound may have an appropriate energy level depending on the substituents. Thus, electron transport capability of an organic photoelectric device may be enhanced, and excellent effects on efficiency and driving voltage may be achieved. Also, the compound may have excellent electrochemical and thermal stability and thus, may help improve life-span characteristic during the operation of the organic photoelectric device.

In an implementation, the compound for an organic photoelectric device may be represented by the following Chemical Formula 1.

[Chemical Formula 1]

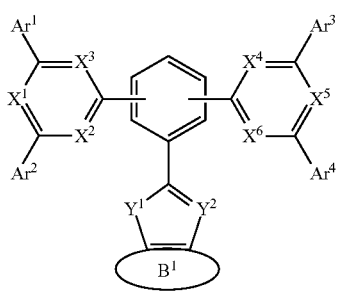

In Chemical Formula 1, $Ar^1$ to $Ar^4$ may each independently be a substituted or unsubstituted C6 to C30 aryl group or a substituted or unsubstituted C3 to C30 heteroaryl group, $X^1$ to $X^6$ may each independently be —N— or —CH—, $Y^1$ may be selected from the group of —O—, —S—, —NH— and —NR—, wherein R is selected from the group of a substituted or unsubstituted C6 to C30 aryl group, a substituted or unsubstituted C3 to C30 heteroaryl group, a substituted or unsubstituted C1 to C6 alkyl group, a substituted or unsubstituted C3 to C30 cycloalkyl group, a substituted or unsubstituted cyano group, a substituted or unsubstituted nitro group, a substituted or unsubstituted carbonyl group, and a substituted or unsubstituted amide group, $Y^2$ may be —CH— or —N—, and $B^1$ may be a substituted or unsubstituted C6 to C30 aryl group or a substituted or unsubstituted C3 to C30 heteroaryl group. In an implementation, $B^1$ may form a fused ring with an adjacent element, e.g., the moiety including $Y^1$ and $Y^2$.

In an implementation, at least 2 of the three substituents bonded with the core benzene may be heteroaryl groups. For example, at least one of $X^1$ to $X^3$ may be —N—, and at least one of $X^4$ to $X^6$ may be —N—.

Each heteroaryl group may include various numbers of heteroatoms in various combinations. Each combination of the heteroatoms may vary characteristics of the compound. Thus, a particular combination may be selected to satisfy desired characteristics.

In an implementation, the heteroatom may be N. However, it is not limited thereto.

In an implementation, the compound represented by the above Chemical Formula 1 may be a compound represented by the following Chemical Formula 2.

[Chemical Formula 2]

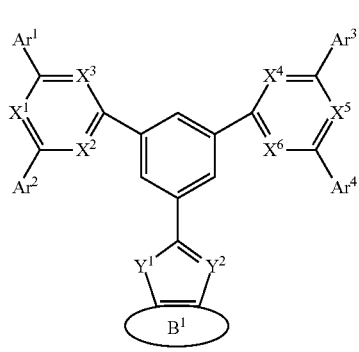

In Chemical Formula 2, $Ar^1$ to $Ar^4$, $X^1$ to $X^6$, $Y^1$, $Y^2$ and $B^1$ may be the same as defined in Chemical Formula 1.

For example, $Ar^1$ to $Ar^4$ may each independently be a substituted or unsubstituted C6 to C30 aryl group or a substituted or unsubstituted C3 to C30 heteroaryl group. For example, $Ar^1$ to $Ar^4$ may each independently be selected from the group of a substituted or unsubstituted phenyl group, a substituted or unsubstituted naphthyl group, a substituted or unsubstituted anthracenyl group, a substituted or unsubstituted phenanthrenyl group, a substituted or unsubstituted perylenyl group, a substituted or unsubstituted chrysenyl group, a substituted or unsubstituted pyridinyl group, a substituted or unsubstituted pyridazinyl group, a substituted or unsubstituted quinolinyl group, and a substituted or unsubstituted isoquinolinyl group.

$Ar^1$ to $Ar^4$ may play a role of smoothing transport of electrons. For example, $Ar^1$ to $Ar^4$ may be a functional group for withdrawing electrons and adjusting a transport rate of the electrons to be similar to that of holes. Accordingly, the substituent may be selected or modified depending on desired characteristics of a device.

In addition, $Ar^1$ to $Ar^4$ may be adjusted regarding a π-conjugation length, so that light emission in a visible region may be controlled. Accordingly, the compound may be very usefully applied to an emission layer for an organic photoelectric device. For example, by maintaining a carbon number thereof within the described range, sufficient effects of a device may be achieved.

The compound including the above-described substituents may exhibit excellent thermal stability or resistance against oxidation. Thus, the compound may help improve life-span characteristics of an organic photoelectric device.

The substituents may vary electron transport capability of the compound, depending on the kind of the substituents. In addition, the compound may have a bulky and/or asymmetric structure and thus may have lower crystallinity. The compound having lower crystallinity may help improve efficiency characteristic and life-span of a device.

$B^1$ may be a substituted or unsubstituted C6 to C30 aryl group or a substituted or unsubstituted C3 to C30 heteroaryl group. In an implementation, $B^1$ may form a fused ring with an adjacent element, e.g., the moiety including $Y^1$ and $Y^2$. Examples of substituted or unsubstituted C6 to C30 aryl groups and substituted or unsubstituted C3 to C30 heteroaryl groups for $B^1$ may include a substituted or unsubstituted phenyl group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted perylenyl group, a substituted or unsubstituted chrysenyl group, a substituted or unsubstituted pyridinyl group, a substituted or unsubstituted quinolinyl group, a substituted or unsubstituted benzoquinolinyl group, and a substituted or unsubstituted phenanthrolinyl group.

The substituent may play a role of smoothing transport of electrons. For example, the substituent may work as a functional group for pulling the electrons and thus, may help adjust a transport rate of the electrons to be similar to that of holes. In addition, an aryl group as the substituent may help increase thermal stability. Accordingly, the substituent may be selected or modified depending on desired characteristics of a device.

In an implementation, the compound for an organic photoelectric device may include a compound represented by one of the following Chemical Formulae 3 to 186.

[Chemical Formula 3]
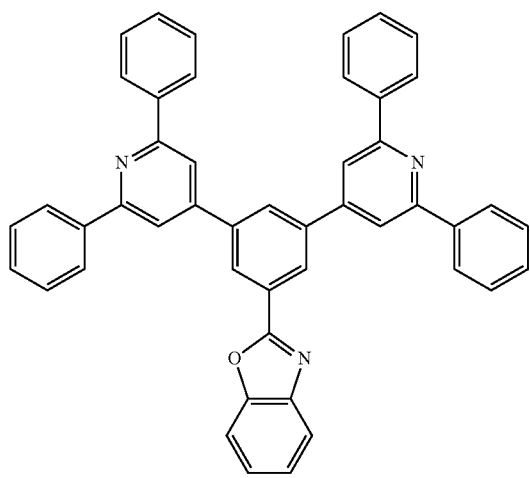
[Chemical Formula 4]
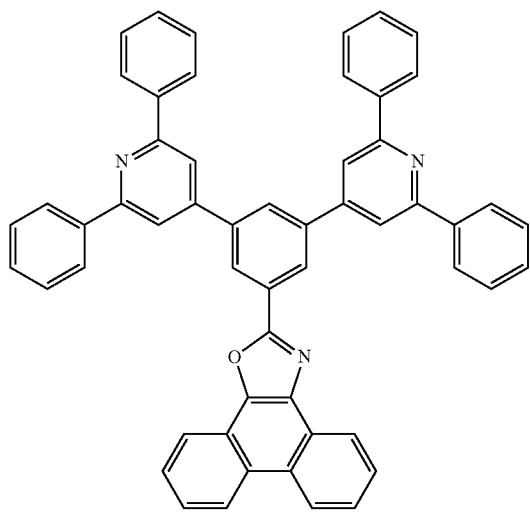
[Chemical Formula 5]
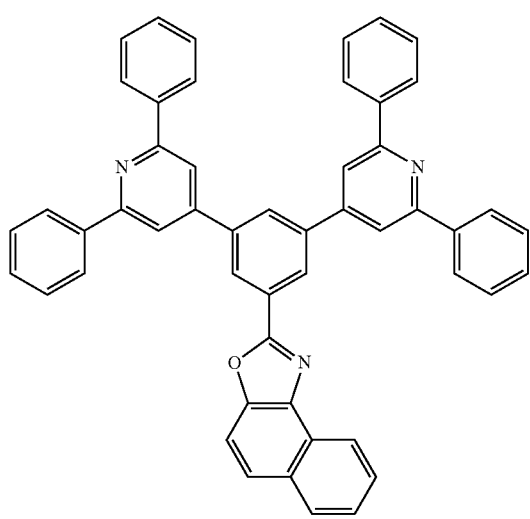
[Chemical Formula 6]
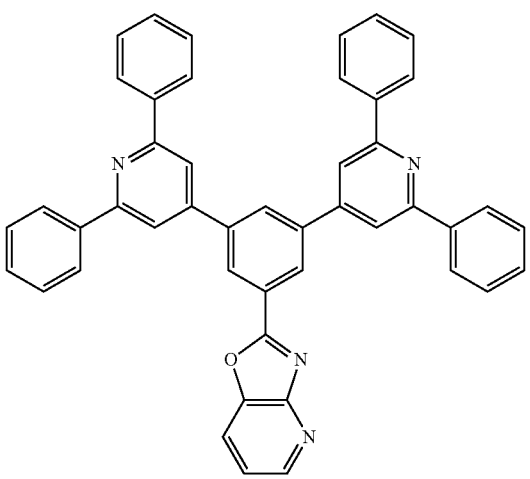
[Chemical Formula 7]
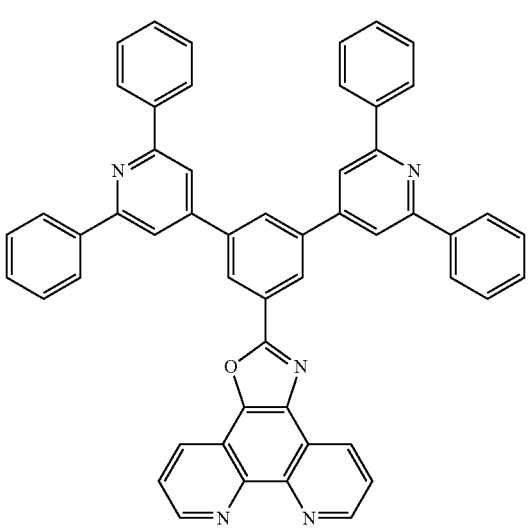
[Chemical Formula 8]
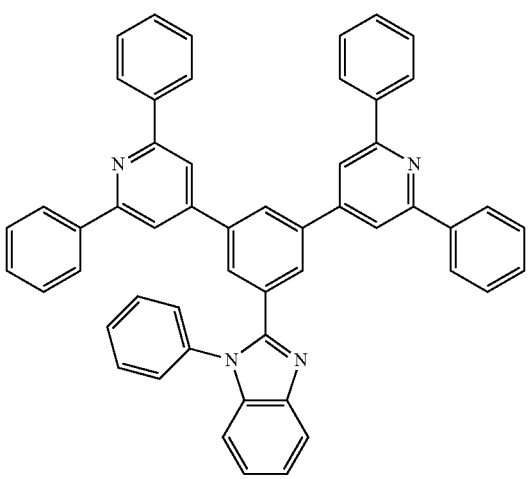

71
-continued
[Chemical Formula 9]
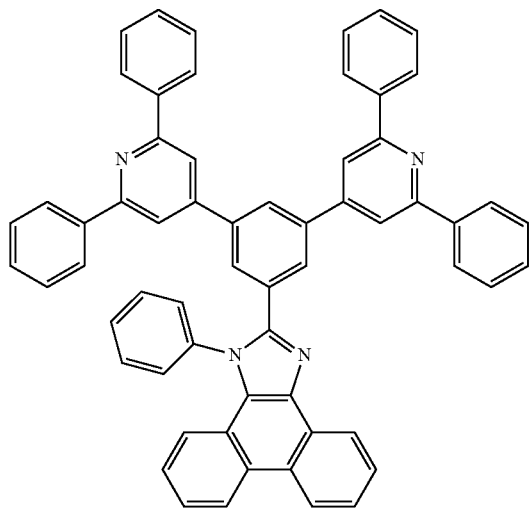
[Chemical Formula 10]
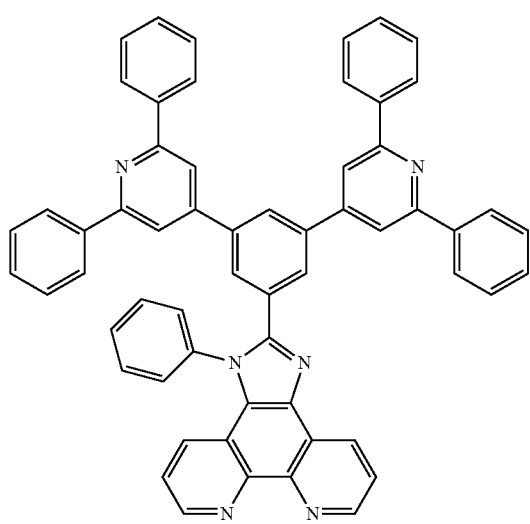
[Chemical Formula 11]
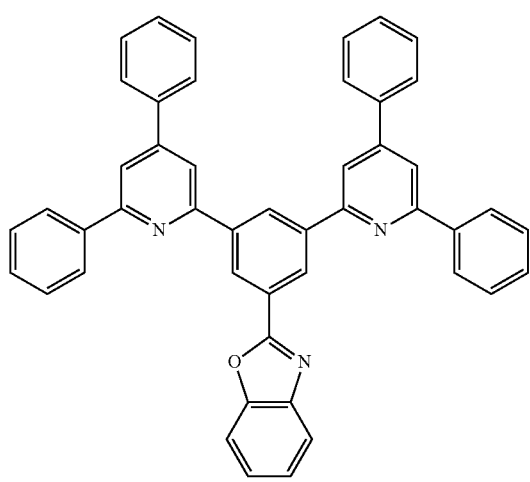 [SMILES: c1ccc(-c2cc(-c3ccccc3)nc(-c3cc(-c4cc(-c5ccccc5)cc(-c5ccccc5)n4)cc(-c4nc5ccccc5o4)c3)c2)cc1]
72
-continued
[Chemical Formula 12]
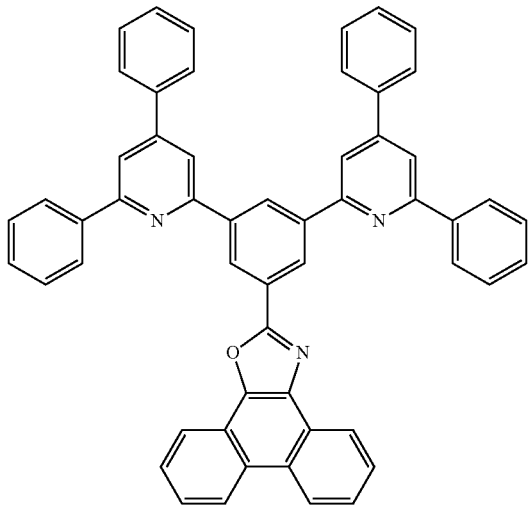
[Chemical Formula 13]
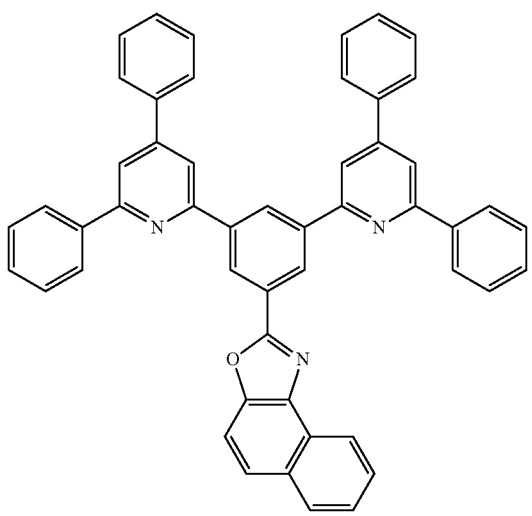
[Chemical Formula 14]
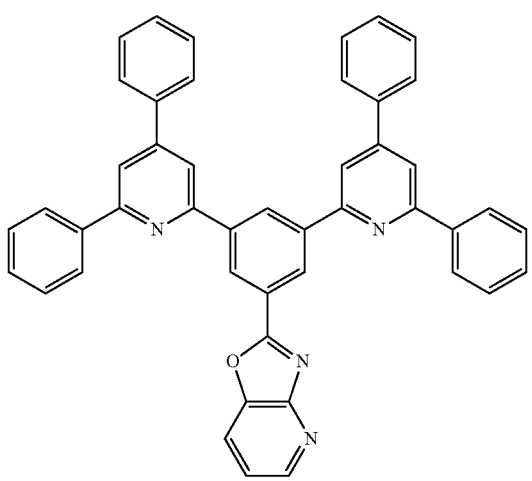

[Chemical Formula 15]
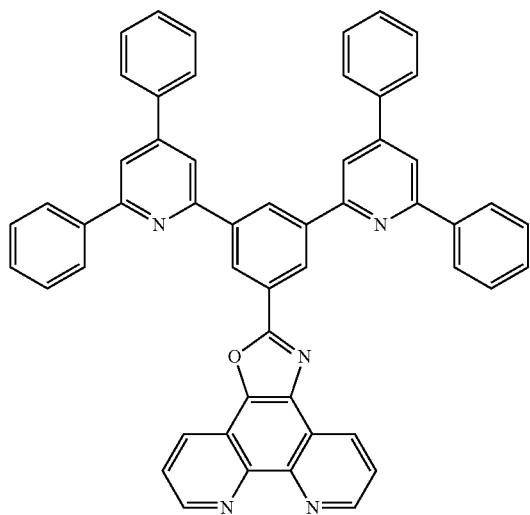
[Chemical Formula 16]
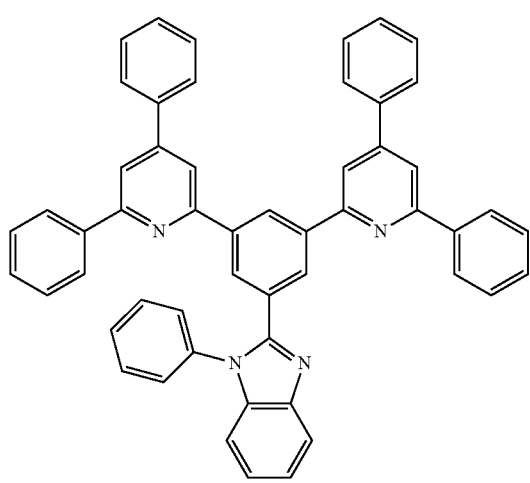
[Chemical Formula 17]
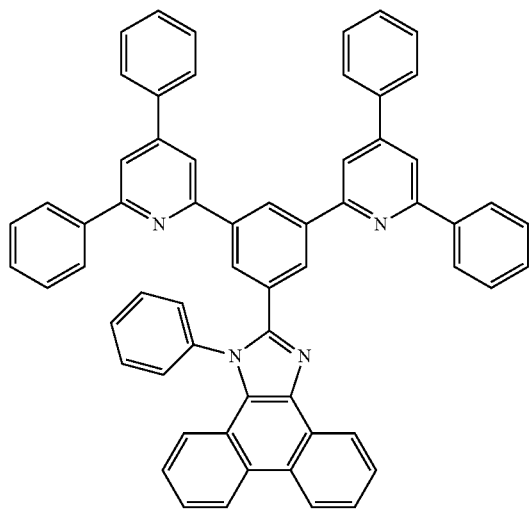
[Chemical Formula 18]
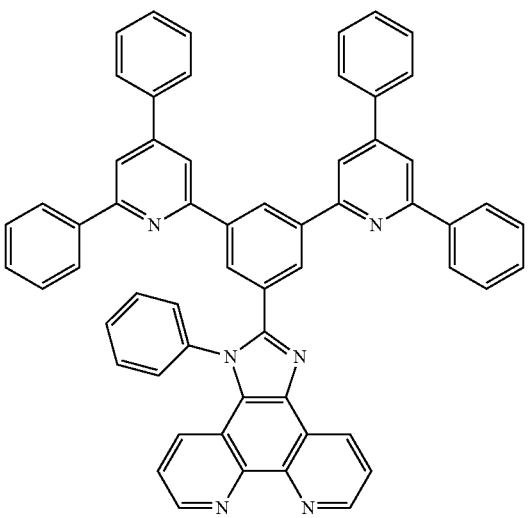
[Chemical Formula 19]
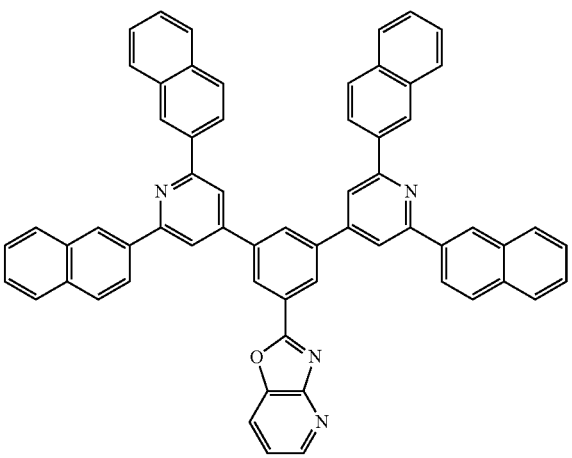
[Chemical Formula 20]
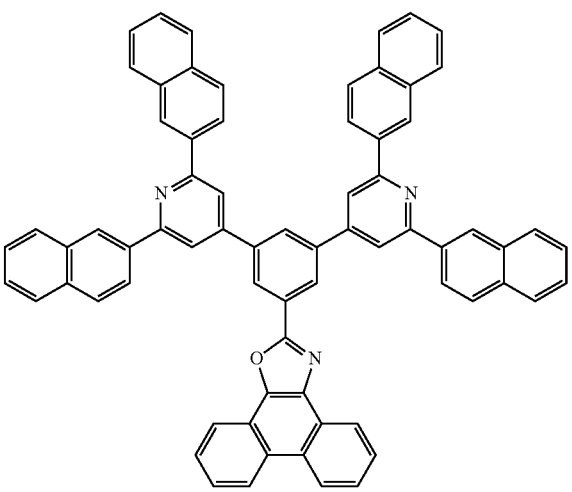

-continued
[Chemical Formula 21]
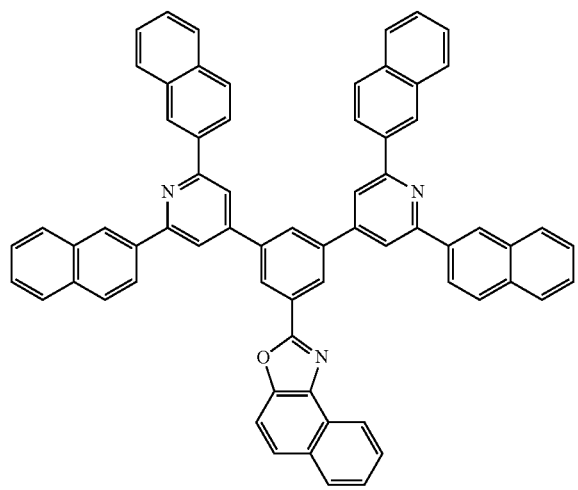
[Chemical Formula 22]
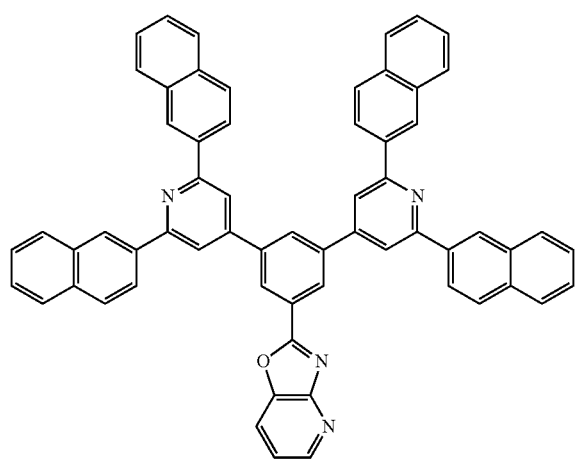
[Chemical Formula 23]
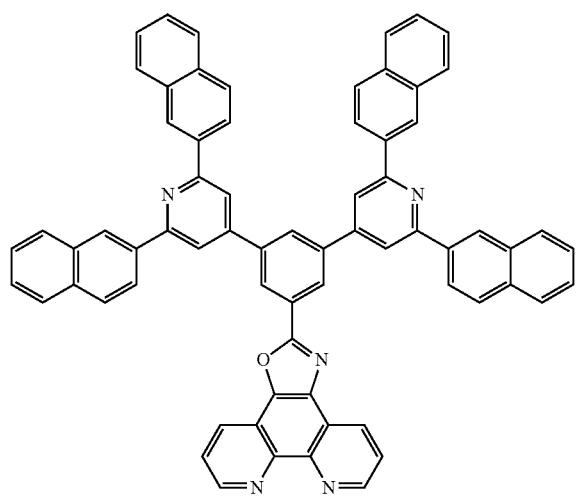
-continued
[Chemical Formula 24]
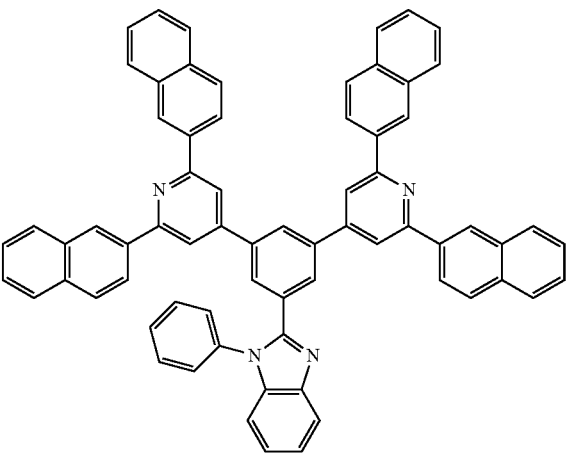
[Chemical Formula 25]
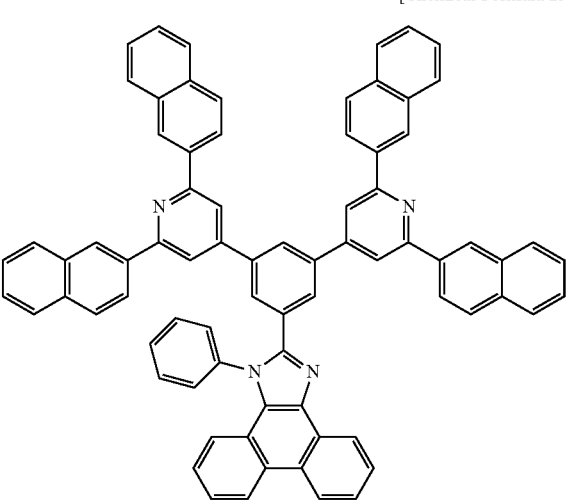
[Chemical Formula 26]
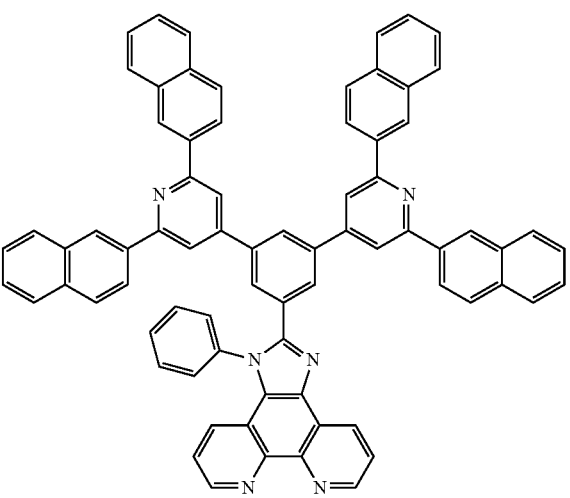

[Chemical Formula 27]
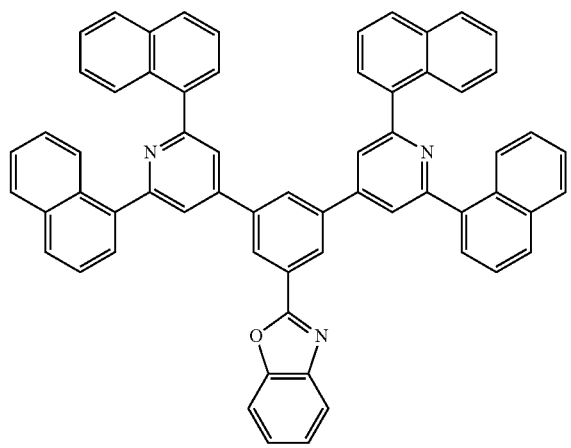
[Chemical Formula 30]
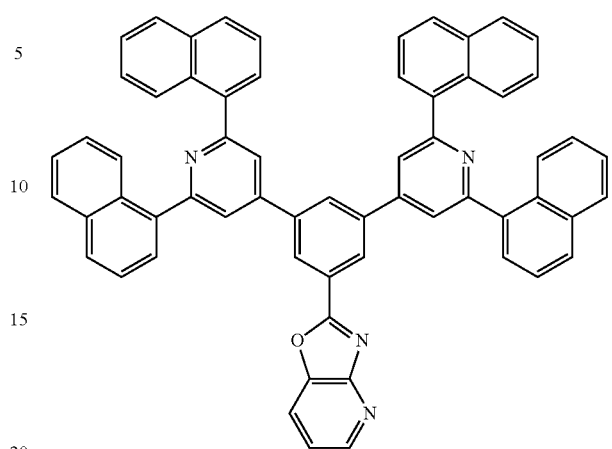
[Chemical Formula 28]
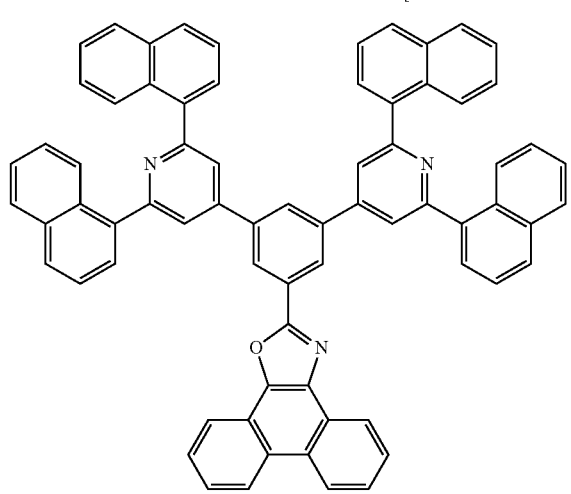
[Chemical Formula 31]
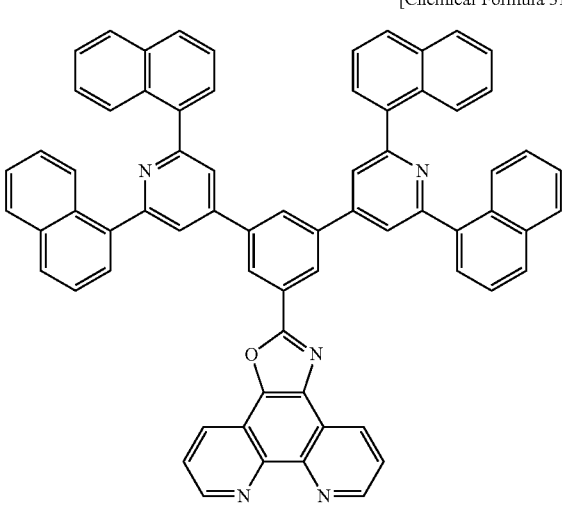
[Chemical Formula 29]
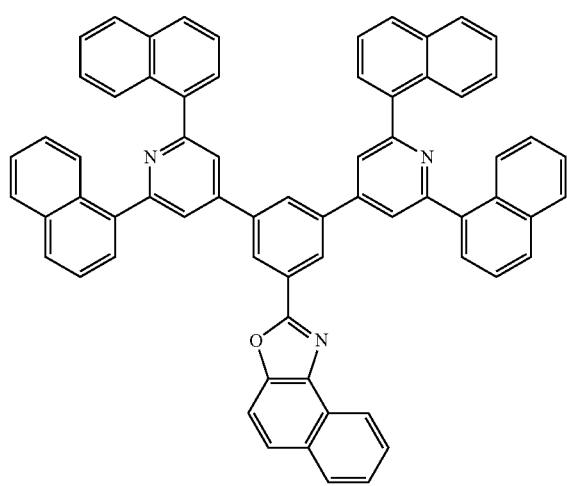
[Chemical Formula 32]
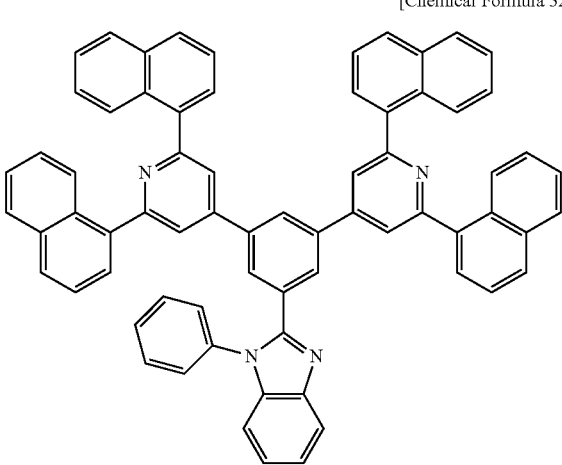

[Chemical Formula 33]
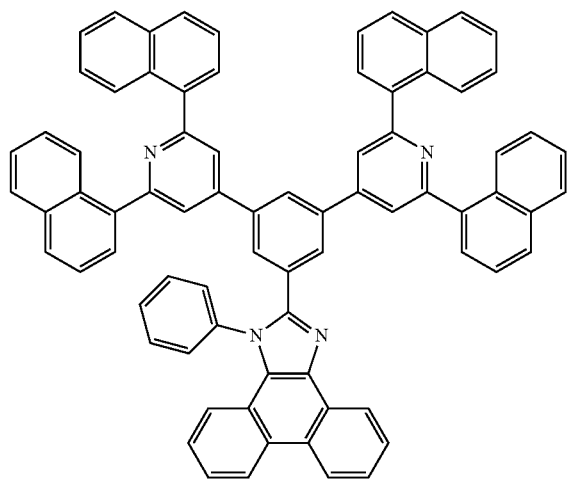
[Chemical Formula 36]
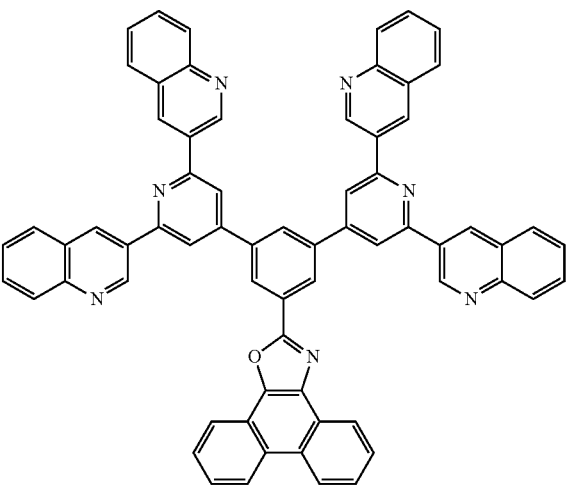
[Chemical Formula 34]
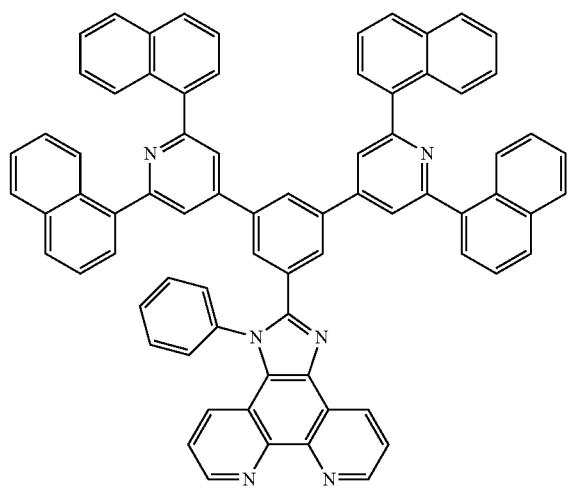
[Chemical Formula 37]
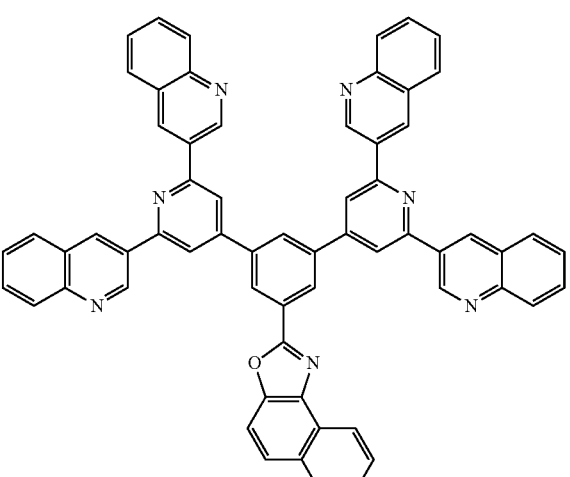
[Chemical Formula 35]
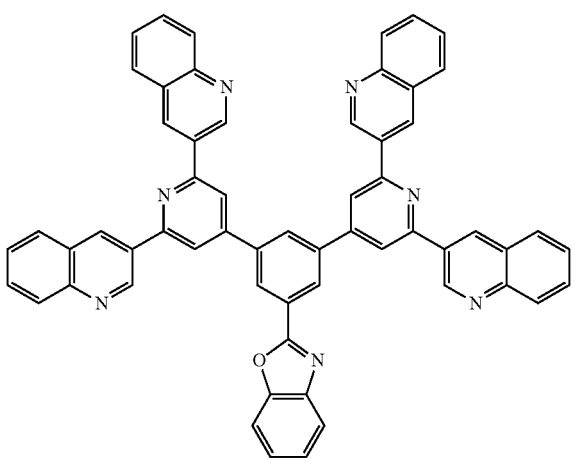
[Chemical Formula 38]
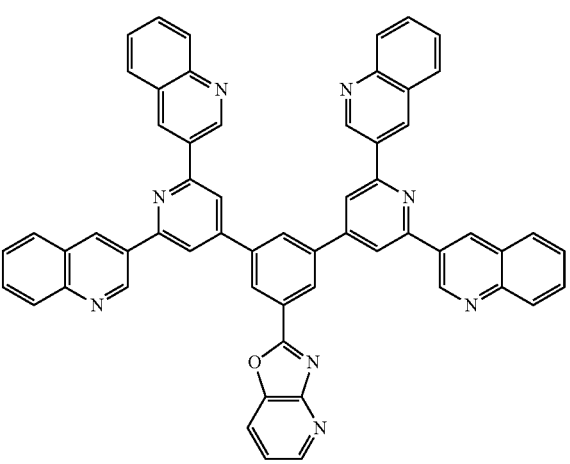

[Chemical Formula 39]
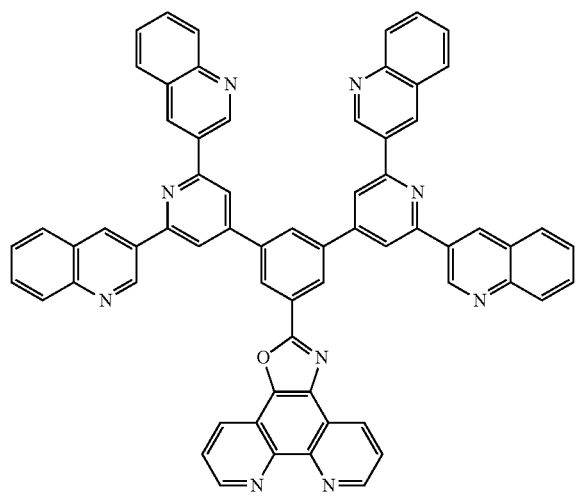
[Chemical Formula 40]
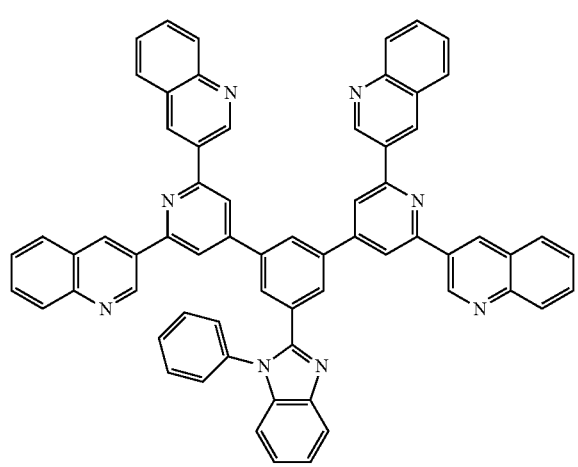
[Chemical Formula 41]
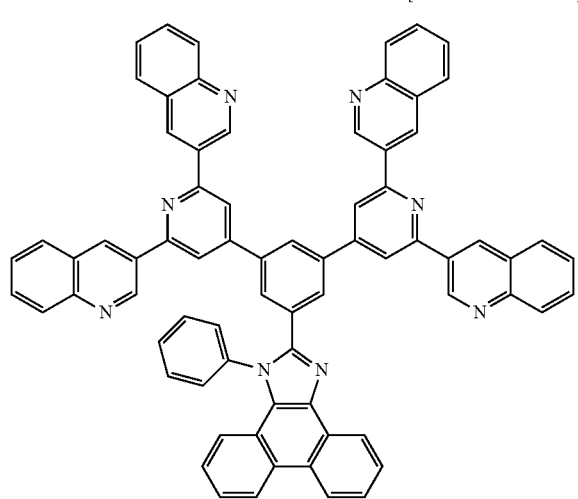
[Chemical Formula 42]
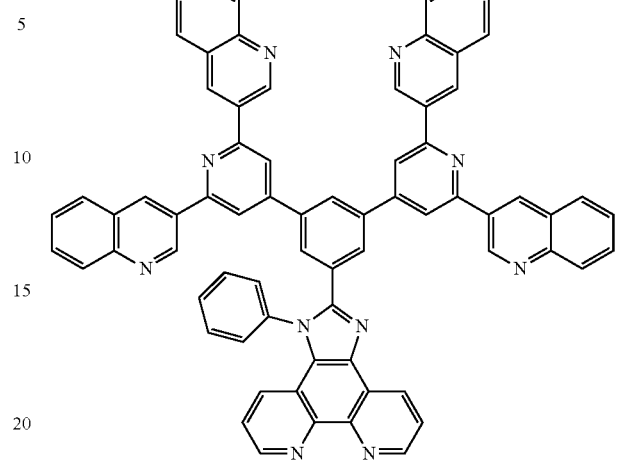
[Chemical Formula 43]
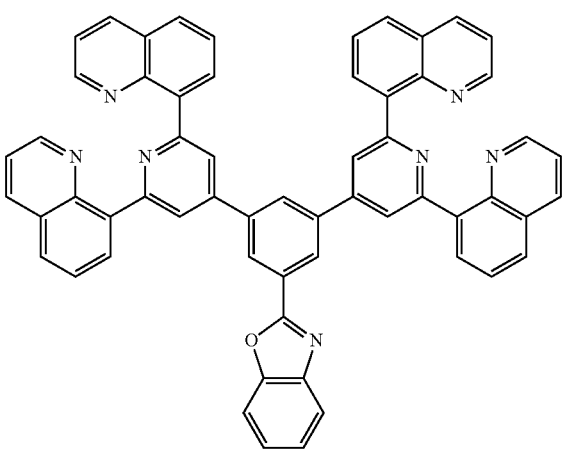
[Chemical Formula 44]
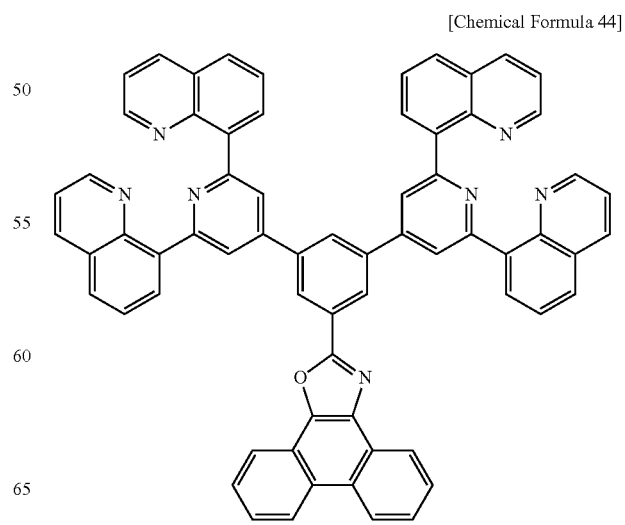

[Chemical Formula 45]
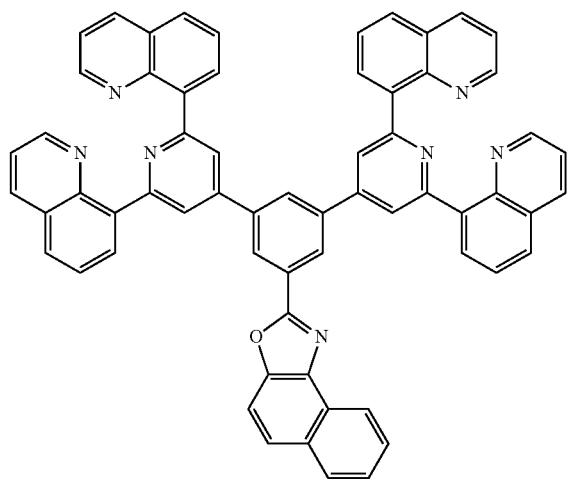
[Chemical Formula 46]
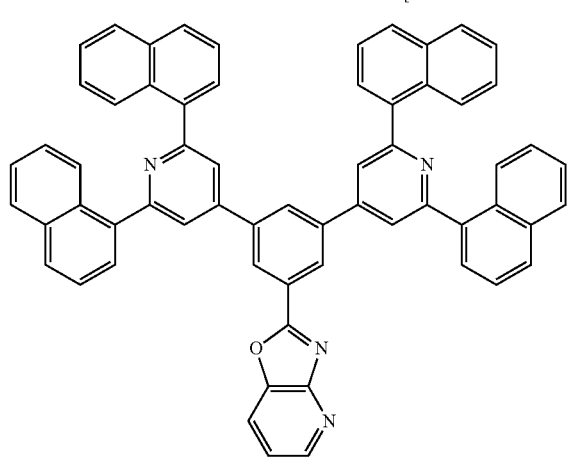
[Chemical Formula 47]
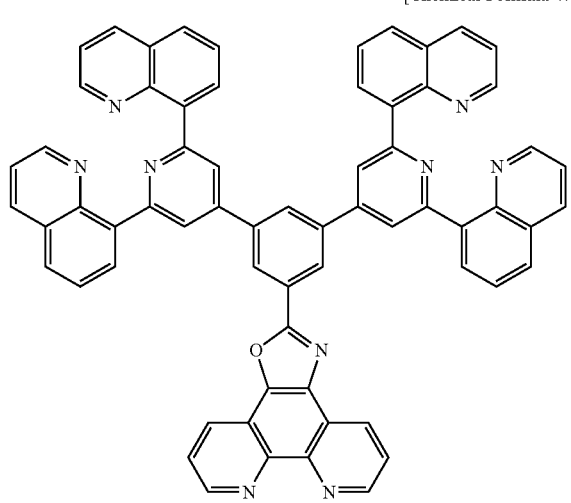
[Chemical Formula 48]
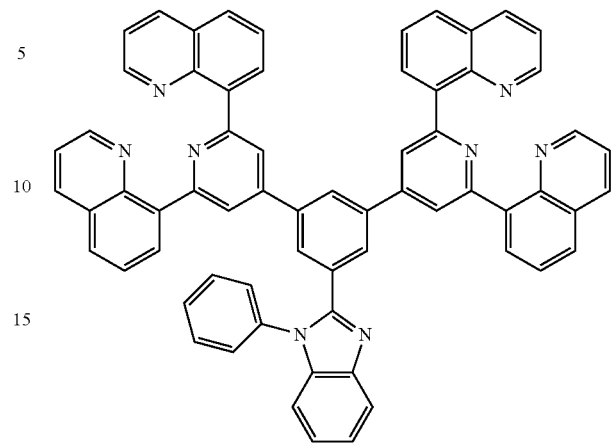
[Chemical Formula 49]
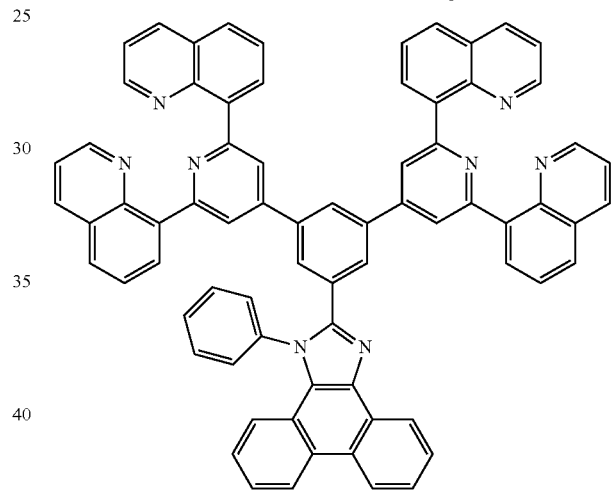
[Chemical Formula 50]
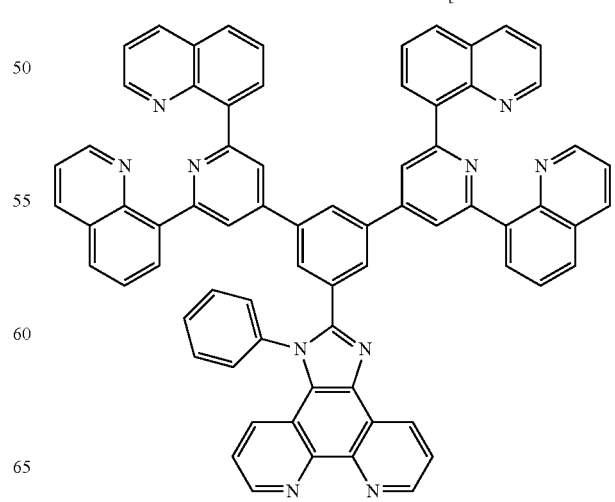

[Chemical Formula 51]
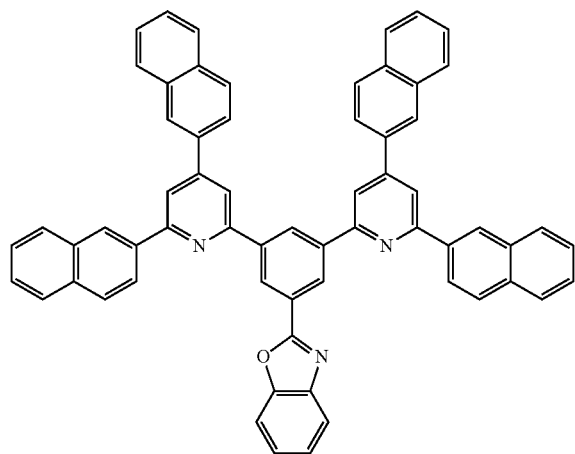
[Chemical Formula 52]
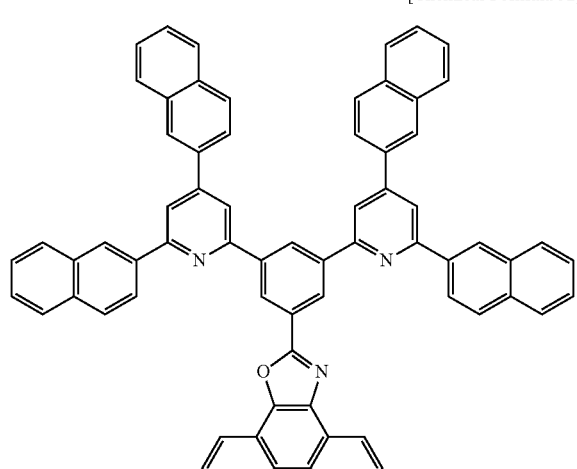
[Chemical Formula 53]
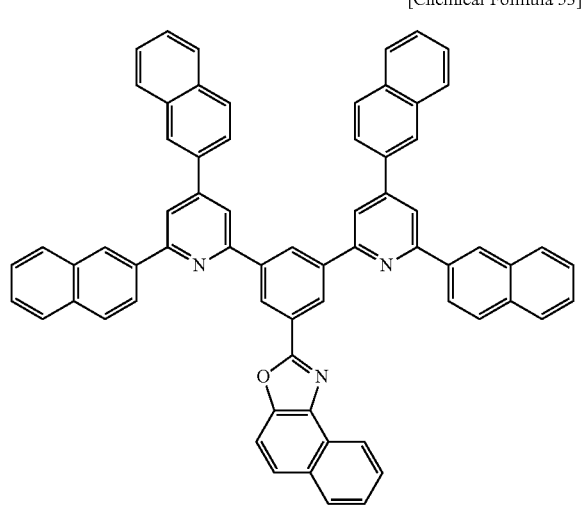
[Chemical Formula 54]
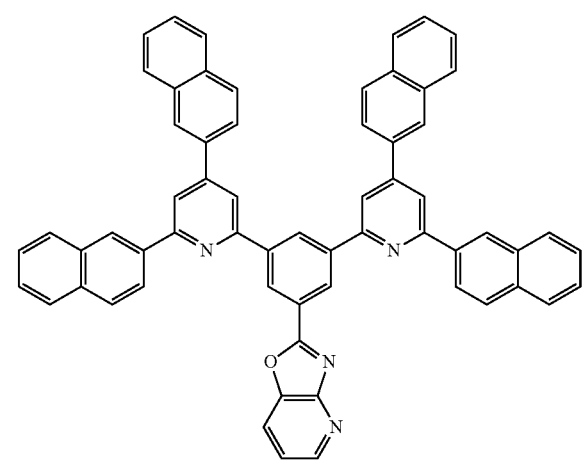
[Chemical Formula 55]
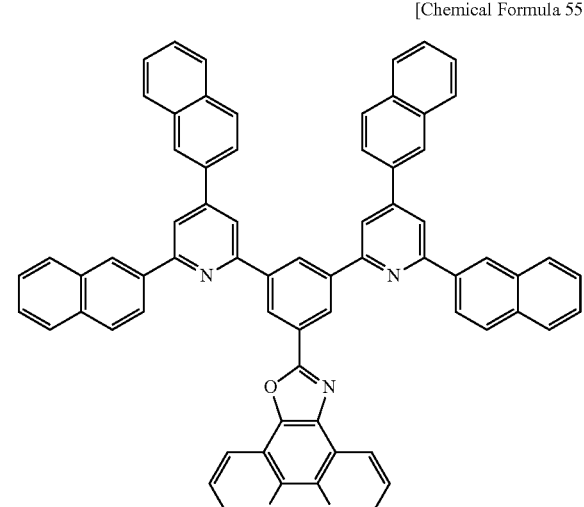
[Chemical Formula 56]
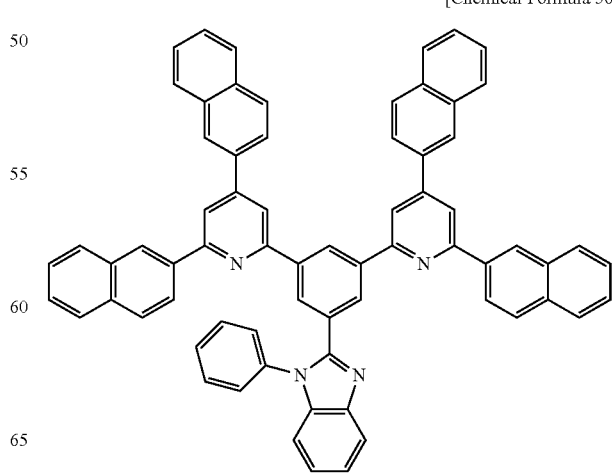

[Chemical Formula 57]
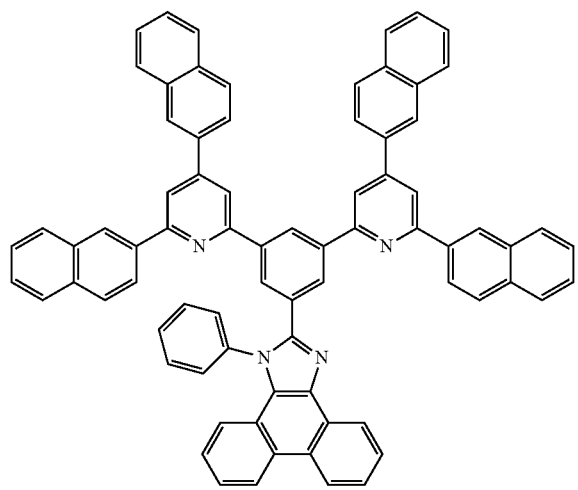
[Chemical Formula 58]
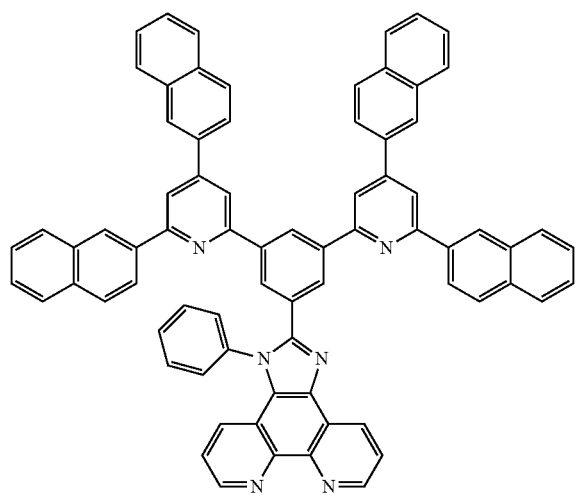
[Chemical Formula 59]
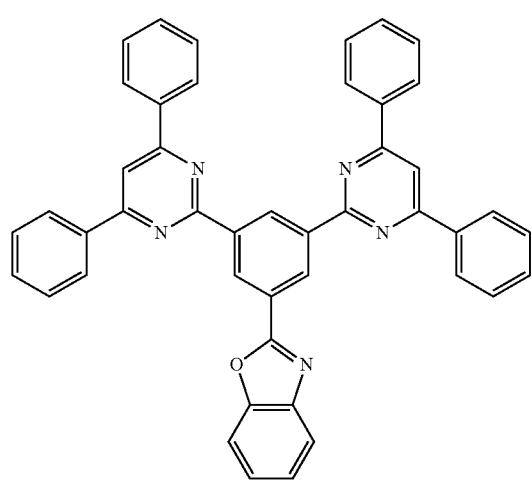
[Chemical Formula 60]
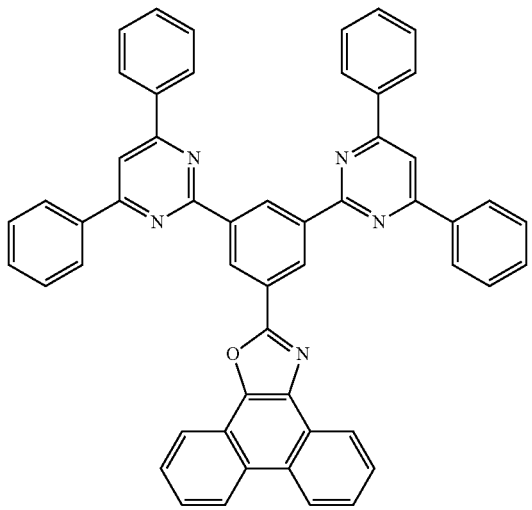
[Chemical Formula 61]
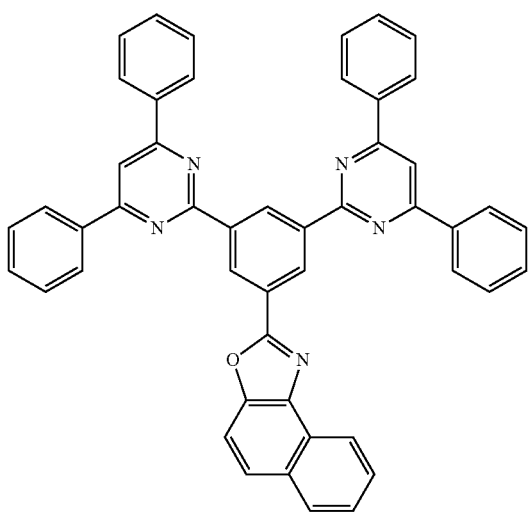
[Chemical Formula 62]
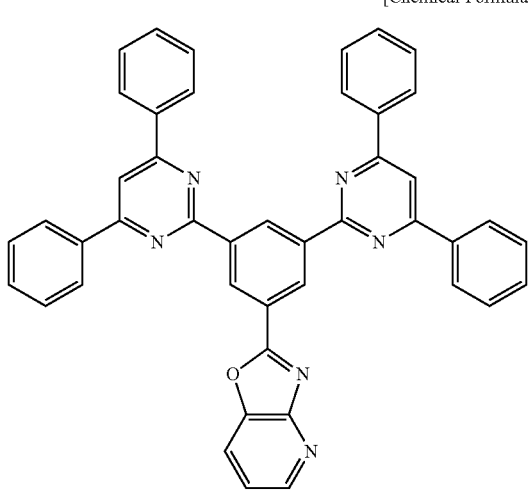

[Chemical Formula 63]
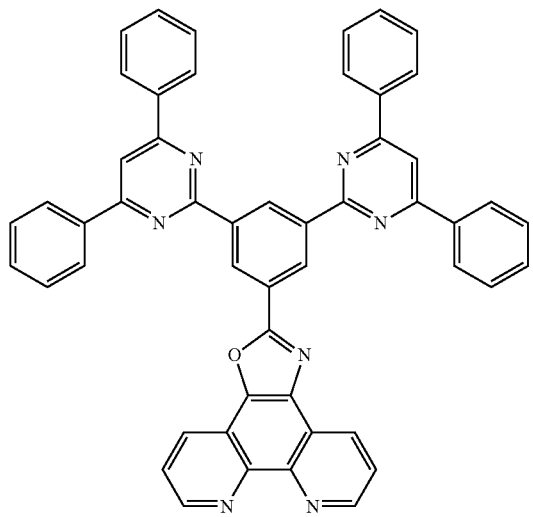
[Chemical Formula 64]
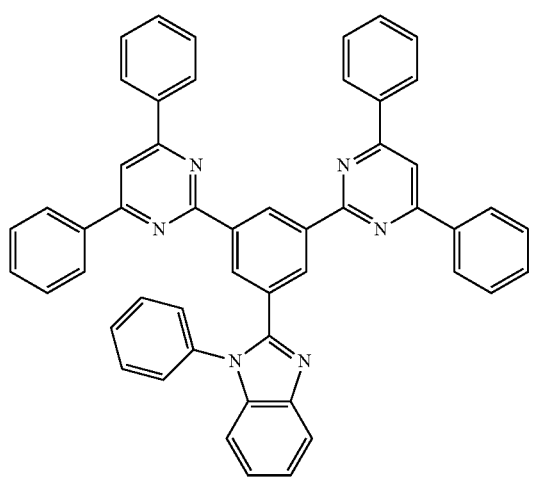
[Chemical Formula 65]
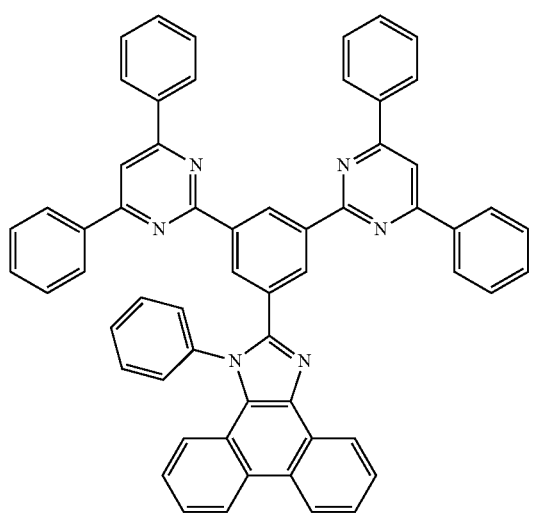
[Chemical Formula 66]
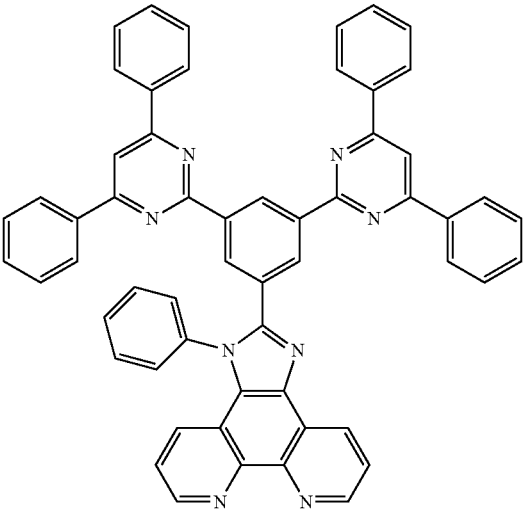
[Chemical Formula 67]
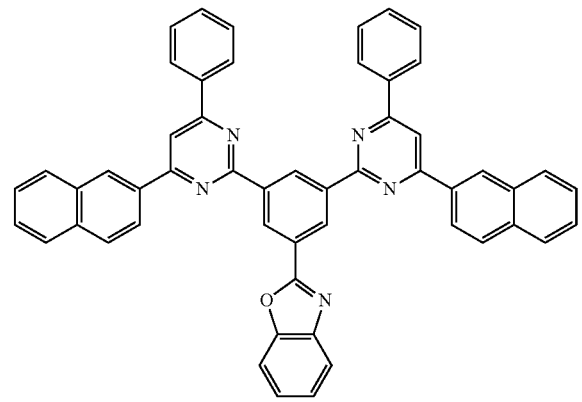
[Chemical Formula 68]
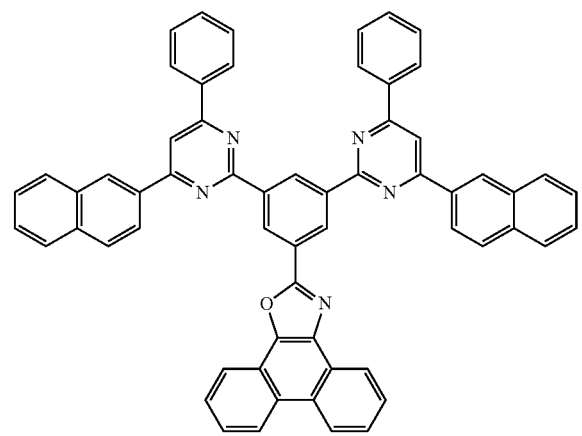

[Chemical Formula 69]
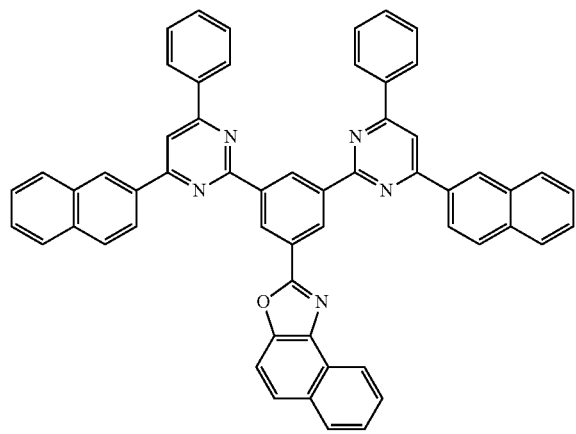
[Chemical Formula 72]
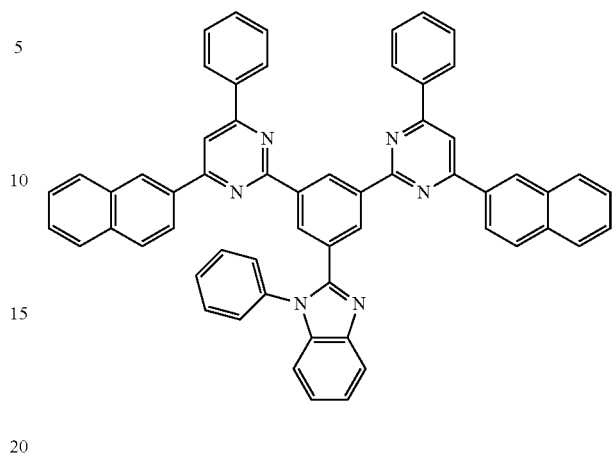
[Chemical Formula 70]
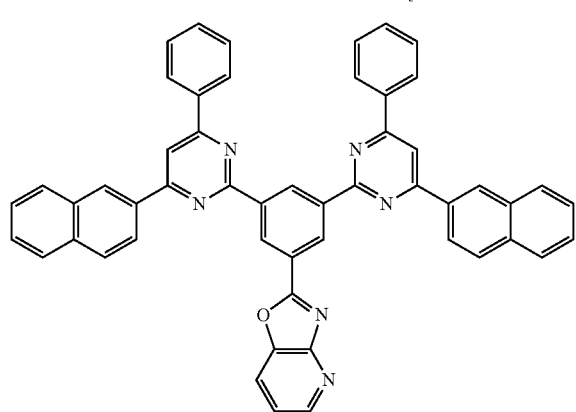
[Chemical Formula 73]
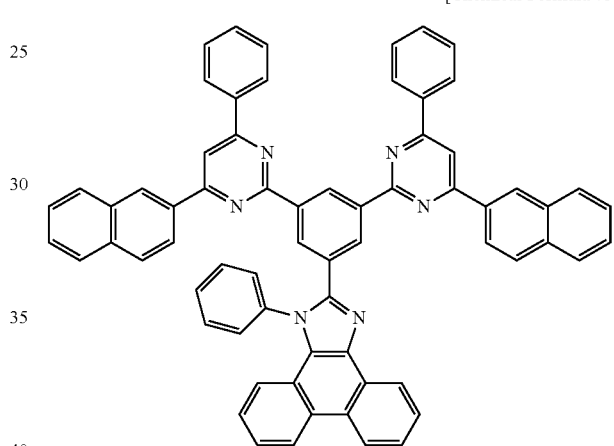
[Chemical Formula 71]
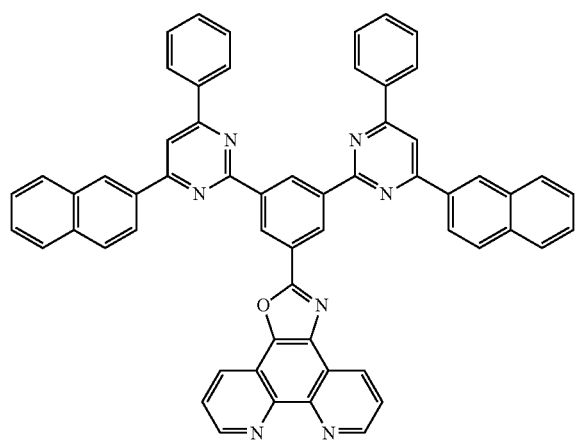
[Chemical Formula 74]
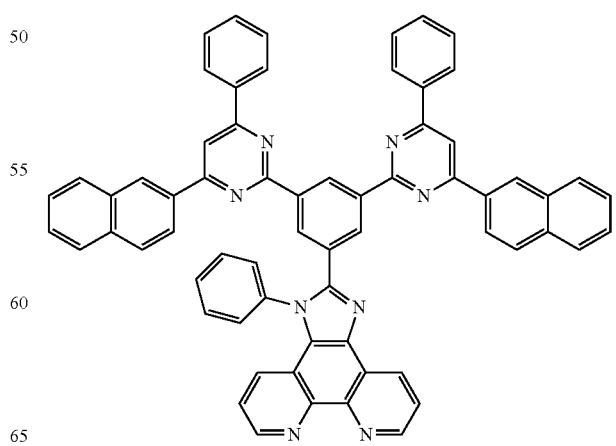

[Chemical Formula 75]
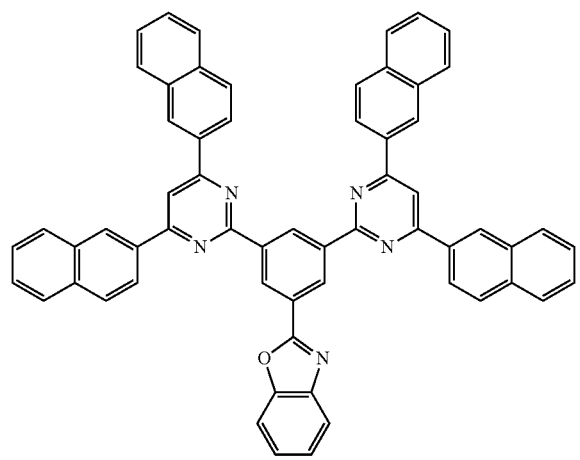
[Chemical Formula 76]
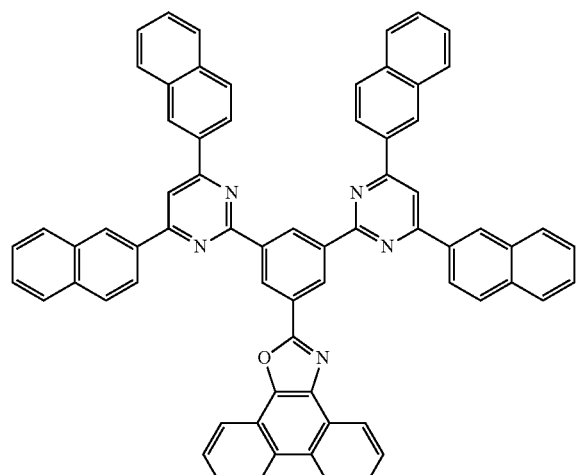
[Chemical Formula 77]
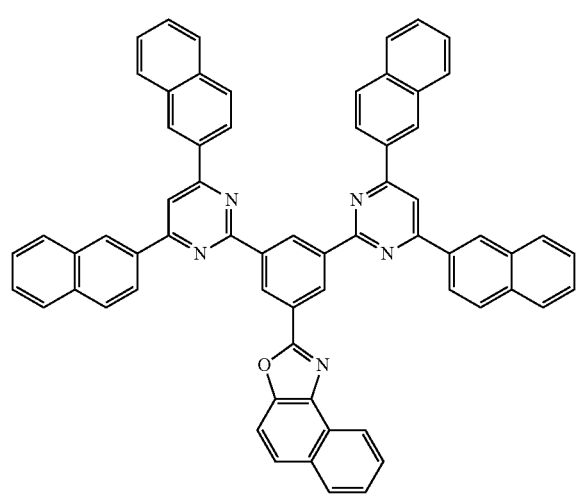
[Chemical Formula 78]
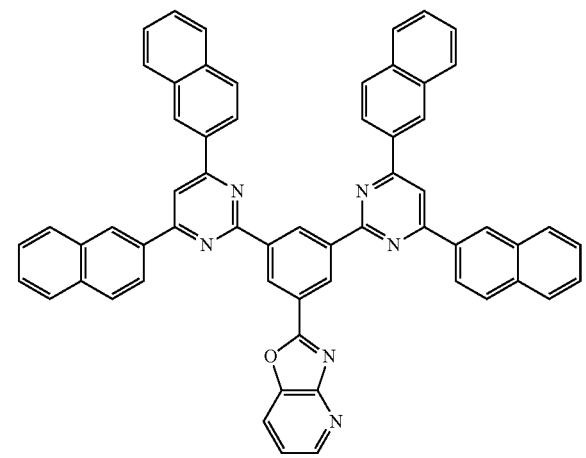
[Chemical Formula 79]
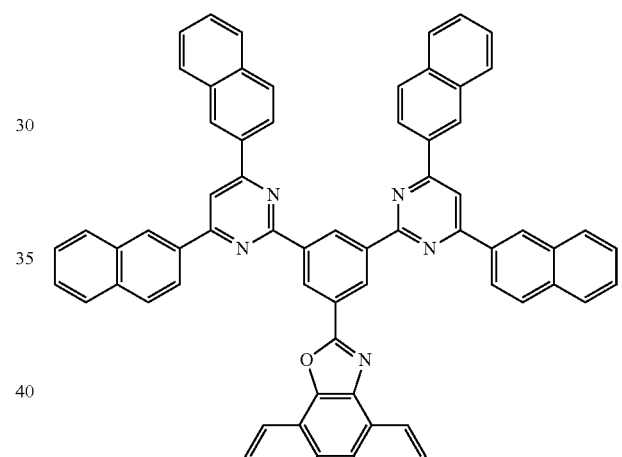
[Chemical Formula 80]
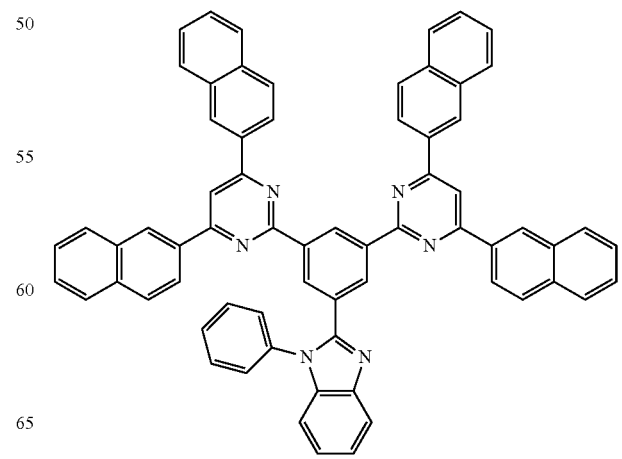

[Chemical Formula 81]
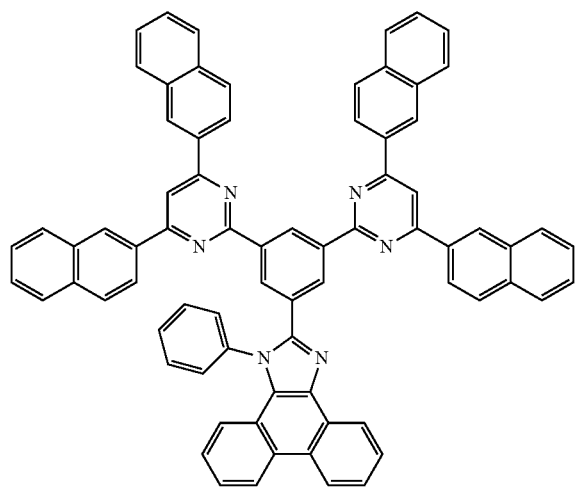
[Chemical Formula 82]
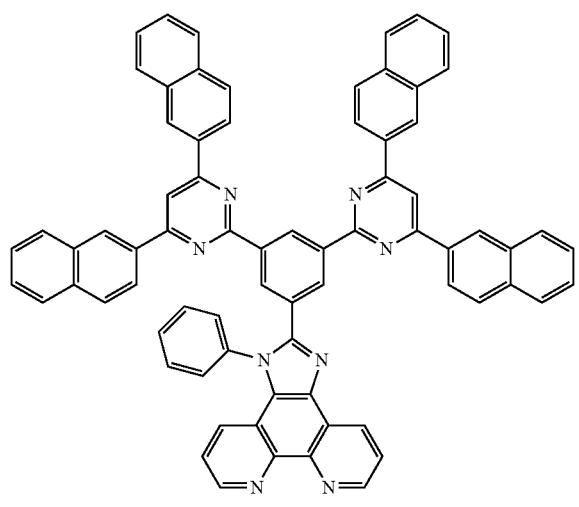
[Chemical Formula 83]
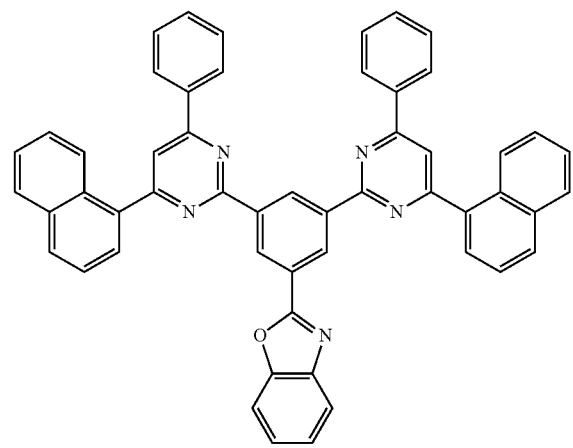
[Chemical Formula 84]
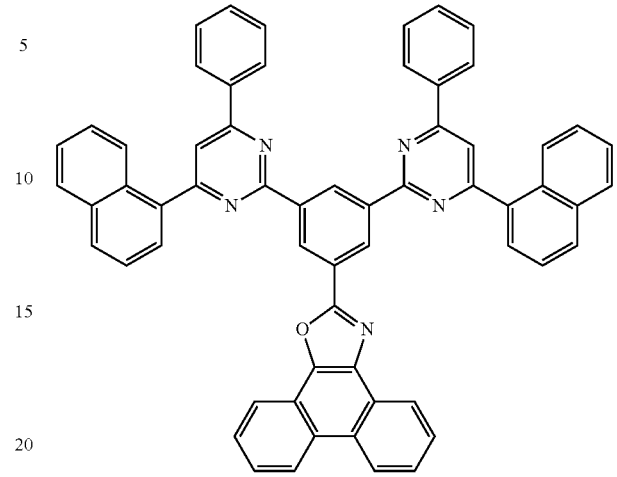
[Chemical Formula 85]
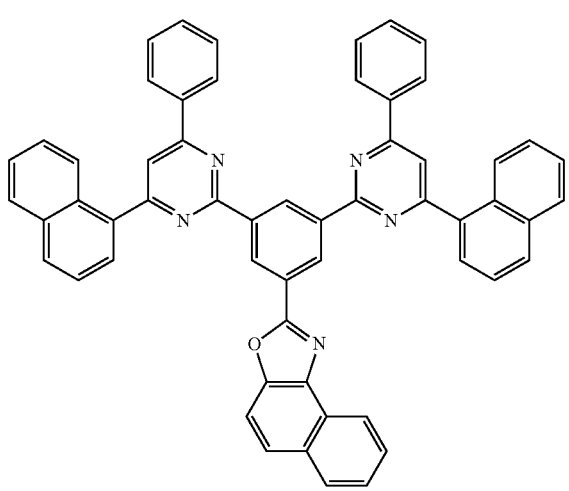
[Chemical Formula 86]
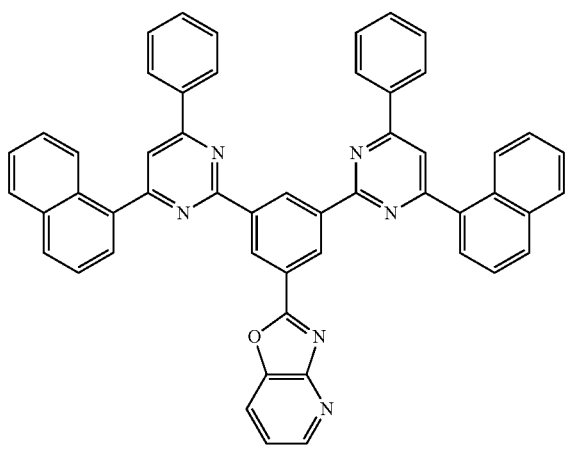

[Chemical Formula 87]
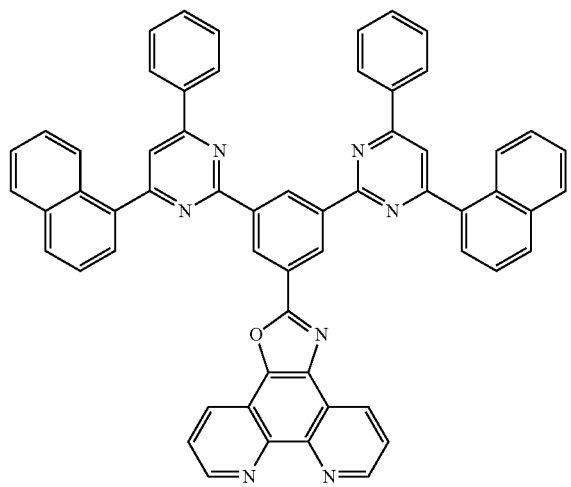
[Chemical Formula 88]
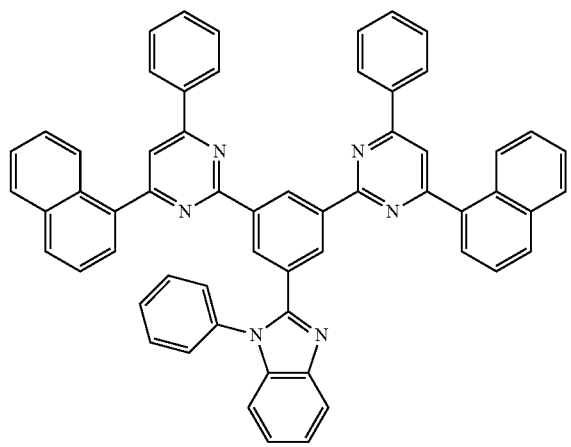
[Chemical Formula 89]
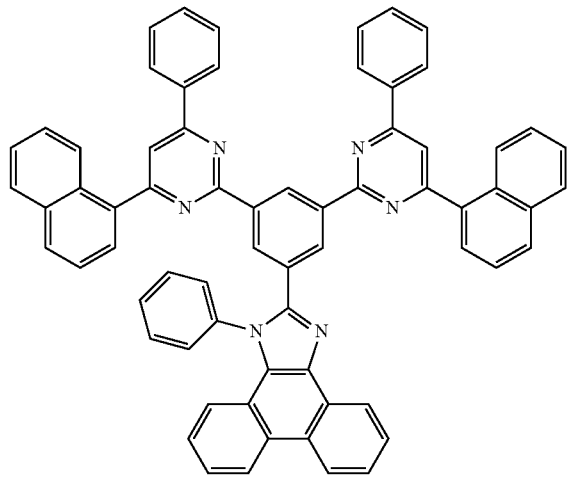
[Chemical Formula 90]
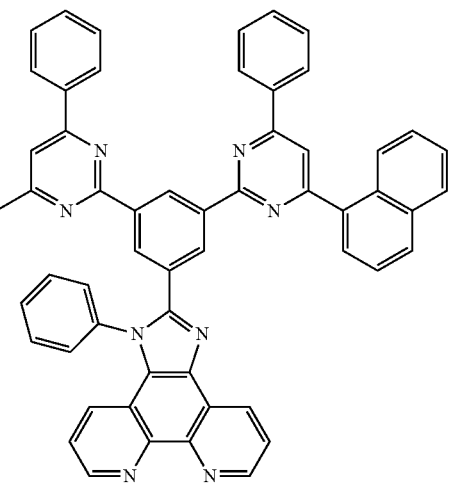
[Chemical Formula 91]
[Chemical Formula 92]
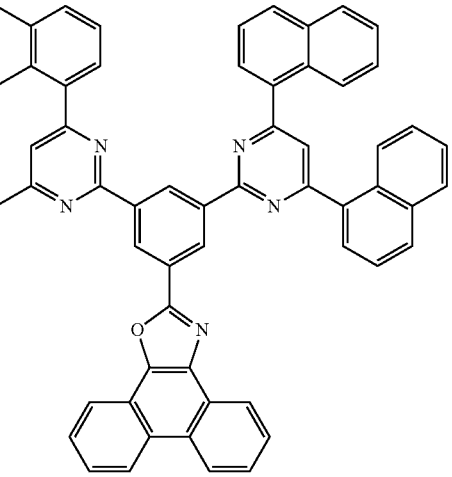

[Chemical Formula 93]
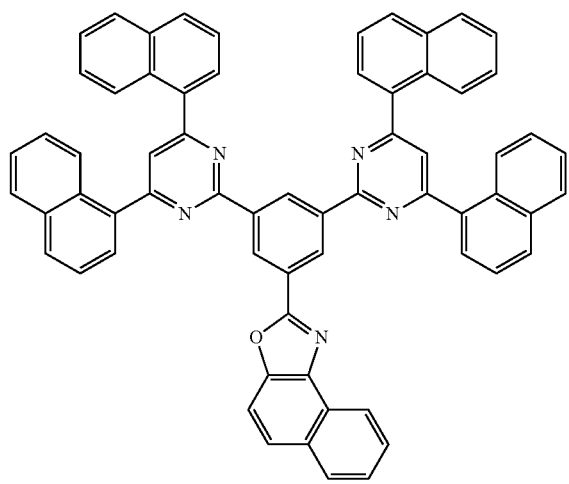
[Chemical Formula 94]
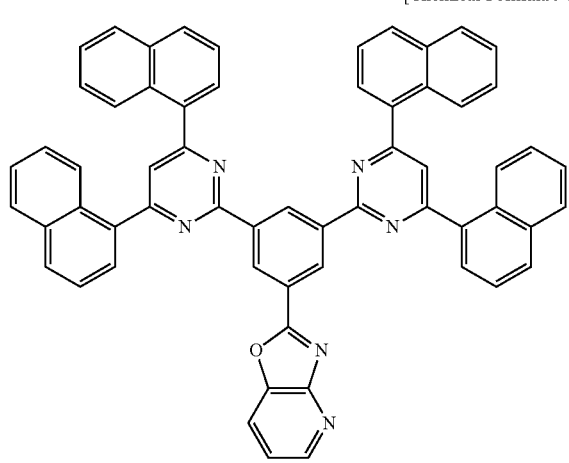
[Chemical Formula 95]
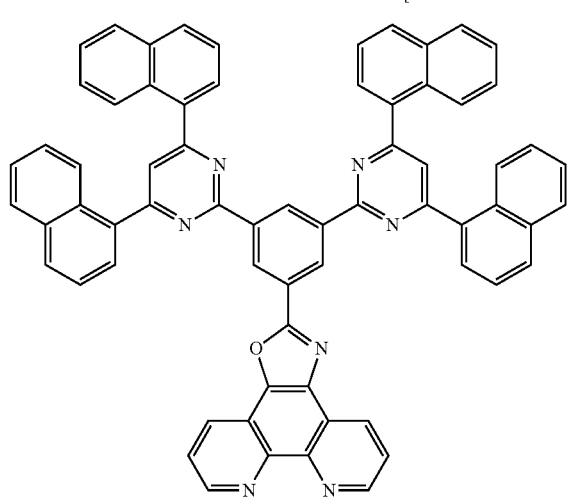
[Chemical Formula 96]
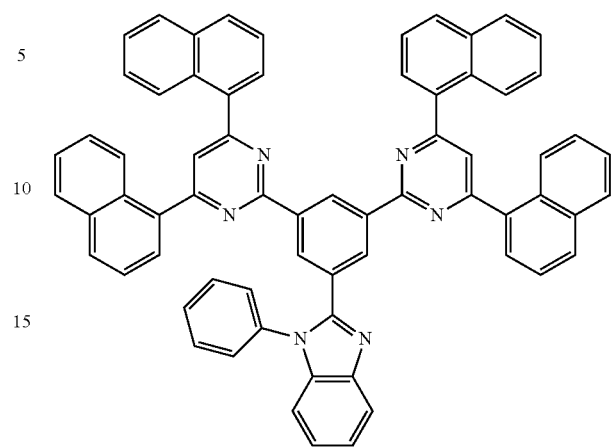
[Chemical Formula 97]
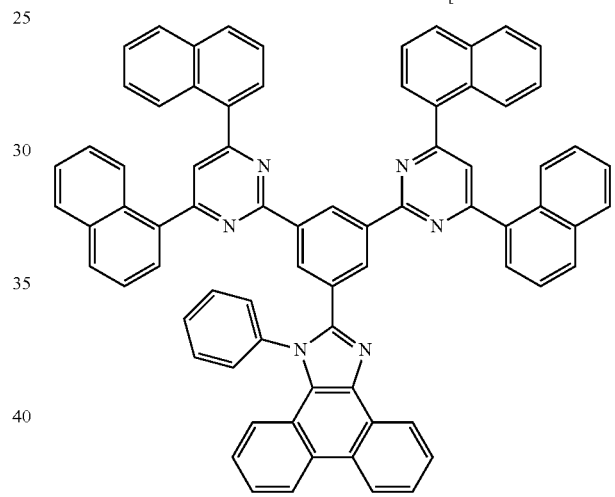
[Chemical Formula 98]
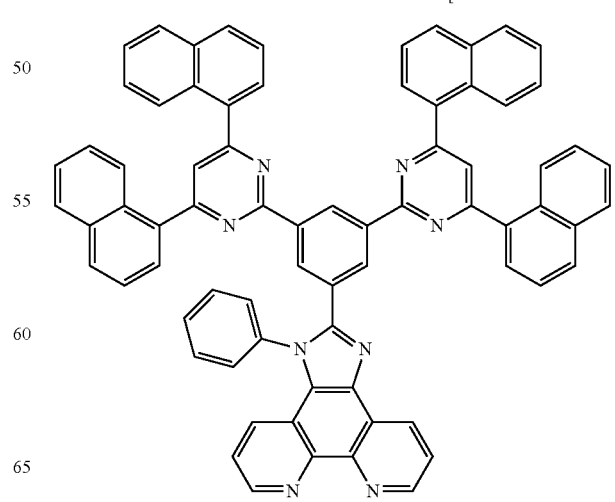

[Chemical Formula 99]
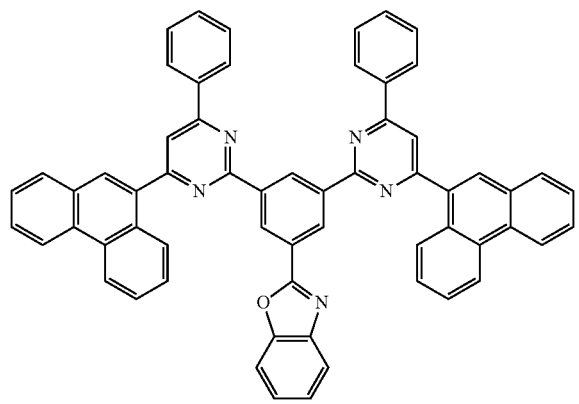
[Chemical Formula 102]
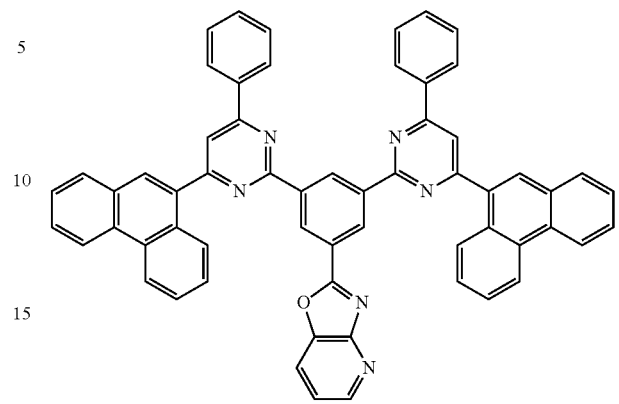
[Chemical Formula 100]
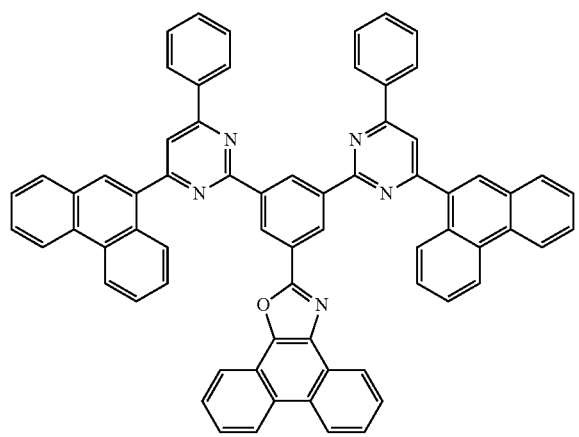
[Chemical Formula 103]
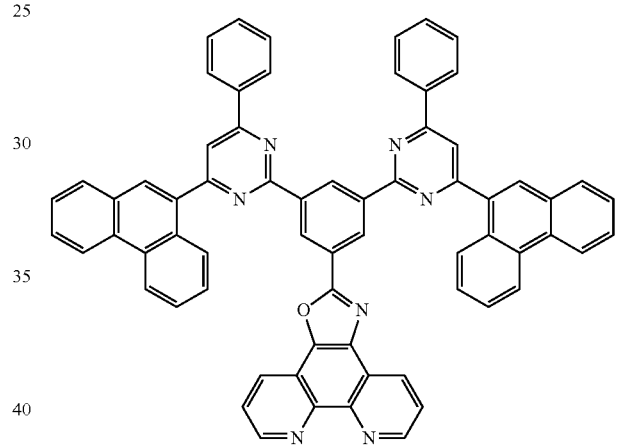
[Chemical Formula 101]
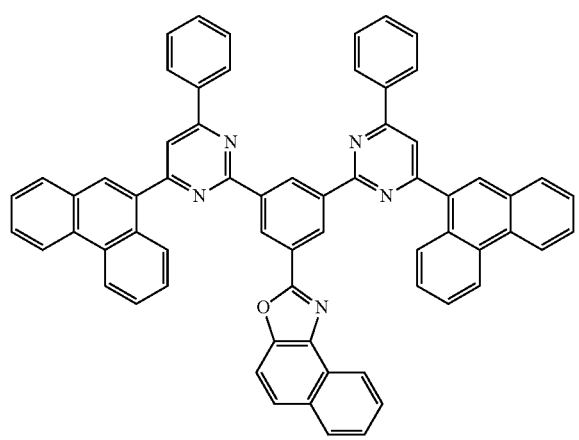
[Chemical Formula 104]
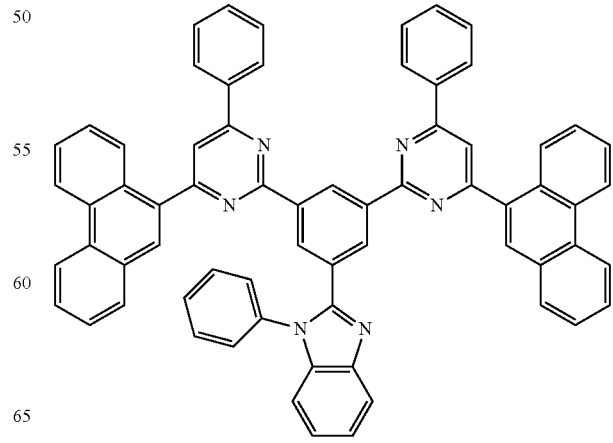

[Chemical Formula 105]
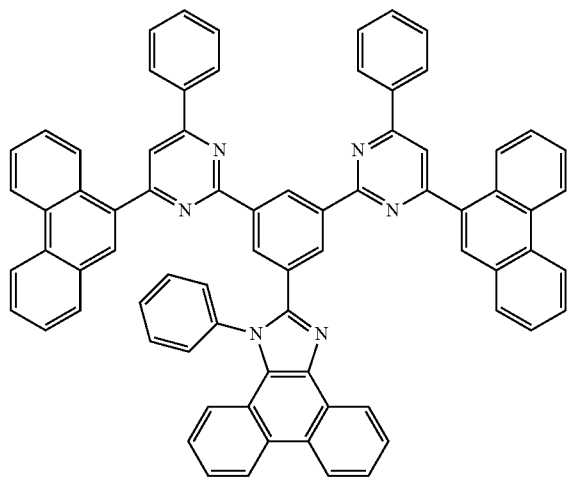
[Chemical Formula 106]
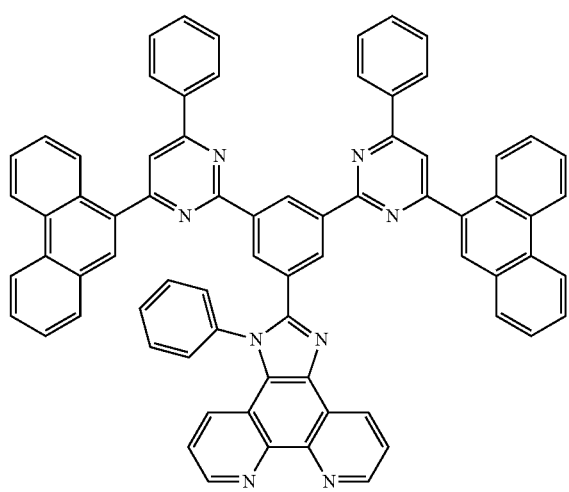
[Chemical Formula 107]
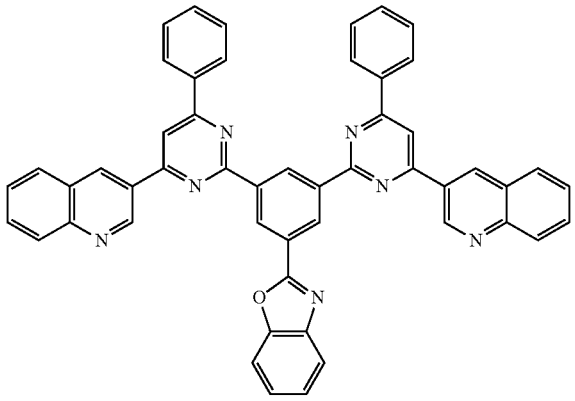
[Chemical Formula 108]
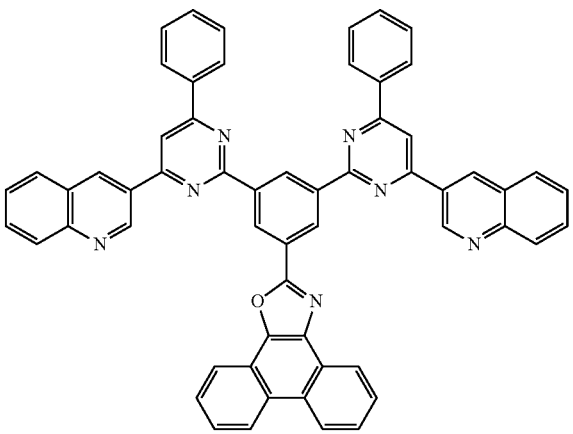
[Chemical Formula 109]
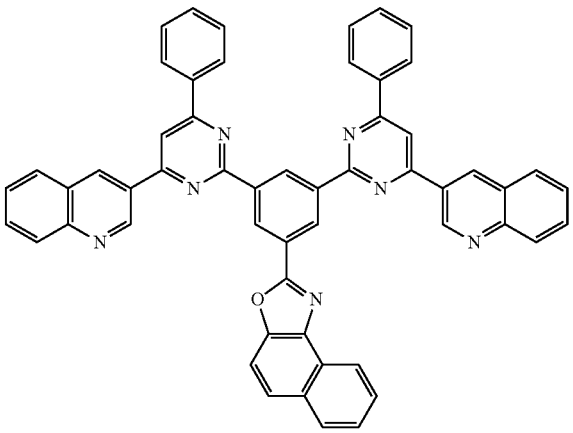
[Chemical Formula 110]
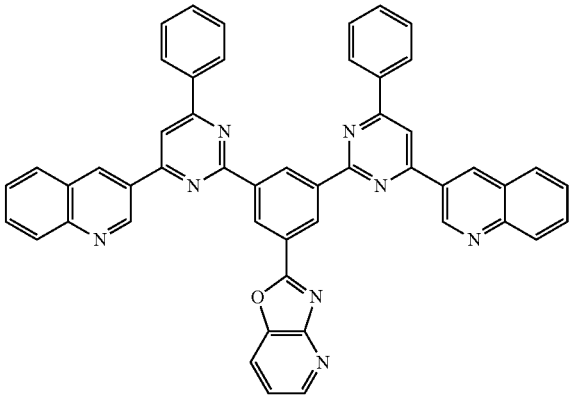

[Chemical Formula 111]
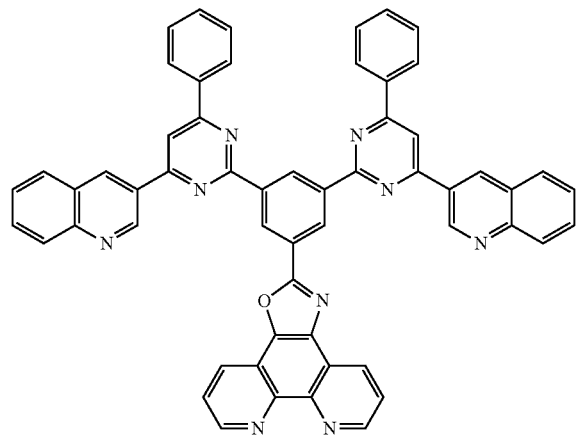
[Chemical Formula 112]
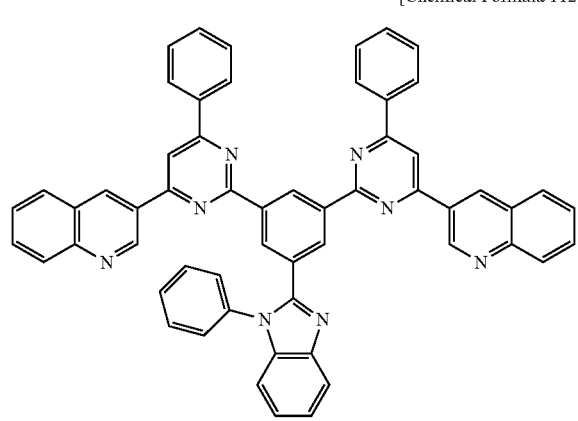
[Chemical Formula 113]
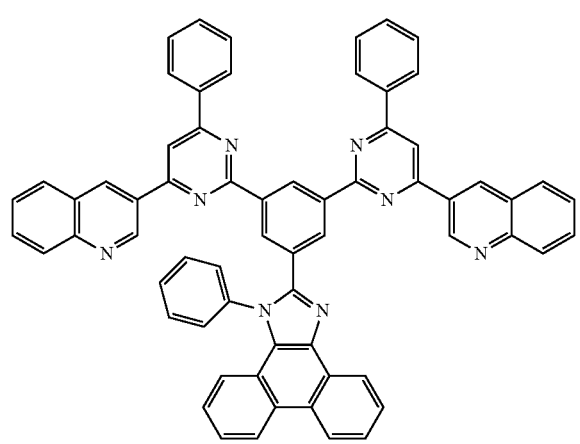
[Chemical Formula 114]
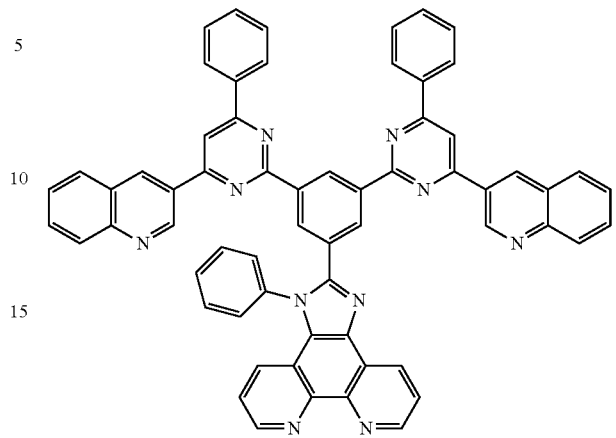
[Chemical Formula 115]
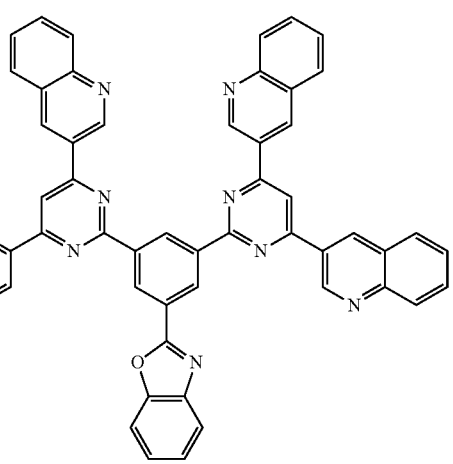
[Chemical Formula 116]
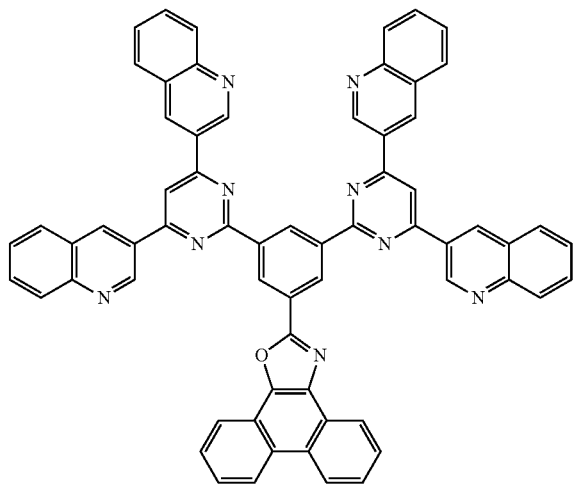

[Chemical Formula 117]
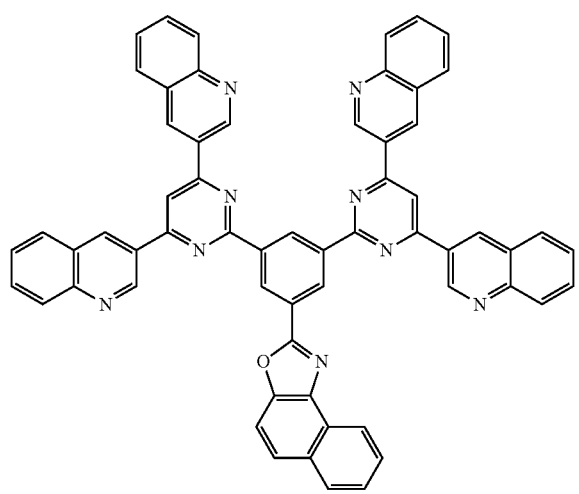
[Chemical Formula 118]
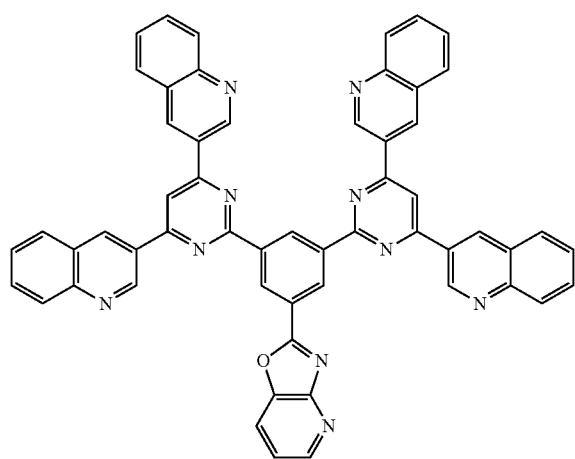
[Chemical Formula 119]
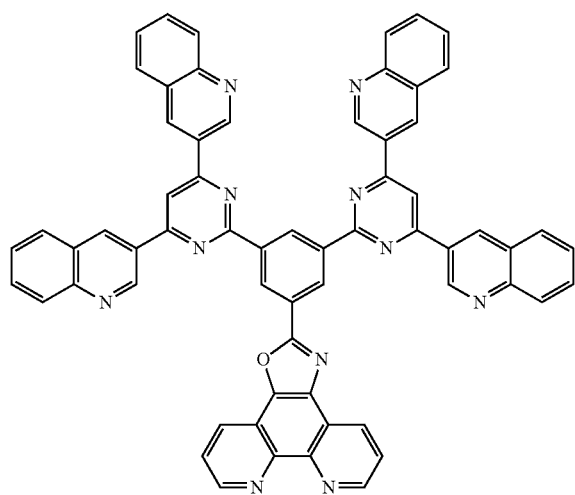
[Chemical Formula 120]
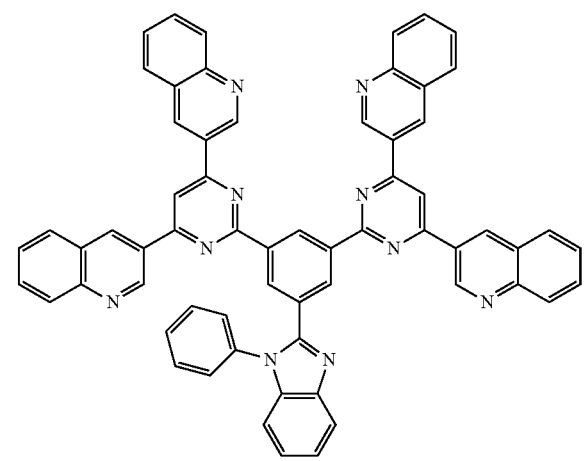
[Chemical Formula 121]
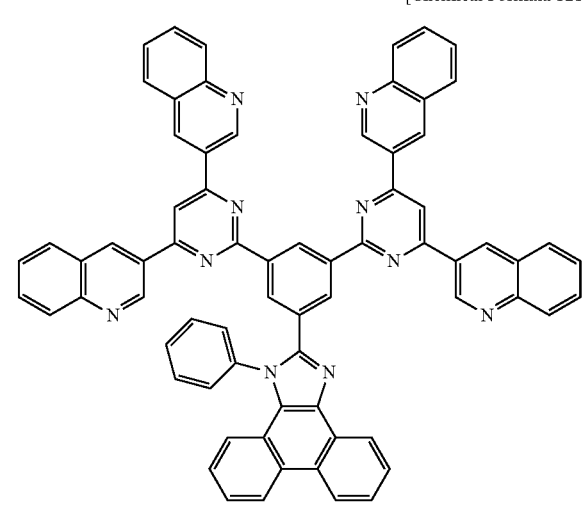
[Chemical Formula 122]
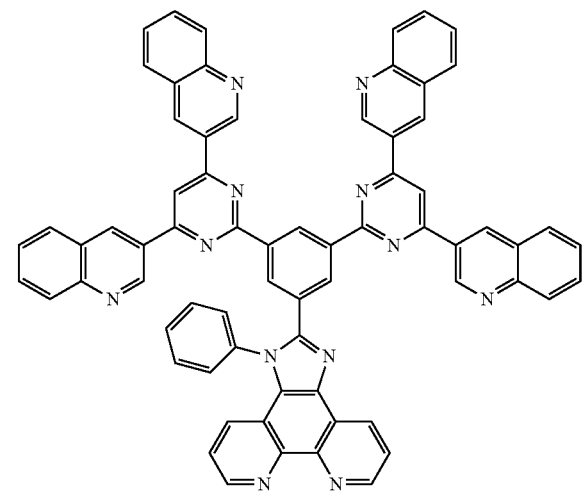

-continued
[Chemical Formula 123]
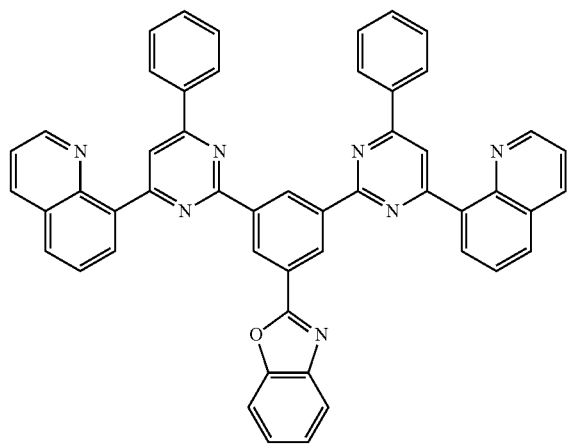
[Chemical Formula 124]
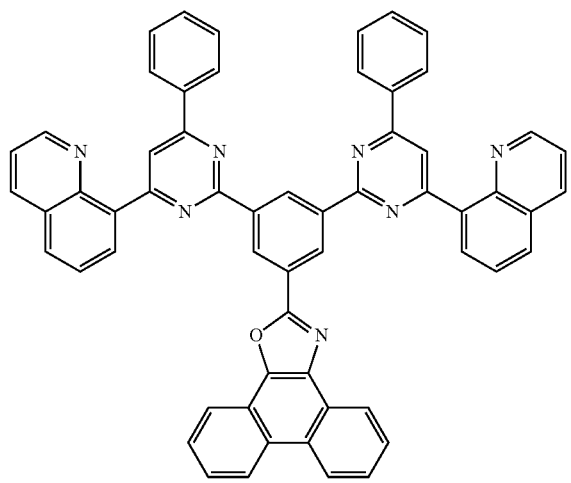
[Chemical Formula 125]
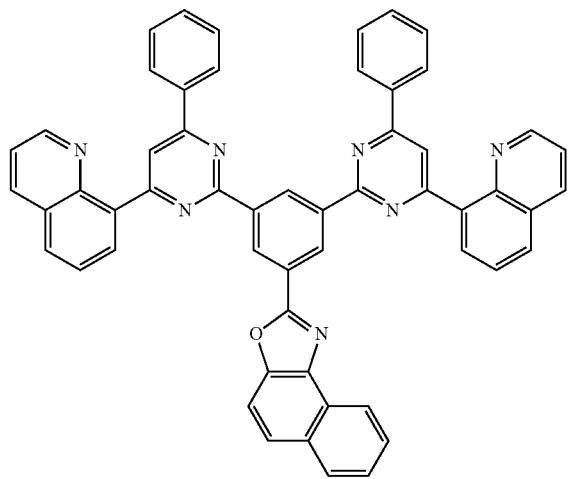
[Chemical Formula 126]
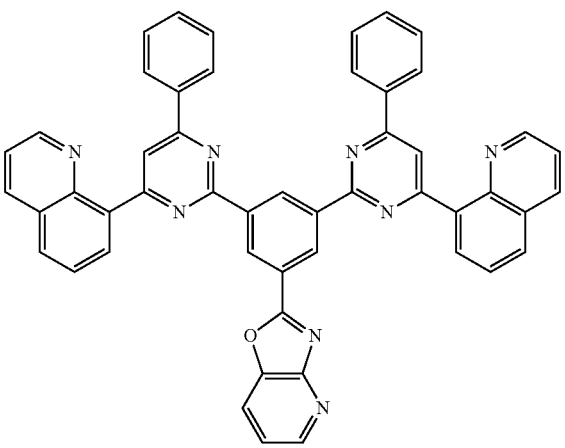
[Chemical Formula 127]
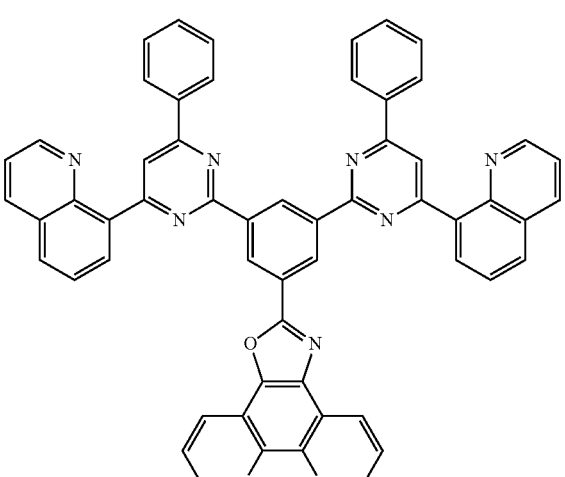
[Chemical Formula 128]
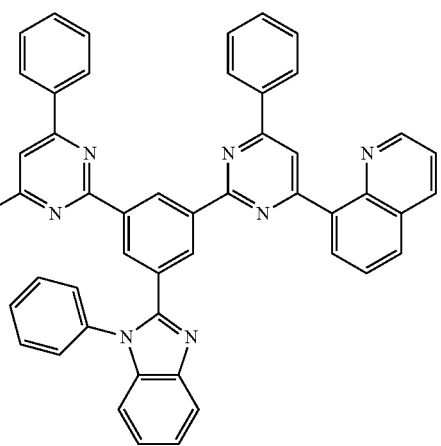

-continued
[Chemical Formula 129]
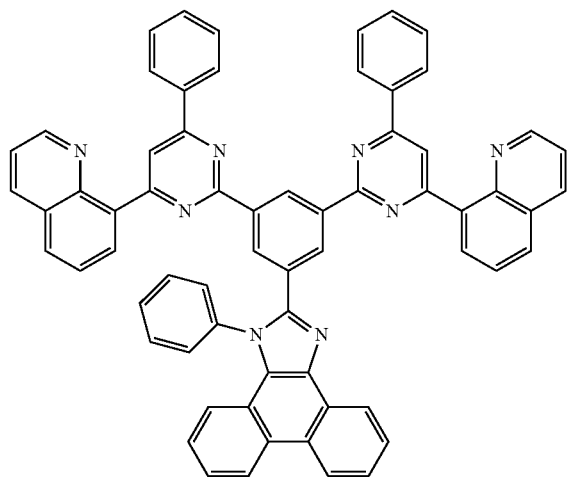
[Chemical Formula 130]
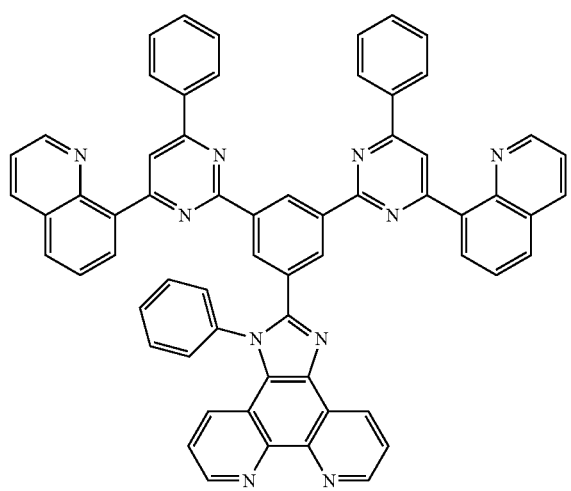
[Chemical Formula 131]
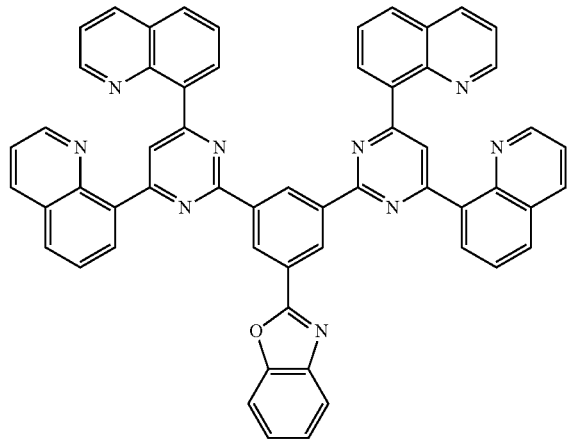
-continued
[Chemical Formula 132]
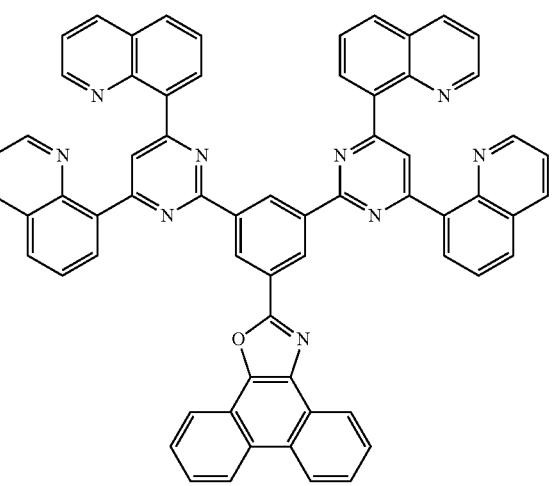
[Chemical Formula 133]
[Chemical Formula 134]
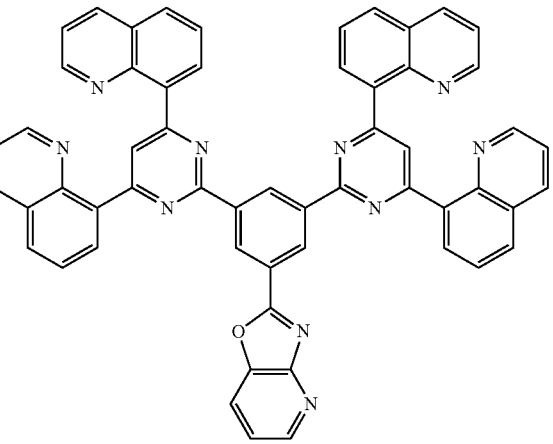

[Chemical Formula 135]
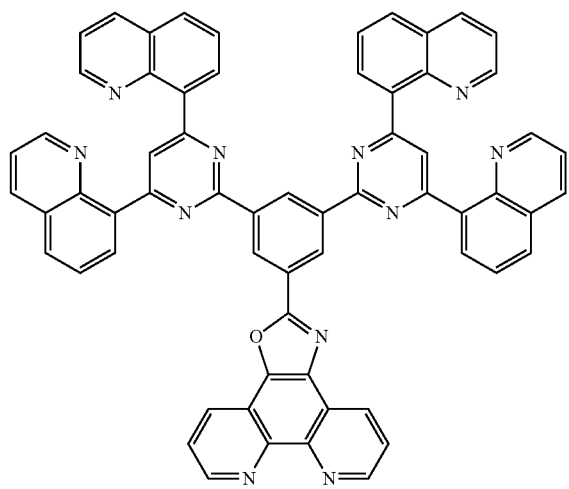
[Chemical Formula 138]
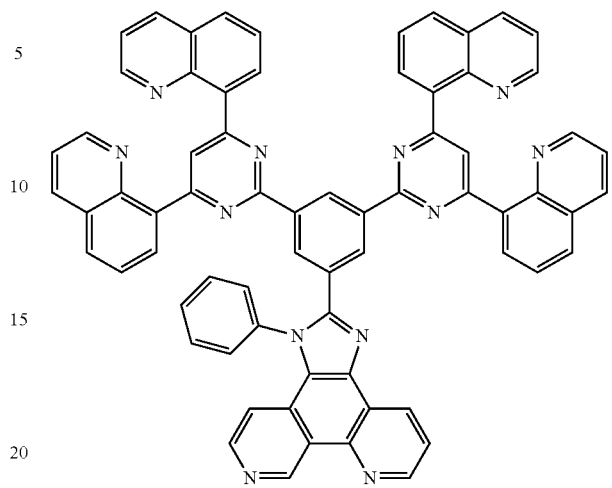
[Chemical Formula 136]
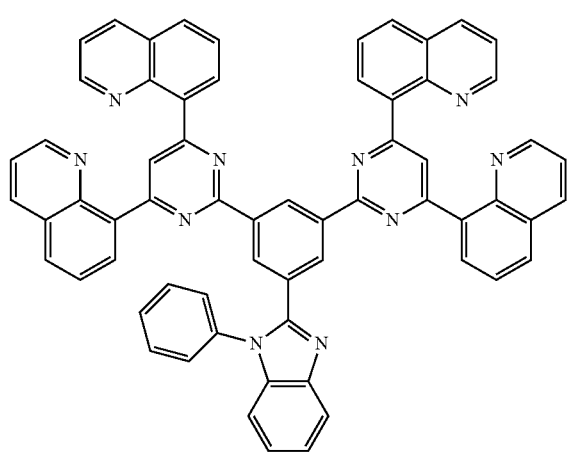
[Chemical Formula 139]
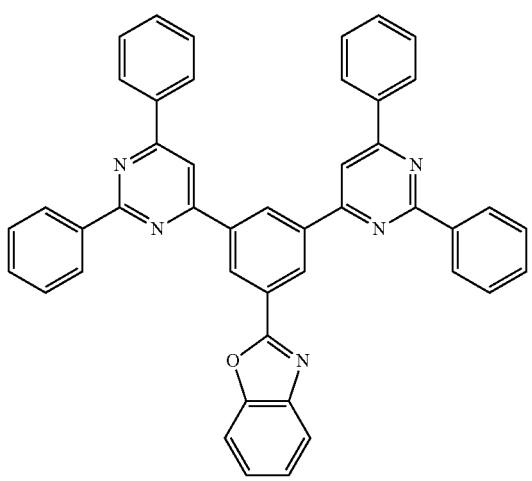
[Chemical Formula 137]
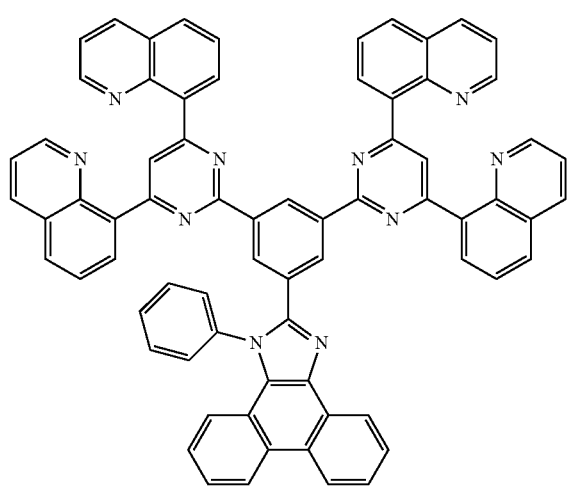
[Chemical Formula 140]
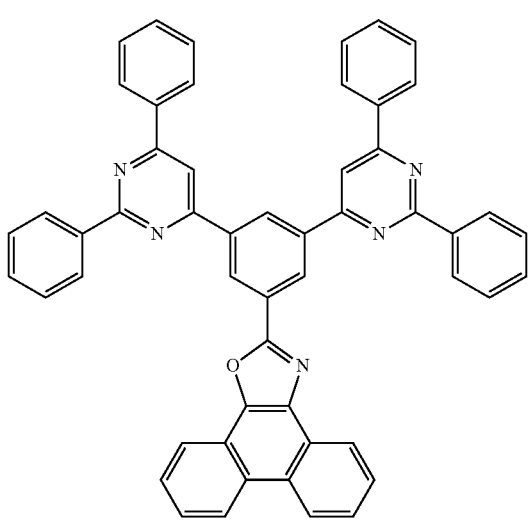

115
-continued
[Chemical Formula 141]
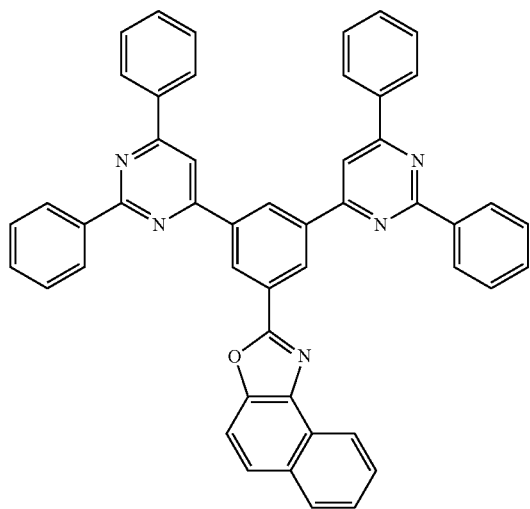
[Chemical Formula 142]
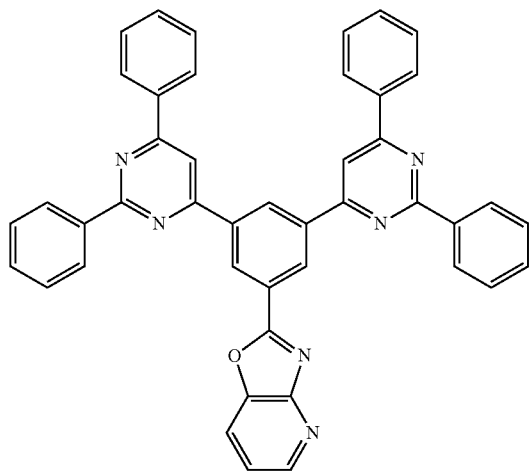
[Chemical Formula 143]
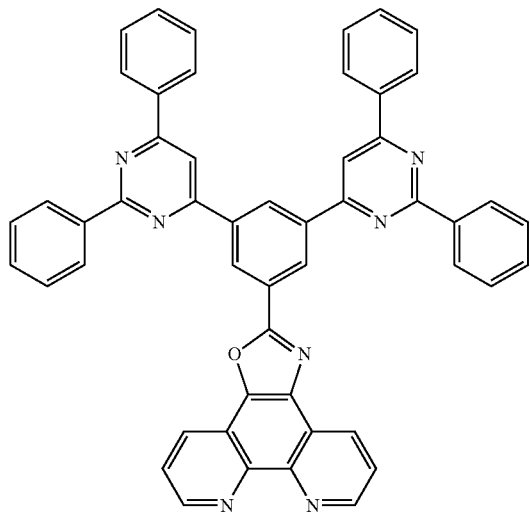
116
-continued
[Chemical Formula 144]
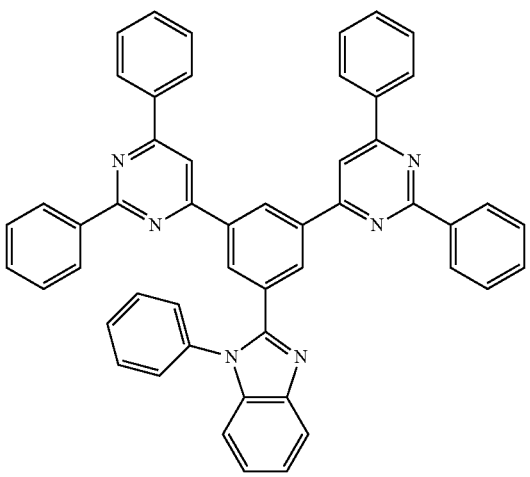
[Chemical Formula 145]
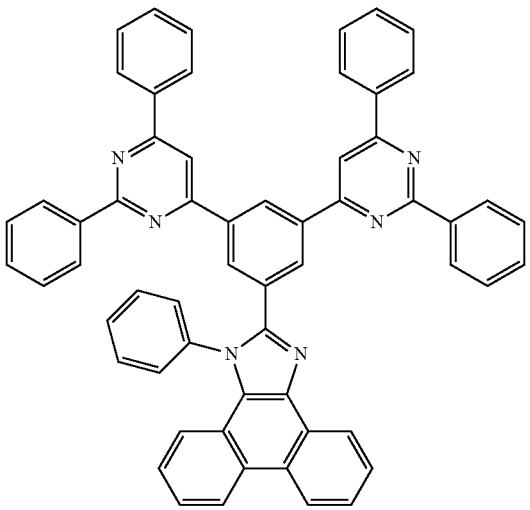
[Chemical Formula 146]
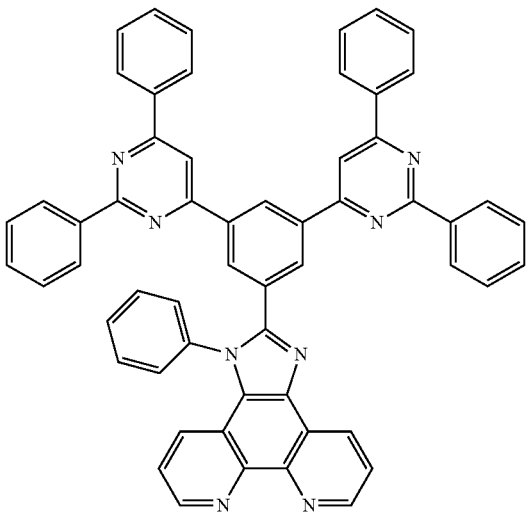

[Chemical Formula 147]
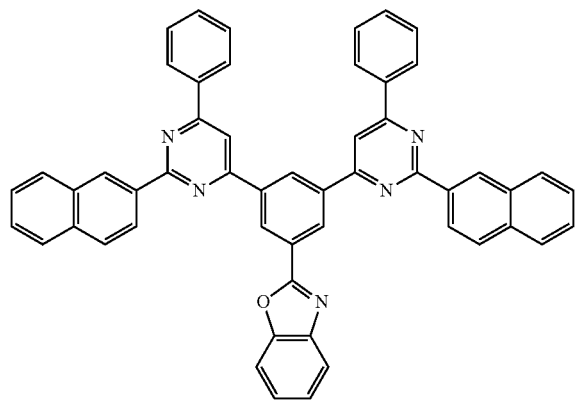
[Chemical Formula 150]
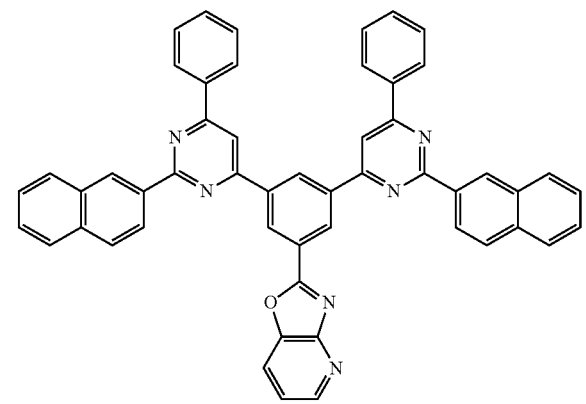
[Chemical Formula 148]
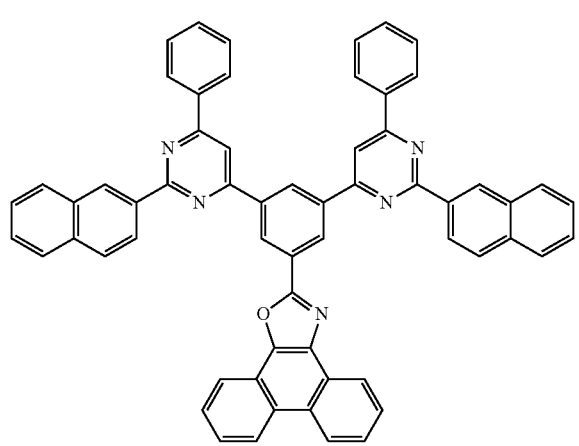
[Chemical Formula 151]
[Chemical Formula 149]
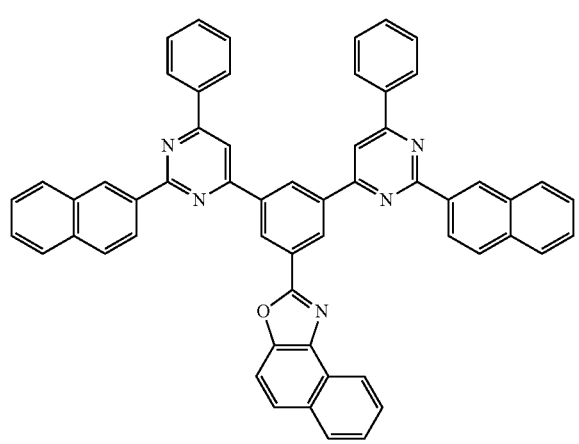
[Chemical Formula 152]
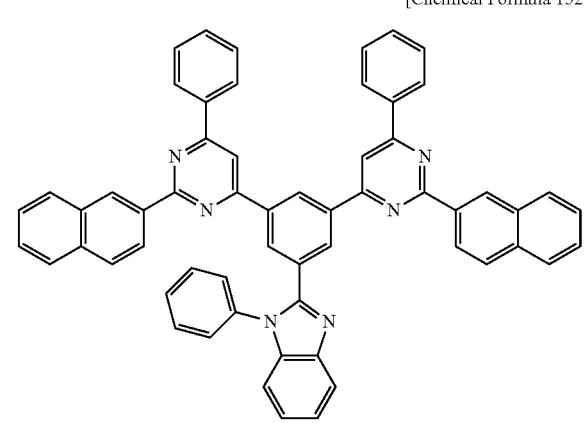

[Chemical Formula 153]
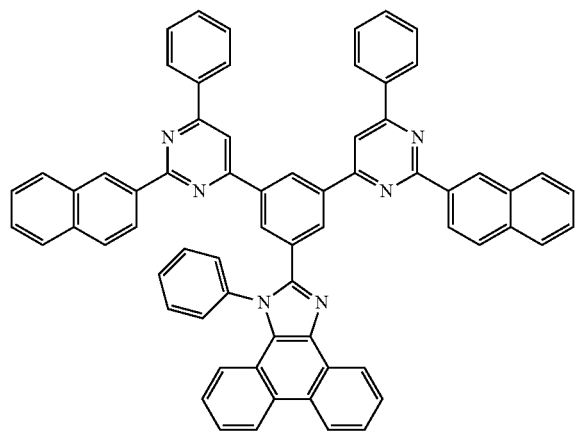
[Chemical Formula 154]
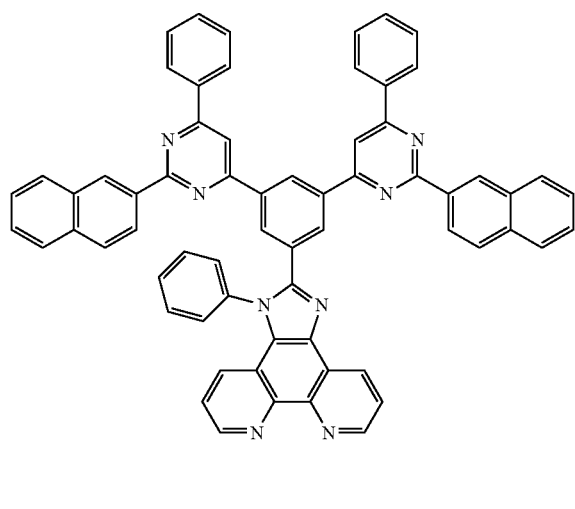
[Chemical Formula 155]
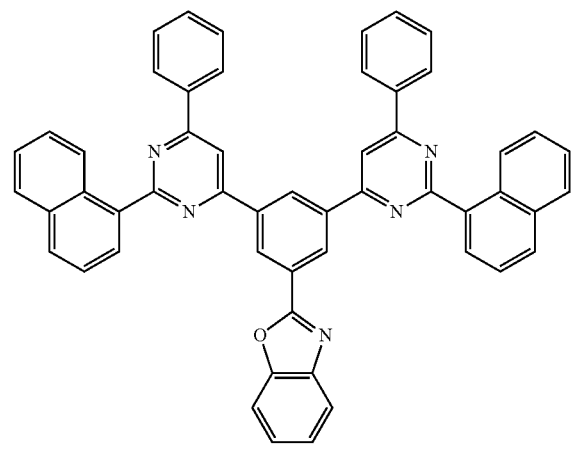
[Chemical Formula 156]
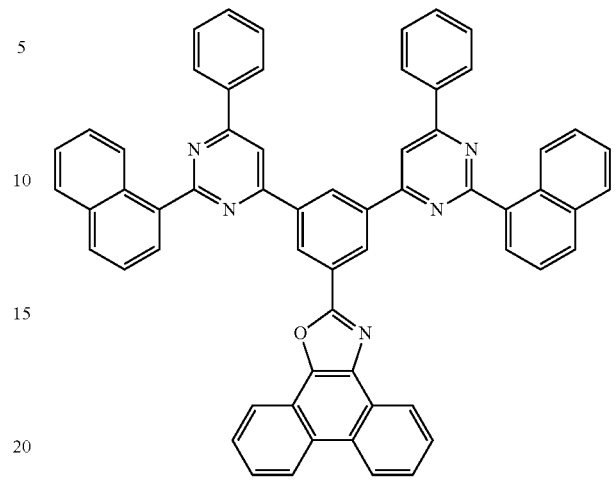
[Chemcial Formula 157]
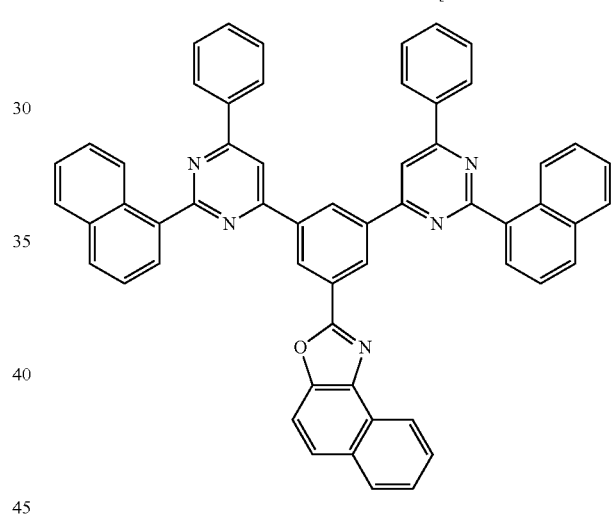
[Chemical Formula 158]
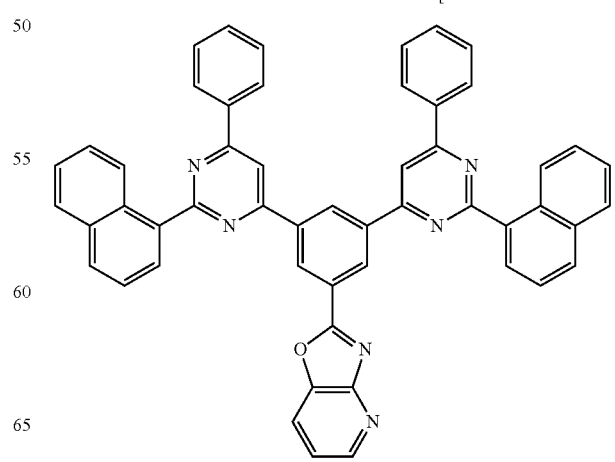

[Chemical Formula 159]
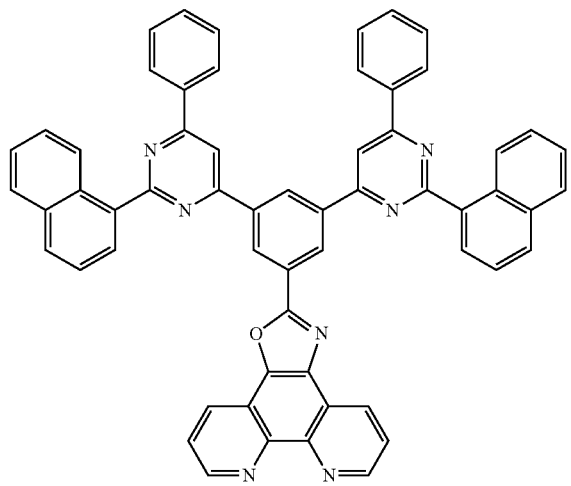
[Chemical Formula 160]
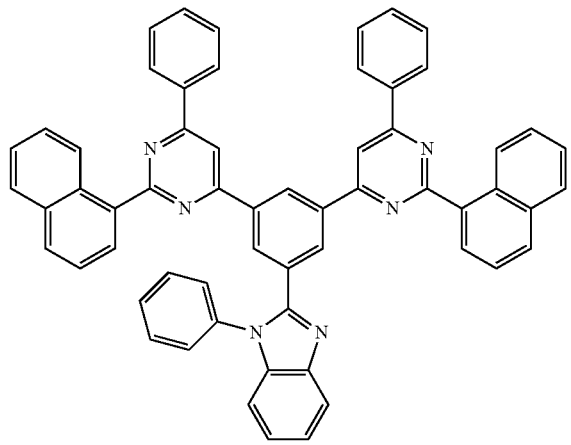
[Chemical Formula 161]
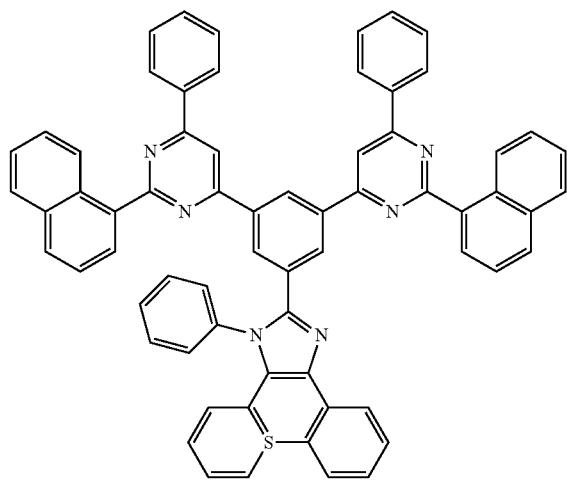
[Chemical Formula 162]
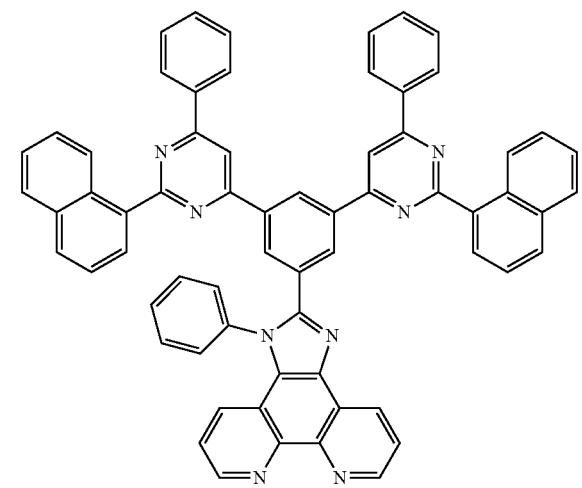
[Chemical Formula 163]
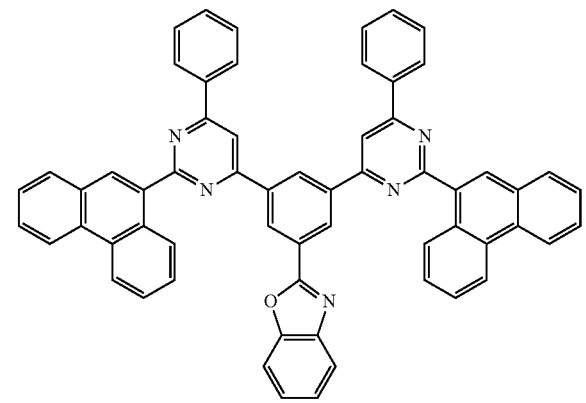
[Chemical Formula 164]
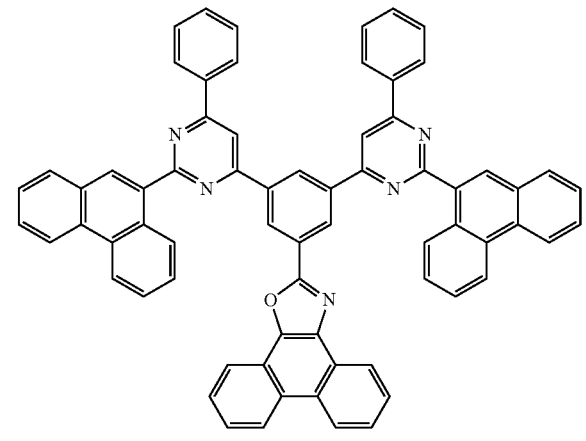

[Chemical Formula 165]
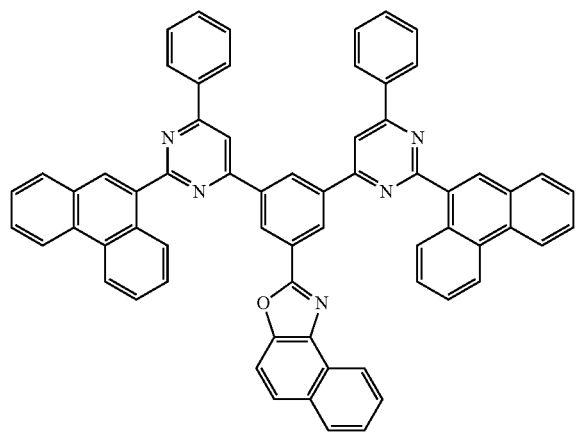
[Chemical Formula 166]
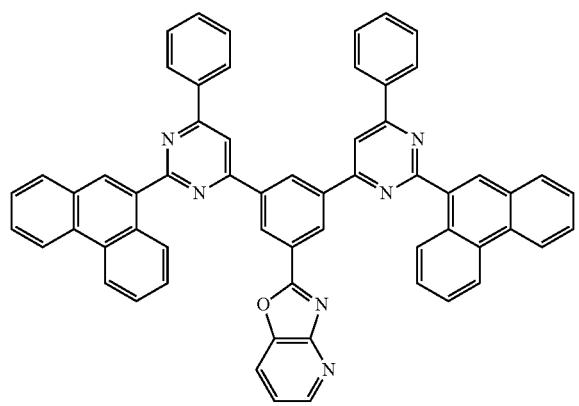
[Chemical Formula 167]
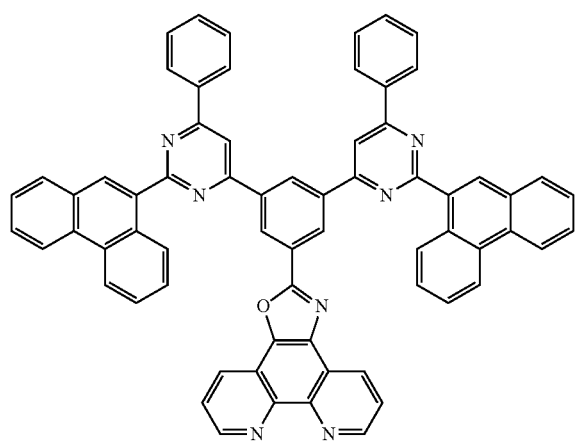
[Chemical Formula 168]
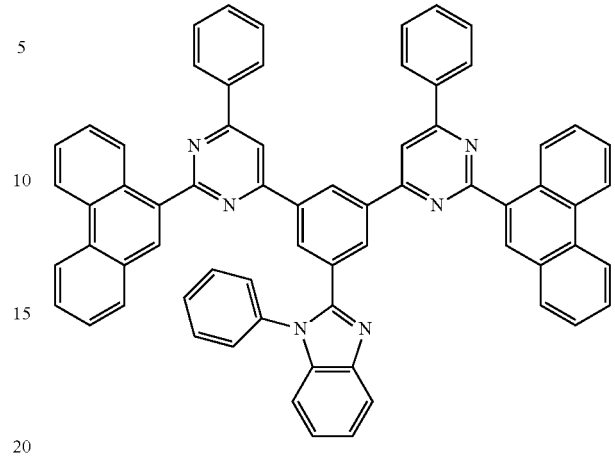
[Chemical Formula 169]
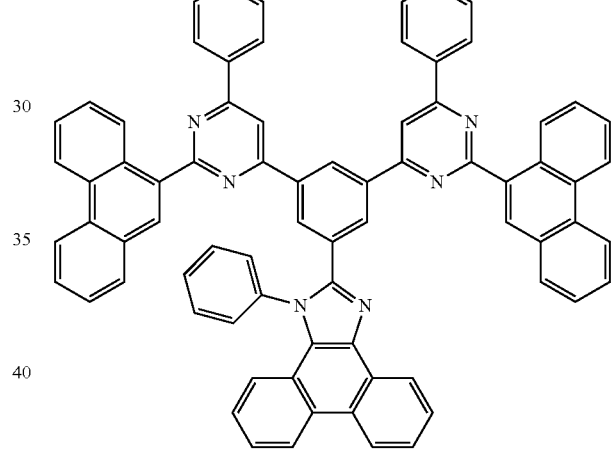
[Chemical Formula 170]
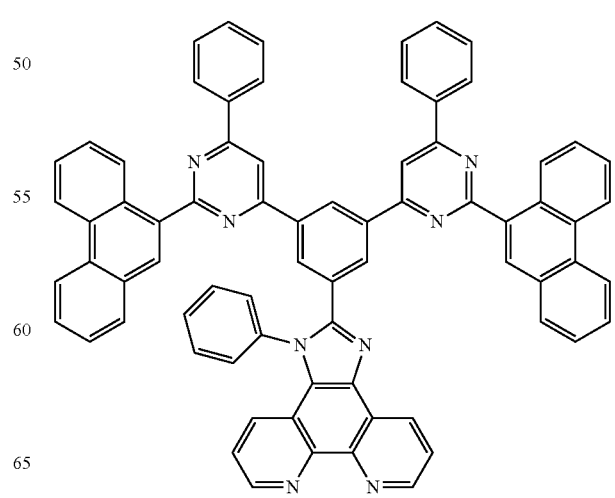

[Chemical Formula 171]
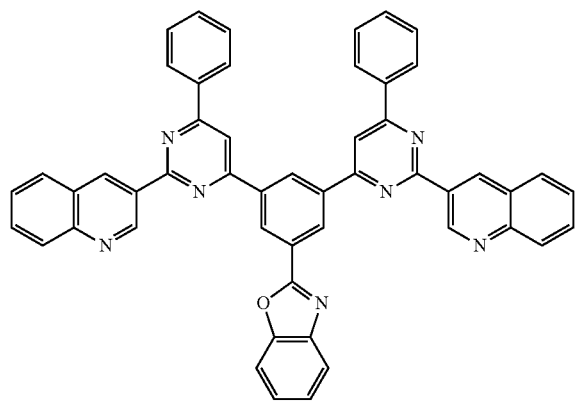
[Chemical Formula 172]
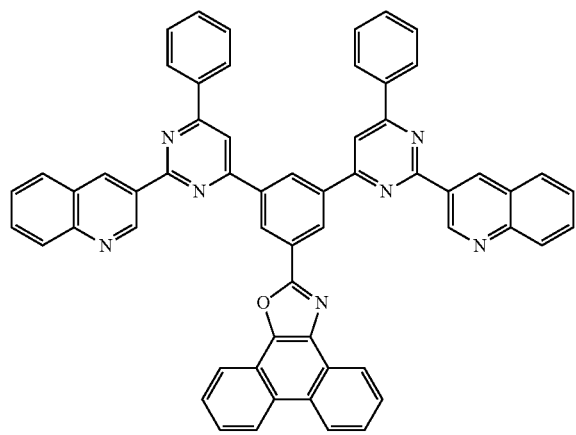
[Chemical Formula 173]
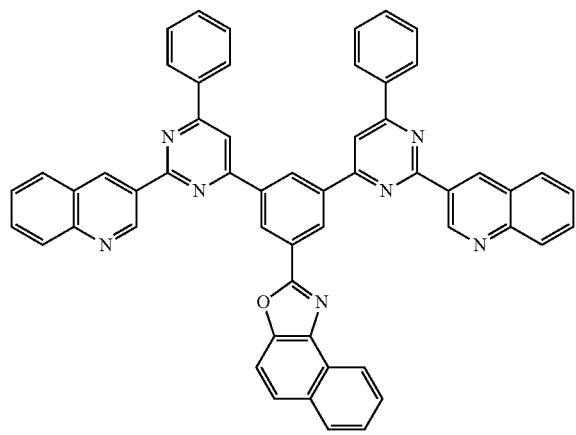
[Chemical Formula 174]
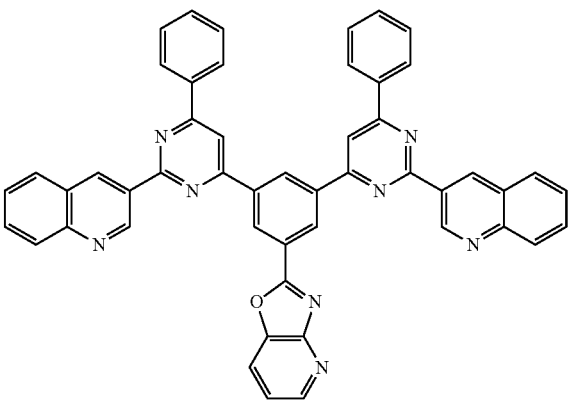
[Chemical Formula 175]
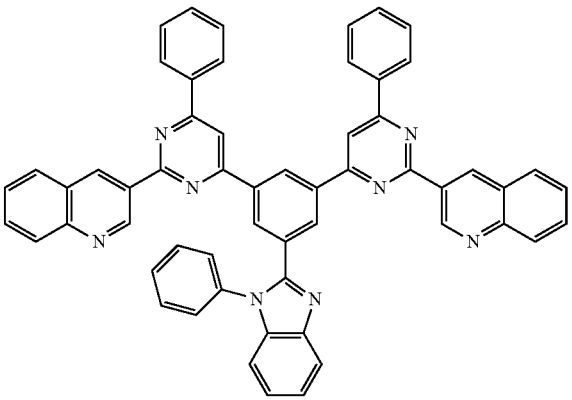
[Chemical Formula 176]

-continued
[Chemical Formula 177]
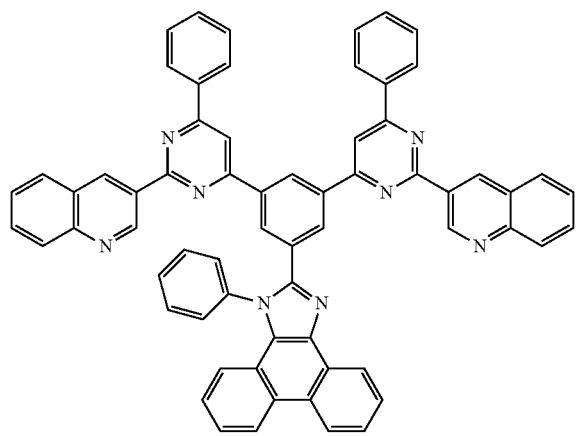
[Chemical Formula 178]
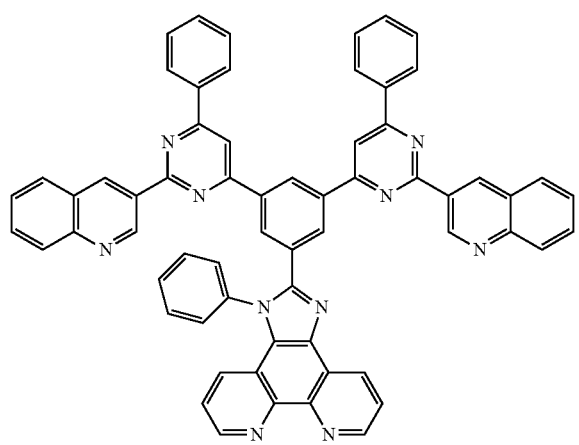
[Chemical Formula 179]
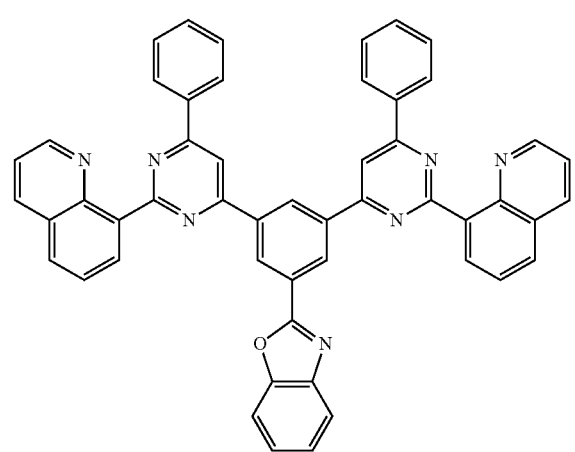
[Chemical Formula 180]
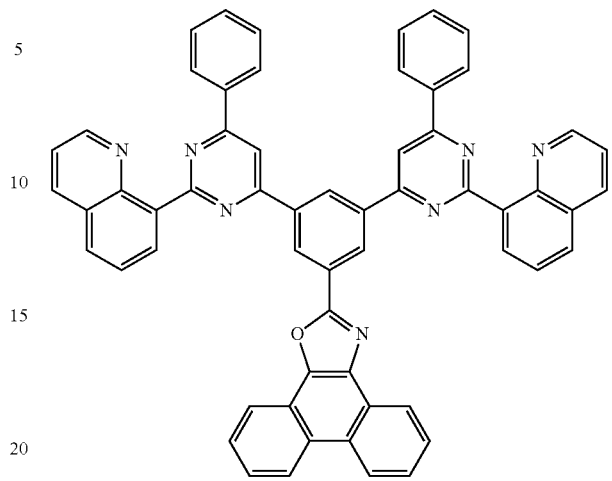
[Chemical Formula 181]
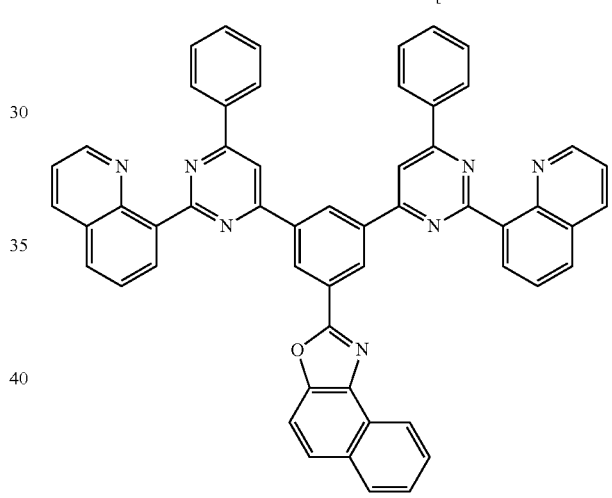
[Chemical Formula 182]
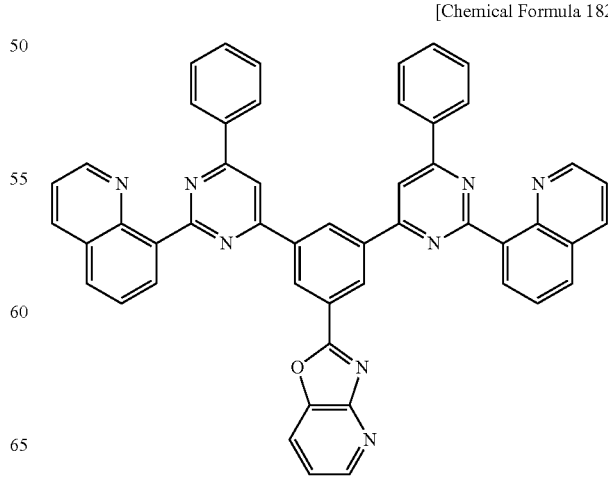

129
-continued

[Chemical Formula 183]

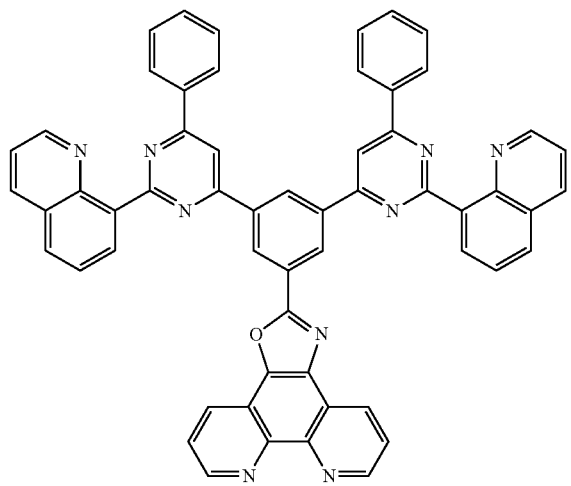

[Chemical Formula 184]

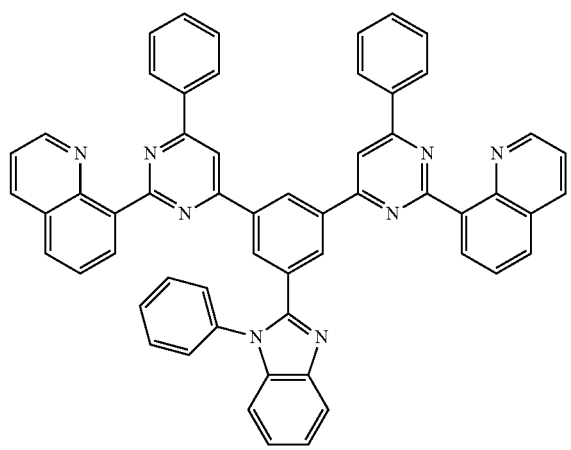

[Chemical Formula 185]

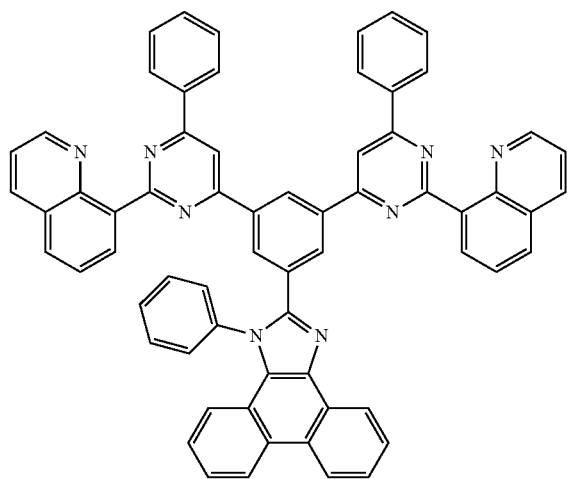

130
-continued

[Chemical Formula 186]

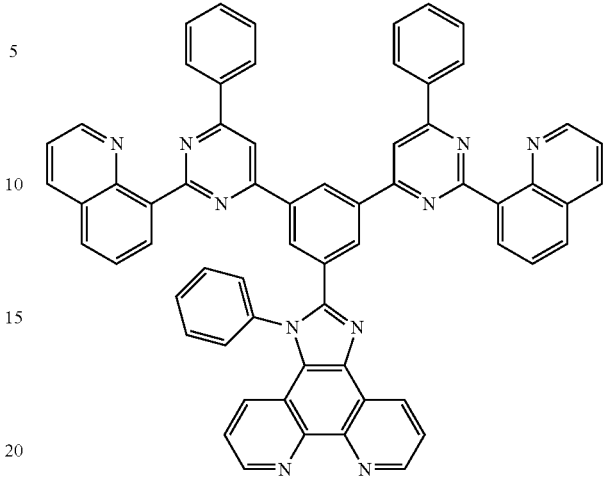

The compound for an organic photoelectric device according to an embodiment, e.g., represented by one of Chemical Formula 1 to 186 or Chemical Formula 3 to 186, may have a glass transition temperature of greater than or equal to about 120° C. and a thermal decomposition temperature of greater than or equal to about 400° C., indicating improved thermal stability. Accordingly, it is possible to produce an organic photoelectric device having a high efficiency.

The compound for an organic photoelectric device according to an embodiment may play a role in emitting light or injecting and/or transporting electrons, and may also act as a light emitting host with an appropriate dopant. For example, the compound for an organic photoelectric device may be used as a phosphorescent or fluorescent host material, a blue light emitting dopant material, or an electron transport material.

The compound for an organic photoelectric device according to an embodiment may be used for an organic thin layer. Thus, the compound may help improve the life-span characteristic, efficiency characteristic, electrochemical stability, and thermal stability of an organic photoelectric device and may help decrease the driving voltage thereof.

An embodiment provides an organic photoelectric device that includes the compound for an organic photoelectric device described above. The organic photoelectric device may include, e.g., an organic light emitting diode, an organic light emitting diode, an organic solar cell, an organic transistor, an organic photo conductor drum, an organic memory device, or the like. For example, the compound for an organic photoelectric device according to an embodiment may be included in an electrode or an electrode buffer layer in the organic solar cell to help improve the quantum efficiency, and may be used as an electrode material for a gate, a source-drain electrode, or the like in the organic transistor.

Hereinafter, an organic light emitting diode will be described in detail.

The embodiments provide an organic light emitting diode including an anode, a cathode, and at least one organic thin layer between the anode and the cathode. The at least one organic thin layer may include the compound for an organic photoelectric device.

The at least one organic thin layer may include a layer selected from the group of an emission layer, a hole transport layer (HTL), a hole injection layer (HIL), an electron transport layer (ETL), an electron injection layer (EIL), a hole blocking layer, and a combination thereof. The at least one organic thin layer may include the compound for an organic photoelectric device according to an embodiment. For example, the compound for an organic photoelectric device according to an embodiment may be included in an electron transport layer (ETL) or an electron injection layer (EIL). In an implementation, when the compound for an organic photoelectric device is included in the emission layer, the compound for an organic photoelectric device may be included as a phosphorescent or fluorescent host, e.g., as a fluorescent blue dopant material.

FIGS. 1 to 5 illustrate cross-sectional views showing organic photoelectric devices including the compound for an organic photoelectric device according to an embodiment.

Referring to FIGS. 1 to 5, organic photoelectric devices 100, 200, 300, 400, and 500 according to an embodiment may include at least one organic thin layer 105 interposed between an anode 120 and a cathode 110.

The anode 120 may include an anode material having a large work function to facilitate hole injection into an organic thin layer. The anode material may include a metal such as nickel, platinum, vanadium, chromium, copper, zinc, and gold, or alloys thereof; a metal oxide such as zinc oxide, indium oxide, indium tin oxide (ITO), and indium zinc oxide (IZO); a combined metal and oxide such as ZnO:Al or SnO$_2$:Sb; or a conductive polymer such as poly(3-methylthiophene), poly[3,4-(ethylene-1,2-dioxy)thiophene] (PEDT), polypyrrole, and polyaniline, but is not limited thereto. In an implementation, the anode 120 may include a transparent electrode including indium tin oxide (ITO).

The cathode 110 may include a cathode material having a small work function to facilitate electron injection into an organic thin layer. The cathode material may include a metal such as magnesium, calcium, sodium, potassium, titanium, indium, yttrium, lithium, gadolinium, aluminum, silver, tin, and lead, or alloys thereof; or a multi-layered material such as LiF/Al, Liq/Al, LiO$_2$/Al, LiF/Ca, LiF/Al, and BaF$_2$/Ca, but is not limited thereto. In an implementation, the cathode 110 may include a metal electrode including aluminum.

Referring to FIG. 1, the organic photoelectric device 100 may include an organic thin layer 105 including only an emission layer 130.

Figure 2:
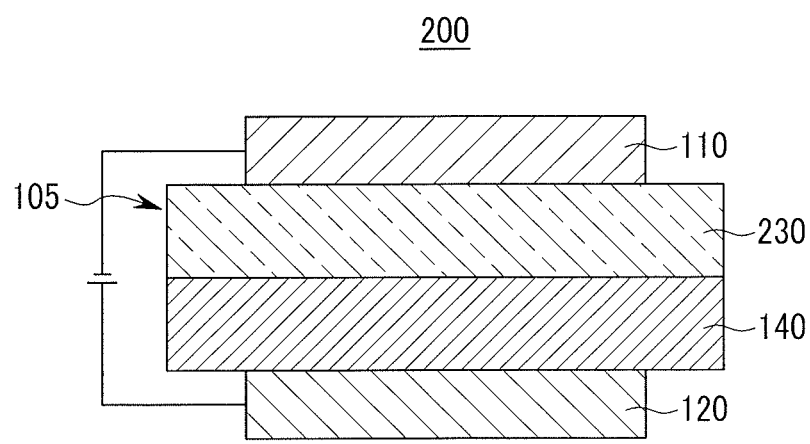

Referring to FIG. 2, a double-layered organic photoelectric device 200 may include an organic thin layer 105 including an emission layer 230 (including an electron transport layer (ETL)) and a hole transport layer (HTL) 140. As shown in FIG. 2, the organic thin layer 105 may include a double layer of the emission layer 230 and the hole transport layer (HTL) 140. The emission layer 130 may also function as an electron transport layer (ETL), and the hole transport layer (HTL) 140 layer may have an excellent binding property with a transparent electrode such as ITO or an excellent hole transport capability.

Figure 3:
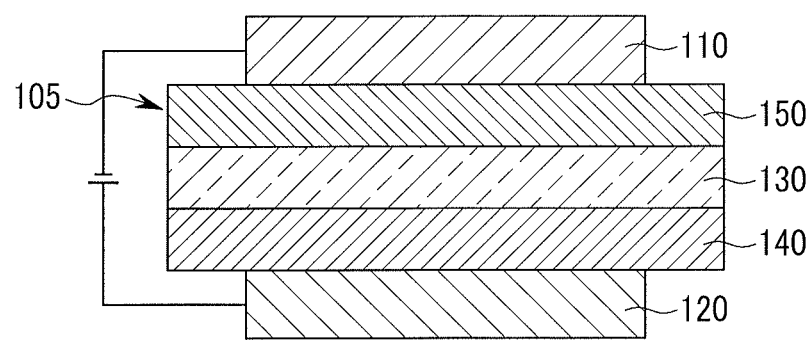

Referring to FIG. 3, a three-layered organic photoelectric device 300 may include an organic thin layer 105 including an electron transport layer (ETL) 150, an emission layer 130, and a hole transport layer (HTL) 140. The emission layer 130 may be independently installed, and layers having an excellent electron transport capability or an excellent hole transport capability may be separately stacked.

Figure 4:
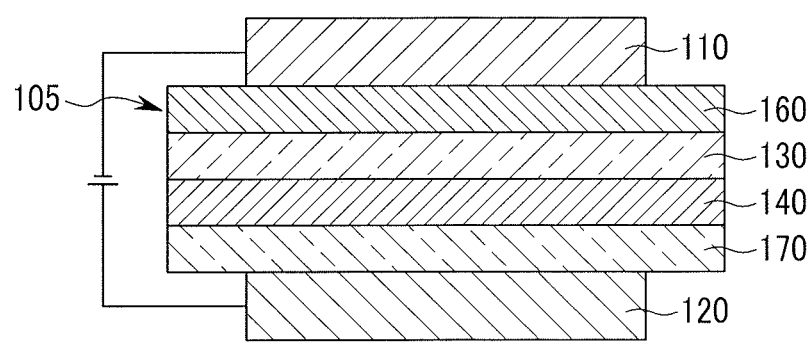

As shown in FIG. 4, a four-layered organic photoelectric device 400 may include an organic thin layer 105 including an electron injection layer (EIL) 160, an emission layer 130, a hole transport layer (HTL) 140, and a hole injection layer (HIL) 170 for adherence with the anode 120 formed of, e.g., ITO.

Figure 5:
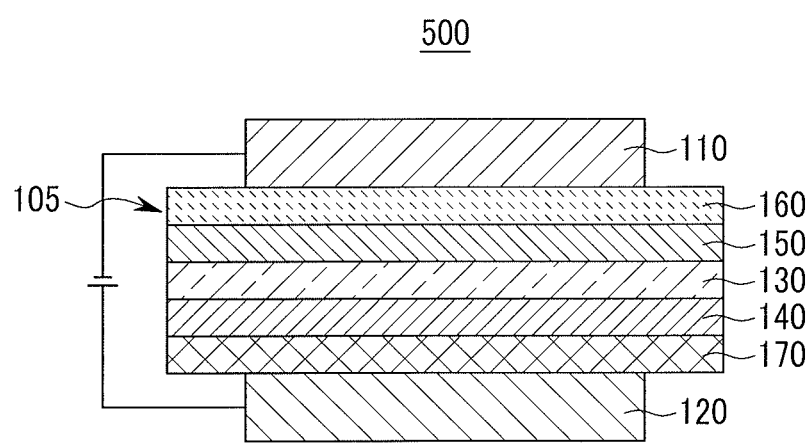

As shown in FIG. 5, a five layered organic photoelectric device 500 may include an organic thin layer 105 including an electron transport layer (ETL) 150, an emission layer 130, a hole transport layer (HTL) 140, and a hole injection layer (HIL) 170, and may further include an electron injection layer (EIL) 160 to achieve a low voltage.

In FIGS. 1 to 5, the organic thin layer 105 including at least one selected from the group of an electron transport layer (ETL) 150, an electron injection layer (EIL) 160, emission layers 130 and 230, a hole transport layer (HTL) 140, a hole injection layer (HIL) 170, and combinations thereof may include the compound for an organic photoelectric device according to an embodiment. The compound for an organic photoelectric device may be used for an electron transport layer (ETL) 150 or electron injection layer (EIL) 160. When the compound is used for the electron transport layer (ETL), it is possible to provide an organic photoelectric device having a simplified structure because an additional hole blocking layer (not shown) may be omitted.

Furthermore, when the compound for an organic photoelectric device is included in the emission layers 130 and 230, the material for the organic photoelectric device may be included as a phosphorescent or fluorescent host or a fluorescent blue dopant.

The organic light emitting diode may be fabricated by, e.g., forming an anode on a substrate; forming an organic thin layer in accordance with a dry coating method such as evaporation, sputtering, plasma plating, and ion plating or a wet coating method such as spin coating, dipping, and flow coating; and providing a cathode thereon.

Another embodiment provides a display device including the organic photoelectric device according to the above embodiment.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Preparation of Compound for Organic Photoelectric Device

EXAMPLE 1

Synthesis of Compound Represented by Chemical Formula 3

The compound represented by Chemical Formula 3 was synthesized according to the following Reaction Scheme 1.

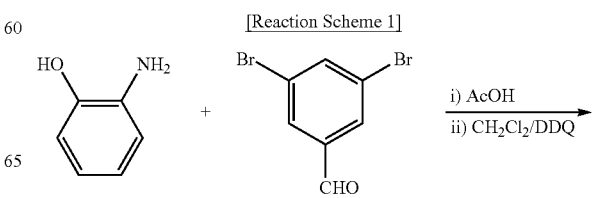

[Reaction Scheme 1]

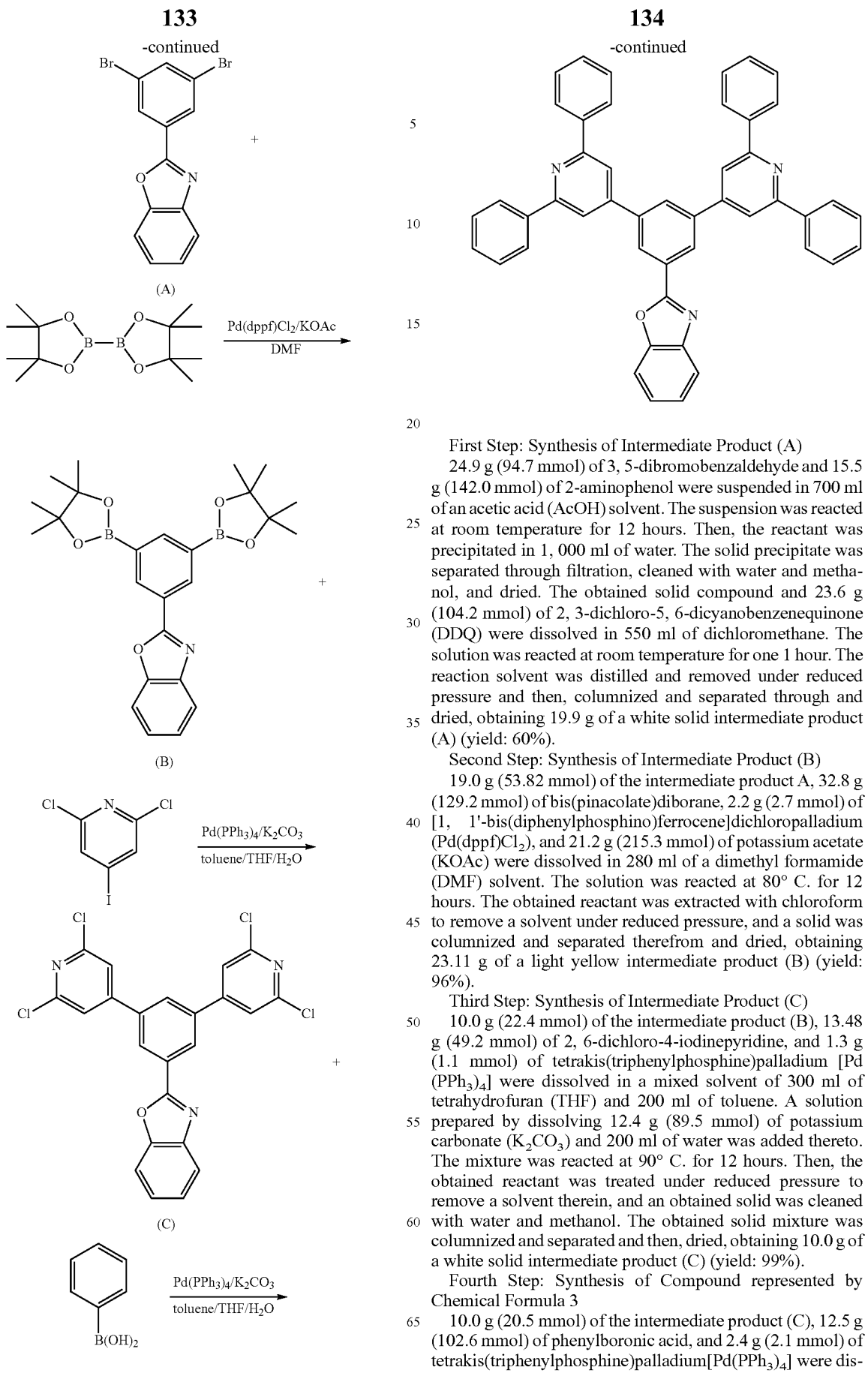

First Step: Synthesis of Intermediate Product (A)

24.9 g (94.7 mmol) of 3, 5-dibromobenzaldehyde and 15.5 g (142.0 mmol) of 2-aminophenol were suspended in 700 ml of an acetic acid (AcOH) solvent. The suspension was reacted at room temperature for 12 hours. Then, the reactant was precipitated in 1, 000 ml of water. The solid precipitate was separated through filtration, cleaned with water and methanol, and dried. The obtained solid compound and 23.6 g (104.2 mmol) of 2, 3-dichloro-5, 6-dicyanobenzenequinone (DDQ) were dissolved in 550 ml of dichloromethane. The solution was reacted at room temperature for one 1 hour. The reaction solvent was distilled and removed under reduced pressure and then, columnized and separated through and dried, obtaining 19.9 g of a white solid intermediate product (A) (yield: 60%).

Second Step: Synthesis of Intermediate Product (B)

19.0 g (53.82 mmol) of the intermediate product A, 32.8 g (129.2 mmol) of bis(pinacolate)diborane, 2.2 g (2.7 mmol) of [1, 1'-bis(diphenylphosphino)ferrocene]dichloropalladium (Pd(dppf)Cl$_2$), and 21.2 g (215.3 mmol) of potassium acetate (KOAc) were dissolved in 280 ml of a dimethyl formamide (DMF) solvent. The solution was reacted at 80° C. for 12 hours. The obtained reactant was extracted with chloroform to remove a solvent under reduced pressure, and a solid was columnized and separated therefrom and dried, obtaining 23.11 g of a light yellow intermediate product (B) (yield: 96%).

Third Step: Synthesis of Intermediate Product (C)

10.0 g (22.4 mmol) of the intermediate product (B), 13.48 g (49.2 mmol) of 2, 6-dichloro-4-iodinepyridine, and 1.3 g (1.1 mmol) of tetrakis(triphenylphosphine)palladium [Pd(PPh$_3$)$_4$] were dissolved in a mixed solvent of 300 ml of tetrahydrofuran (THF) and 200 ml of toluene. A solution prepared by dissolving 12.4 g (89.5 mmol) of potassium carbonate (K$_2$CO$_3$) and 200 ml of water was added thereto. The mixture was reacted at 90° C. for 12 hours. Then, the obtained reactant was treated under reduced pressure to remove a solvent therein, and an obtained solid was cleaned with water and methanol. The obtained solid mixture was columnized and separated and then, dried, obtaining 10.0 g of a white solid intermediate product (C) (yield: 99%).

Fourth Step: Synthesis of Compound represented by Chemical Formula 3

10.0 g (20.5 mmol) of the intermediate product (C), 12.5 g (102.6 mmol) of phenylboronic acid, and 2.4 g (2.1 mmol) of tetrakis(triphenylphosphine)palladium[Pd(PPh$_3$)$_4$] were dissolved in a mixed solvent of 300 ml of tetrahydrofuran (THF) and 200 ml of toluene. A solution prepared by dissolving 17.0 g (123.2 mmol) of potassium carbonate ($K_2CO_3$) in 200 ml of water was added thereto. The solution mixture was reacted at 100° C. 12 hours. The obtained reactant was treated under reduced pressure to remove a solvent therein, and a solid obtained therefrom was cleaned with water and methanol. The obtained solid mixture was columnized and separated and then, dried, obtaining 10.8 g of a white solid compound represented by Chemical Formula 3 (yield: 81%). (calculation value: 653.77/measurement value: MS[M+1] 654.25)

EXAMPLE 2

Synthesis of Compound Represented by Chemical Formula 4

The compound represented by Chemical Formula 4 was synthesized according to the following Reaction Scheme 2.

[Reaction Scheme 2]

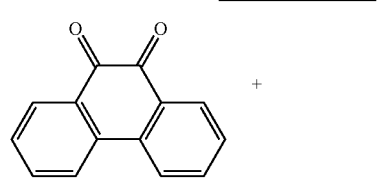

+

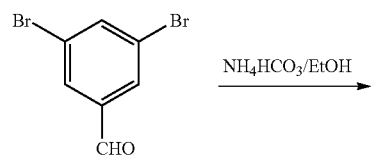

(D)

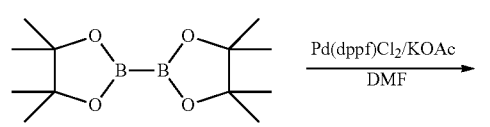

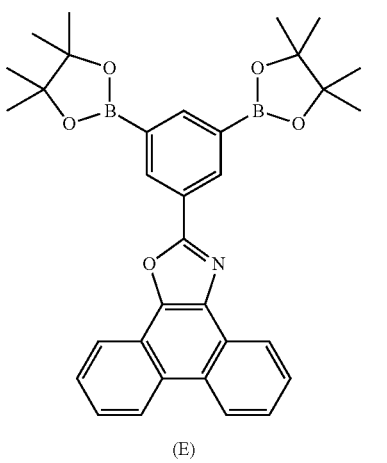

(E)

+

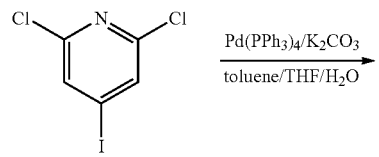

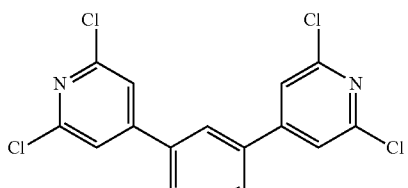

+

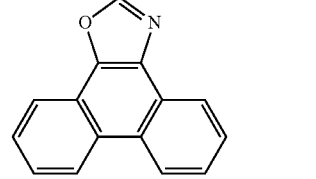

(F)

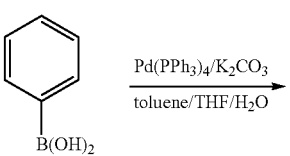

-continued

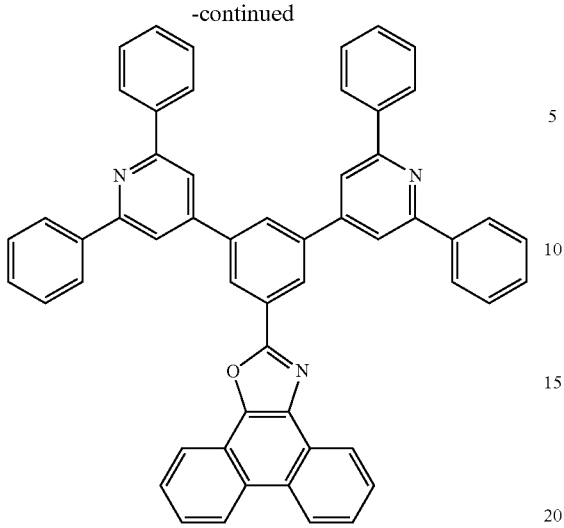

First Step; Synthesis of Intermediate Product (D)

13.0 g (62.4 mmol) of 9, 10-phenanthrenequinone, 24.7 g (93.7 mmol) of 3, 5-dibromobenzaldehyde, and 24.7 g (312.2 mmol) of ammonium bicarbonate ($NH_4HCO_3$) were dissolved in 700 ml of ethanol. The solution was reacted at 100° C. for 12 hours. The obtained reactant was filtered, separated, cleaned with ethanol, and dried, obtaining 89.4 g of a light yellow intermediate product (D) (yield: 73%).

Second Step: Synthesis of Intermediate Product (E)

20.0 g (44.4 mmol) of the intermediate product (D), 26.9 g (105.9 mmol) of bis(pinacolate)diborane, 1.8 g (2.2 mmol) of [1, 1'-bis(diphenylphosphino)ferrocene]dichloropalladium (Pd(dppf)$Cl_2$), and 17.3 g (215.3 mmol) of potassium acetate (KOAc) were dissolved in 300 ml of a dimethyl formamide (DMF) solvent. The solution was reacted at 80° C. for 12 hours. The obtained reactant was extracted with chloroform and treated under reduced pressure to remove a solvent therein, and an obtained extract was columnized and separated and then dried, obtaining 22.65 g of a white solid intermediate product (E) (yield: 94%).

Third Step: Synthesis of Intermediate Product (F)

10.0 g (18.3 mmol) of the intermediate product (E), 11.0 g (40.2 mmol) of 2, 6-dichloro-4-iodinepyridine, and 1.1 g (0.9 mmol) of tetrakis(triphenylphosphine)palladium [Pd(PPh3)4] were dissolved in a mixed solvent of 300 ml of tetrahydrofuran (THF) and 200 ml of toluene. A solution prepared by dissolving 10.1 g (73.1 mmol) of potassium carbonate ($K_2CO_3$) in 200 ml of water. The mixture was reacted at 90° C. for 12 hours. The obtained reactant was treated under reduced pressure to remove a solvent therein and then cleaned with water and methanol. The obtained solid mixture was columnized and separated and then, dried, obtaining 10.3 g of a white solid intermediate product (F) (yield: 96%).

Fourth Step: Synthesis of Compound Represented by Chemical Formula 4

10.0 g (17.0 mmol) of the intermediate product (F), 10.4 g (85.1 mmol) of phenylboronic acid, and 2.0 g (1.7 mmol) of tetrakis(triphenylphosphine)palladium[Pd(PPh$_3$)$_4$] were dissolved in a mixed solvent of 300 ml of tetrahydrofuran (THF) and 200 ml of toluene. A solution prepared by dissolving 14.1 g (102.2 mmol) of potassium carbonate ($K_2CO_3$) was added thereto. The mixture was reacted at 100° C. for 12 hours. The obtained reactant was treated under reduced pressure to remove a solvent therein and cleaned with water and methanol. The obtained solid mixture was columnized and separated and then, dried, obtaining 9.8 g of a white solid compound represented by Chemical Formula 4 (yield: 98%). (calculation value: 753.89/measurement value: MS[M+1] 754.28)

EXAMPLE 3

Synthesis of Compound Represented by Chemical Formula 11

The compound represented by Chemical Formula 11 was synthesized according to the following Reaction Scheme 3.

[Reaction Scheme 3]

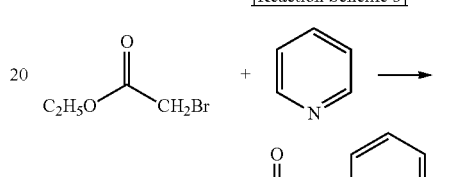

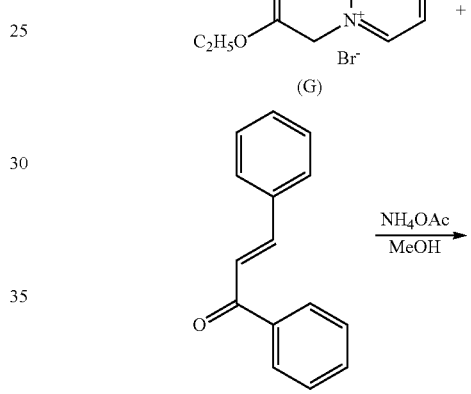

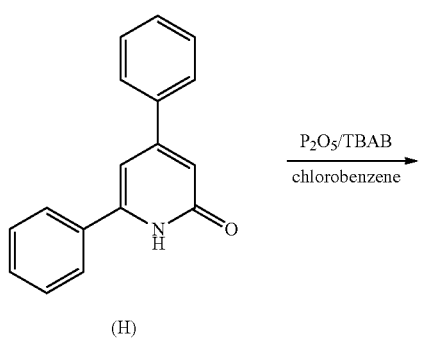

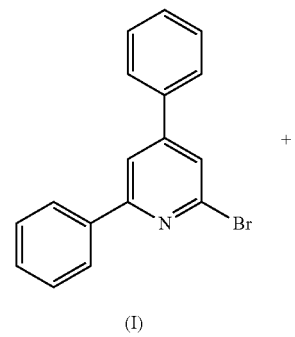

-continued

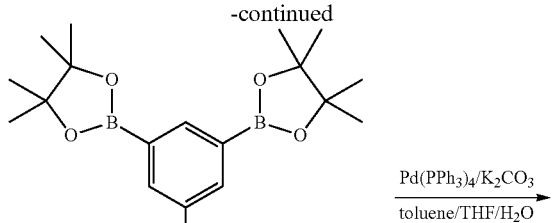

(B)

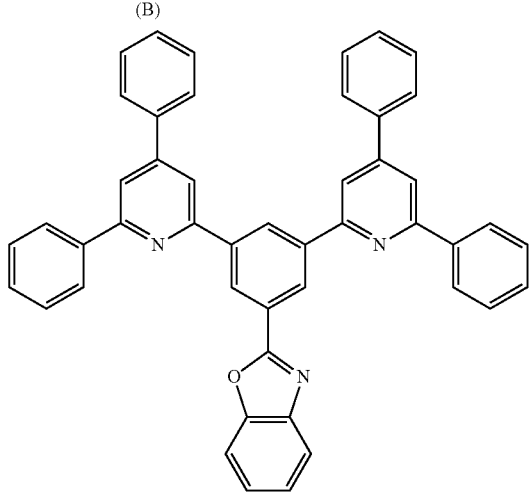

First Step: Synthesis of Intermediate Product (G)

105.0 g (628.4 mmol) of ethylbromoacetate and 994.67 g (12.6 mol) of pyridine were suspended in a solvent, and the suspended solution was reacted at room temperature for 2 hours. Then, the obtained reactant was precipitated by adding 1,000 ml of diethylether thereto. The precipitated solid compound was filtered, separated, cleaned with diethylether, and dried, obtaining 152.3 g of a light yellow solid intermediate product (G) (yield: 98%).

Second Step: Synthesis of Intermediate Product (H)

150.0 g (609.5 mmol) of the intermediate product (G), 105.8 g (609.5 mmol) of transchalcone, and 375.85 g (4.8 mol) of ammonium acetate ($NH_4OAC$) were dissolved in 1,500 ml of methanol. The solution was reacted at 100° C. for 12 hours. The obtained reactant was precipitated in 2,000 ml of water, and the precipitated solid compound was filtered, separated, cleaned with water and methanol, and dried, obtaining 98.15 g of a white solid intermediate product (H) (yield: 78%).

Third Step: Synthesis of Intermediate Product (I)

98.0 g (396.3 mmol) of the intermediate product (H), 168.7 g (1.2 mol) of phosphorus oxide ($P_2O_5$), and 191.6 g (594.4 mol) of tetrabutylammoniumbromide (TBAB) were dissolved in 1,400 ml of chlorobenzene. The solution was reacted at 140° C. for 12 hours. The obtained reactant was treated under reduced pressure to remove a solvent therein, and the obtained solid mixture was cleaned with 500 ml of water. The obtained reactant was extracted with chloroform and treated under reduced pressure to remove a solvent therein. The extract was cleaned with 500 ml of methanol and dried, obtaining 89.4 g of a white solid intermediate product (I) (yield: 73%).

Fourth Step: Synthesis of Compound Represented by Chemical Formula 11

17.0 g (38.0 mmol) of the intermediate product (B), 28.3 g (91.3 mmol) of the intermediate product (I), and 2.2 g (1.9 mmol) of tetrakis(triphenylphosphine)palladium[$Pd(PPh_3)_4$] were dissolved in a mixed solvent of 500 ml of tetrahydrofuran (THF) and 300 ml of toluene. A solution prepared by dissolving 21.0 g (152 mmol) of potassium carbonate ($K_2CO_3$) in 300 ml of water was added thereto. The mixture was reacted at 110° C. for 24 hours. The obtained reactant was treated under reduced pressure to remove a solvent and then cleaned with water and methanol. The obtained solid mixture was columnized and separated and then, dried, obtaining 23.0 g of a white solid compound represented by Chemical Formula 11 (yield: 93%). (calculation value: 653.77/measurement value: MS[M+1] 654.25)

EXAMPLE 4

Synthesis of Compound Represented by Chemical Formula 12

The compound represented by Chemical Formula 12 was synthesized according to the following Reaction Scheme 4.

[Reaction Scheme 4]

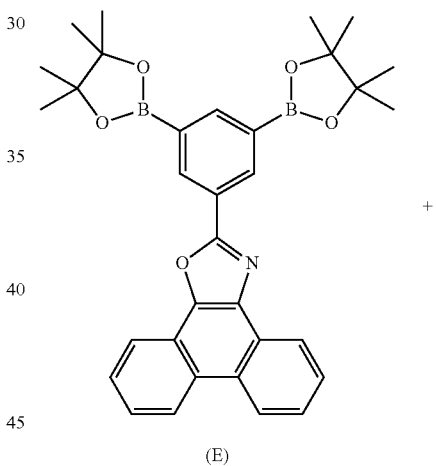

(E)

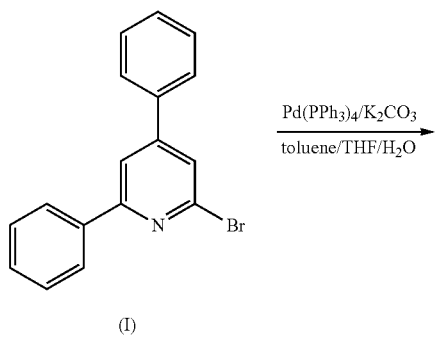

(I)

-continued

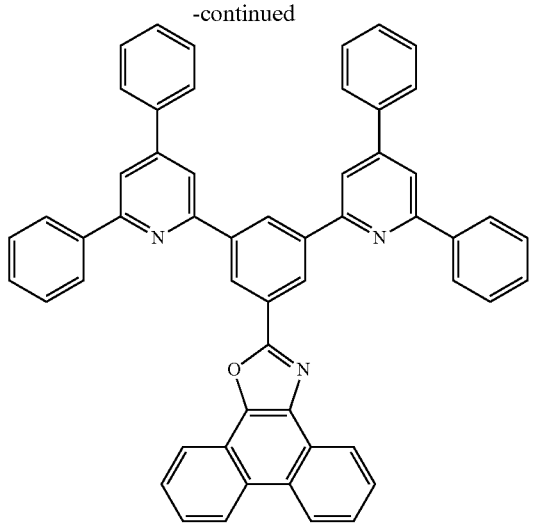

10.0 g (18.3 mmol) of the intermediate product (E), 13.6 g (43.9 mmol) of the intermediate product (I), and 1.1 g (0.9 mmol) of tetrakis(triphenylphosphine)palladium[Pd(PPh$_3$)$_4$] were dissolved in a mixed solvent of 300 ml of tetrahydrofuran (THF) and 200 ml of toluene. A solution prepared by dissolving 10.1 g (73.1 mmol) of potassium carbonate (K$_2$CO$_3$) in 200 ml of water was added thereto. The mixture was reacted at 110° C. for 24 hours. The obtained reactant was treated under reduced pressure to remove a solvent therein and cleaned with water and methanol. Then, the obtained solid compound was recrystallized in chloroform and methanol and dried, obtaining 11.5 g of a white solid compound represented by Chemical Formula 12 (yield: 83%). (calculation value: 753.89/measurement value: MS[M+1] 754.28)

Fabrication of Organic Photoelectric Device

EXAMPLE 5

Fabrication of Organic Photoelectric Device Using the Compound Prepared in Example 1

As an anode, ITO having a thickness of 1,000 Å was used, and as a cathode, aluminum (Al) having a thickness of 1,000 Å was used.

Specifically, organic photoelectric devices were fabricated as follows: an ITO glass substrate having sheet resistance of 15Ω/cm$^2$ was cut to a size of 50 mm×50 mm×0.7 mm and ultrasonic wave cleaned in acetone, isopropyl alcohol, and pure water for 5 minutes each, and UV ozone cleaned for 30 minutes to provide an anode.

N1, N1'-(biphenyl-4, 4'-diyl)bis(N1-(naphthalen-2-yl)-N4, N4-diphenylbenzene-1, 4-diamine) was deposited on the glass substrate to be 585 Å thick, and N, N-di(1-naphthyl)-N, N-diphenylbenzidine was sequentially deposited to form a 50 Å-thick hole injection layer (HIL).

4% of N, N, N', N'-tetrakis (3, 4-dimethylphenyl)chrysene-6, 12-diamine and 96% of 9-(3-(naphthalen-1-yl)phenyl)-10-(naphthalen-2-yl)anthracene were deposited to provide a 200 Å-thick emission layer.

Then, the compound synthesized in Example 1 and Liq were deposited at a 1:1 ratio (a weight ratio) to provide a 300 Å-thick electron transport layer (ETL).

Liq was vacuum-deposited on the electron transport layer (ETL) to provide a 5 Å thick electron injection layer (EIL), and Al was vacuum-deposited to form a 1,000 Å thick Liq/Al electrode.

EXAMPLE 6

Fabrication of Organic Photoelectric Device Using Example 2

An organic photoelectric device was fabricated according to the same method as Example 5 except for using the compound according to Example 2 instead of the compound according to Example 1 to form an electron transport layer (ETL).

EXAMPLE 7

Fabrication of Organic Photoelectric Device Using Example 4

An organic photoelectric device was fabricated according to the same method as Example 5 except for using the compound according to Example 4 instead of the compound according to Example 1 to form an electron transport layer (ETL).

COMPARATIVE EXAMPLE 1

Fabrication of Organic Photoelectric Device Using Alq3

An organic photoelectric device was fabricated according to the same method as Example 5 except for using 300 Å thick tris(8-hydroxyquinolinato)aluminum (Alq3) and Liq instead of the compound according to Example 1 to form an electron transport layer (ETL).

Performance of Organic Photoelectric Device Measurement

Each organic photoelectric device was measured regarding current density and luminance changes and luminous efficiency depending on voltage. Specifically, the measurement was performed as follows.

1) Current Density Change Depending on Voltage Change

Figure 6:
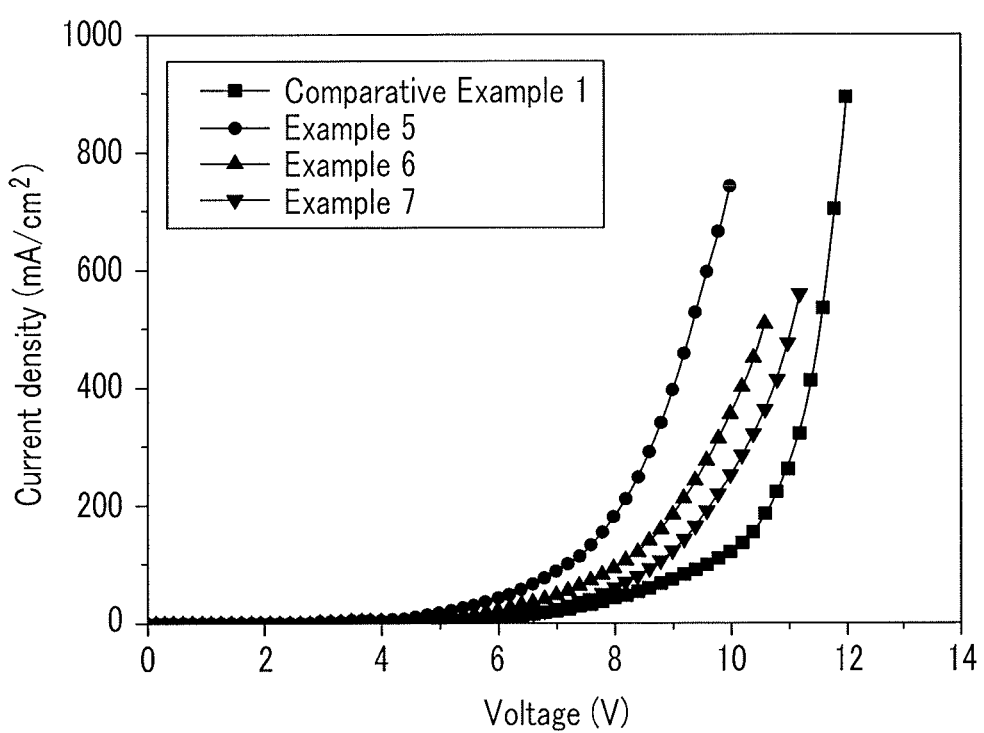
FIG. 6 illustrates a graph showing current density change data of an organic photoelectric device depending on a voltage according to Examples and Comparative Examples.

Each organic photoelectric device was measured regarding current value flowing in a unit device using a current-voltage meter (Keithley 2400) while its voltage was increased from 0 V to 14 V, and the current value was divided by an area. The results are provided in FIG. 6.

2) Luminance Change Depending on Voltage Change

Figure 7:
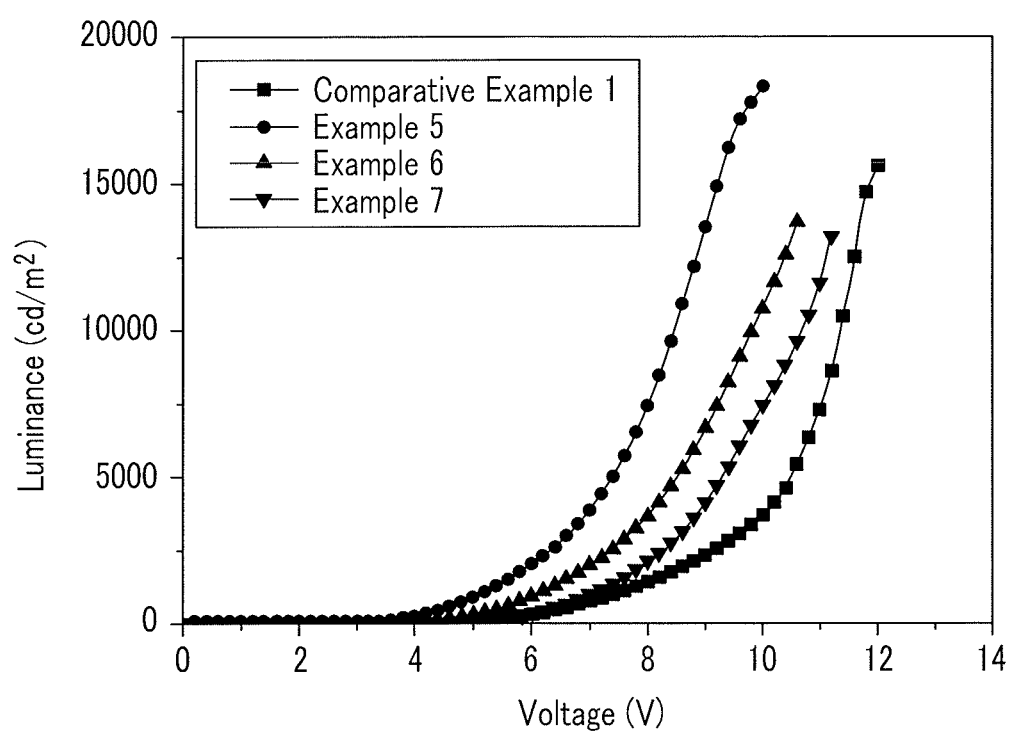
FIG. 7 illustrates a graph showing light emitting luminance change data of an organic photoelectric device depending on a voltage according to Examples and Comparative Examples.

Each organic photoelectric device was measured regarding luminance using a luminance meter (Minolta Cs-1000A) while its voltage was increased from 0 V to 14 V. The results are provided in FIG. 7.

3) Luminous Efficiency and Electric Power Efficiency

Figure 8:
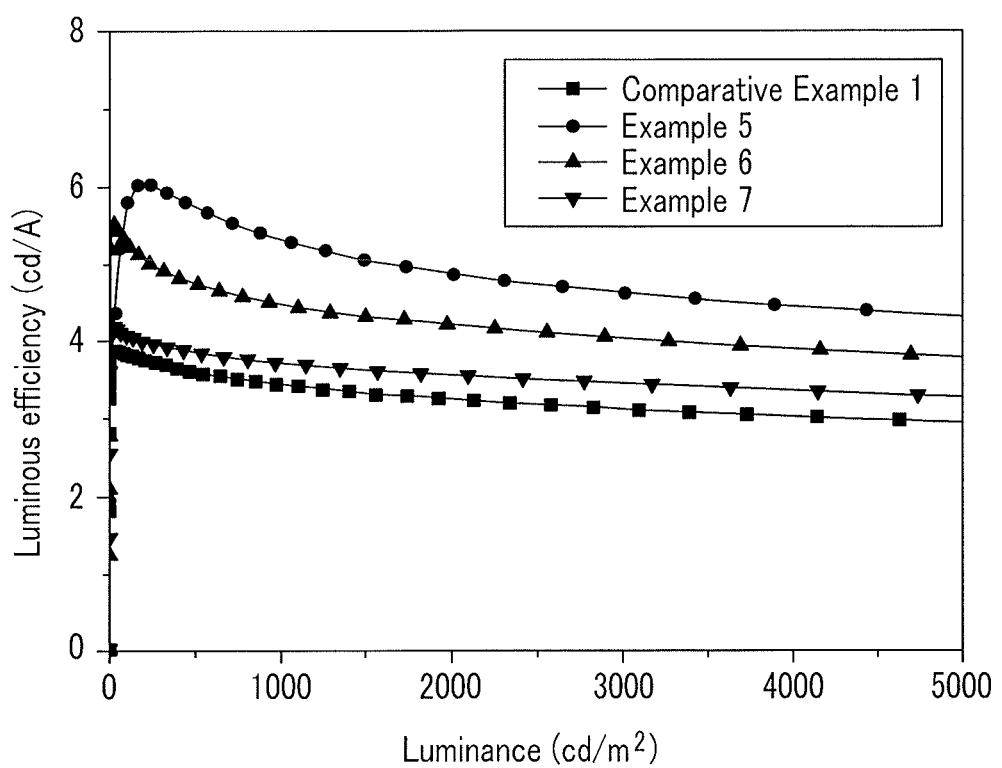
FIG. 8 illustrates a graph showing luminous efficiency measurement data of an organic photoelectric device according to Examples and Comparative Examples.
Figure 9:
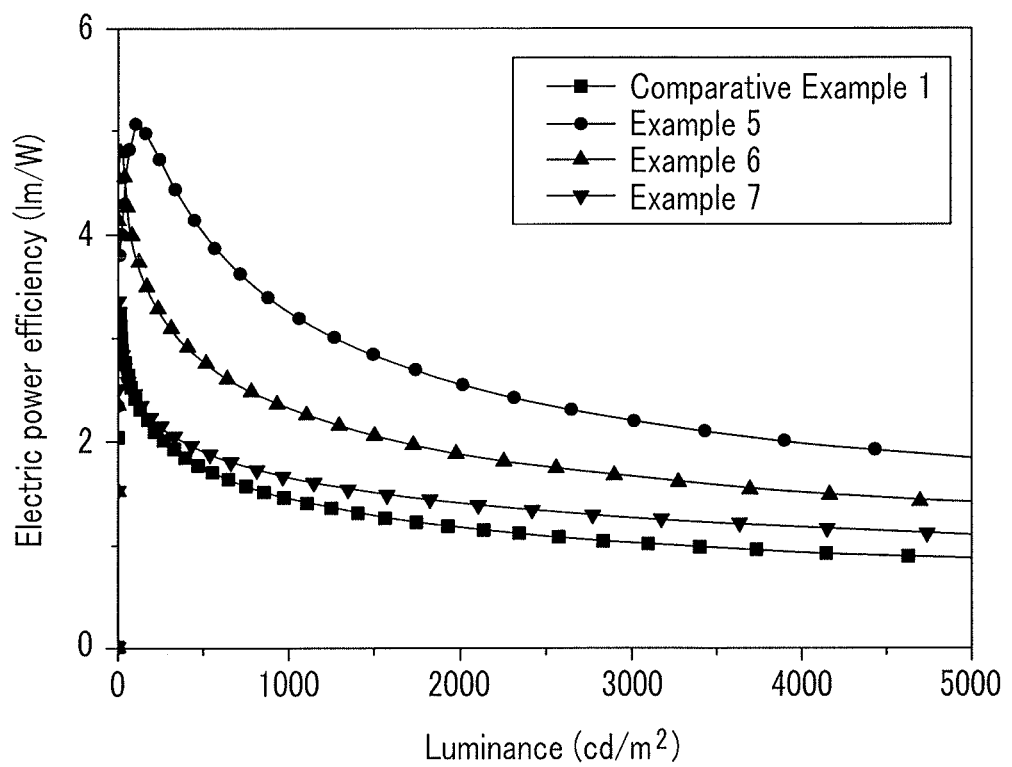
FIG. 9 illustrates a graph showing electric power efficiency measurement data of an organic photoelectric device according to Examples and Comparative Examples.

The luminance, current density, and voltage obtained in 1) and 2) were used to calculate Luminous efficiency (cd/A) and electric power efficiency (1 m/W) at the same brightness (1,000 cd/m$^2$). The results are provided in FIGS. 8 and 9.

Measurement Result

The measurement results are provided in the following Table 1.

TABLE 1

| | Luminance 500 cd/m$^2$ | | |
| --- | --- | --- | --- |
| | Driving voltage (V) | Luminous efficiency (cd/A) | Electric power efficiency (lm/W) |
| Example 5 | 4.4 | 5.80 | 4.14 |
| Example 6 | 5.4 | 4.75 | 2.76 |

TABLE 1-continued

| | Luminance 500 cd/m² | | |
|---|---|---|---|
| | Driving voltage (V) | Luminous efficiency (cd/A) | Electric power efficiency (lm/W) |
| Example 7 | 6.4 | 3.84 | 1.88 |
| Comparative Example 1 | 6.6 | 3.58 | 1.70 |

Referring to Table 1, the organic light emitting diodes according to Examples 5 to 7 had excellent driving voltage, luminous efficiency, and electric power efficiency. Accordingly, the organic light emitting diodes had an increased device life-span.

By way of summation and review, an organic light emitting diode may transform electrical energy into light by applying current to an organic light emitting material. It may have a structure in which a functional organic material layer is interposed between an anode and a cathode. The organic material layer may include a multi-layer including different materials, e.g., a hole injection layer (HIL), a hole transport layer (HTL), an emission layer, an electron transport layer (ETL), and/or an electron injection layer (EIL), in order to help improve efficiency and stability of an organic photoelectric device.

In such an organic photoelectric device, when a voltage is applied between an anode and a cathode, holes from the anode and electrons from the cathode may be injected to an organic material layer and recombined to generate excitons having high energy. The generated excitons may generate light having certain wavelengths while shifting to a ground state.

One type of organic light emitting diode may include a low molecular weight aromatic diamine and aluminum complex as an emission layer forming material. The organic layer may have a structure in which a thin film (hole transport layer (HTL)) of a diamine derivative and a thin film of tris(8-hydroxy-quinolate)aluminum ($Alq_3$) are laminated.

Recently, a phosphorescent light emitting material for a light emitting material of an organic light emitting diode has been considered, in addition to the fluorescent light emitting material. Such a phosphorescent material may emit light by transiting the electrons from a ground state to an exited state, non-radiance transiting of a singlet exciton to a triplet exciton through intersystem crossing, and transiting a triplet exciton to a ground state to emit light.

As described above, in an organic light emitting diode, an organic material layer may include a light emitting material and a charge transport material, e.g., a hole injection material, a hole transport material, an electron transport material, an electron injection material, or the like.

The light emitting material may be classified as blue, green, and red light emitting materials according to emitted colors, and yellow and orange light emitting materials to emit colors approaching natural colors.

When one material is used as a light emitting material, a maximum light emitting wavelength may be shifted to a long wavelength or color purity may decrease because of interactions between molecules, or device efficiency may decrease because of a light emitting quenching effect. Therefore, a host/dopant system may be included as a light emitting material in order to improve color purity and increase luminous efficiency and stability through energy transfer.

In order to achieve excellent performance of an organic photoelectric device, a material constituting an organic material layer, e.g., a hole injection material, a hole transport material, a light emitting material, an electron transport material, an electron injection material, and a light emitting material such as a host and/or a dopant, should be stable and have good efficiency.

A low molecular weight organic light emitting diode may be manufactured as a thin film in a vacuum deposition method and may have good efficiency and life-span performance. A polymer organic light emitting diode may be manufactured in an Inkjet or spin coating method may have an advantage of low initial cost and being large-sized.

Both low molecular weight organic light emitting and polymer organic light emitting diodes may have an advantage of being self-light emitting and having high speed response, wide viewing angle, ultra-thin, high image quality, durability, large driving temperature range, and the like. For example, they may have good visibility due to self-light emitting characteristics, compared with a conventional LCD (liquid crystal display) and may have an advantage of decreasing thickness and weight up to a third, compared with an LCD, because they do not need a backlight.

In addition, since they have a response speed up to 1,000 times faster than LCD, they can realize a perfect motion picture without after-image. Based on these advantages, they have been developed to have 80 times efficiency and more than 100 times life-span. Recently, sizes have rapidly increased, and a 40-inch organic light emitting diode panel has been developed.

The display devices should have improved luminous efficiency and life-span in order to be larger. Herein, luminous efficiency should have a smooth combination between holes and electrons in an emission layer. However, an organic material in general may have slower electron mobility than hole mobility, and may exhibit an inefficient combination between holes and electrons. Accordingly, increasing electron injection and mobility from a cathode and simultaneously preventing movement of holes may be desirable.

In order to improve life-span, a material crystallization caused by Joule heating generated during device operating may be prevented. Accordingly, an organic compound having excellent electron injection and mobility, and high electrochemical stability may be desirable.

The embodiments provide a compound for an organic photoelectric device that may act as a light emitter, or electron injection and/or transport material, and may also act as a light emitting host along with an appropriate dopant.

The embodiments provide an organic photoelectric device having excellent life-span, efficiency, driving voltage, electrochemical stability, and thermal stability using the compound. When the compound is particularly used to form an electron transport layer (ETL) for the organic photoelectric device, the organic photoelectric device may have excellent performance efficiency characteristic.

The compound for an organic photoelectric device may have excellent electrochemical and thermal stability and life-span characteristics, and thus may provide an organic photoelectric device having high luminous efficiency at a low driving voltage.

The embodiments provide an organic photoelectric device having excellent life-span, efficiency, electrochemical stability, and thermal stability.

Example embodiments have been disclosed herein, and although specific terms are employed, they are used and are to be interpreted in a generic and descriptive sense only and not for purpose of limitation. Accordingly, it will be understood by those of skill in the art that various changes in form and details may be made without departing from the spirit and scope of the present invention as set forth in the following claims.

What is claimed is:

1. A compound for an organic photoelectric device, the compound being represented by the following Chemical Formula 1:

[Chemical Formula 1]

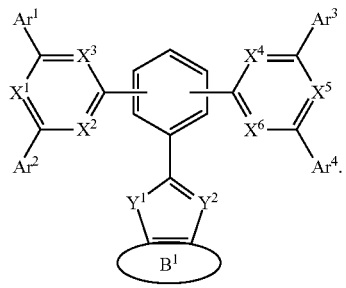

wherein, in Chemical Formula 1:
Ar$^1$ to Ar$^4$ are each independently a substituted or unsubstituted C6 to C30 aryl group or a substituted or unsubstituted C3 to C30 heteroaryl group,
X$^1$ to X$^6$ are each independently N or CH, provided that at least one of X$^1$ to X$^3$ is N and at least one of X$^4$ to X$^6$ is N,
Y$^1$ is selected from the group of O, S, NH and NR, wherein R is selected from the group of a substituted or unsubstituted C6 to C30 aryl group, a substituted or unsubstituted C3 to C30 heteroaryl group, a substituted or unsubstituted C1 to C6 alkyl group, a substituted or unsubstituted C3 to C30 cycloalkyl group, a substituted or unsubstituted cyano group, a substituted or unsubstituted nitro group, a substituted or unsubstituted carbonyl group, and a substituted or unsubstituted amide group,
Y$^2$ is CH or N, and
B$^1$ is selected from the group of a substituted or unsubstituted naphthyl group, a substituted or unsubstituted anthracenyl group, a substituted or unsubstituted phenanthrenyl group, a substituted or unsubstituted pyrenyl group, a substituted or unsubstituted perylenyl group, a substituted or unsubstituted chrysenyl group, a substituted or unsubstituted pyridinyl group, a substituted or unsubstituted quinolinyl group, a substituted or unsubstituted benzoquinolinyl group, and a substituted or unsubstituted phenanthrolinyl group.

2. The compound for an organic photoelectric device as claimed in claim 1, wherein the compound for an organic photoelectric device represented by Chemical Formula 1 is represented by the following Chemical Formula 2:

[Chemical Formula 2]

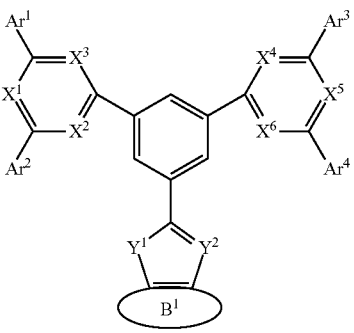

wherein, in Chemical Formula 2,
Ar$^1$ to Ar$^4$ are each independently a substituted or unsubstituted C6 to C30 aryl group or a substituted or unsubstituted C3 to C30 heteroaryl group,
X$^1$ to X$^6$ are each independently N or CH, provided that at least one of X$^1$ to X$^3$ is N and at least one of X$^4$ to X$^6$ is N,
Y$^1$ is selected from the group of O, S, NH, and NR, wherein R is selected from the group of a substituted or unsubstituted C6 to C30 aryl group, a substituted or unsubstituted C3 to C30 heteroaryl group, a substituted or unsubstituted C1 to C6 alkyl group, a substituted or unsubstituted C3 to C30 cycloalkyl group, a substituted or unsubstituted cyano group, a substituted or unsubstituted nitro group, a substituted or unsubstituted carbonyl group, and a substituted or unsubstituted amide group,
Y$^2$ is CH or N, and
B$^1$ is selected from the group of a substituted or unsubstituted naphthyl group, a substituted or unsubstituted anthracenyl group, a substituted or unsubstituted phenanthrenyl group, a substituted or unsubstituted pyrenyl group, a substituted or unsubstituted perylenyl group, a substituted or unsubstituted chrysenyl group, a substituted or unsubstituted pyridinyl group, a substituted or unsubstituted quinolinyl group, a substituted or unsubstituted benzoquinolinyl group, and a substituted or unsubstituted phenanthrolinyl group.

3. The compound for an organic photoelectric device as claimed in claim 1, wherein Ar$^1$ to Ar$^4$ are each independently a substituted or unsubstituted phenyl group, a substituted or unsubstituted naphthyl group, a substituted or unsubstituted anthracenyl group, a substituted or unsubstituted phenanthrenyl group, a substituted or unsubstituted perylenyl group, a substituted or unsubstituted chrysenyl group, a substituted or unsubstituted pyridinyl group, a substituted or unsubstituted pyridazinyl group, a substituted or unsubstituted quinolinyl group, or a substituted or unsubstituted isoquinolinyl group.

4. A compound for an organic photoelectric device, the compound being represented by one of the following Chemical Formulae 4 to 7, 9, 10, 12 to 15, 17, 18, 20 to 23, 25, 26, 28 to 31, 33, 34, 36 to 39, 41, 42, 44 to 47, 49, 50, 52 to 55, 57, 58, 60 to 63, 65, 66, 68 to 71, 73, 74, 76 to 79, 81, 82, 84 to 87, 89, 90, 92 to 95, 97, 98, 100 to 103, 105, 106, 108 to 111, 113, 114, 116 to 119, 121, 122, 124 to 127, 129, 130, 132 to 135, 137, 138, 140 to 143, 145, 146, 148 to 151, 153, 154, 156 to 159, 161, 162, 164 to 167, 169, 170, 172 to 175, 177, 178, 180 to 183, 185, and 186:

[Chemical Formula 4]

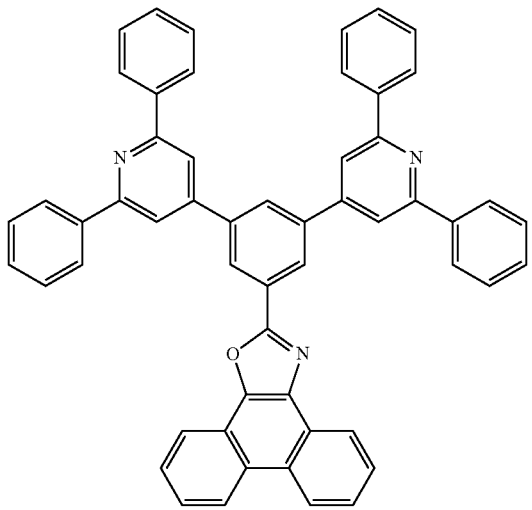

[Chemical Formula 5]
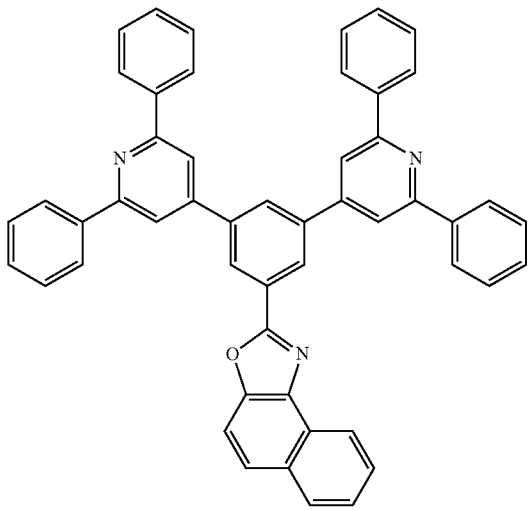
[Chemical Formula 6]
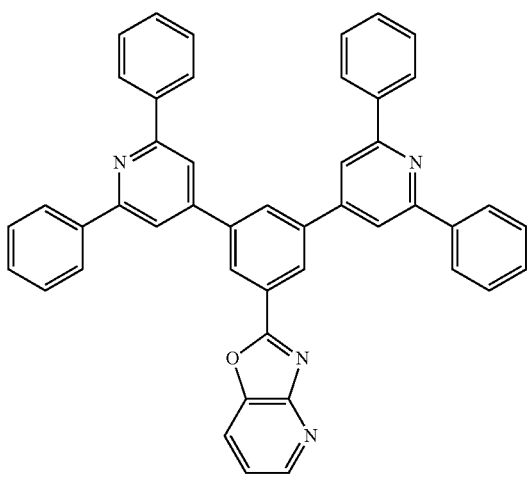
[Chemical Formula 7]
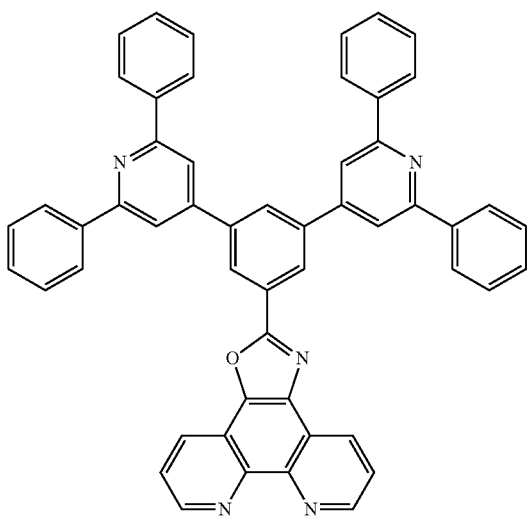
[Chemical Formula 9]
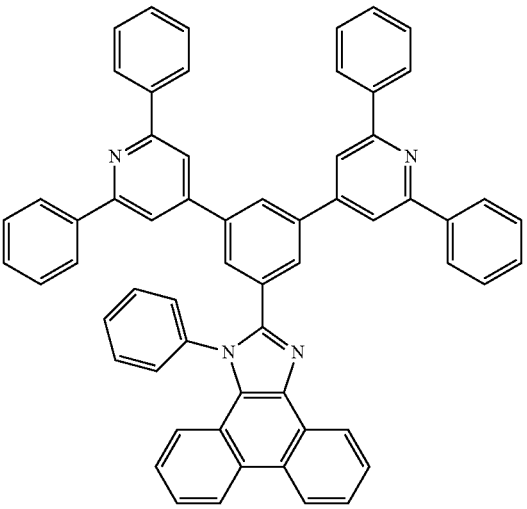
[Chemical Formula 10]
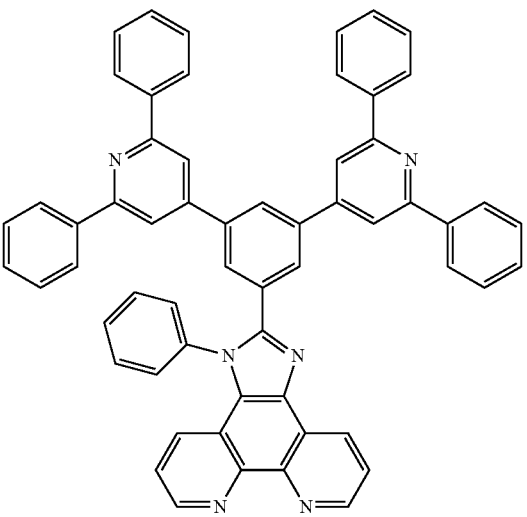
[Chemical Formula 12]
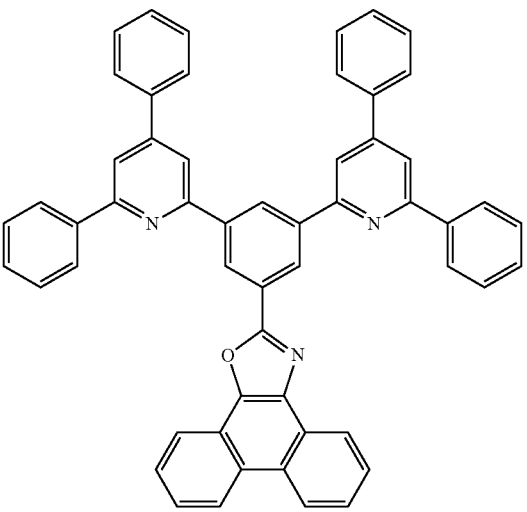

[Chemical Formula 13]
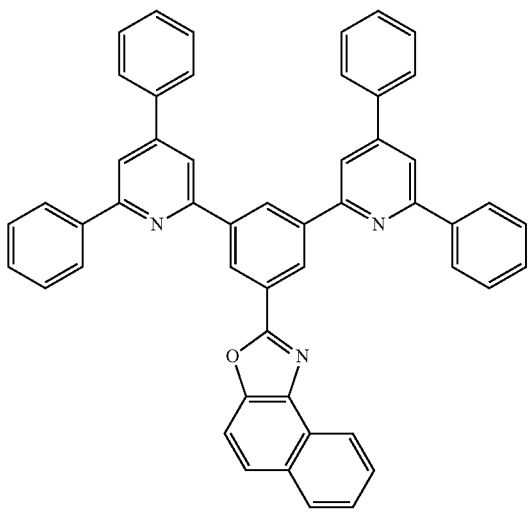
[Chemical Formula 14]
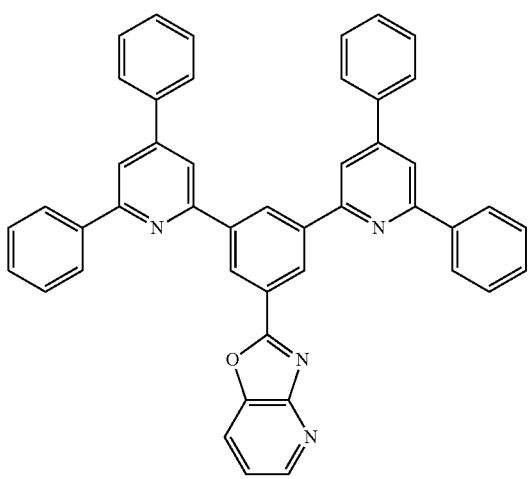
[Chemical Formula 15]
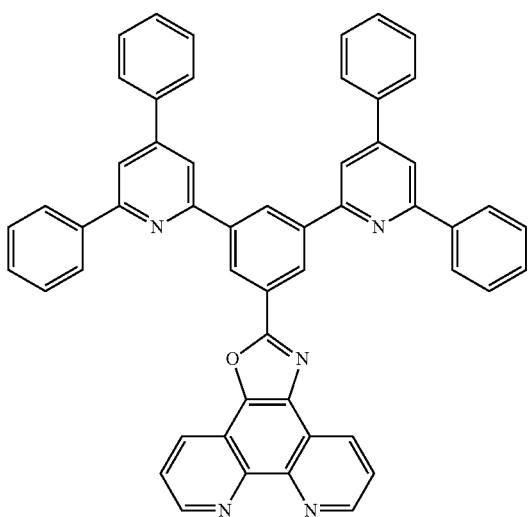
[Chemical Formula 17]
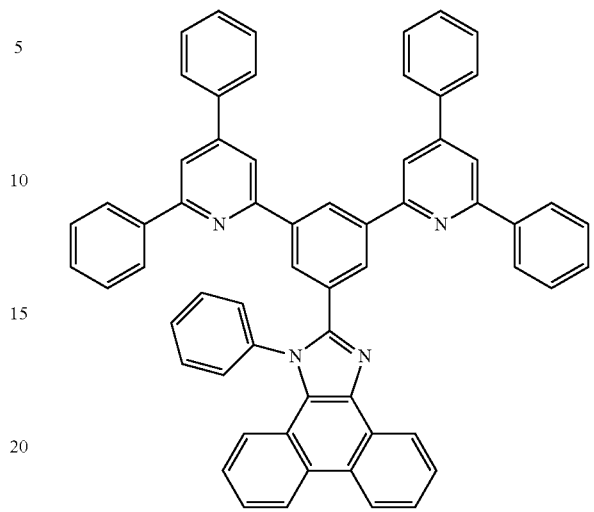
[Chemical Formula 18]
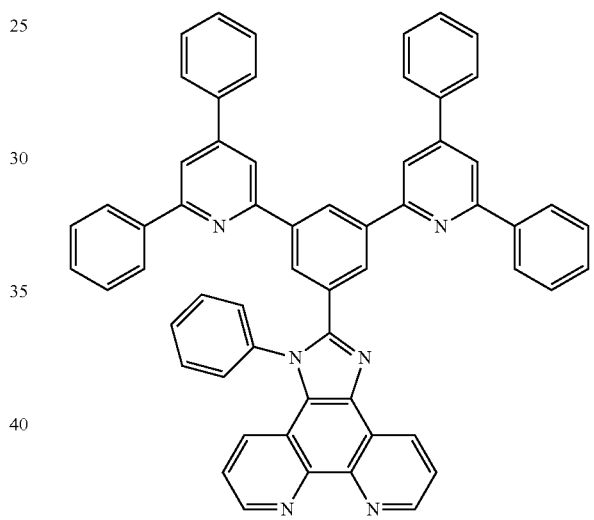
[Chemical Formula 20]
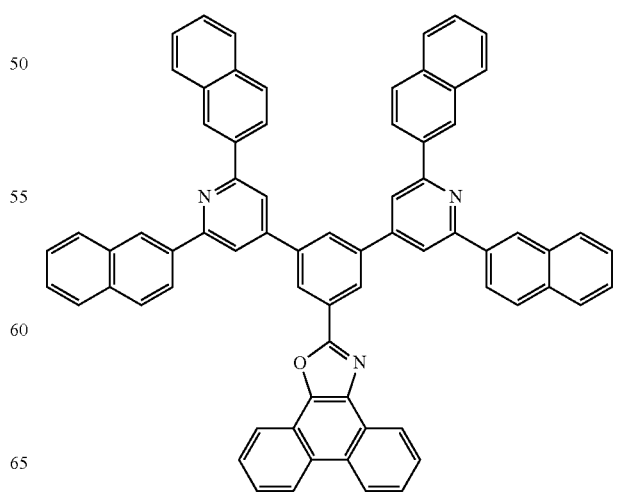

151
-continued
[Chemical Formula 21]
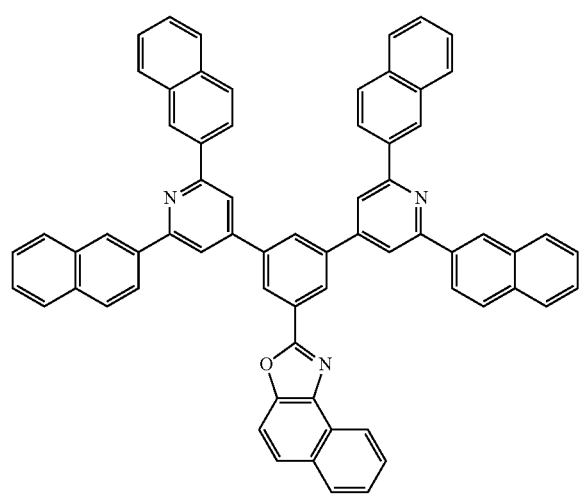
[Chemical Formula 22]
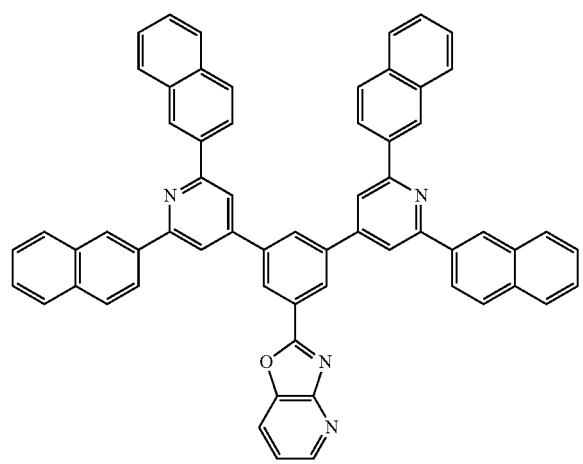
[Chemical Formula 23]
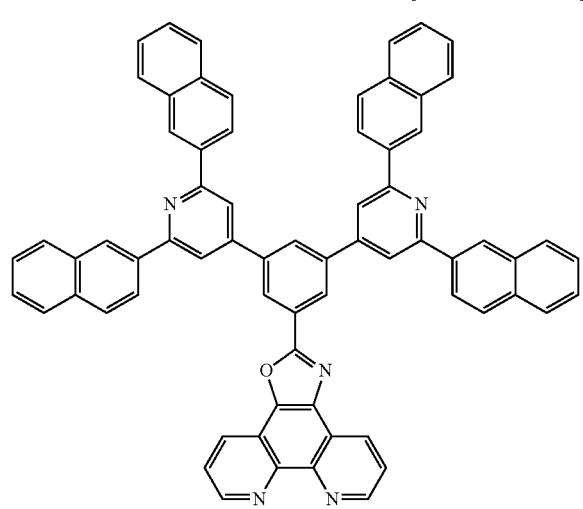
152
-continued
[Chemical Formula 25]
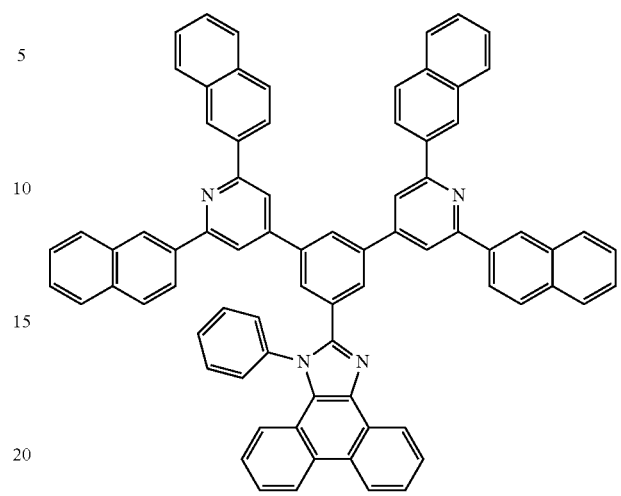
[Chemical Formula 26]
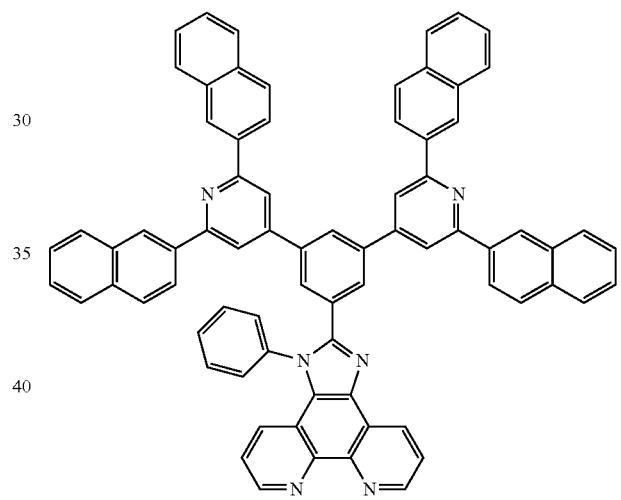
[Chemical Formula 28]
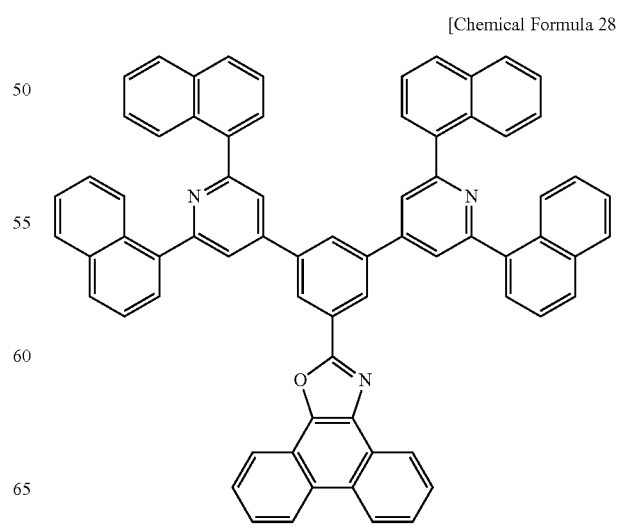

153
-continued
[Chemical Formula 29]
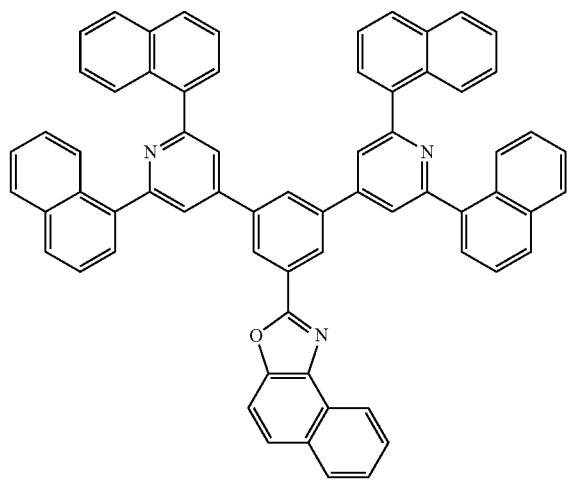
[Chemical Formula 30]
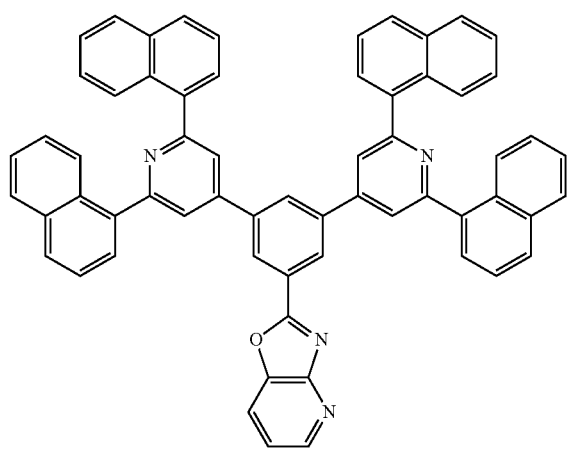
[Chemical Formula 31]
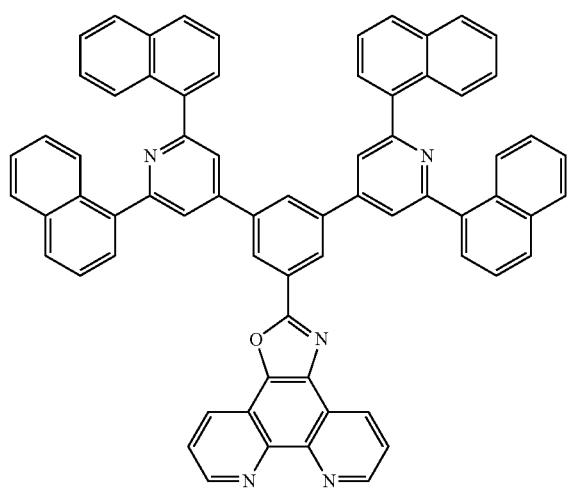
154
-continued
[Chemical Formula 33]
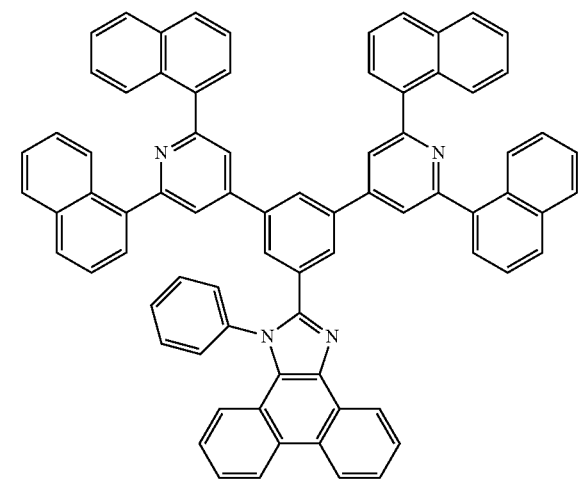
[Chemical Formula 34]
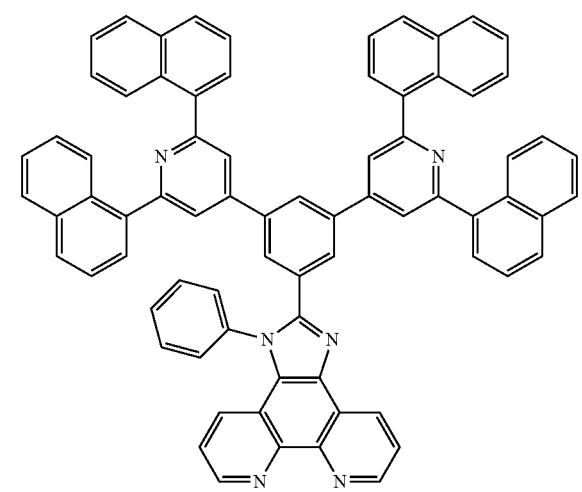
[Chemical Formula 36]
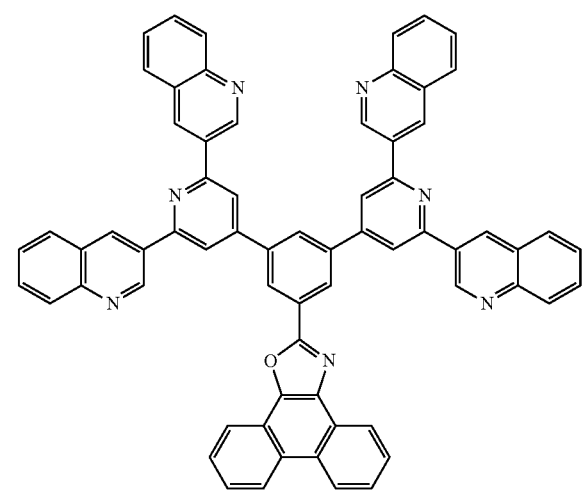

155
-continued
[Chemical Formula 37]
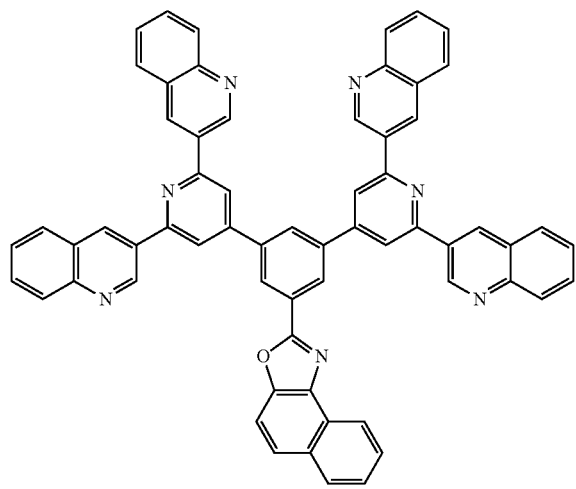
[Chemical Formula 38]
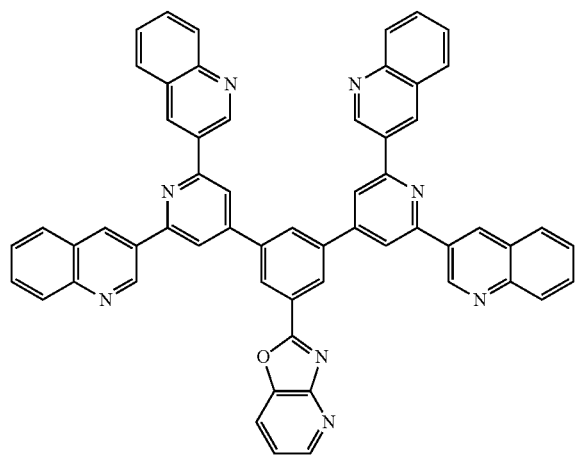
[Chemical Formula 39]
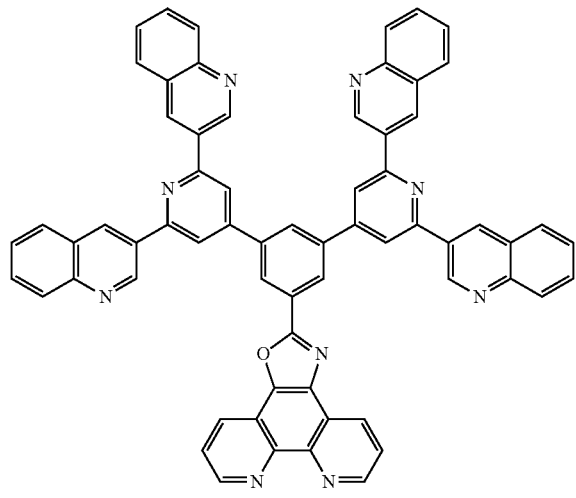
156
-continued
[Chemical Formula 41]
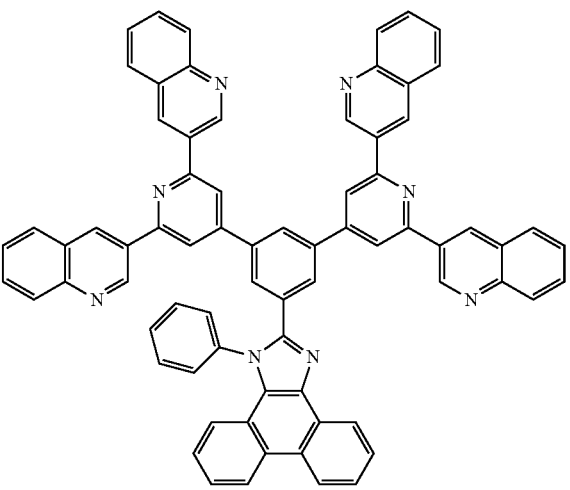
[Chemical Formula 42]
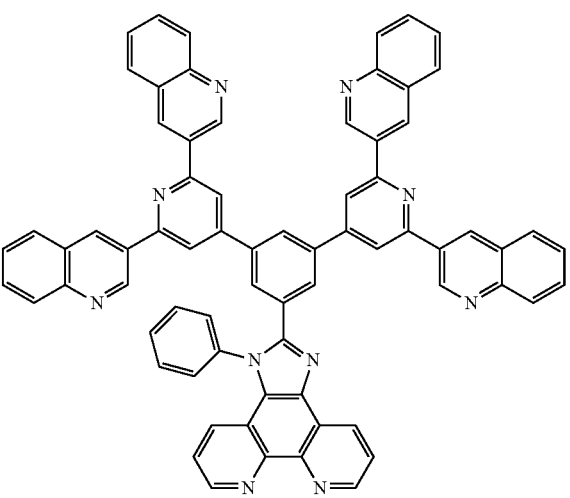
[Chemical Formula 44]
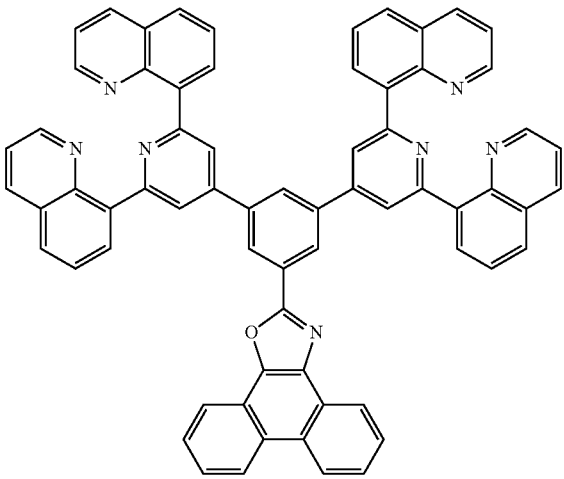

[Chemical Formula 45]
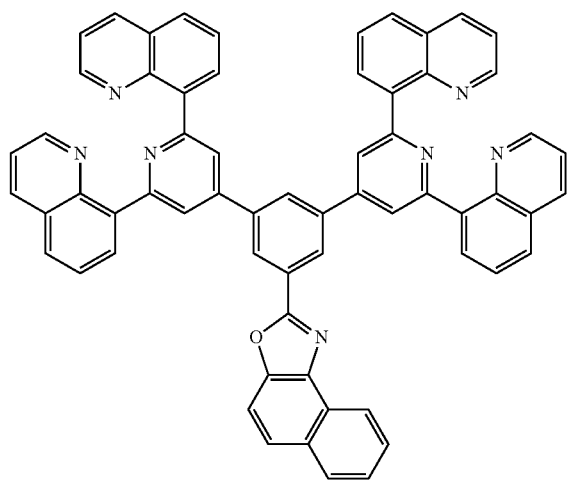
[Chemical Formula 49]
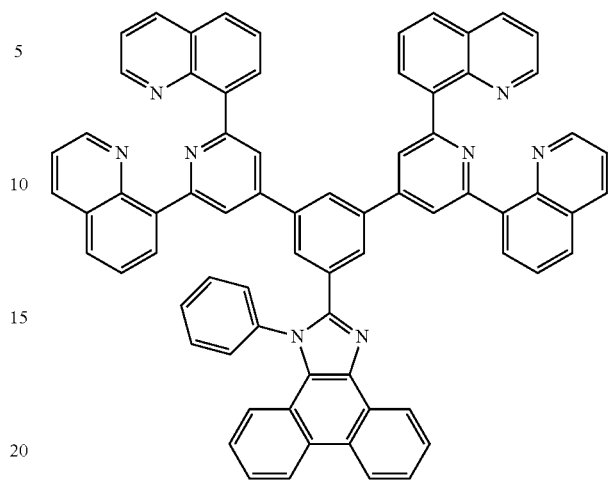
[Chemical Formula 46]
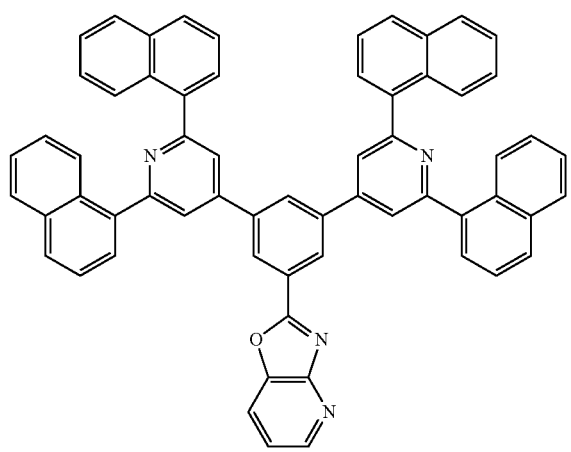
[Chemical Formula 50]
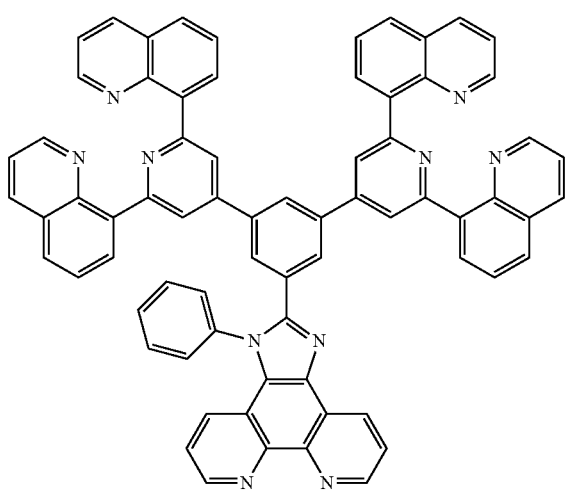
[Chemical Formula 47]
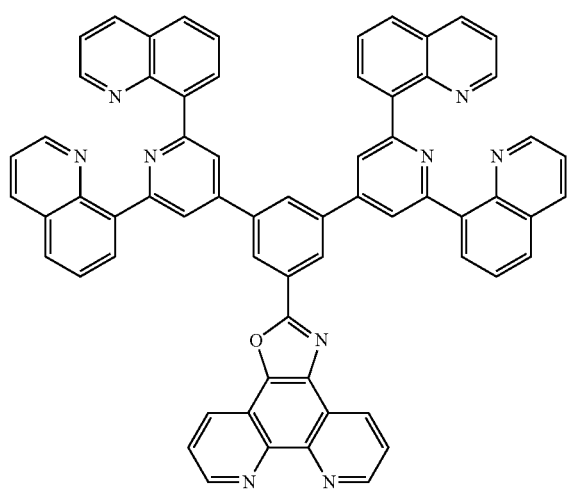
[Chemical Formula 52]
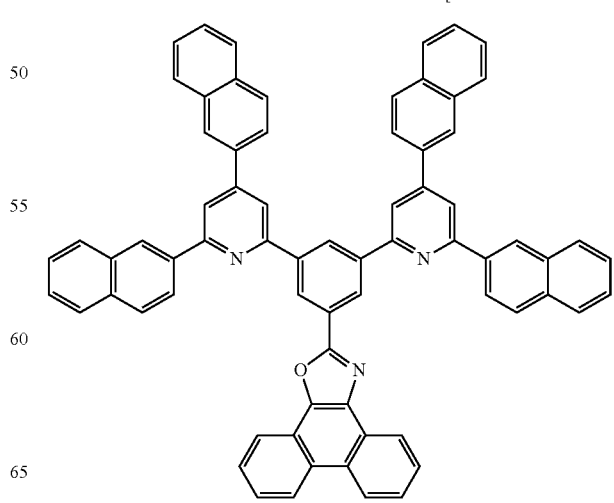

[Chemical Formula 53]
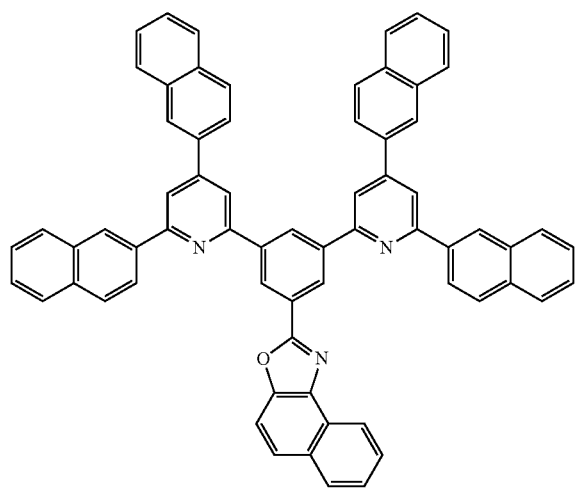
[Chemical Formula 54]
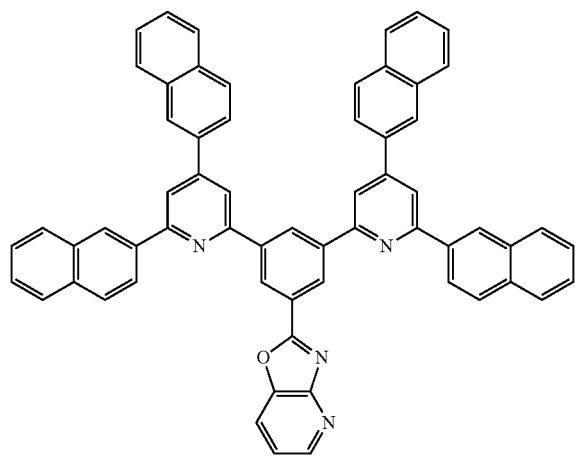
[Chemical Formula 55]
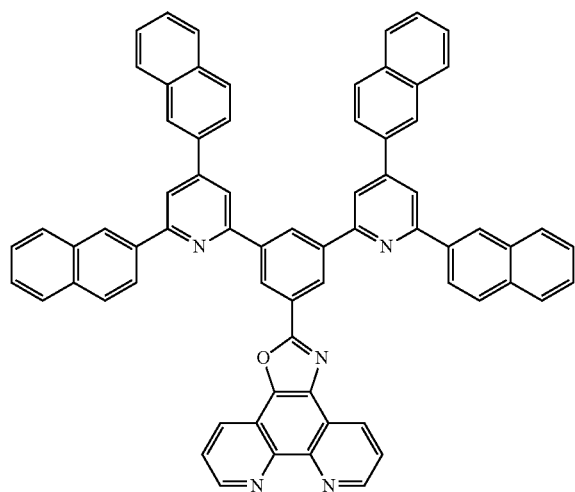
[Chemical Formula 57]
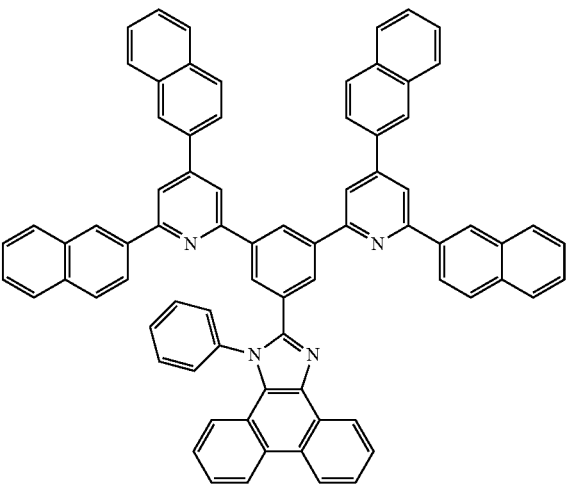
[Chemical Formula 58]
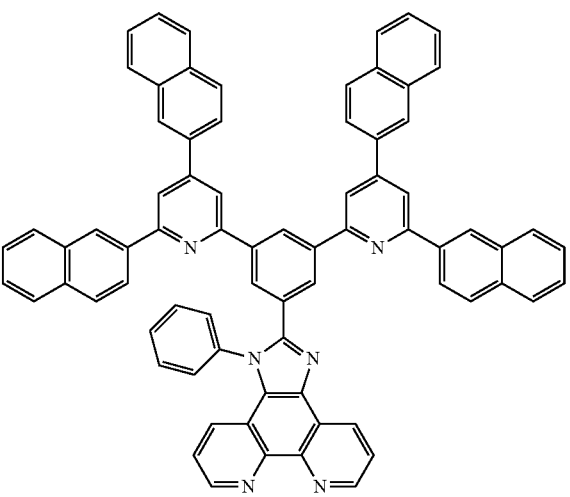
[Chemical Formula 60]
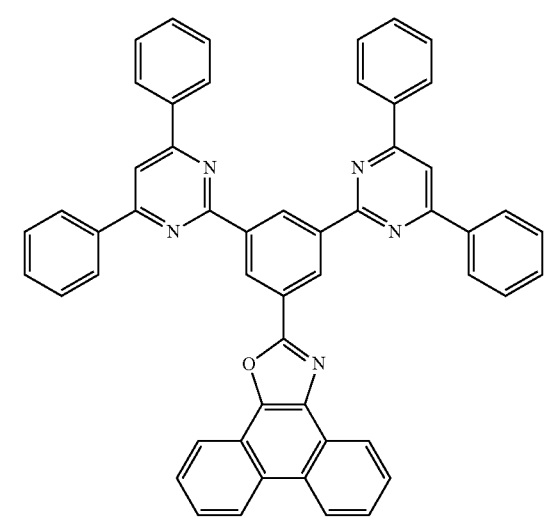

[Chemical Formula 61]
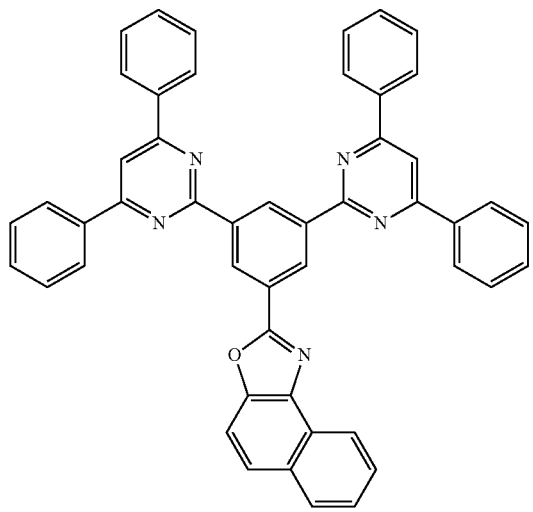
[Chemical Formula 62]
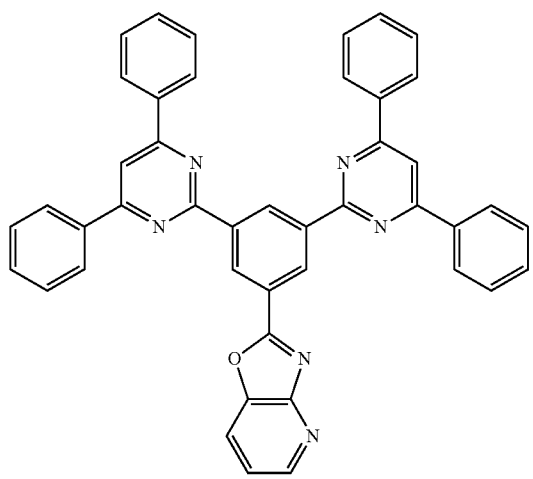
[Chemical Formula 63]
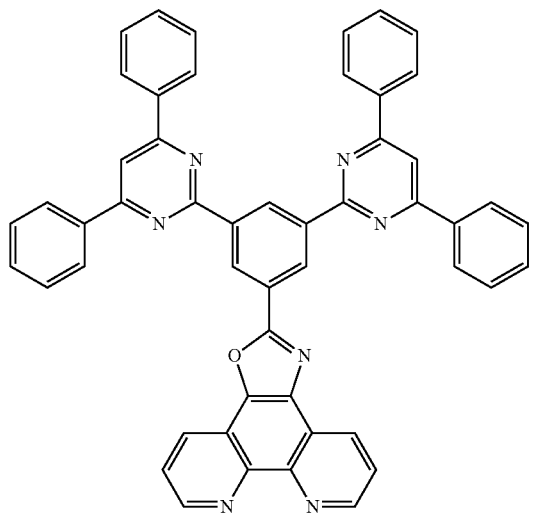
[Chemical Formula 65]
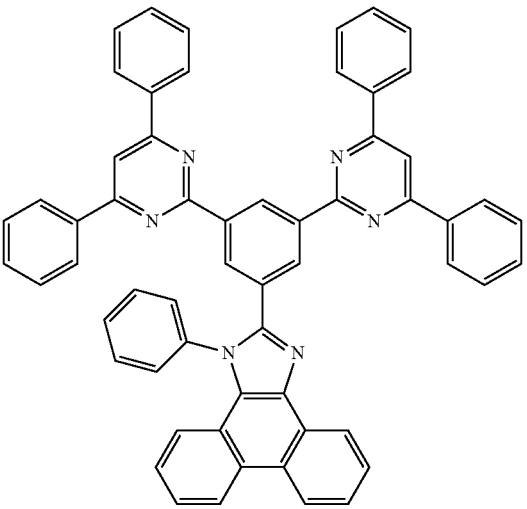
[Chemical Formula 66]
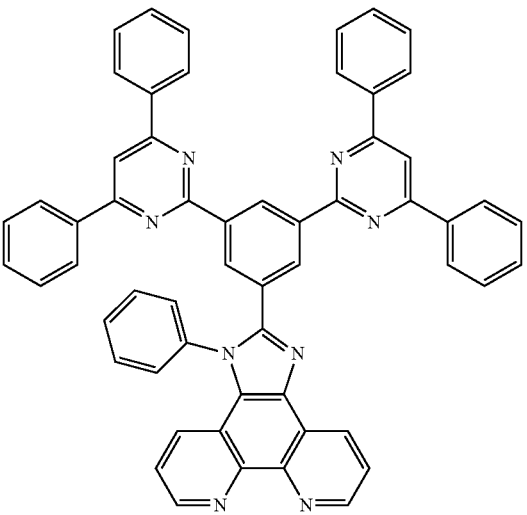
[Chemical Formula 68]
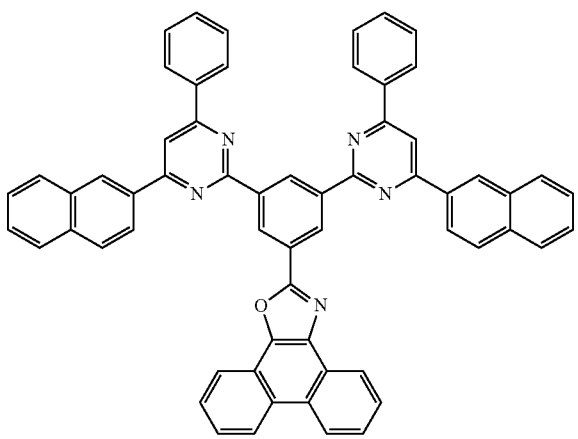

[Chemical Formula 69]
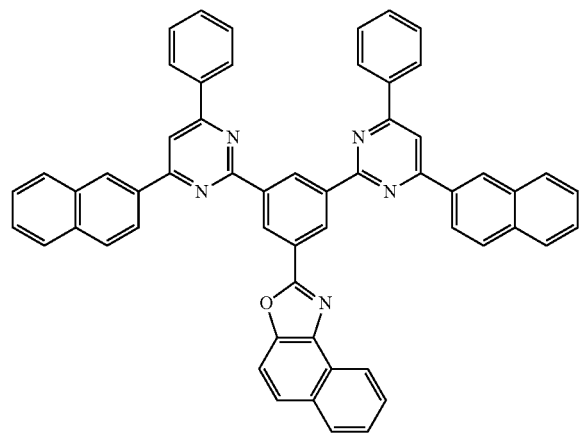
[Chemical Formula 70]
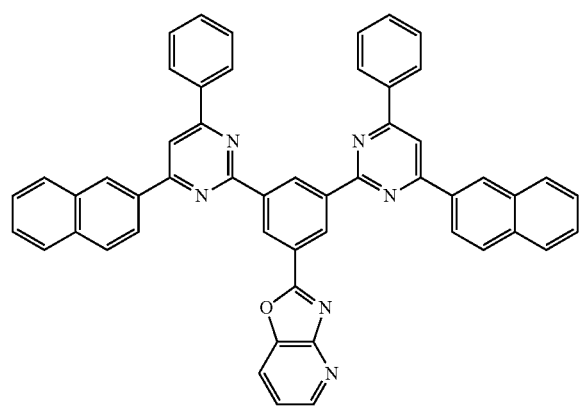
[Chemical Formula 71]
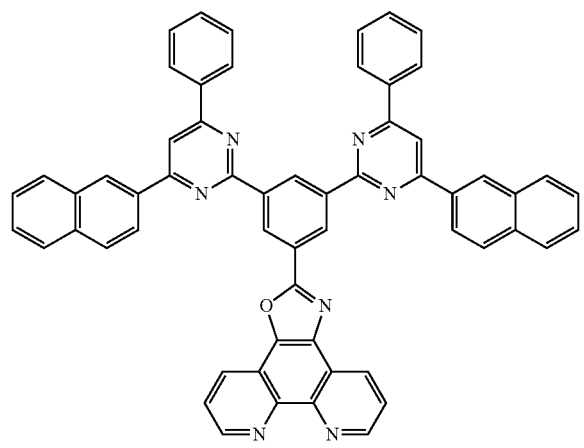
[Chemical Formula 73]
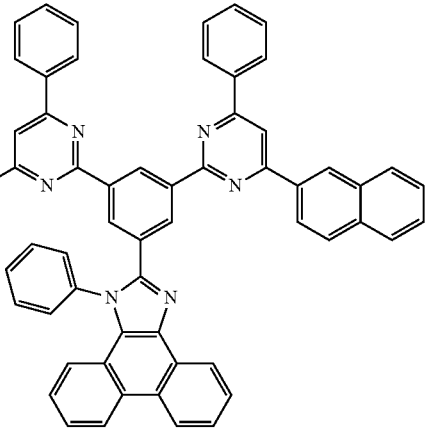
[Chemical Formula 74]
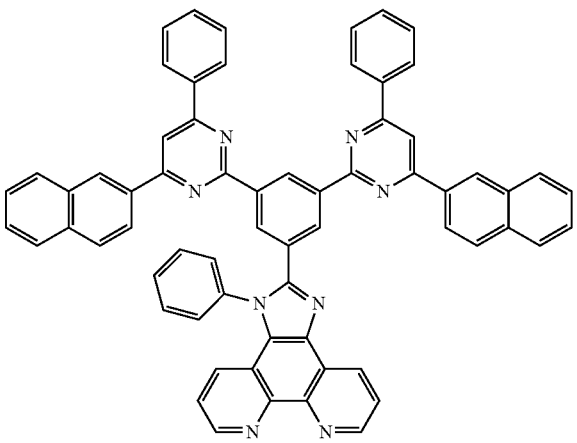
[Chemical Formula 76]
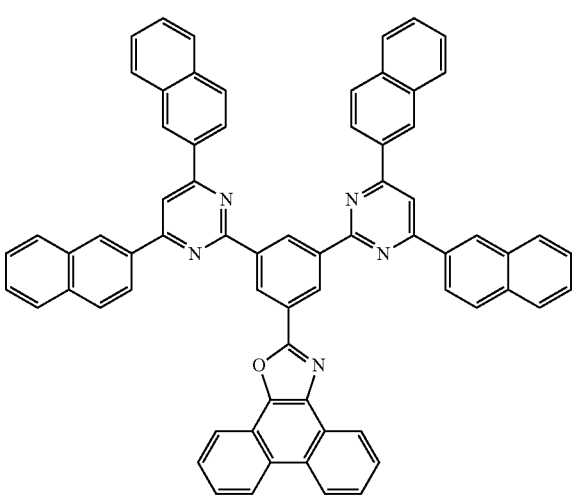

[Chemical Formula 77]
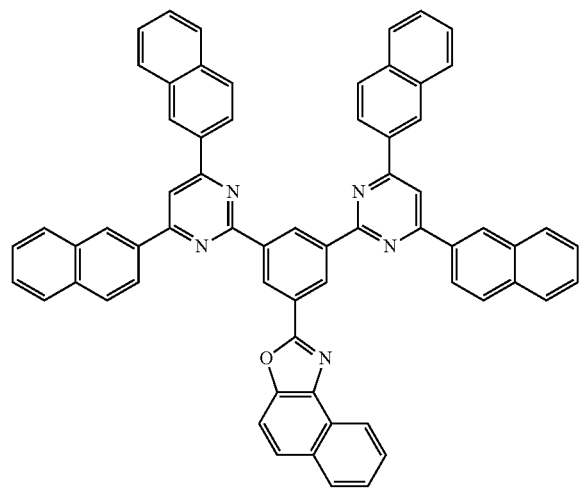
[Chemical Formula 81]
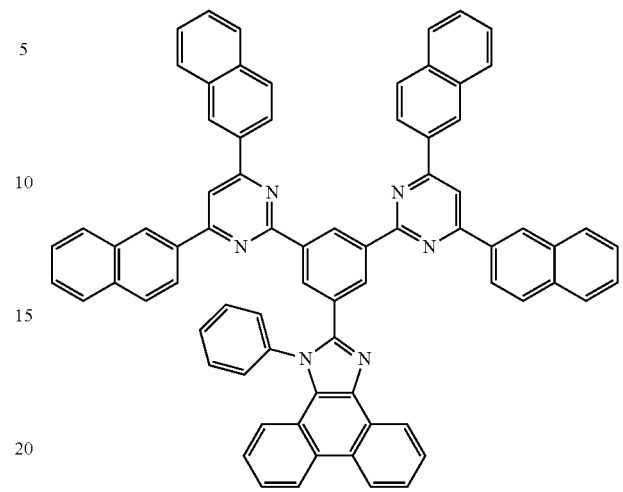
[Chemical Formula 78]
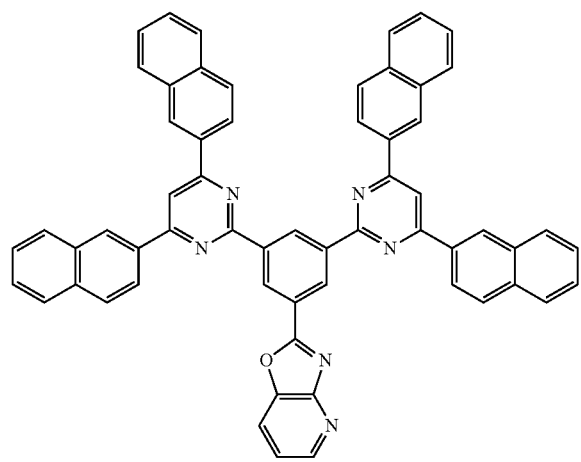
[Chemical Formula 82]
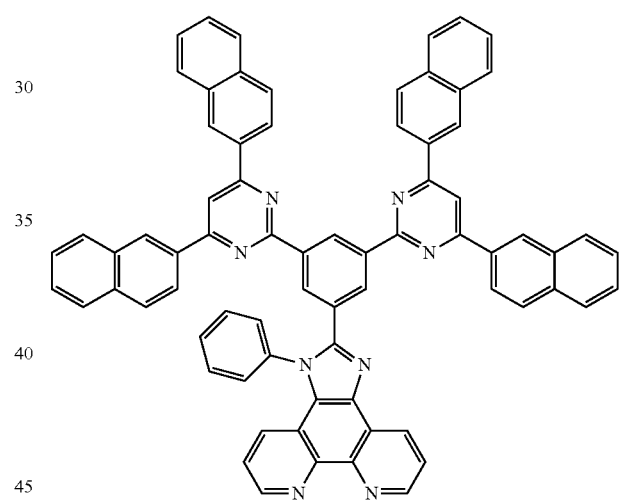
[Chemical Formula 79]
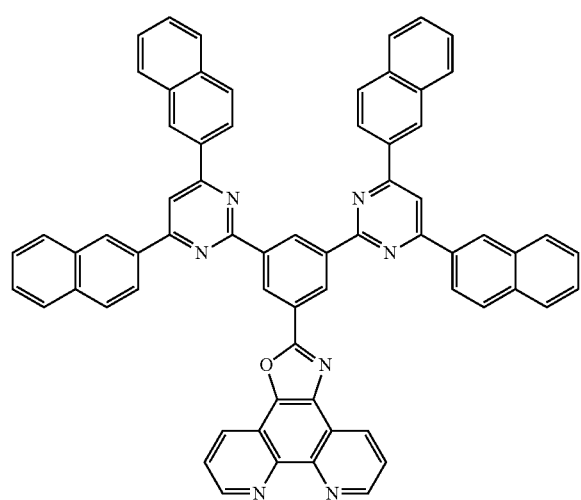
[Chemical Formula 84]
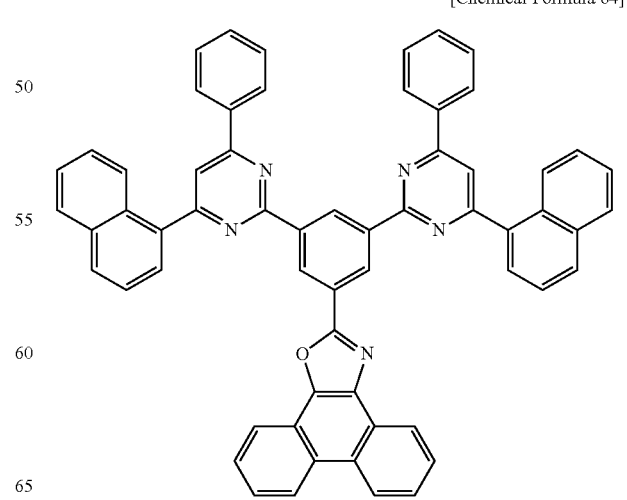

[Chemical Formula 85]
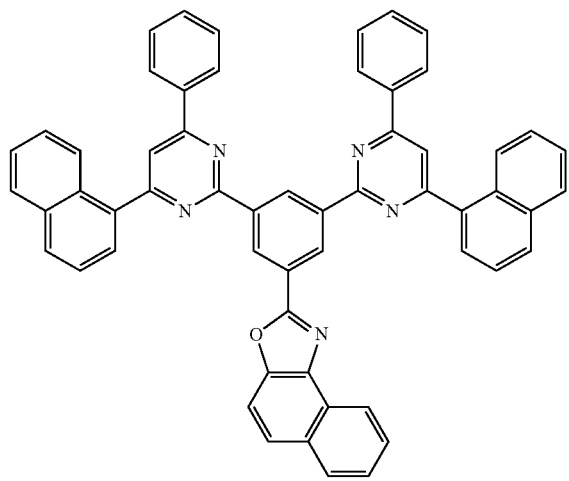
[Chemical Formula 86]
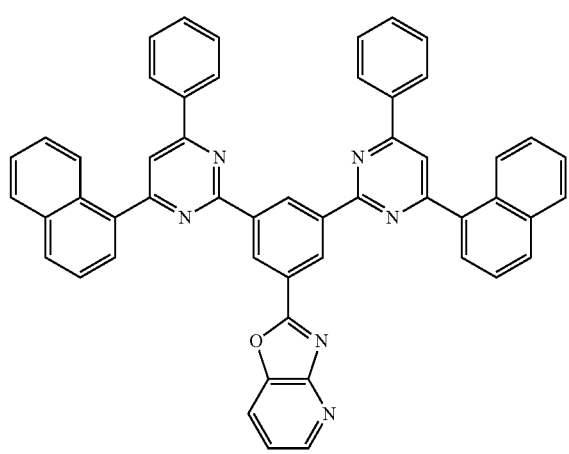
[Chemical Formula 87]
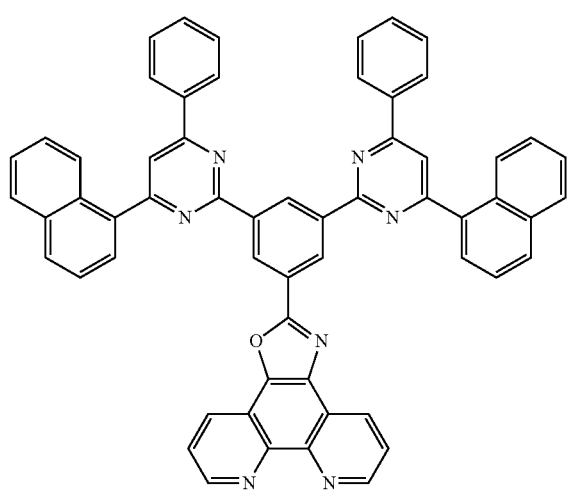
[Chemical Formula 89]
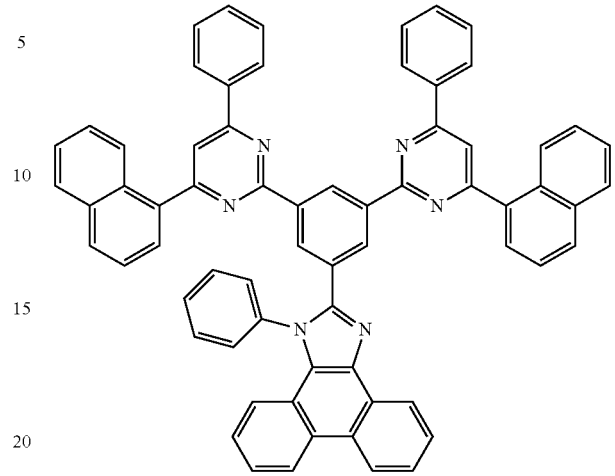
[Chemical Formula 90]
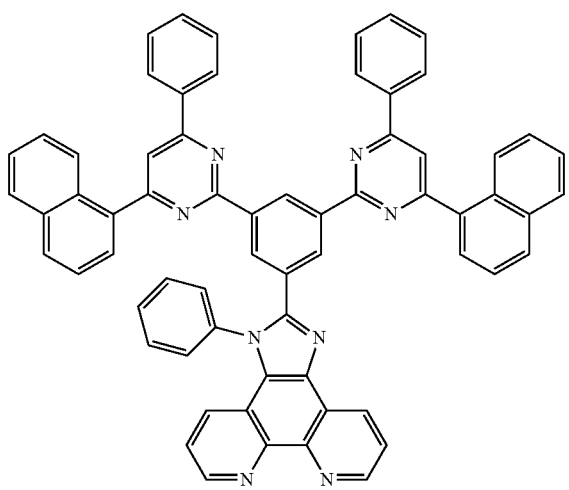
[Chemical Formula 92]
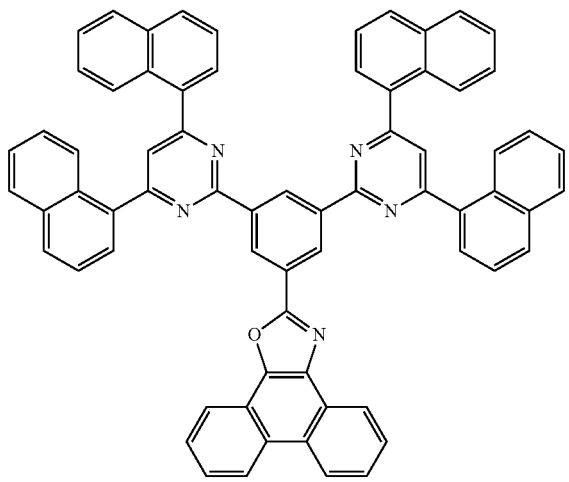

[Chemical Formula 93]
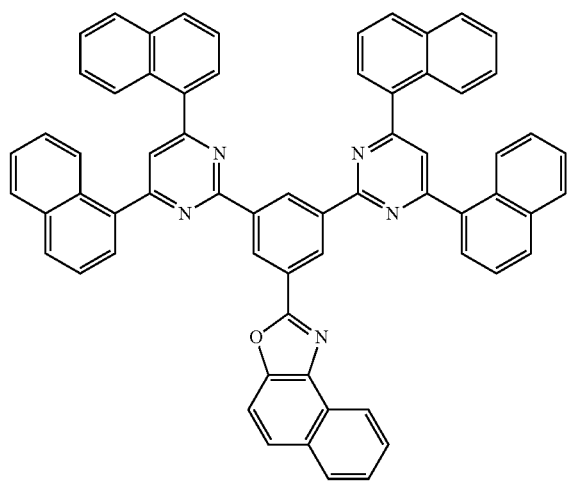
[Chemical Formula 97]
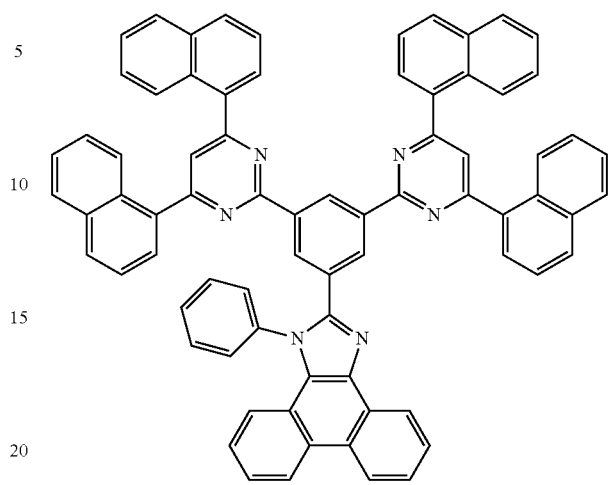
[Chemical Formula 94]
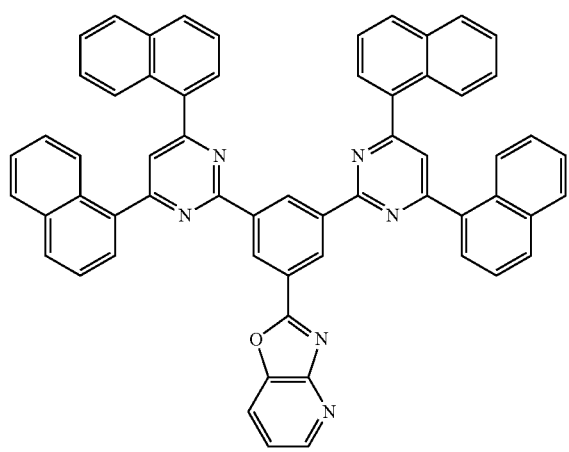
[Chemical Formula 98]
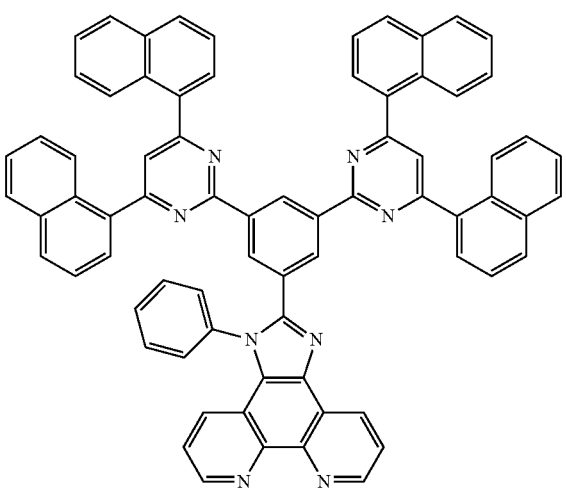
[Chemical Formula 95]
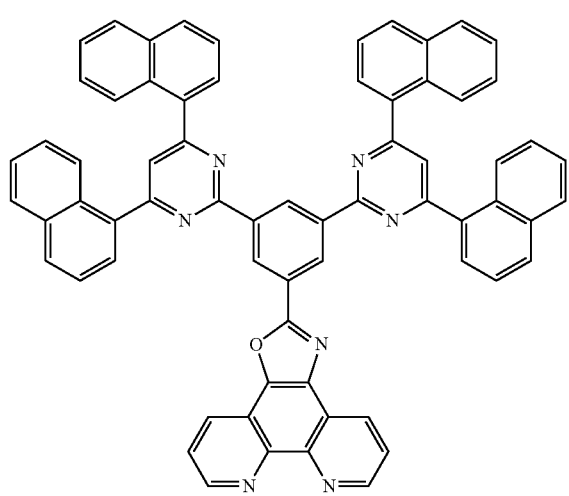
[Chemical Formula 100]
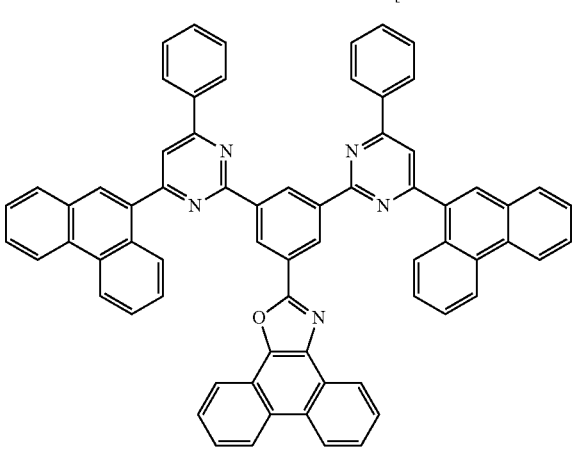

[Chemical Formula 101]
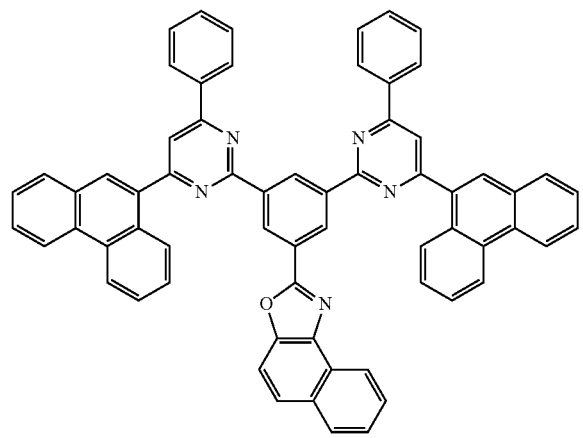
[Chemical Formula 102]
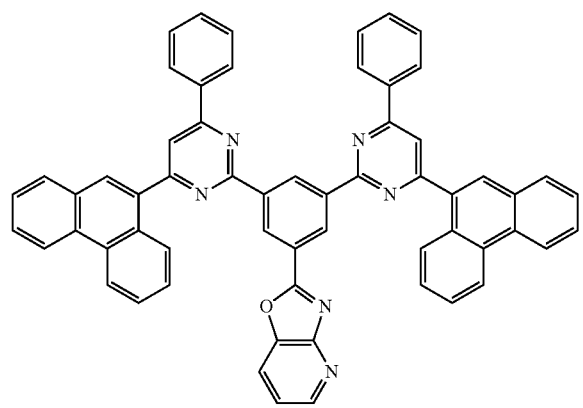
[Chemical Formula 103]
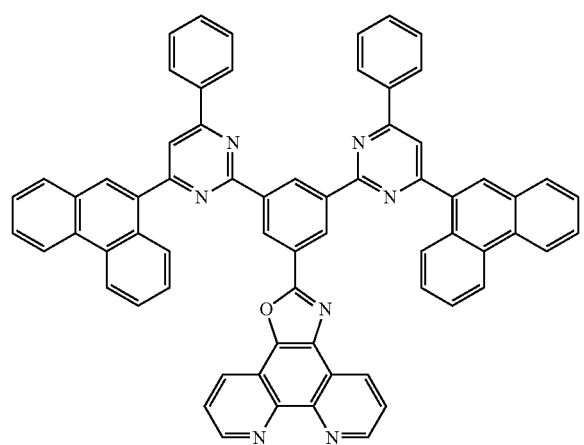
[Chemical Formula 105]
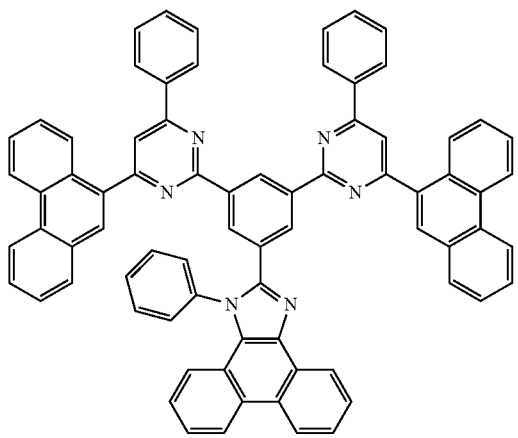
[Chemical Formula 106]
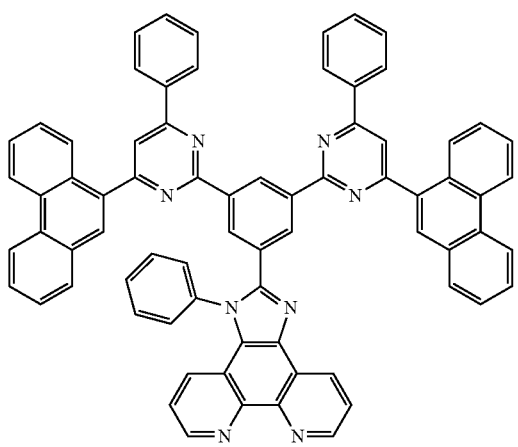
[Chemical Formula 108]
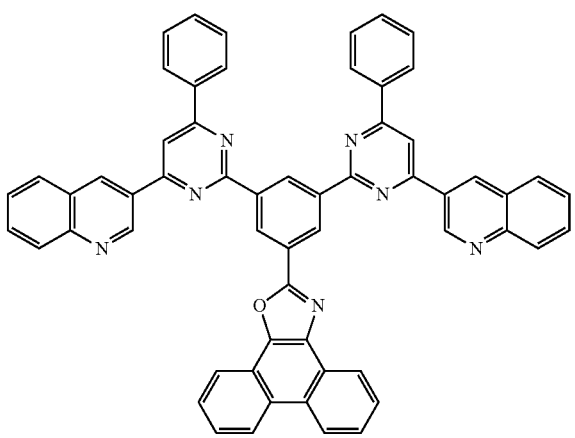

[Chemical Formula 109]
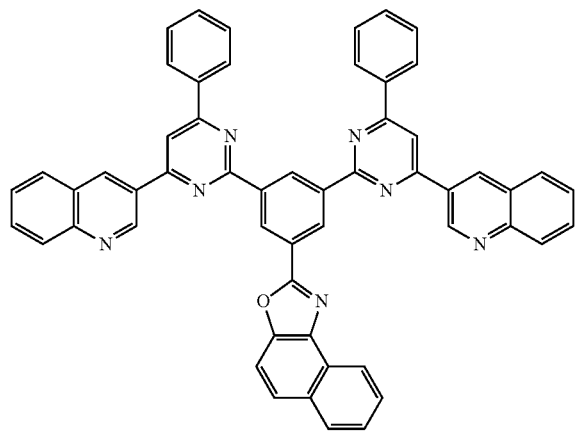
[Chemical Formula 110]
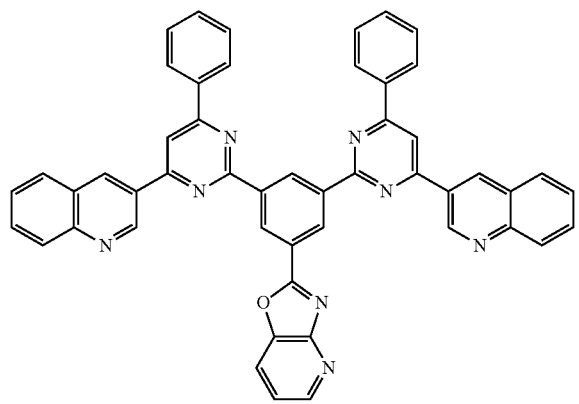
[Chemical Formula 111]
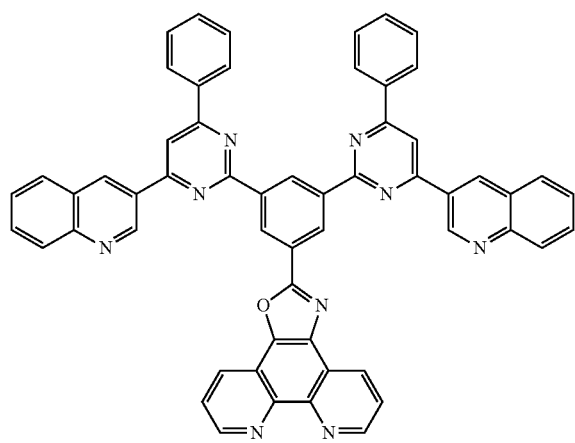
[Chemical Formula 113]
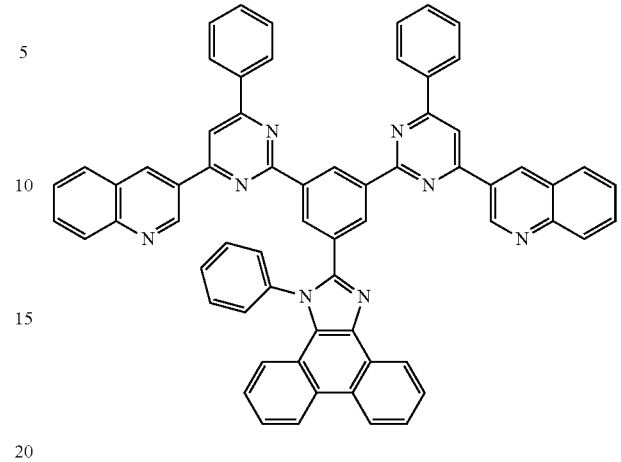
[Chemical Formula 114]
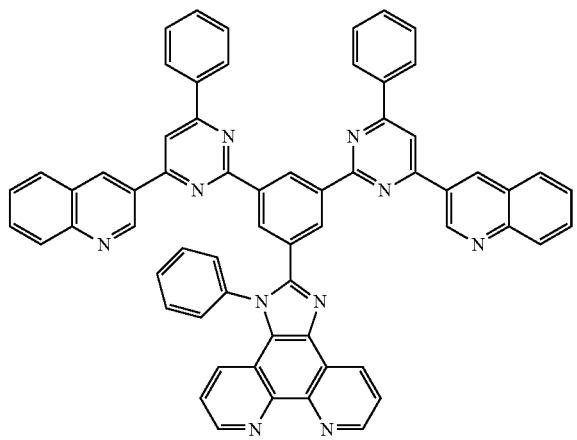
[Chemical Formula 116]
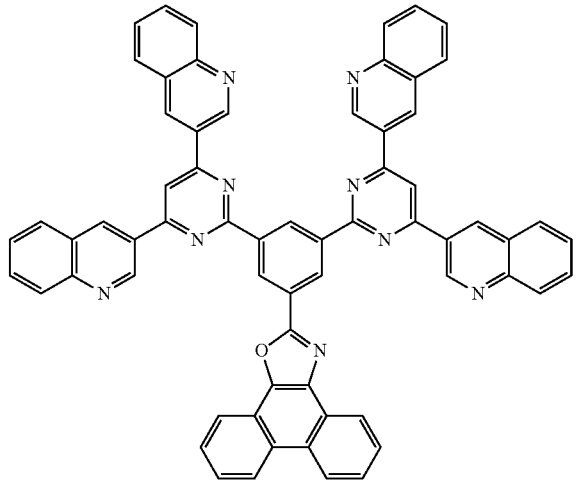

-continued
[Chemical Formula 117]
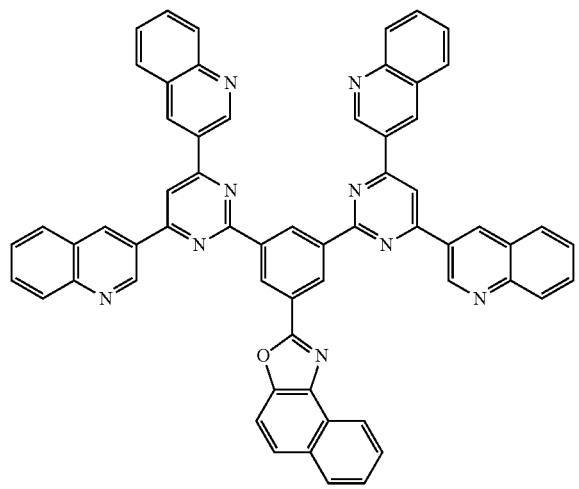
[Chemical Formula 118]
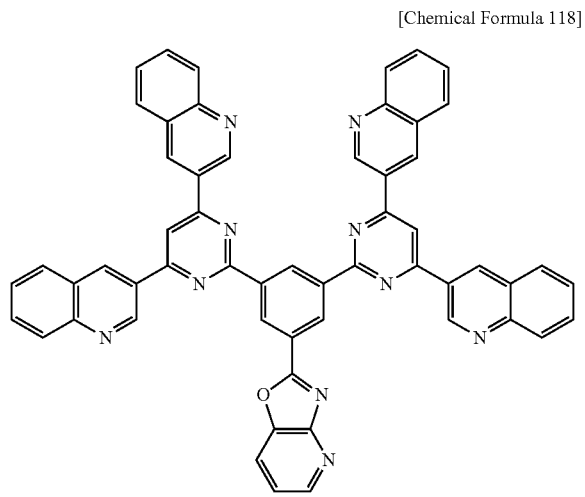
[Chemical Formula 119]
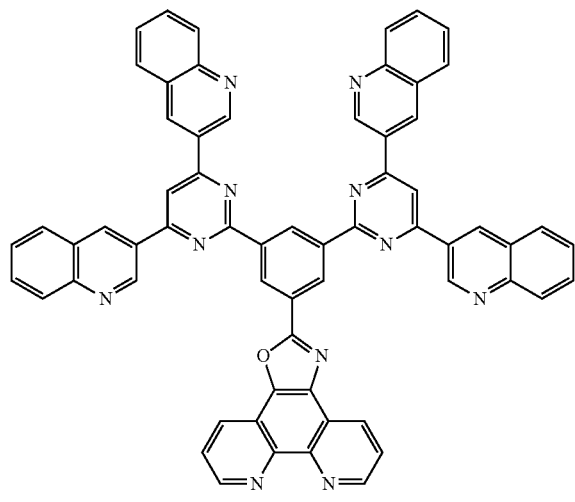
-continued
[Chemical Formula 121]
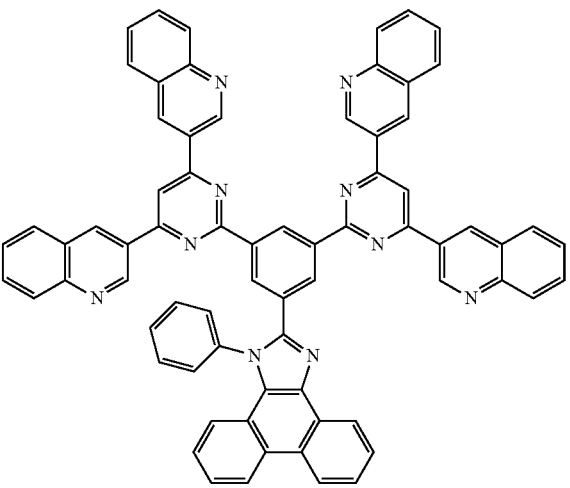
[Chemical Formula 122]
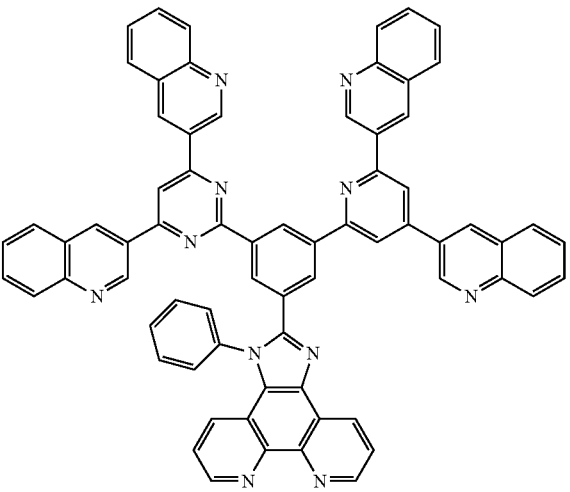
[Chemical Formula 124]

[Chemical Formula 125]
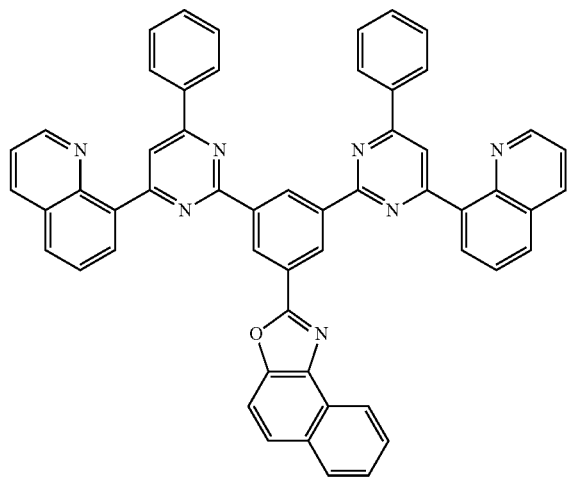
[Chemical Formula 126]
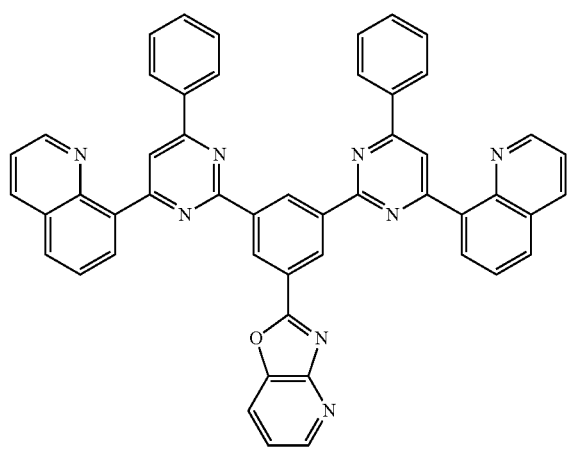
[Chemical Formula 127]
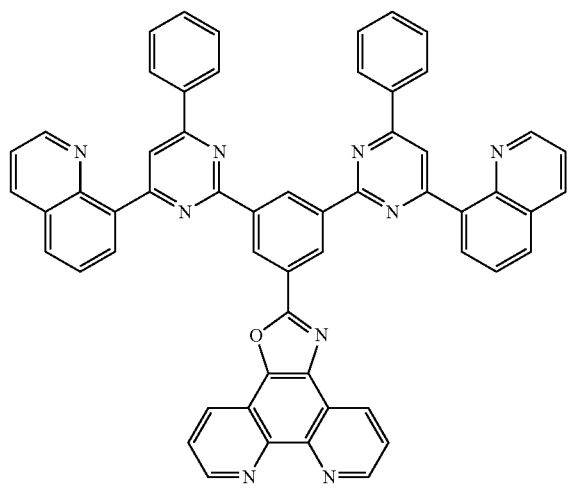
[Chemical Formula 129]
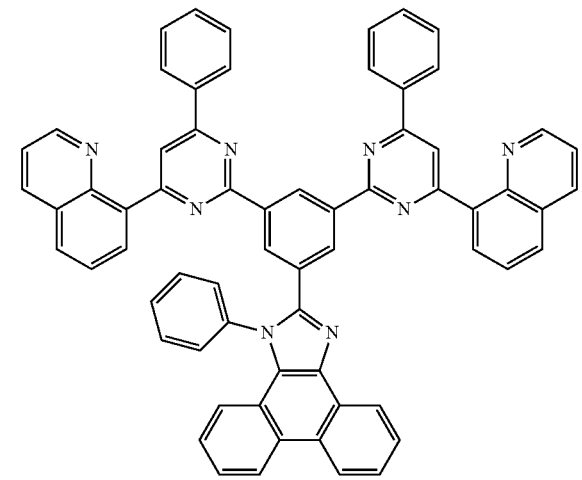
[Chemical Formula 130]
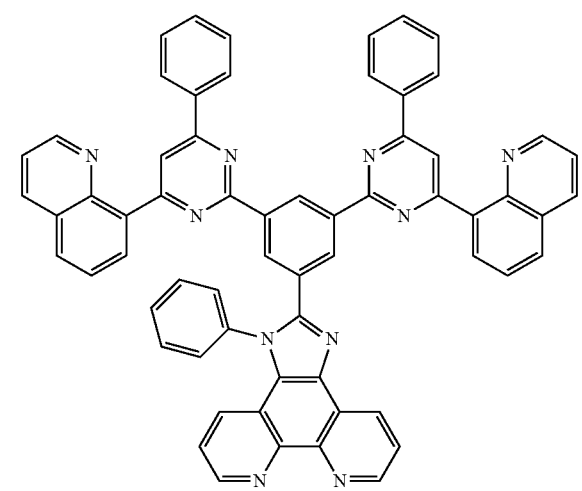
[Chemical Formula 132]
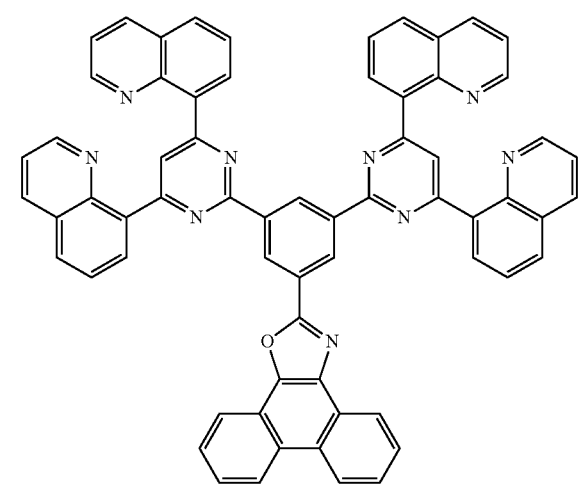

[Chemical Formula 133]
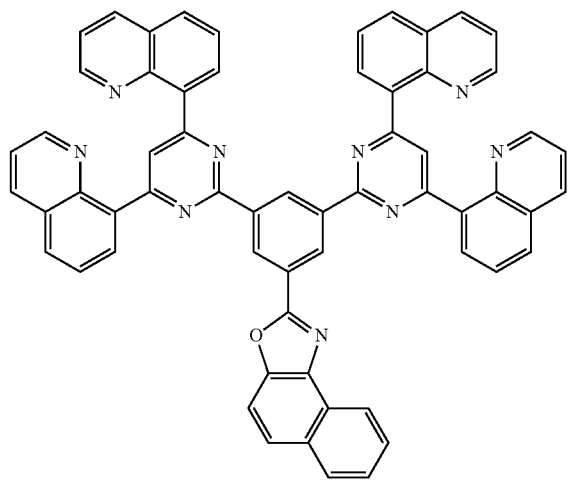
[Chemical Formula 137]
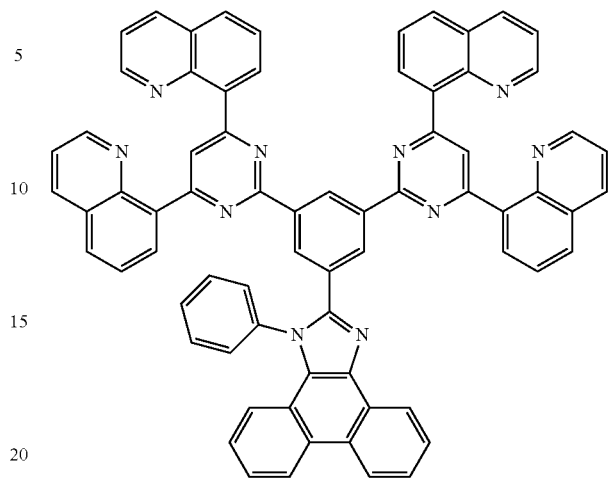
[Chemical Formula 134]
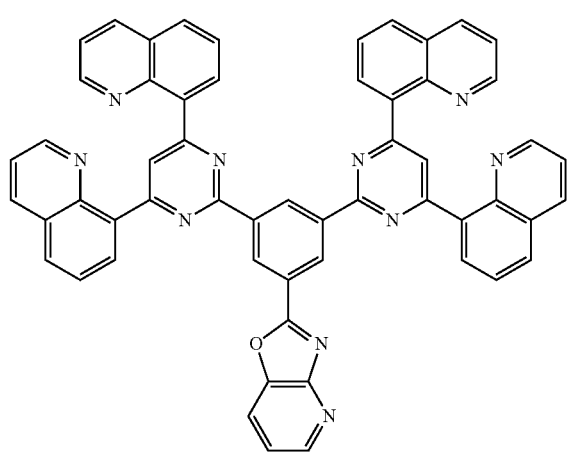
[Chemical Formula 138]
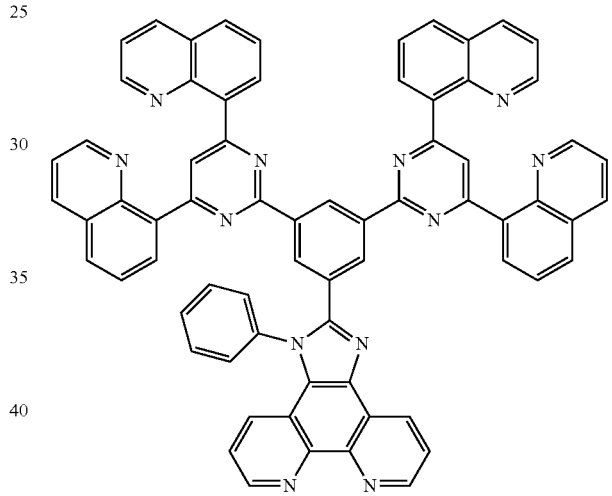
[Chemical Formula 135]
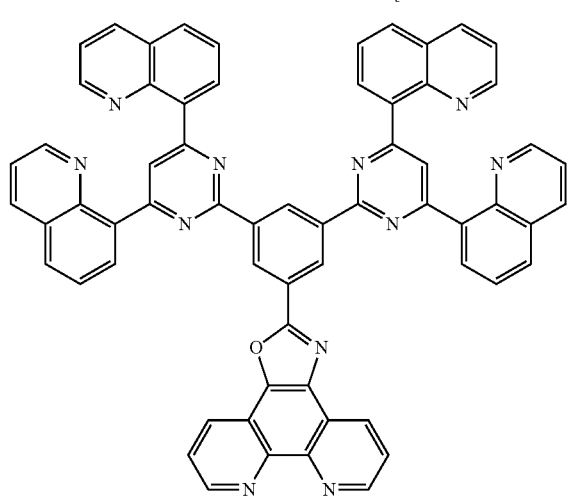
[Chemical Formula 140]
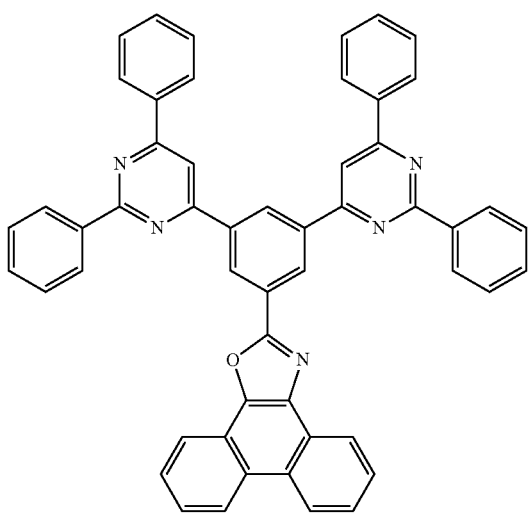

[Chemical Formula 141]
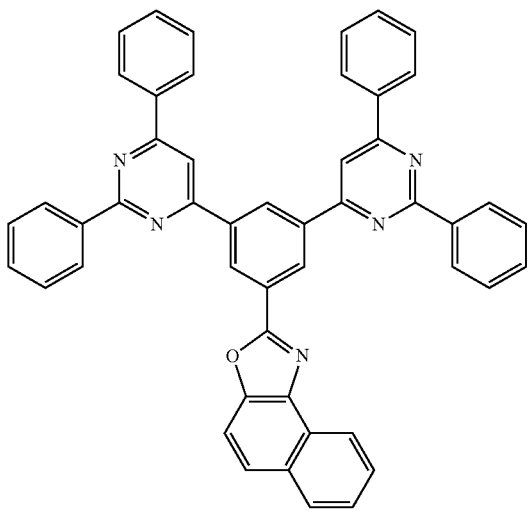
[Chemical Formula 142]
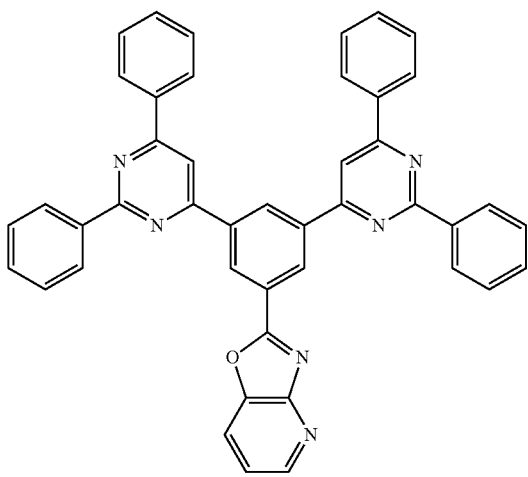
[Chemical Formula 143]
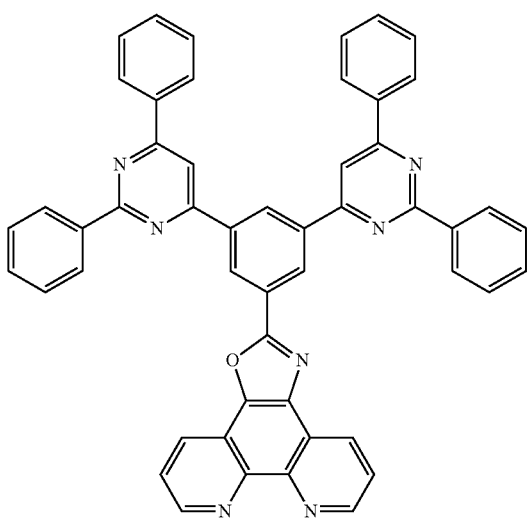
[Chemical Formula 145]
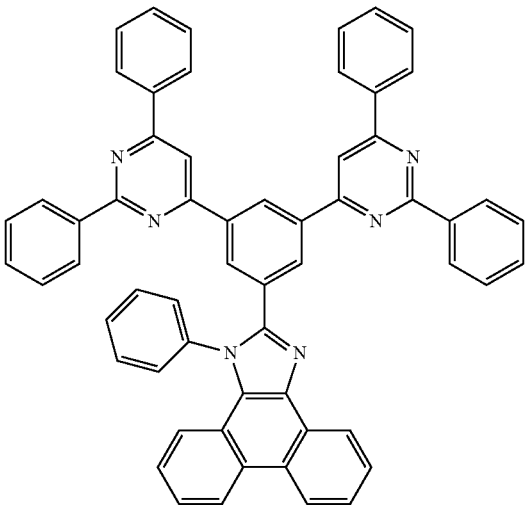
[Chemical Formula 146]
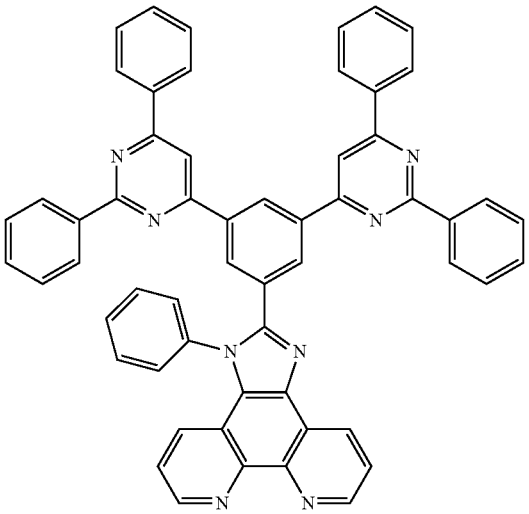
[Chemical Formula 148]
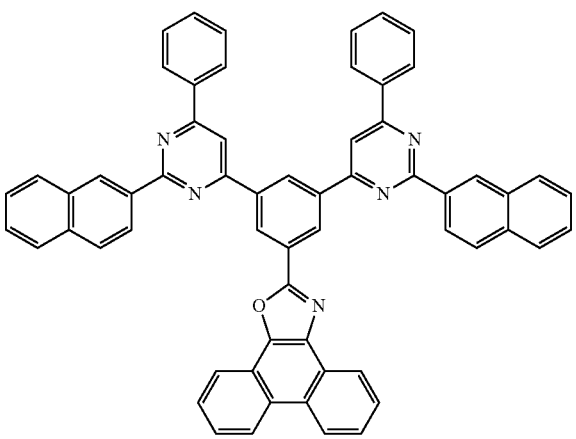

[Chemical Formula 149]
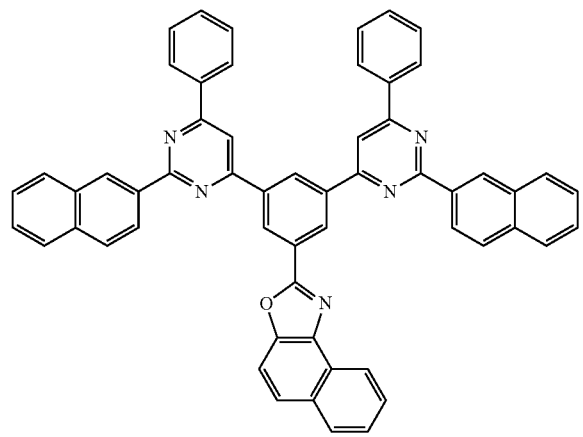
[Chemical Formula 153]
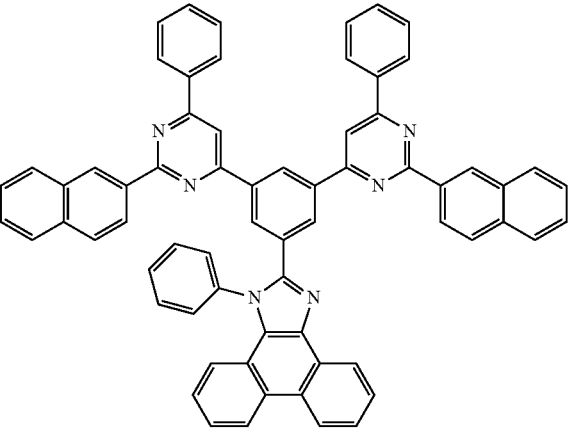
[Chemical Formula 150]
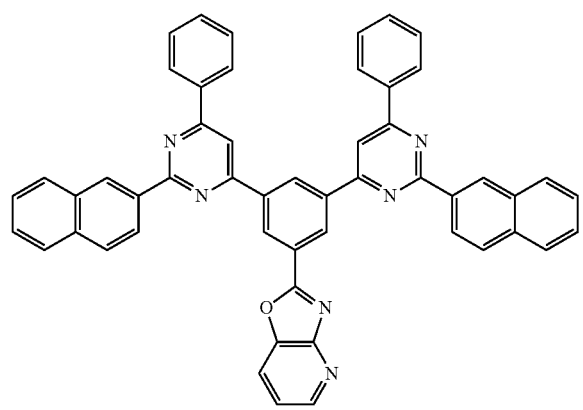
[Chemical Formula 154]
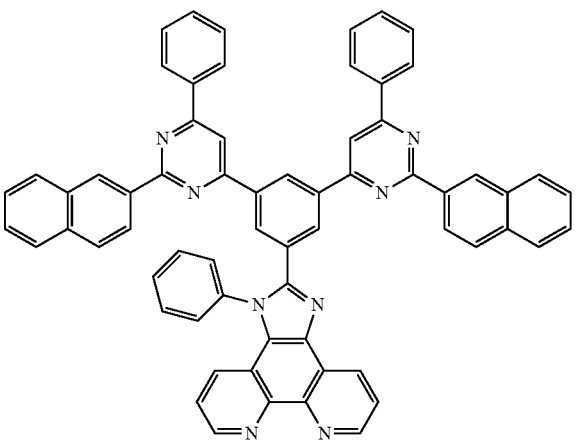
[Chemical Formula 151]
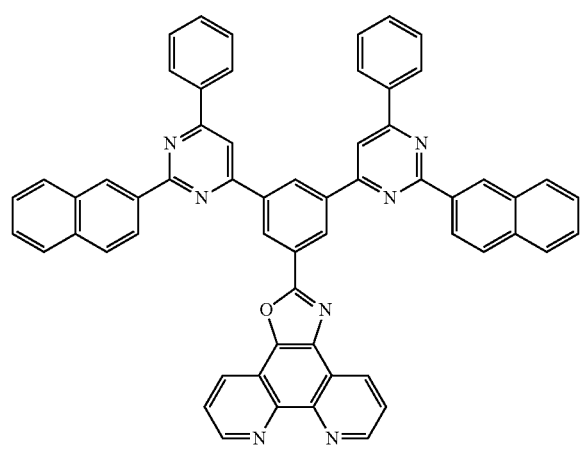
[Chemical Formula 156]
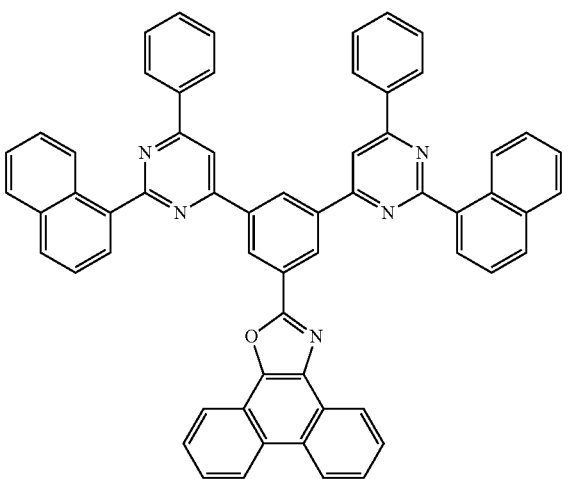

185
-continued
[Chemical Formula 157]
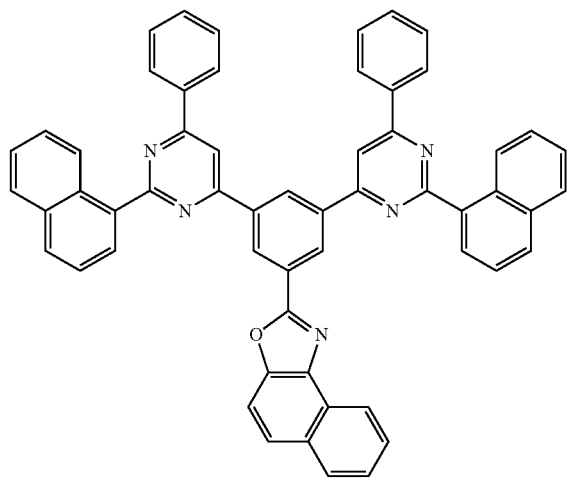
[Chemical Formula 158]
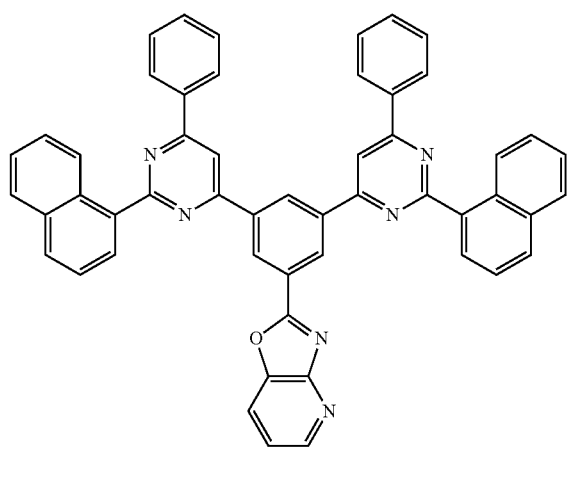
[Chemical Formula 159]
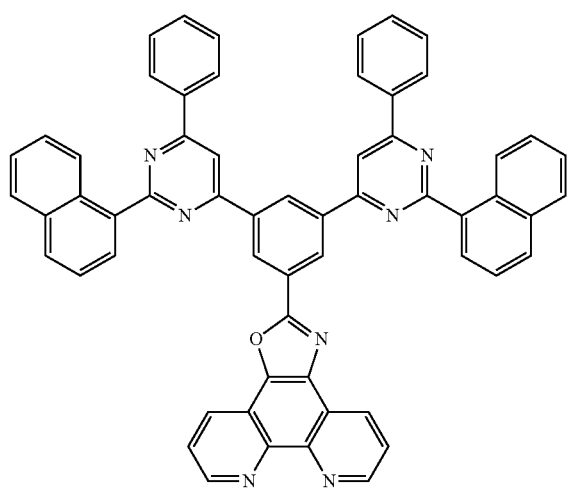
186
-continued
[Chemical Formula 161]
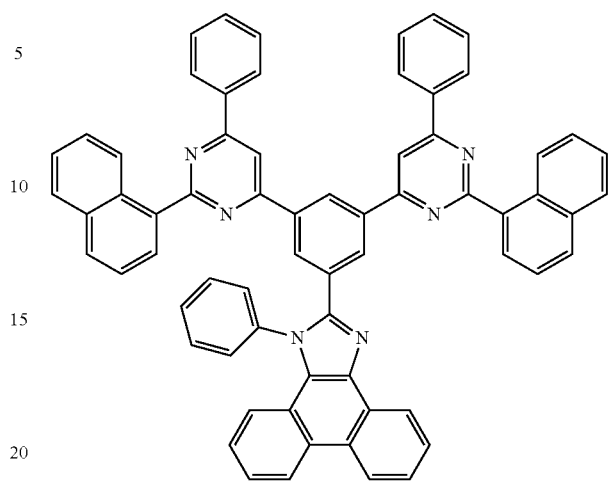
[Chemical Formula 162]
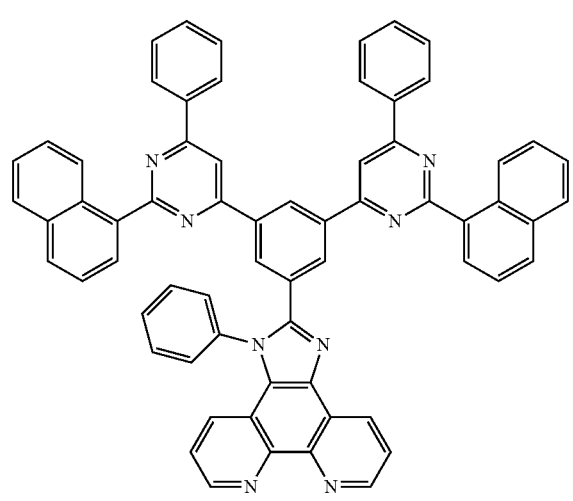
[Chemical Formula 164]
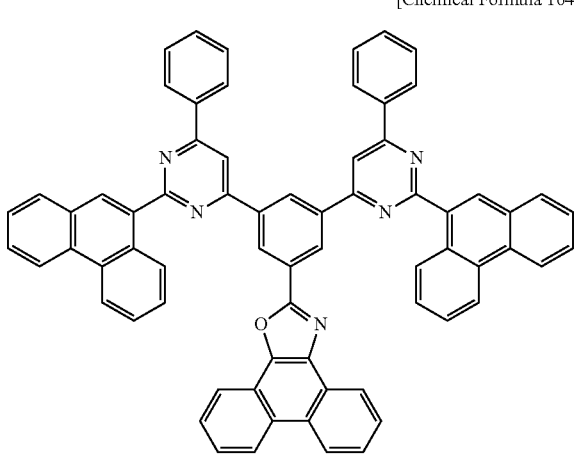

[Chemical Formula 165]
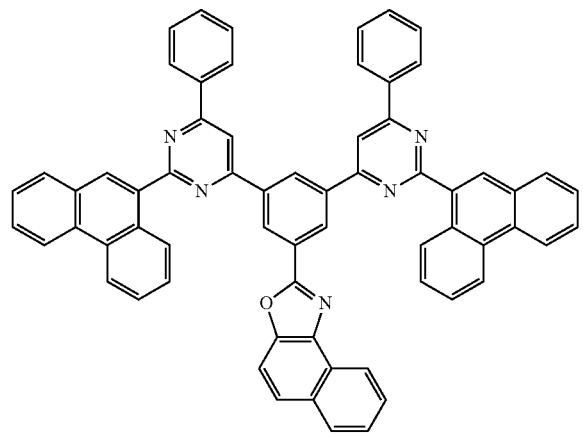
[Chemical Formula 169]
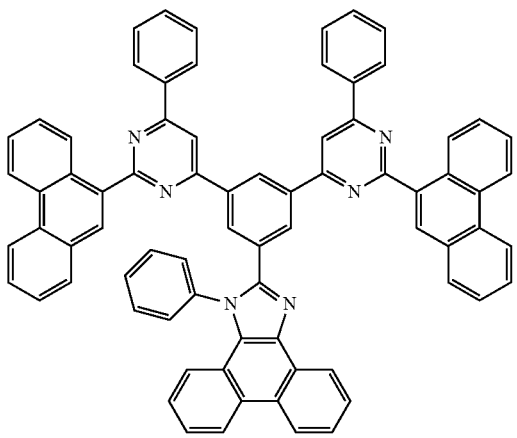
[Chemical Formula 166]
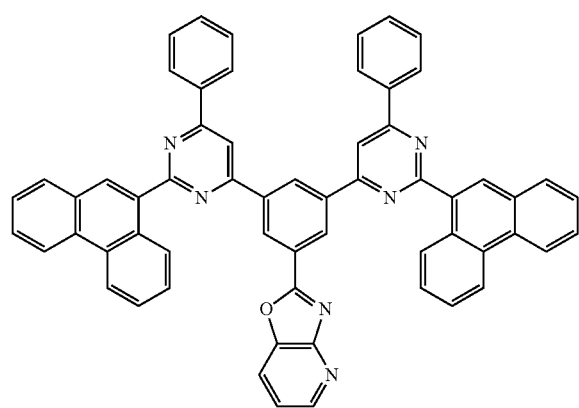
[Chemical Formula 170]
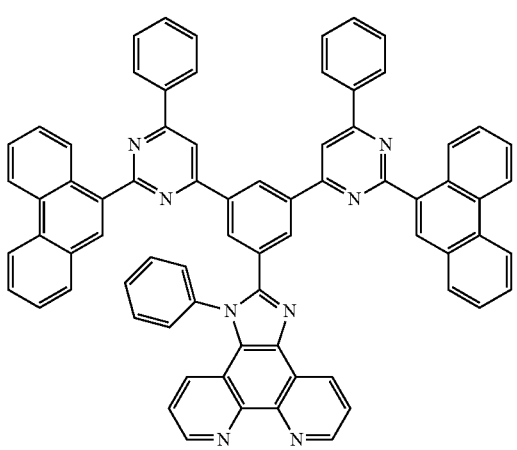
[Chemical Formula 167]
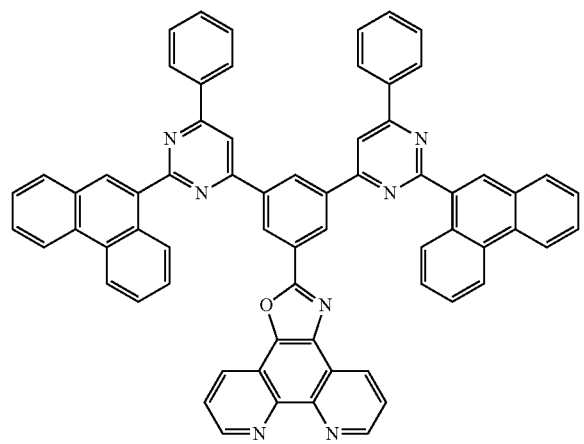
[Chemical Formula 172]
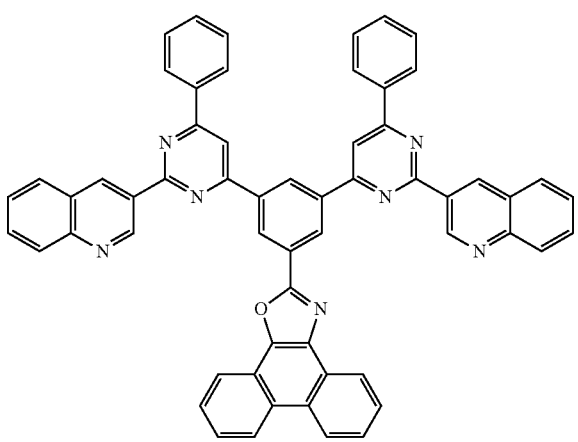

189
-continued
[Chemical Formula 173]
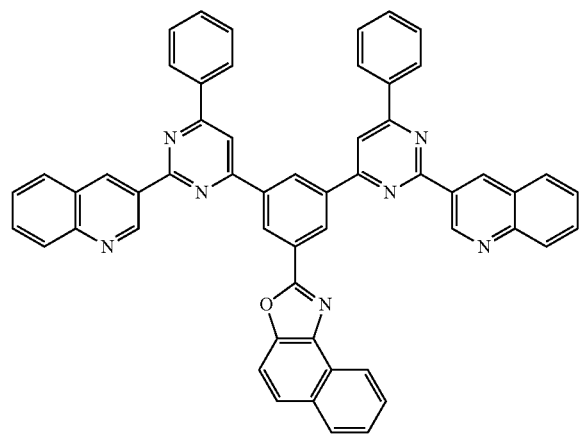
[Chemical Formula 174]
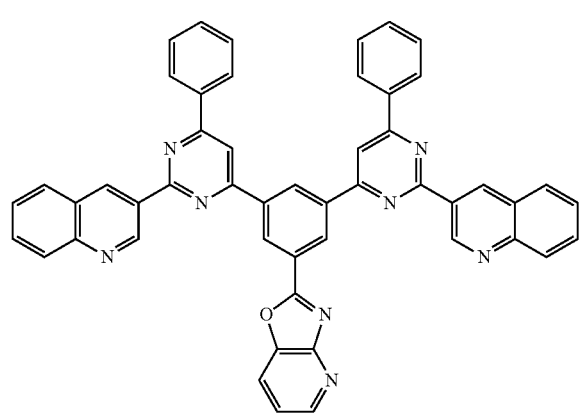
[Chemical Formula 175]
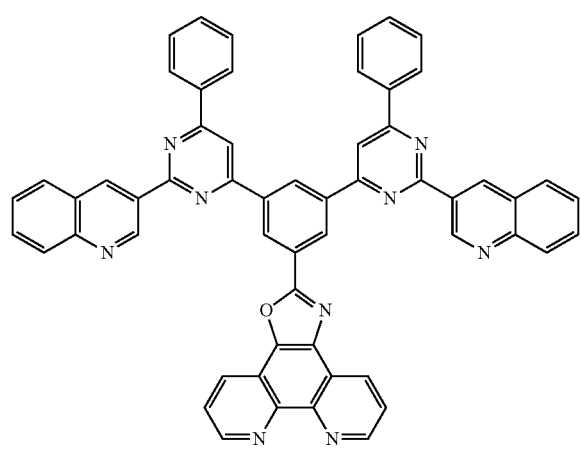
190
-continued
[Chemical Formula 177]
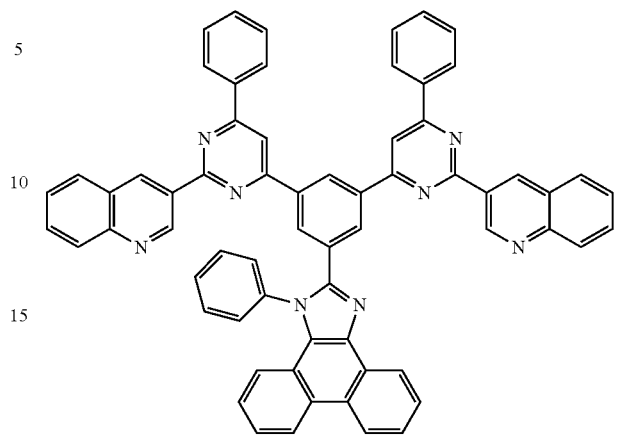
[Chemical Formula 178]
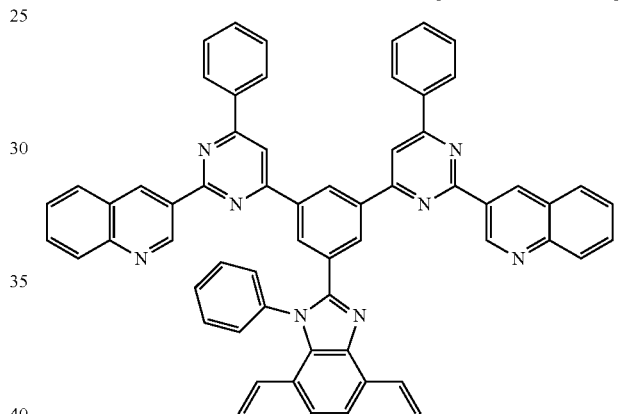
[Chemical Formula 180]
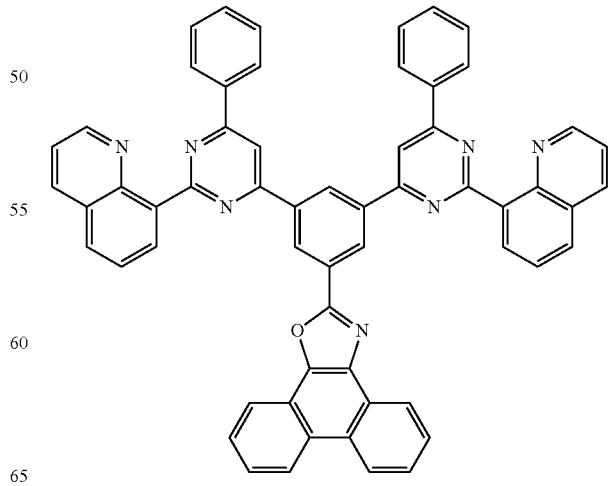

[Chemical Formula 181]

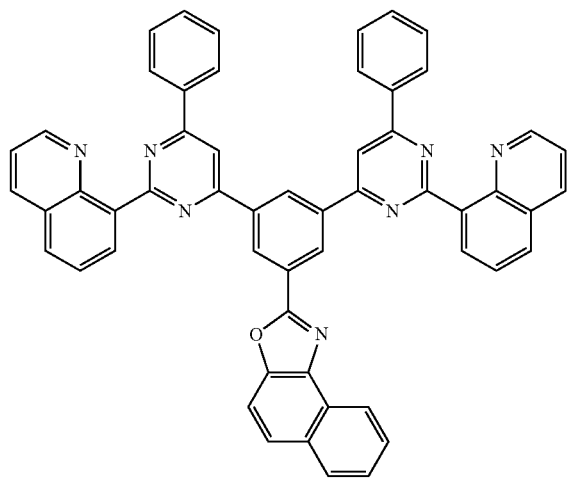

[Chemical Formula 182]

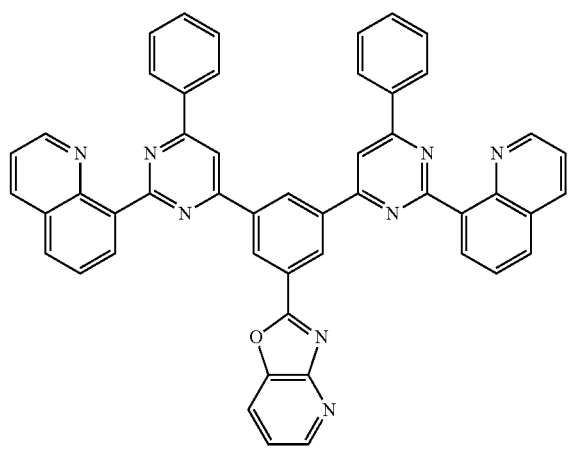

[Chemical Formula 183]

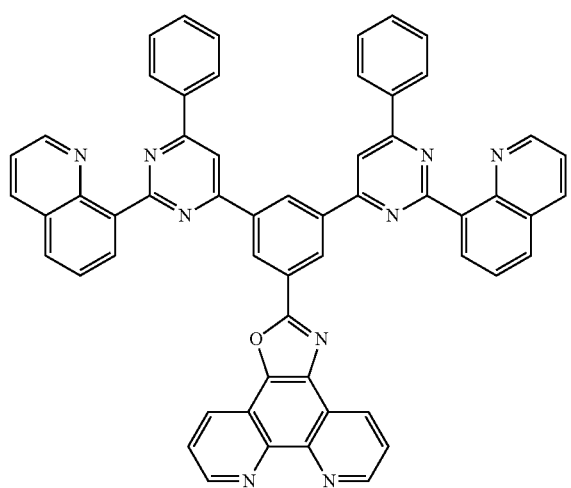

[Chemical Formula 185]

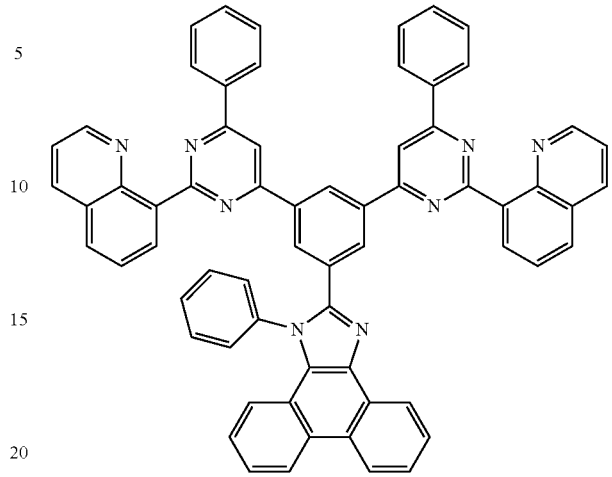

[Chemical Formula 186]

5. An organic photoelectric device, comprising:
an anode,
a cathode, and
at least one organic thin layer between the anode and the cathode, the at least one organic thin layer including the compound for an organic photoelectric device as claimed in claim 1.

6. The organic photoelectric device as claimed in claim 5, wherein the at least one organic thin layer is selected from the group of an emission layer, a hole transport layer (HTL), a hole injection layer (HIL), an electron transport layer (ETL), an electron injection layer (EIL), a hole blocking layer, and a combination thereof.

7. The organic photoelectric device as claimed in claim 5, wherein:
the at least one organic thin layer includes one of an electron transport layer (ETL) and an electron injection layer (EIL), and
the compound for an organic photoelectric device is included in the electron transport layer (ETL) or the electron injection layer (EIL).

8. The organic photoelectric device as claimed in claim 5, wherein:
the at least one organic thin layer includes an emission layer, and the compound for an organic photoelectric device is included in the emission layer.

9. The organic photoelectric device as claimed in claim 5, wherein:
the at least one organic thin layer includes an emission layer, and
the compound for an organic photoelectric device is a phosphorescent or fluorescent host material in the emission layer.

10. The organic photoelectric device as claimed in claim 5, wherein:
the at least one organic thin layer includes an emission layer, and
the compound for an organic photoelectric device is a fluorescent blue dopant material in the emission layer.

11. The organic photoelectric device as claimed in claim 5, wherein the organic photoelectric device is selected from the group of an organic light emitting diode, an organic solar cell, an organic transistor, an organic photo-conductor drum, and an organic memory device.

12. A display device including the organic photoelectric device as claimed in claim 5.

13. An organic photoelectric device, comprising:
an anode,
a cathode, and
at least one organic thin layer between the anode and the cathode, the at least one organic thin layer including the compound for an organic photoelectric device as claimed in claim 2.

14. A display device including the organic photoelectric device as claimed in claim 13.

15. An organic photoelectric device, comprising:
an anode,
a cathode, and
at least one organic thin layer between the anode and the cathode, the at least one organic thin layer including the compound for an organic photoelectric device as claimed in claim 4.

16. The organic photoelectric device as claimed in claim 15, wherein the at least one organic thin layer is selected from the group of an emission layer, a hole transport layer (HTL), a hole injection layer (HIL), an electron transport layer (ETL), an electron injection layer (EIL), a hole blocking layer, and a combination thereof.

17. The organic photoelectric device as claimed in claim 15, wherein:
the at least one organic thin layer includes one of an electron transport layer (ETL) and an electron injection layer (EIL), and
the compound for an organic photoelectric device is included in the electron transport layer (ETL) or the electron injection layer (EIL).

* * * * *